United States Patent
Gewehr et al.

(10) Patent No.: US 6,583,090 B1
(45) Date of Patent: Jun. 24, 2003

(54) HETARYL-SUBSTITUTED BENZYL PHENYL ETHERS, METHOD FOR THE PRODUCTION THEREOF, AND THEIR USE FOR COMBATING HARMFUL FUNGI AND ANIMAL PESTS

(75) Inventors: Markus Gewehr, Kastellaun (DE); Roland Götz, Ludwigshafen (DE); Thomas Grote, Schifferstadt (DE); Hubert Sauter, Mannheim (DE); Norbert Götz, Worms (DE); Herbert Bayer, Mannheim (DE); Wassilios Grammenos, Ludwigshafen (DE); Andreas Gypser, Mannheim (DE); Bernd Müller, Frankenthal (DE); Arne Ptock, Ludwigshafen (DE); Eberhard Ammermann, Heppenheim (DE); Gisela Lorenz, Neustadt (DE); Siegfried Strathmann, Limburgerhof (DE); Volker Harries, Frankenthal (DE); Oliver Cullmann, Mannheim (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 09/623,178
(22) PCT Filed: Feb. 25, 1999
(86) PCT No.: PCT/EP99/01198
§ 371 (c)(1), (2), (4) Date: Aug. 29, 2000
(87) PCT Pub. No.: WO99/46246
PCT Pub. Date: Sep. 16, 1999

(30) Foreign Application Priority Data

Mar. 9, 1998 (DE) ......................... 198 09 995
May 20, 1998 (DE) ......................... 198 22 576

(51) Int. Cl.[7] ........................ A01N 43/56; C07D 231/12
(52) U.S. Cl. ..................... 504/280; 548/377.1
(58) Field of Search .............. 548/377.1; 504/280

(56) References Cited

PUBLICATIONS

Al–Smadi et al., Liebigs Ann./Recl. (1997) vol. 11, pp. 2357–2361 –Abstract.*

* cited by examiner

*Primary Examiner*—Robert W. Ramsuer
(74) *Attorney, Agent, or Firm*—Keil & Weinkauf

(57) ABSTRACT

The invention relates to hetaryl-substituted benzyl phenyl ethers of formula (I) in which the substituents have the following meanings: (Q):

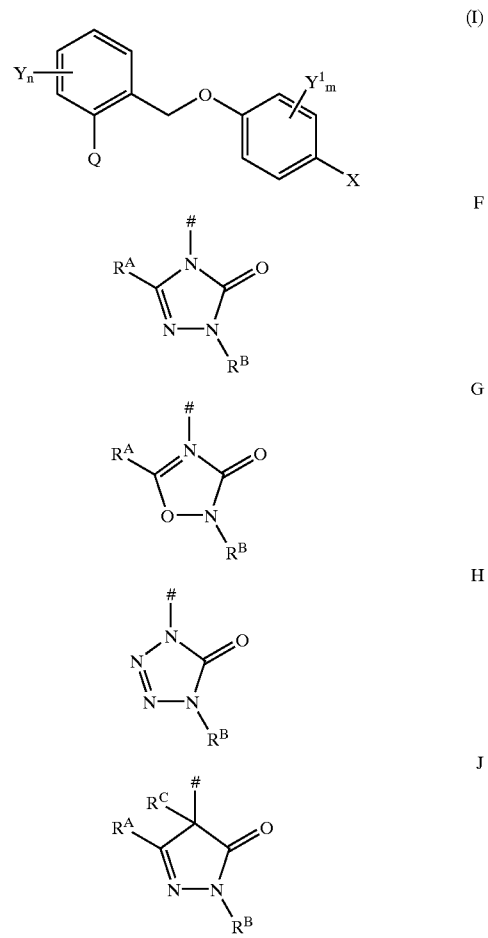

$C(=CHOCH_3)$—$COOCH_3$, $C(=CHCH_3)$—$COOCH_3$, $C(=NOCH_3)$—$COOCH_3$, $C(=NOCH_3)$—$CONHCH_3$, $N(—OCH_3)$—$COOCH_3$ or a group F, G, H or J, whereby # characterizes the bond with the phenyl ring, and (X) five-linked heteroaryl which is optionally substituted by a group $Y^2_p$ and which contains one to four nitrogen atoms or one to three nitrogen atoms and one sulfur or oxygen atom. The invention also relates to the salts of the inventive hetaryl-substituted benzyl phenyl ethers, to the production of compounds (I), and to the use of compounds (I) for combating harmful fungi and animal pests.

10 Claims, No Drawings

HETARYL-SUBSTITUTED BENZYL PHENYL ETHERS, METHOD FOR THE PRODUCTION THEREOF, AND THEIR USE FOR COMBATING HARMFUL FUNGI AND ANIMAL PESTS

The present invention relates to hetaryl-substituted benzyl phenyl ethers of the formula I

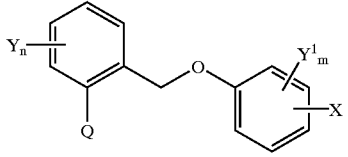

(I)

where:

Q is $C(=CHOCH_3)—COOCH_3$, $C(=CHCH_3)—COOCH_3$, $C(=NOCH_3)—COOCH_3$, $C(=NOCH_3)—CONHCH_3$, $N(—OCH_3)—COOCH_3$ or
a group F, G, H, or J

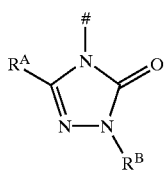

F

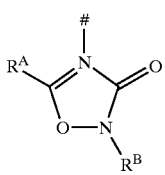

G

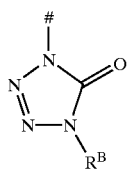

H

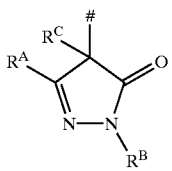

J where
# denotes the bond with the phenyl ring and
$R^A$ is hydrogen, cyano, halogen,
$C_1$–$C_6$-alkyl, $C_1$–$C_6$-haloalkyl, $C_3$–$C_6$-cycloalkyl, $C_3$–$C_6$-halocycloalkyl, $C_2$–$C_6$-alkenyl, $C_2$–$C_6$-haloalkenyl, $C_2$–$C_6$-alkynyl, $C_2$–$C_6$-haloalkynyl, $C_1$–$C_6$-alkoxy, $C_1$–$C_6$-haloalkoxy, $C_3$–$C_6$-cycloalkyloxy, $C_3$–$C_6$-halocycloalkyloxy, $C_2$–$C_6$-alkenyloxy, $C_2$–$C_6$-haloalkenyloxy, $C_2$–$C_6$-alkynyloxy, $C_2$–$C_6$-haloalkynyloxy, acetyloxy, $C_1$–$C_6$-alkylthio, $C_1$–$C_6$-haloalkylthio, $C_3$–$C_6$-cycloalkylthio, $C_2$–$C_6$-alkenylthio, $C_2$–$C_6$-haloalkenylthio, $C_2$–$C_6$-alkynylthio, $C_2$–$C_6$-haloalkynylthio, $C_1$–$C_6$-alkylsulfinyl, $C_1$–$C_6$-haloalkylsulfinyl, $C_3$–$C_6$-cycloalkylsulfinyl, $C_2$–$C_6$-alkenylsulfinyl, $C_2$–$C_6$-haloalkenylsulfinyl, $C_2$–$C_6$-alkynylsulfinyl, $C_2$–$C_6$-haloalkynylsulfinyl, $C_1$–$C_6$-alkylsulfonyl, $C_1$–$C_6$-haloalkylsulfonyl, $C_3$–$C_6$-cycloalkylsulfonyl, $C_2$–$C_6$-alkenylsulfonyl, $C_2$–$C_6$-haloalkenylsulfonyl, $C_2$–$C_6$-alkynylsulfonyl, $C_2$–$C_6$-haloalkynylsulfonyl,
amino, $C_1$–$C_6$-alkylamino, $C_1$–$C_6$-dialkylamino, $C_1$–$C_6$-alkoxyamino, $(C_1$–$C_6$-alkyl) $(C_1$–$C_6$-alkoxy) amino, or
unsubstituted heterocyclyl or heterocyclyl which is substituted by one to three groups $R^4$;
$R^B$ is hydrogen, $C_1$–$C_6$-alkyl, $C_1$–$C_6$-haloalkyl, $C_3$–$C_6$-cycloalkyl, $C_2$–$C_6$-alkenyl, $C_2$–$C_6$-haloalkenyl, $C_2$–$C_6$-alkynyl or $C_2$–$C_6$-haloalkynyl;
$R^C$ is hydrogen, $C_1$–$C_6$-alkyl, $C_1$–$C_6$-haloalkyl, $C_3$–$C_6$-cycloalkyl, $C_3$–$C_6$-halocycloalkyl, $C_2$–$C_6$-alkenyl, $C_2$–$C_6$-haloalkenyl, $C_2$–$C_6$-alkynyl, $C_2$–$C_6$-haloalkynyl, hydroxyl, $C_1$–$C_2$-alkoxy, acetyloxy, $C_2$–$C_4$-alkylcarbonyl or $C_2$–$C_4$-alkoxycarbonyl;
X is five-membered hetaryl which is unsubstituted or substituted by a group $Y^2_p$ and contains one to four nitrogen atoms or one to three nitrogen atoms and one sulfur or oxygen atom;
Y, $Y^1$ are halogen, cyano, nitro, $C_1$–$C_4$-alkyl, $C_1$–$C_4$-haloalkyl, $C_2$–$C_6$-alkenyl, $C_2$–$C_6$-haloalkenyl or $C_1$–$C_4$-alkoxy;
$Y^2$ is halogen, cyano, nitro, $C_1$–$C_4$-alkyl, $C_1$–$C_4$-haloalkyl, $C_2$–$C_6$-alkenyl, $C_2$–$C_6$-haloalkenyl, $C_2$–$C_6$-alkynyl, $C_1$–$C_4$-alkoxy, $C_1$–$C_4$-haloalkoxy, $C_1$–$C_4$-alkylamino or $C_1$–$C_4$-alkylthio, or
phenyl, phenoxy or benzyl, where the aromatic rings may be partially or fully halogenated or may carry one to three groups $R^4$:
$R^4$ is halogen, cyano, nitro, hydroxyl, mercapto, amino, carboxyl, aminocarbonyl, aminothiocarbonyl, alkyl, haloalkyl, alkenyl, alkenyloxy, alkynyloxy, alkoxy, haloalkoxy, alkylthio, alkylamino, dialkylamio, formyl, alkylcarbonyl, alkylsulfonyl, alkylsulfoxyl, alkoxycarbonyl, alkylcarbonyloxy, alkylaminocarbonyl, dialkylaminocarbonyl, alkylaminothiocarbonyl, dialkylaminothiocarbonyl, where the alkyl groups in these radicals contain 1 to 6 carbon atoms and the abovementioned alkenyl or alkynyl groups in these radicals contain 2 to 8 carbon atoms;
and/or one to three of the following radicals
cycloalkyl, cycloalkoxy, heterocyclyl, heterocyclyloxy, where the cyclic systems contain 3 to 10 ring members; aryl, aryloxy, arylthio, aryl-$C_1$–$C_6$-alkoxy, aryl-$C_1$–$C_6$-alkyl, hetaryl, hetaryloxy, hetarylthio, where the aryl radicals preferably contain 6 to 10 ring members, the hetaryl radicals 5 or 6 ring members, where the cyclic systems may be partially or fully halogenated or may be substituted by one to three groups $R^5$ or by one or two groups $R^6$:
$R^5$ is halogen, cyano, nitro, hydroxyl, $C_1$–$C_6$-alkyl, $C_1$–$C_6$-haloalkyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_3$–$C_6$-alkynyloxy and $C_1$–$C_4$-alkylenedioxy which may be halogenated; and
$R^6$ is $C(=NOR^d)$ -$\Gamma_l$-$R^{d_1}$, where $R^d$ is hydrogen or $C_1$–$C_6$-alkyl, $\Gamma$ is oxygen, sulfur or $NR^d$ and l is 0 or 1;

m, n are 0, 1 or 2, where the radicals Y and $Y^1$ may be different if m or n=2;

p is 0, 1, 2 or 3, where the radicals $Y^2$ may be different if p=2 or 3;

and salts thereof.

Additionally, the invention relates to processes for preparing the compounds I and to the use of the compounds I for controlling harmful fungi and animal pests.

Phenoxymethylenephenylacetic acid methyl esters and methyl amides are known from EP-A 253 213, EP-A 254 426, EP-A 251 082, EP-A 278 595, EP-A 280 185, EP-A 299 694, EP-A 386 561, EP-A 398 692 and EP-A 477 631, and the corresponding methoxycarbamates are known from WO-A 93/15046. Hetaryl-substituted phenylacetic acid derivatives are disclosed in EP-A 811 614.

Cyclic amides which carry an ortho-substituted phenyl ring in the position ortho to the amide carbonyl group are disclosed in WO-A 95/14009, WO-A 96/17851, WO-A 96/26191, WO-A 96/36229, WO-A 96/36615, WO-A 96/36616, WO-A 96/38425, WO-A 97/00612, WO-A 97/02255, WO-A 97/05120, WO-A 97/19935, WO-A 98/05652, WO-A 98/20003 and WO-A 98/23155, and JP-A 09/104676 and JP-A 09/208565. Cyclic amides which carry a substituted heterocycle in the position ortho to the amide carbonyl group are disclosed in WO-A 96/36633.

The compounds described in the abovementioned publications are suitable for use as crop protection agents against harmful fungi and in some cases against animal pests.

However, their action is in many cases unsatisfactory.

It is an object of the invention to provide compounds having improved activity.

This object was achieved by the substituted benzyl phenyl ethers of the formula I. Furthermore, intermediates and processes for preparing the compounds I, and also the use of the compounds I and of compositions comprising them for controlling harmful fungi and animal pests, were found. The fungicidal action is preferred.

Compared with the known compounds, the compounds of the formula I have increased activity against harmful fungi and animal pests.

The compounds of the formula I differ from the compounds known from the abovementioned publications by the design of the phenoxy group, which is substituted by five-membered nitrogen heterocycles or heteroaromatics.

The compounds I can be obtained by different routes, and it is immaterial for the synthesis whether the group Q or the phenoxy group E is constructed first.

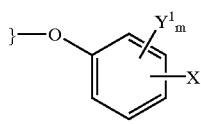

The bracket } in the formula E denotes the linkage point with the benzyl skeleton in the formula I.

The construction of the group —Q is known, for example, from the publications cited at the outset, and also from the following publications:

EP-A 254 426, EP-A 370 629, EP-A 463 488, EP-A 472 300 and EP-A 513 580.

Thus, for clarity, the term

Q# is used for $C(=CHOCH_3)$—$COOCH_3$, $C(-CHCH_3)$—$COOCH_3$, $C(=NOCH_3)$—$COOCH_3$, $N(-OCH_3)$—$COOCH_3$ or the group F, G, H or J, or a suitable precursor thereof, and L# is used for the phenoxy group E, or a suitable precursor thereof, in the descriptions of the reactions below.

For compounds of the formulae IF and IH

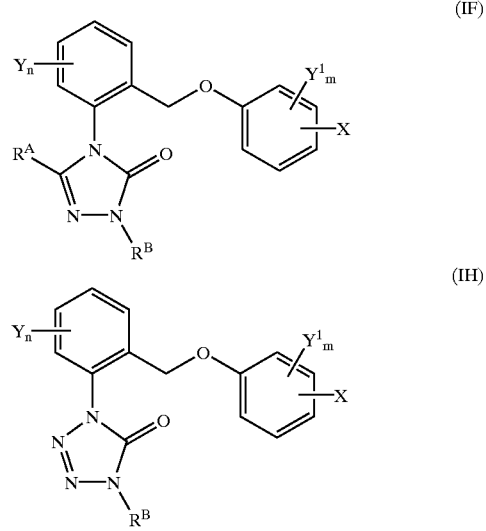

preference is given to introducing the phenoxy group in the steps in which Q# is nitro or, in the case of IF, is the group F, and, in the case IH, is the group H.

For compounds of the formulae IG and IJ

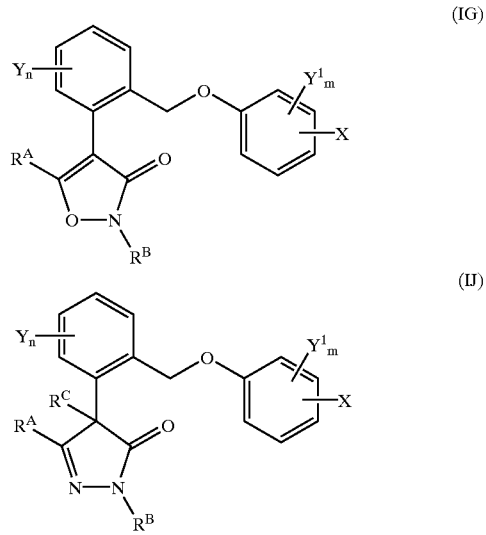

preference is given to introducing the phenoxy group in the steps in which Q# is the group G and the group J, respectively.

The synthesis of the compounds I is generally carried out by reacting phenols of the formula II with benzyl derivatives of the formula III#.

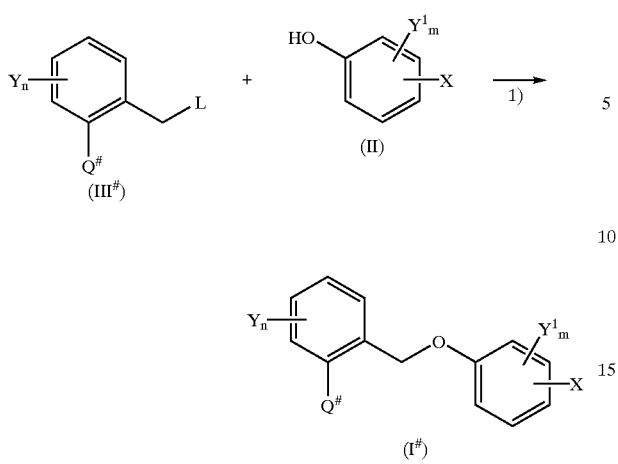

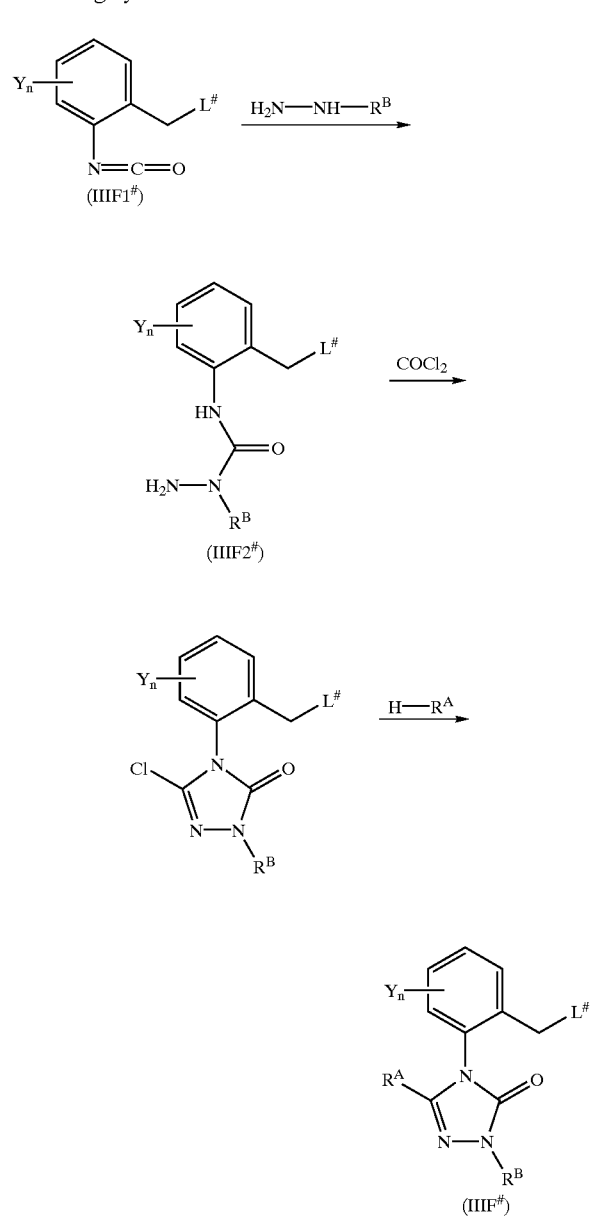

In the formula III#, L is a nucleofuge leaving group, such as halogen or alkyl- or arylsulfonate, preferably bromine, chlorine, mesylate, tosylate or triflate.

1) This reaction is usually carried out at 0° C. to 180° C., preferably at 20° C. to 60° C., in an inert organic solvent in the presence of a base [cf. EP-A 254 426; EP-A 463 488; WO-A 93/15046; WO-A 95/18789; WO-A 95/29896].

The benzyl compounds III# are known (EP-A 513 580, EP-A 477 631, EP-A 463 488, EP-A 251 082, EP-A 400 417, EP-A 585 751, WO-A 93/15046) or they can be prepared by the methods described in these publications or by the routes outlined below:

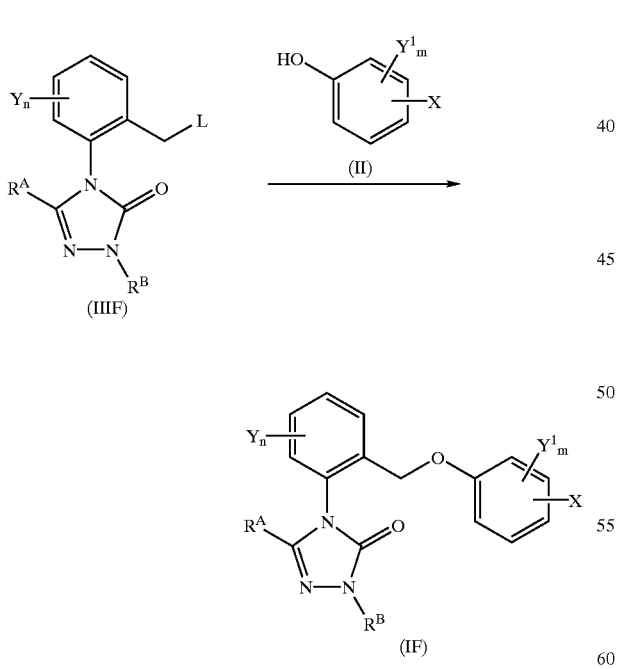

For compounds of the formula IF and the corresponding precursors IIIF, the group Q is preferably synthesized by the following route:

The benzyl compounds IIIF# required for preparing the compounds IF in which $R^A$ is hydroxyl, alkoxy, haloalkoxy, cycloalkoxy, halocycloalkoxy, alkenyloxy, haloalkenyloxy, alkynyloxy or haloalkynyloxy are known from the literature [cf. WO-A 97/02255], or they can be obtained by the methods of the cited literature. They can be obtained by the following synthesis route:

This route is suitable not only for preparing the benzyl compounds IIIF# but also, in principle, for synthesizing the group F at each stage of the synthesis of the group L#. The group Q is particularly preferably synthesized at the stage of the compounds IIIF1# or IIIF# in which L# is hydrogen.

The isocyanates of the formula IIIF1# are obtainable by known methods from the corresponding nitrobenzene derivatives via reduction and reaction of the resulting anilines with phosgene [cf. WO-A 97/02255].

The benzyl compounds IIIF# required for preparing the compounds IF in which $R^A$ is alkyl, haloalkyl, cycloalkyl, halocycloalkyl, alkenyl, haloalkenyl, alkynyl or haloalkynyl are known from the literature [cf. WO-A 96/36229], or they can be obtained by the methods of the cited literature. They can be obtained by reacting the carbamates of the formula IIIF2# with orthoesters:

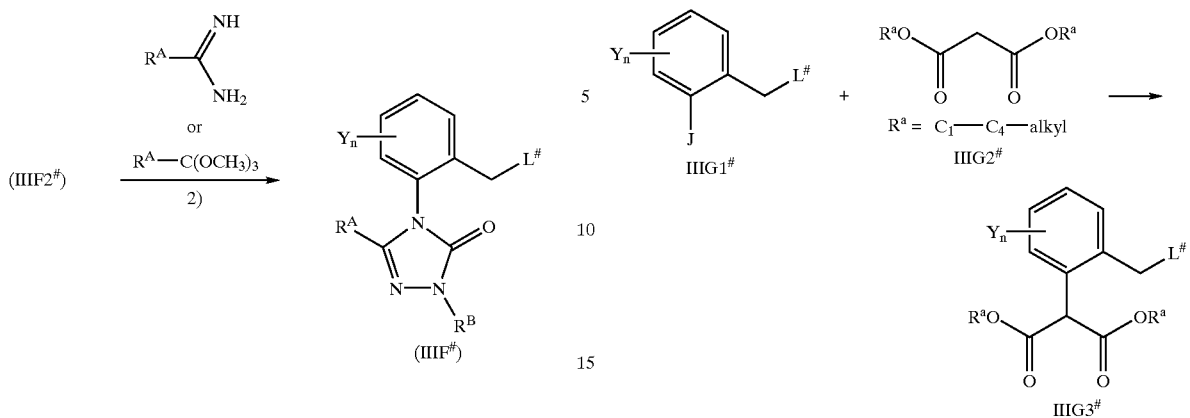

2) This reaction is generally carried out at from 0° C. to 200° C., preferably from 50° C. to 120° C., in an inert organic solvent [cf. J. Org. Chem., 43 (1978), 936].

Suitable solvents are aliphatic hydrocarbons, aromatic hydrocarbons, such as toluene, o-, m- and p-xylene, halogenated hydrocarbons, ethers, such as diethyl ether, diisopropyl ether, tert-butyl methyl ether, dioxane and tetrahydrofuran, nitriles, ketones, and also dimethyl sulfoxide, dimethylformamide and dimethylacetamide, particularly preferably dimethylformamide, tetrahydrofuran or toluene. It is also possible to use mixtures of the abovementioned solvents.

The starting materials are generally reacted with each other in equimolar amounts. In terms of yield, it may be advantageous to employ an excess of orthoester, based on IIIF2#.

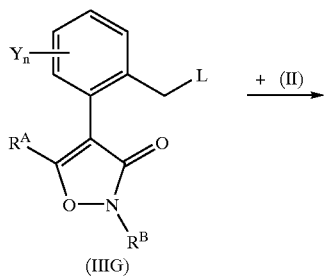

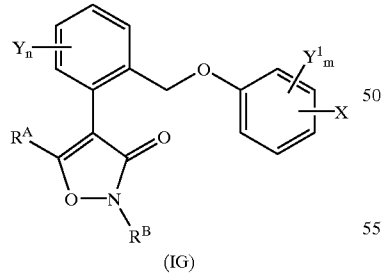

For compounds of the formula IG and the corresponding precursors IIIG, the group Q is preferably synthesized by the following route:

The benzyl compounds IIIG# required for preparing the compounds IG are known from the literature [WO-A 95/14009; WO-A 97/02255], or they are obtainable by the methods of the cited literature. They can be obtained by the following synthesis routes:

These routes are not only suitable for preparing the benzyl compounds IIIG# but, in principle, at each stage of the synthesis of the isoxazolinone group for synthesizing the phenoxy group E. The group Q is particularly preferably synthesized at the stage of the compounds IIIG or IIIG5 in which L# is hydrogen.

Compounds of the formula IIIG in which $R^A$ is alkyl are obtained, by the route known from U.S. Pat. No. 4,952,573, from the corresponding phenylacetic esters IIIG4#.

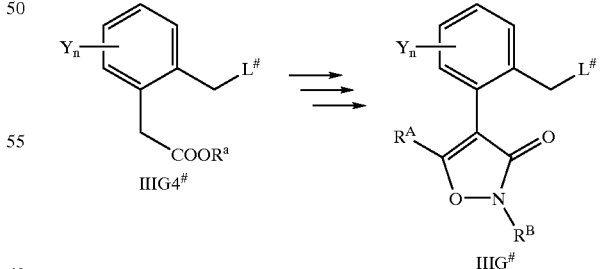

The benzyl compounds IIIH1#–IIIH3# in which L# is a leaving group L and which are required for preparing the compounds IH are known from the literature [cf. WO-A 96/36229].

The tetrazolinone group H can be synthesized by the synthesis route outlined below.

This route is not only suitable for preparing the benzyl compounds IIIH# and IIIH1#/IIIH5# but also, in principle, at each stage of the synthesis of the group L# for synthesizing the tetrazolinone group. The phenoxy group is particularly preferably synthesized at the nitrobenzene stage.

The isocyanates of the formula IIIF1# are obtainable by known methods from the corresponding nitrobenzene derivatives via reduction and reaction of the resulting anilines with phosgene [cf. WO-A 97/02255].

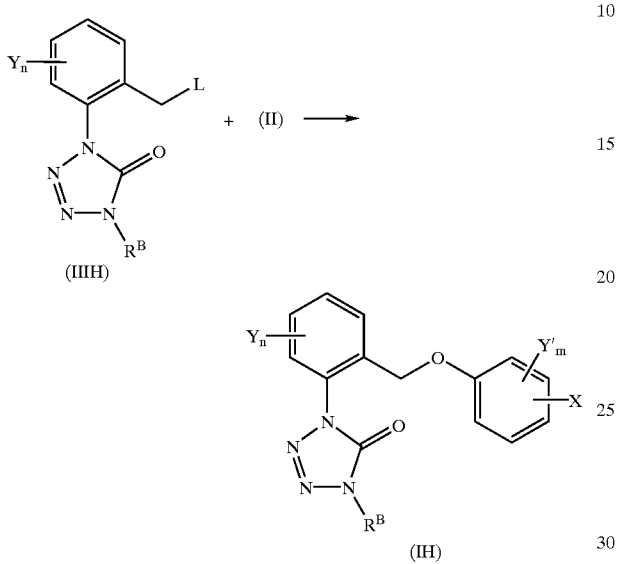

For compounds of the formula IH and the corresponding precursors IIIH, the group Q is preferably synthesized by the following route:

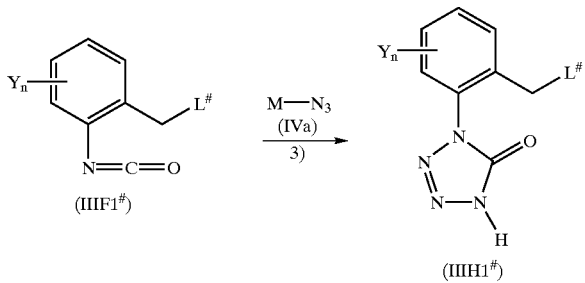

3) The reaction of the isocyanates IIIA1# with the azides IVa is generally carried out at from −10° C. to 200° C., preferably from 20° C. to 140° C., in an inert organic solvent, in the presence or absence of a base or an acid [cf. J. Org. Chem. 45 (1980), 5130; J. Am. Chem. Soc. 81 (1959), 3076; Tetrahedron 31 (1975), 765; J. Org. Chem. 38 (1973), 675].

Suitable solvents are aliphatic hydrocarbons, aromatic hydrocarbons, such as toluene, o-, m- and p-xylene, halogenated hydrocarbons, such as methylene chloride, chloroform and chlorobenzene, ethers, nitriles, and also dimethyl sulfoxide, dimethyl formamide and dimethyl acetamide, particularly preferably toluene, xylene, dimethylformamide and chloroform. If the azide IVa employed is liquid, it can also be used as solvent. It is also possible to employ mixtures of the abovementioned solvents.

The starting materials are generally reacted with each other in equimolar amounts. In terms of yield, it may be advantageous to employ an excess of IVa, based on IIIF1#.

In the formula IVa, M is a cation from the group consisting of the alkali metals and alkaline earth metals, trialkylsilyl and alkyl. Preference is given to using trimethylsilyl azide.

Compounds of the formula IIIH2# in which $R^B$ is $C_1$–$C_6$-alkyl, $C_1$–$C_6$-haloalkyl, $C_3$–$C_6$-cycloalkyl, $C_2$–$C_6$-alkenyl, $C_2$–$C_6$-haloalkenyl, $C_2$–$C_6$-alkynyl or $C_2$–$C_6$-haloalkynyl are obtained from tetrazolinones of the formula IIIH1# by alkylation. If L# in the formula IIIH2# is the phenoxy group E, the compounds IIIH2# correspond to the compounds IH.

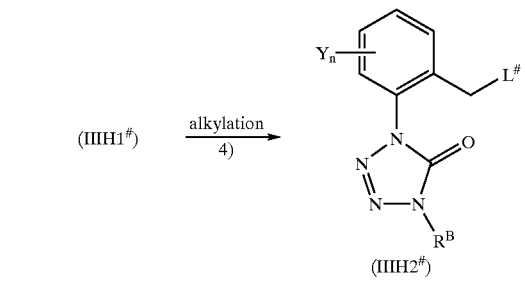

4) The alkylation of the tetrazolinones IIIH1# to give IIIH2# is generally carried out at from −20° C. to 180° C., preferably from 20° C. to 120° C., in an inert organic solvent in the presence of a base [cf. Synth. Commun. 18 (1988),2011; J. Chem. Soc. Chem. Commun., (1987), 735].

Suitable solvents are aliphatic hydrocarbons, aromatic hydrocarbons, such as toluene, o-, m- and p-xylene, halogenated hydrocarbons, ethers, such as diethyl ether, diisopropyl ether, tert-butyl methyl ether, dioxane, anisole and tetrahydrofuran, nitriles, alcohols, and also dimethyl sulfoxide, dimethylformamide and dimethylacetamide, particularly preferably dimethylformamide, tetrahydrofuran, dimethyl sulfoxide, diethyl ether and toluene. It is also possible to employ mixtures of the abovementioned solvents.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, alkali metal and alkaline earth metal hydrides, such as lithium hydride, sodium hydride, potassium hydride and calcium hydride, alkali metal amides, alkali metal and alkaline earth metal carbonates, such as lithium carbonate, potassium carbonate and calcium carbonate, and also alkali metal bicarbonates, such as sodium bicarbonate, organometallic compounds, in particular alkali metal alkyls, alkylmagnesium halides, and also alkali metal and alkaline earth metal alkoxides and dimethoxymagnesium, furthermore organic bases, for example tertiary amines, pyridine, substituted pyridines and also bicyclic amines. Particular preference is given to sodium hydride, sodium bicarbonate, sodium carbonate and sodium hydroxide and potassium hydroxide.

The bases are generally employed in equimolar amounts or in excess, but they can also be employed in catalytic amounts or, if appropriate, as solvent.

Suitable alkylating agents are, for example, alkyl halides, alkyl sulfonates, alkyl p-toluenesulfonates, alkyl trifluoromethanesulfonates, alcohols, ethers or alkyl p-bromophenylsulfonates, in particular methyl iodide or dimethyl sulfate.

The starting materials are generally reacted with each other in equimolar amounts. In terms of yield, it may be advantageous to employ an excess of alkylating agent, based on IIIH1#.

Compounds of the formula IIIH3# in which $R^B$ is $C_1$-$C_6$-alkylcarbonyl or $C_1$-$C_6$-alkoxycarbonyl are obtained from tetrazolinones of the formula IIIH1# by reaction with acylating agents, such as carbonyl halides, carboxylic anhydrides, carboxylic esters or chloroformates.

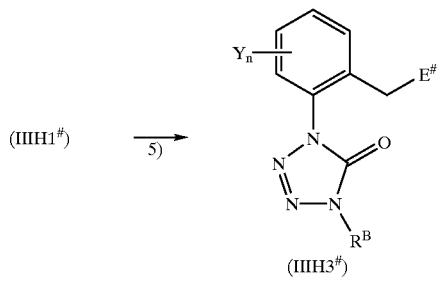

(IIIH1#) $\xrightarrow{5)}$ (IIIH3#)

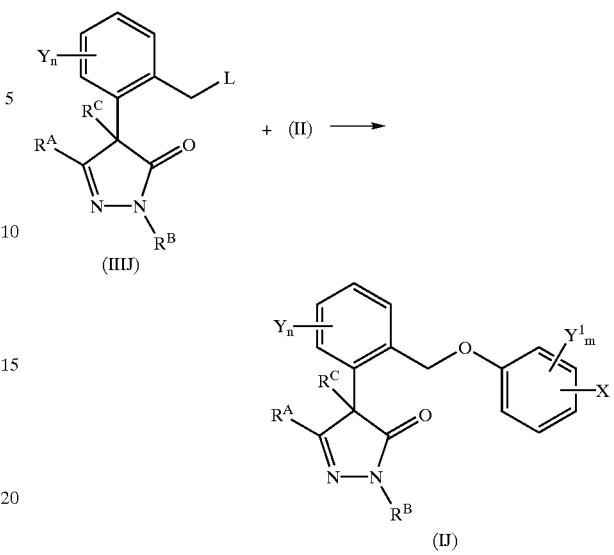

(IIIJ)

+ (II) ⟶

(IJ)

5) The acylation of the tetrazolinones IIIH1# to give IIIH3# is generally carried out at from −20° C. to 180° C., preferably from 20° C. to 120° C., in an inert organic solvent in the presence of a base [cf. Synth. Commun. 18 (1988), 2011; J. Chem. Soc. Chem. Commun., (1987), 735].

Suitable solvents are aliphatic hydrocarbons, aromatic hydrocarbons, such as toluene, o-, m- and p-xylene, halogenated hydrocarbons, ethers, such as diethyl ether, diisopropyl ether, tert-butyl methyl ether, dioxane and tetrahydrofuran, nitriles, and also dimethyl sulfoxide, dimethylformamide and dimethylacetamide, particularly preferably dimethylformamide, tetrahydrofuran, dimethyl sulfoxide, diethyl ether and toluene. It is also possible to employ mixtures of the abovementioned solvents.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, alkali metal and alkaline earth metal hydrides, such as lithium hydride, sodium hydride, potassium hydride and calcium hydride, alkali metal amides, alkali metal and alkaline earth metal carbonates, such as lithium carbonate, potassium carbonate and calcium carbonate, and also alkali metal bicarbonates, such as sodium bicarbonate, furthermore organic bases, for example tertiary amines, such as trimethylamine, triethylamine, diisopropylethylamine and N-methylpiperidine, pyridine, substituted pyridines, and also bicyclic amines. Particular preference is given to sodium hydride, sodium bicarbonate, sodium carbonate and sodium hydroxide and potassium hydroxide, triethylamine and pyridine.

The bases are generally employed in equimolar amounts or in excess, but they can also be employed in catalytic amounts or, if appropriate, as solvent.

The starting materials are generally reacted with each other in equimolar amounts. In terms of yield, it may be advantageous to employ an excess of acylating agent, based on IIIH1#.

The benzyl compounds IIIJ# required for preparing the compounds IJ in which $R^B$ is alkyl, haloalkyl, cycloalkyl, alkenyl, haloalkenyl, alkynyl or haloalkynyl are known from the literature [WO-A 96/36229], or they can be obtained by the methods of the cited literature. They can be obtained by the following synthesis route:

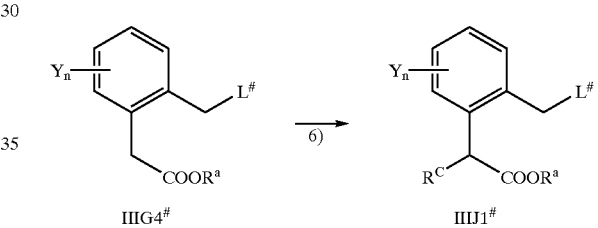

IIIG4#     IIIJ1#

6) The alkylation or acylation of the phenylacetic acid derivatives IIIG4# to give IIIJ1# is generally carried out at from −20° C. to 180° C., preferably from 20° C. to 120° C., in an inert organic solvent in the presence of a base, if appropriate under phase-transfer conditions [cf. Houben-Weyl, Vol. 8 (1952), p.600–610; Org. Syntheses 55 (1976), 91; Org. Reactions 9 (1957), 107; Org. Reactions 17 (1969), 155; J. Am. Chem. Soc., 92 (1970), 1397].

Suitable solvents are aliphatic hydrocarbons, aromatic hydrocarbons, such as toluene, o-, m- and p-xylene, halogenated hydrocarbons, ethers, such as diethyl ether, diisopropyl ether, tert-butyl methyl ether, dioxane and tetrahydrofuran, nitriles, and also dimethyl sulfoxide, dimethylformamide and dimethylacetamide, particularly preferably dimethylformamide, tetrahydrofuran, dimethyl sulfoxide, diethyl ether and toluene. It is also possible to employ mixtures of the abovementioned solvents.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, alkali metal and alkaline earth metal hydrides, lithium hydride, sodium hydride, potassium hydride and calcium hydride, alkali metal amides, alkali metal and alkaline earth metal carbonates, such as lithium carbonate, potassium carbonate and calcium carbonate, and also alkali metal bicarbonates, such as sodium bicarbonate, organometallic compounds, in particular alkali metal alkyls, alkylmagnesium halides, and also alkali metal and alkaline earth metal alkoxides and dimethoxymagnesium, furthermore organic bases, for example tertiary amines, pyridine, substituted pyridines and also bicyclic amines. Particular preference is given to sodium hydride, sodium bicarbonate, sodium carbonate and sodium hydroxide and potassium hydroxide.

The bases are generally employed in equimolar amounts or in excess, but it is also possible to employ them in catalytic amounts or, if appropriate, as solvent.

Suitable alkylating agents are, for example, alkyl halides, alkyl sulfonates, alkyl p-toluenesulfonates, alkyl trifluoromethane-sulfonates, ethers or alkyl p-bromophenylsulfonates, in particular methyl iodide or dimethyl sulfate.

Suitable acylating agents are, for example, carbonyl halides, carboxylic anhydrides, carboxylic esters or chloroformates.

The starting materials are generally reacted with each other in equimolar amounts. In terms of yield, it may be advantageous to employ an excess of alkylating or acylating agent, based on IIIG4#.

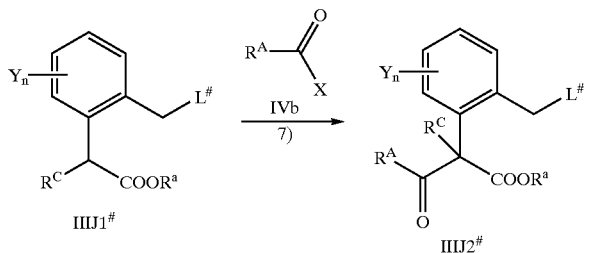

7) The acylation of the phenylacetic acid derivatives IIIJ1# with the carboxylic acid derivatives IVb is generally carried out at from −20° C. to 180° C., preferably from 20° C. to 120° C., in an inert organic solvent in the presence of a base [cf. Houben-Weyl, Vol. 8 (1952), p. 560–589 and 610–612; Org. Reactions 8 (1954), 59 and 266]. In the formula IVb, X is a customary leaving group, such as halogen, alkoxy or alkylcarbonyloxy.

Suitable solvents are aliphatic hydrocarbons, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane and tetrahydrofuran, nitriles, and also dimethyl sulfoxide, dimethyl formamide and dimethyl acetamide, particularly preferably dimethylformamide, tetrahydrofuran, dimethyl sulfoxide, diethyl ether and toluene. It is also possible to employ mixtures of the abovementioned solvents.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, alkali metal and alkaline earth metal hydrides, such as lithium hydride, sodium hydride, potassium hydride and calcium hydride, alkali metal amides, alkali metal and alkaline earth metal carbonates, such as lithium carbonate, potassium carbonate and calcium carbonate, and also alkali metal bicarbonates, such as sodium bicarbonate, organometallic compounds, in particular alkali metal alkyls, alkylmagnesium halides, and also alkali metal and alkaline earth metal alkoxides and dimethoxymagnesium, furthermore organic bases, for example tertiary amines, pyridine, substituted pyridines and also bicyclic amines. Particular preference is given to sodium hydride, sodium bicarbonate, sodium carbonate and sodium hydroxide and potassium hydroxide.

The bases are generally employed in equimolar amounts or in excess, but they can also be employed in catalytic amounts or, if appropriate, as solvent.

Suitable acylating agents are, for example, carbonyl halides, carboxylic anhydrides, chloroformates or carboxylic esters.

The starting materials are generally reacted with each other in equimolar amounts. In terms of yield, it may be advantageous to employ an excess of acylating agent, based on IIIJ1#.

Compounds IIIJ# in which $R^B$ is alkyl, haloalkyl, cycloalkyl, alkenyl, haloalkenyl, alkynyl or haloalkynyl are obtained by reacting the dicarbonyl compounds IIIJ2# with alkylhydrazines IVc. If the group L# is the phenoxy group E, the compounds IIIJ# correspond to the compounds IJ.

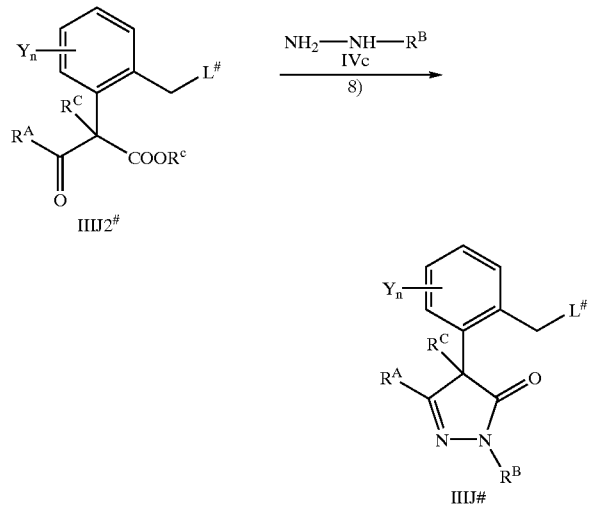

8) This reaction with alkylhydrazines is generally carried out at from −20° C. to 200° C., preferably from 20° C. to 150° C., in an inert organic solvent [cf. Org. Synthesis 55 (1976), 73; J. Am. Chem. Soc. 112 (1990), 7305; J. Org. Chem. 47 (1982), 214].

Suitable solvents are aliphatic hydrocarbons, aromatic hydrocarbons, halogenated hydrocarbons, ethers, nitriles, alcohols, such as methanol, ethanol, n-propanol, isopropanol, n-butanol and tert-butanol, and also dimethyl sulfoxide, dimethylformamide and dimethylacetamide, particularly preferably methanol, ethanol or dimethylformamide. It is also posisble to employ mixtures of the abovementioned solvents.

The starting materials are generally reacted with each other in equimolar amounts. In terms of yield, it may be advantageous to employ an excess of the alkylhydrazines, based on IIIJ2#.

The compounds IIIJ# in which $R^B$ is hydrogen are obtained by reacting the dicarbonyl compounds IIIJ2# with hydrazine.

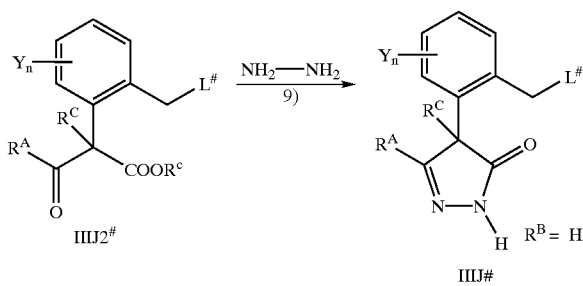

9) This reaction can be carried out similarly to the conditions described in Section 8) above.

Compounds IIIJ# in which $R^B$ is alkyl, haloalkyl, cycloalkyl, alkenyl, haloalkenyl, alkynyl or haloalkynyl can alternatively also be obtained from the compounds IIIJ# in which $R^B$ is hydrogen by alkylation. If the group L# is the phenoxy group E, the compounds IIIJ# correspond to the compounds IJ.

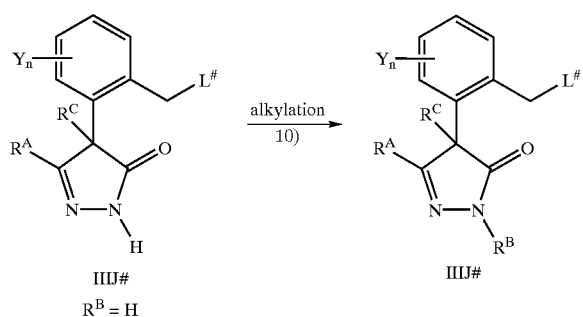

10) The alkylation of the diazolidinones IIIJ# is generally carried out at from −20° C. to 180° C., preferably from 20° C. to 120° C., in an inert organic solvent in the presence of a base [cf. Synth. Commun. 18 (1988), 2011; J. Chem. Soc. Chem. Commun., (1987), 735].

Suitable solvents are aliphatic hydrocarbons, aromatic hydrocarbons, such as toluene, o-, m- and p-xylene, halogenated hydrocarbons, ethers, such as diethyl ether, diisopropyl ether, tert-butyl methyl ether, dioxane, anisole and tetrahydrofuran, nitriles, alcohols, and also dimethyl sulfoxide, dimethylformamide and dimethylacetamide, particularly preferably dimethylformamide, tetrahydrofuran, dimethyl sulfoxide, diethyl ether and toluene. It is also possible to employ mixtures of the abovementioned solvents.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, alkali metal and alkaline earth metal hydrides, such as lithium hydride, sodium hydride, potassium hydride and calcium hydride, alkali metal amides, alkali metal and alkaline earth metal carbonates, such as lithium carbonate, potassium carbonate and calcium carbonate, and also alkali metal bicarbonates, such as sodium bicarbonate, organometallic compounds, in particular alkali metal alkyls, alkylmagnesium halides, and also alkali metal and alkaline earth metal alkoxides and dimethoxymagnesium, furthermore organic bases, for example tertiary amines, pyridine, substituted pyridines and also bicyclic amines. Particular preference is given to sodium hydride, sodium bicarbonate, sodium carbonate and sodium hydroxide and potassium hydroxide.

The bases are generally employed in equimolar amounts or in excess, but they can also be employed in catalytic amounts or, if appropriate, as solvent.

Suitable alkylating agents are, for example, alkyl halides, alkyl sulfonates, alkyl p-toluenesulfonates, alkyl trifluoromethane-sulfonates, alcohols, ethers or alkyl p-bromophenylsulfonates, in particular methyl iodide or dimethyl sulfate.

The starting materials are generally reacted with each other in equimolar amounts. In terms of yield, it may be advantageous to employ an excess of alkylating agent, based on IIIJ#.

Alternatively to the access route from the phenylacetic acid derivatives of the formula IIIG4#, the compounds IIIJ# can also be synthesized from carboxylic acid derivatives of the formula IIIJ3#. In the formula IIIJ3#, X is a leaving group, such as halogen or imidazolyl.

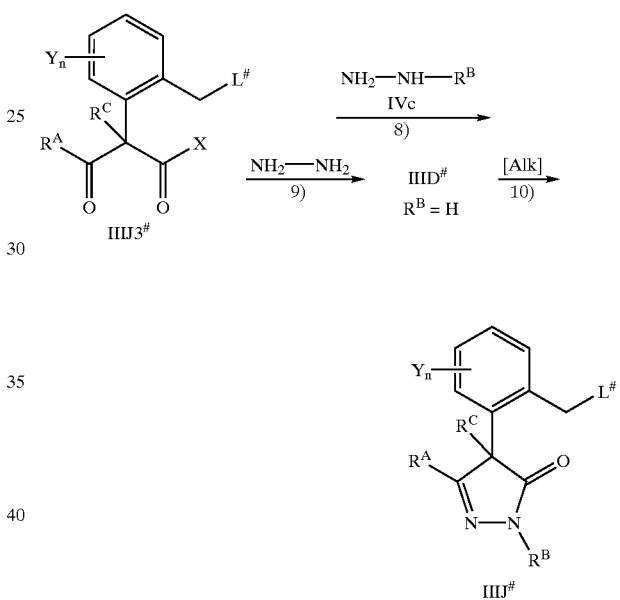

The reactions of IIIJ3# with hydrazine to give the compounds IIIJ# ($R^B$=H) and alkylation with alkylating agents [Alk] to give the compounds IIIJ#, or with alkylhydrazines IVc directly to give the compounds IIIJ#, are carried out by the methods of the reactions described in sections 9) to 11).

The compounds IIIJ3# are known from the literature [cf. WO-A 96/36229], or they can be prepared by the methods of the cited literature.

Alternatively, the dicarbonyl compounds IIIJ2# can also be prepared from aryl halides of the formula IIIJ4# by reaction with β-keto esters IVd under transition metal catalysis and subsequent alkylation.

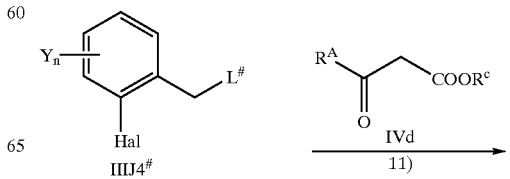

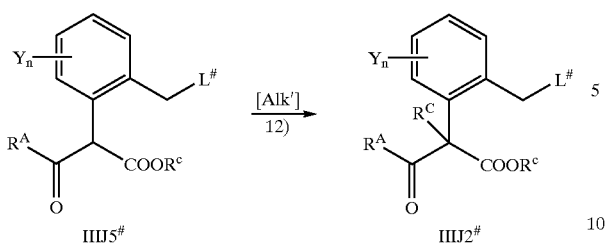
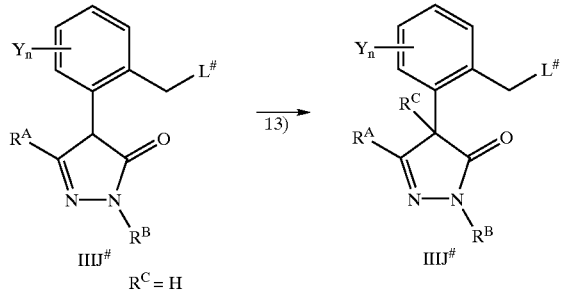

11) This reaction is generally carried out at from −20° C. to 200° C., preferably from 20° C. to 150° C., in an inert organic solvent in the presence of a base and a catalyt [cf. Angew. Chem. Int. Ed. Engl. 13 (1974), 340; J. Am. Chem. Soc. 102 (1980), 7765; J. Am. Chem. Soc. 81 (1959), 627; Chem. Lett. 1981, 367].

Suitable solvents are aliphatic hydrocarbons, aromatic hydrocarbons, such as toluene, o-, m- and p-xylene, halogenated hydrocarbons, ethers, ketones, and also dimethyl sulfoxide, dimethyl formamide and dimethylacetamide, particularly preferably dimethylformamide, toluene or xylene. It is also possible to use mixtures of the abovementioned solvents.

Suitable bases are, in general, inorganic compounds, such as alkali metal and alkaline earth metal hydroxides, alkali metal and alkaline earth metal oxides, alkali metal and alkaline earth metal hydrides, such as lithium hydride, sodium hydride, potassium hydride and calcium hydride, alkali metal amides, alkali metal and alkaline earth metal carbonates, and also alkali metal bicarbonates, organometallic compounds, in particular alkali metal alkyls, alkylmagnesium halides, and also alkali metal and alkaline earth metal alkoxides, furthermore organic bases, for example tertiary amines, pyridine, substituted pyridines and bicyclic amines. Particular preference is given to sodium hydride. The bases are generally employed in catalytic amounts, but they can also be employed in equimolar amounts, in excess or, if appropriate, as solvent.

Suitable catalysts are transition metals, such as, for example, copper, or their salts, in particular the halides, such as CuBr or CuCl.

The starting materials are generally reacted with each other in equimolar amounts. In terms of yield, it may be advantageous to employ an excess of β-keto ester IVd, based on IIIJ4#.

12) The alkylation of IIIJ5# is carried out by the method of the reaction described in Section 6).

Compounds of the formulae IJ and IIIJ in which $R^C$ is hydrogen are obtainable by reacting phenylacetic acid derivatives IIIG4# according to the acylation described in Section 7) directly to form compounds of the formula IIIJ2#, and carrying out the other steps analogously.

Alternatively, the radical $R^C$ can also be introduced at the stage of the phenyldiazolidinone of the formula IIIJ#. If the group L# is the phenoxy group E, the compounds IIIJ# correspond to the compounds IJ.

13) This reaction is carried out similarly to the reaction described in Section 6).

The benzyl compounds IIIJ# required for preparing the compounds IJ in which $R^B$ is hydroxyl, alkoxy, haloalkoxy, cycloalkyloxy, halocycloalkoxy, alkenyloxy, haloalkenyloxy, alkynyloxy, haloalkynyloxy or acetyloxy are obtainable by the following synthesis route:

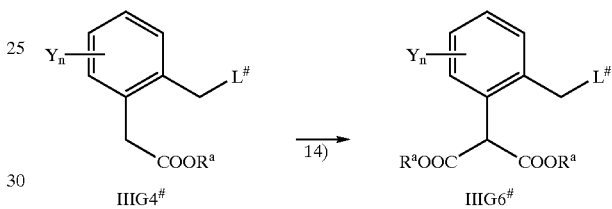

14) This acylation with chloroformic esters is carried out similarly to the reaction described in Section 6).

Phenylmalonic esters IIIJ6# can alternatively be prepared from aryl halides of the formula IIIJ4# by reaction with malonic esters IVe under transition metal catalysis.

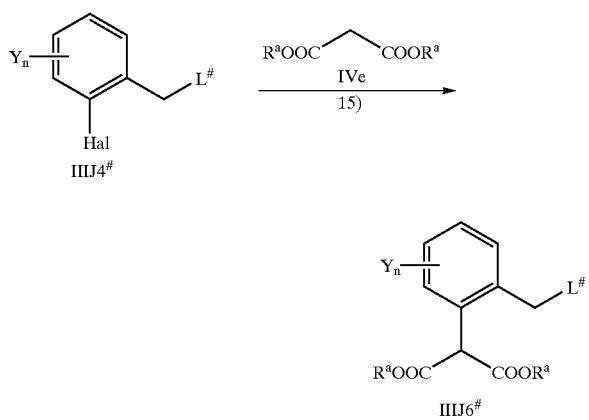

15) This reaction is carried out under the conditions described in Section 11).

The reaction of the phenylmalonic esters IIIJ6# with alkylhydrazines of the formula IVc leads to phenyldiazolidinediones of the formula IIIJ7#.

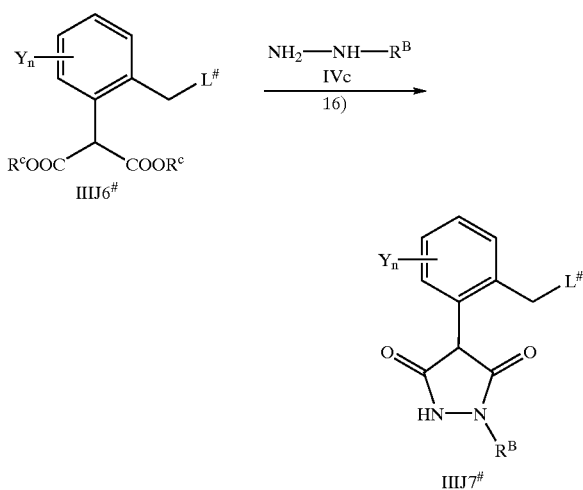

16) This reaction is carried out under the conditions described in Section 8).

The reaction of the phenylmalonic esters IIIJ6# with hydrazine likewise leads to phenyldiazolidinediones of the formula IIIJ7'#.

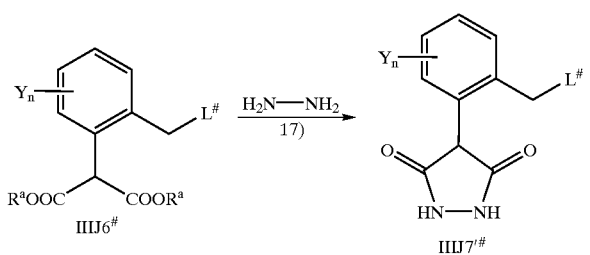

17) This reaction is carried out under the conditions described in Section 9).

Alkylations of the phenyldiazolidinediones IIIJ7# and IIIJ7'# lead to the compounds IIIJ'# and IIIJ"#.

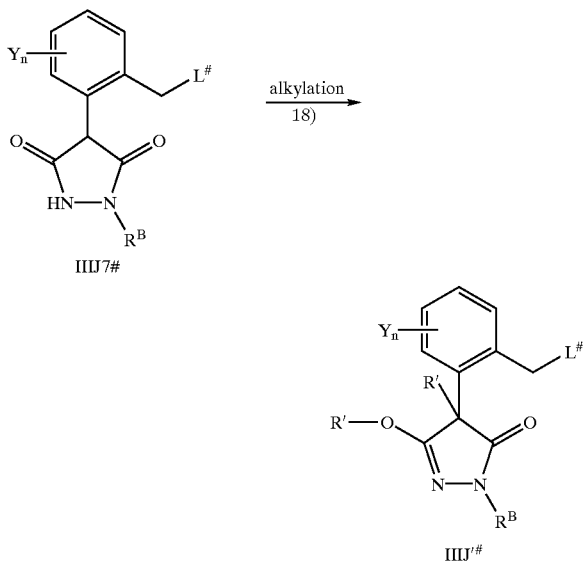

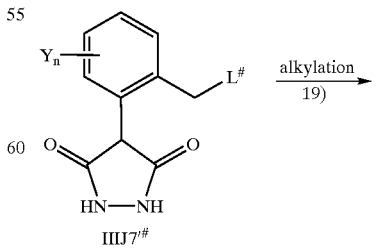

In the formula IIIJ'#, R' is alkyl, haloalkyl, cycloalkyl, halocycloalkyl, alkenyl, haloalkenyl, alkynyl or haloalkynyl.

18) The alkylation is generally carried out at from 0° C. to 150° C., preferably from 20° C. to 100° C., in an inert organic solvent, if appropriate in the presence of a base [Arch. Pharm. 298 (1965), 580 ff.].

Suitable solvents are aliphatic hydrocarbons, aromatic hydrocarbons, halogenated hydrocarbons, such as methylene chloride, chloroform and chlorobenzene, ethers, such as diethyl ether, diisopropyl ether, tert-butyl methyl ether, dioxane and tetrahydrofuran, nitriles, ketones, alcohols, and also dimethyl sulfoxide, dimethylformamide and dimethylacetamide, particularly preferably dimethylformamide, methylene chloride or tetrahydrofuran. It is also possible to employ mixtures of the abovementioned solvents.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, alkali metal and alkaline earth metal hydrides, alkali metal amides, alkali metal and alkaline earth metal carbonates, such as lithium carbonate, potassium carbonate and calcium carbonate, and also alkali metal bicarbonates, such as sodium bicarbonate, organometallic compounds, in particular alkali metal alkyls, alkylmagnesium halides, and also alkali metal and alkaline earth metal alkoxides and dimethoxymagnesium, furthermore organic bases, for example tertiary amines, such as trimethylamine, triethylamine, diisopropylethylamine and N-methylpiperidine, pyridine, substituted pyridines, and also bicyclic amines. Particular preference is given to potassium hydroxide, sodium hydroxide, potassium carbonate, triethylamine or pyridine. The bases are generally employed in equimolar amounts, in excess or, if appropriate, as solvent.

Suitable alkylating agents are, for example, diazoalkane compounds, alkyl halides, alkyl sulfonates, alkyl p-toluenesulfonates, alkyl trifluoromethanesulfonates, alcohols, ethers or alkyl p-bromophenylsulphonates, in particular methyl iodide, dimethyl sulfate or trimethylsilyldiazomethane.

The starting materials are generally reacted with each other in equimolar amounts. In terms of yield, it may be advantageous to employ an excess of alkylating agent, based on IIIJ7#.

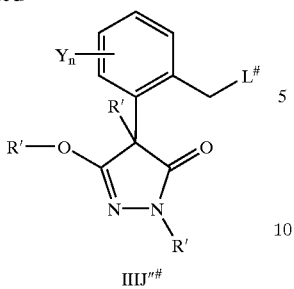

IIIJ''#

In the formula IIIJ''#, R' is alkyl, haloalkyl, cycloalkyl, halocycloalkyl, alkenyl, haloalkenyl, alkynyl or haloalkynyl.

19) The alkylation is carried out similarly to the reaction described in Section 18) above.

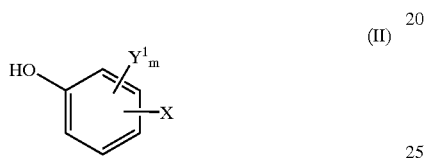
(II)

The phenols of the formula II are known from the literature, and/or can be prepared similar to known methods [cf. EP-A 811 614; J. Org. Chem., Vol. 59 (1994) p. 1589; Bull. Chem. Soc. Jpn., Vol. 62 (1989) p. 618; J. Heterocycl. Chem., Vol. 27 (1990) p. 343; Chem. Lett. 1983, p. 1355; J. Heterocycl. Chem., Vol. 25 (1988) p. 1003; Tetrahedron Lett.; Vol. 29 (1988) p. 1425; Tetrahedron Lett., Vol. 27 (1986) p. 4407; Khim. Geterotsikl. Soedin 1991, p. 334; J. Chem. Soc., Perkin Trans., Vol. I 1990, p. 3112; Khim. Geterotsikl. Soedin (1968) p. 372; Chem. Ber., Vol. 94 (1961) p. 1868; J. Chem. Soc. (1952) p. 3418; J. Org. Chem., Vol. 53 (1988) p. 4349; Synth. Comm., Vol. 20 (1990) p. 3161; Chem. Lett. (1985) p. 1049; Synth. Comm., Vol. 20 (1990) p. 3161; Chem. Ber., Vol. 117 (1984) p. 1194].

The syntheses of the phenols II start either from phenols IIa or from phenyl compounds where a hydroxyl group can be generated from a suitable substituent Z. During the synthesis of the hetaryl group X, it may be necessary to block the hydroxyl function of the phenol derivative employed by a suitable protective group.

A suitable substituent Z may be, for example, a nitro group, which can be converted into a hydroxyl function by generally known methods via the reaction sequence: reduction, diazotization, reduction and boildown.

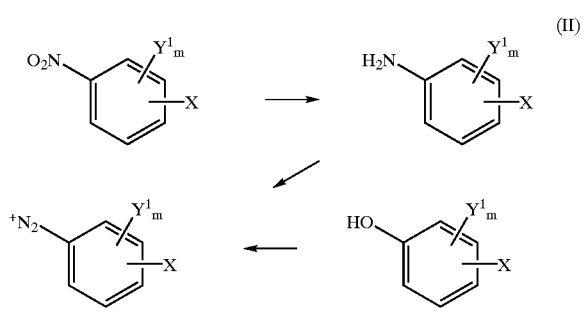
(II)

In the synthesis schemes below, [OH] denotes a hydroxyl group, which may be protected, or a suitable precursor thereof.

Phenols of the formula II in which X is pyrazol-1-yl are preferably obtained by the following method:

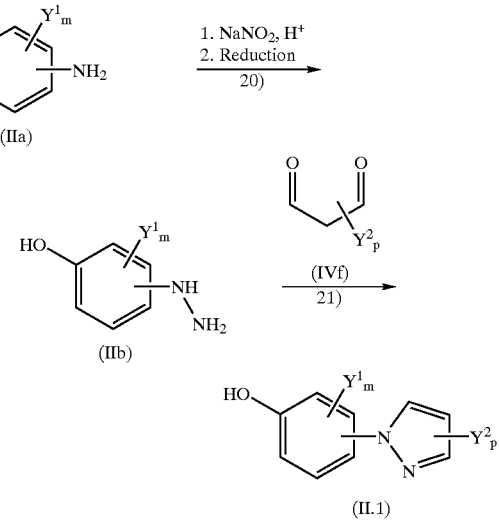

20a) The reaction of IIa with nitrite is carried out at −10° C. to 25° C., preferably at −5° C. to 10° C., in water or an inert organic solvent in the presence of an acid under generally customary conditions [cf. Organikum, 15th edition 1976, p. 654ff., VEB Verlag der Wissenschaften, Berlin].

The acids are generally used in equimolar amounts, in excess or, if appropriate, as solvents.

Nitrosating agents which are usually used are alkali metal or alkaline earth metal nitrites, in particular sodium nitrite or potassium nitrite.

The starting materials are generally reacted with one another in equimolar amounts. In terms of yield, it may be advantageous to employ an excess of nitrosating agent, based on IIa.

20b) The reduction of the diazo compound can be carried out under generally customary conditions, preferably by reduction with iron, tin or zinc or salts thereof in the presence of an acid or by reduction with alkali metals in the presence of a base [cf. Houben-Weyl, Vol. IV/1c, 4th edition, p. 506ff., Thieme Verlag Stuttgart and New York (1980); ibid. Vol. IV/1d, 4th edition, p. 473ff. (1981); Heterocycles, Vol. 31, p. 2201 (1990)]. Preference is furthermore given to reducing the diazonium salts with sulfite or disulfite [cf: Organikum, 15th ed., VEB Verlag der Wissenschaften, Berlin, p. 662, 1976; J. Chem. Soc, 1927, p. 1325ff.; Chem. Ber., Vol. 55, p. 1827, 1922; Houben-Weyl, Vol. 10/2, p. 182, Thieme Verlag, Stuttgart].

The bases are generally employed in catalytic amounts, but it is also possible to employ them in equimolar amounts, in excess, or if appropriate, as solvents.

Suitable reducing agents are in particular $NaHSO_3$, $Na_2S_2O_5$ or $SnCl_2$.

The starting materials are generally reacted with one another in equimolar amounts. In terms of yield, it may be advantageous to employ an excess of reducing agent, based on the nitroso compound.

21) The reaction of the hydrazine IIb with the β-keto compound IVf is usually carried out at −10° C. to 80° C., preferably at 0° C. to 30° C., in an inert organic solvent [cf. Synthesis (1991) p. 18; Heterocycles, Vol. 31 (1990) p. 855; J. Heterocycl. Chem., Vol. 24 (1987) p. 1309].

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisol and tetrahydrofuran, nitriles, such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and also dimethyl sulfoxide, dimethyl formamide and dimethylacetamide, particularly preferably methanol, ethanol or dimethylformamide. It is also possible to employ mixtures of the abovementioned solvents.

The starting materials are generally reacted with one another in equimolar amounts. In terms of yield, it may be advantageous to employ an excess of VIa, based on V#.

β-Ketocompounds IVf are either commercially available or they can be prepared by methods known from the literature.

Phenols of the formula II in which X is pyrazol-3-yl and pyrazol-5-yl, and also isoxazol-3-yl and isoxazol-5-yl, are preferably obtainable by the methods known from EP-A 811 614.

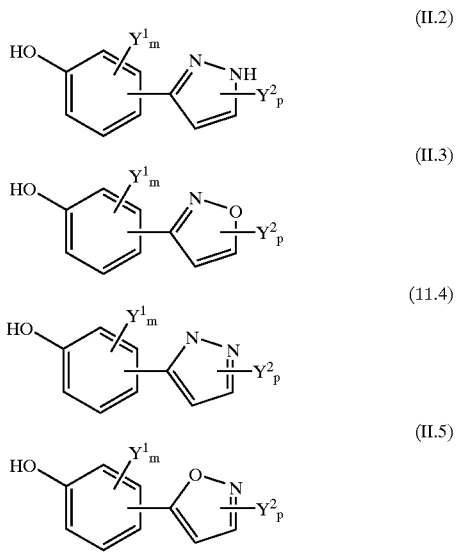

Phenols of the formula II in which X is 1,2,4-triazol-3-yl are obtainable by methods known from the literature, for example from the corresponding benzamides [cf. Liebigs Ann., Vol. 343 (1905) p. 207].

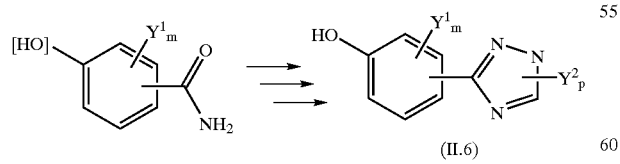

Phenols of the formula II in which Z is 1,3-oxazol-5-yl are obtainable by methods known from the literature from the corresponding α-aminoacetylbenzenes [cf. Chem. Ber., Vol. 47 (1914) p. 3163; J. Chem. Gen. USSR, Vol. 32 (1962) p. 1192].

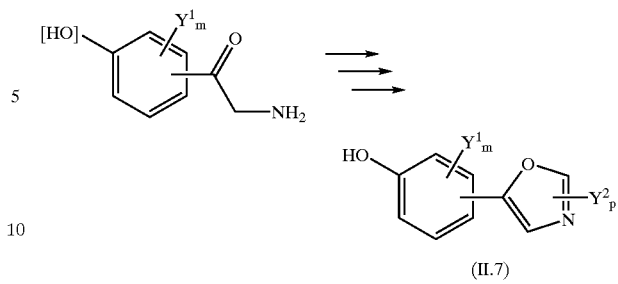

Phenols of the formula II in which X is 1,3-oxazol-4-yl are obtainable by methods known from the literature from the corresponding α-haloacetylbenzenes [cf. Synth. Commun. (1979) p. 789].

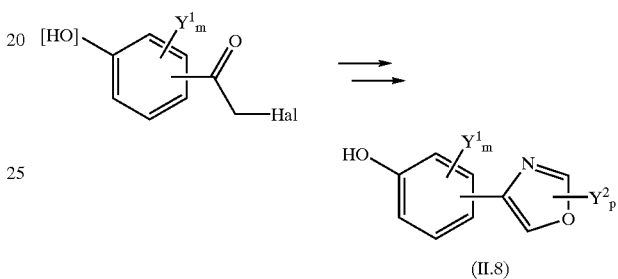

Phenols of the formula II in which X is oxazol-2-yl are obtainable by routes known from the literature [cf. J. Chem. Soc., Perkin Trans., Vol. I (1990) p. 2329; Ind. J. Chem., Vol. 20 (1981) p. 322].

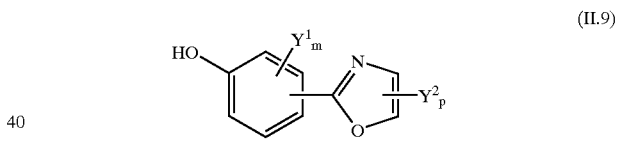

Phenols of the formula II in which X is imidazol-1-yl are obtainable by methods known from the literature [cf. J. Med. Chem., Vol. 31 (1988) p. 2136; J. Fluorine Chem., Vol. 43 (1989) p. 131; U.S. Pat No. 4,966,967].

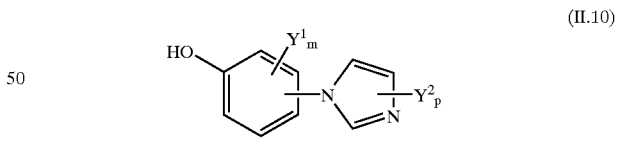

Phenols of the formula II in which X is imidazol-2-yl are obtainable by routes known from the literature from phenyl halides and 2-trialkyltinimidazoles [cf. Bull. Chem. Soc. Jpn., Vol. 59 (1968) p. 677].

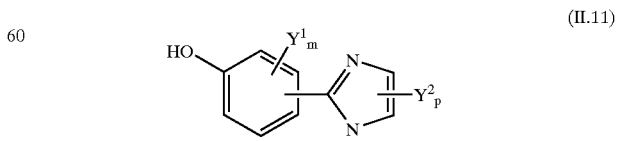

Phenols of the formula II in which X is imidazol-4-yl are obtainable by routes known from the literature from phenyl halides and 4-trialkyltinimidazoles [cf. Tetrahedron, Vol. 52 (1996) p. 13703].

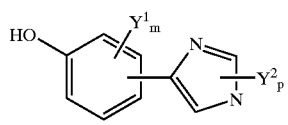
(II.12)

Phenols of the formula II in which X is 1-alkylimidazol-5-yl are obtainable by routes known from the literature [cf. Tetrahedron Lett., Vol. 27 (1986) p. 5019].

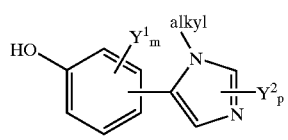
(II.13)

Phenols of the formula II in which X is pyrrol-1-yl are obtainable, for example, by the following route known from the literature [cf. J. Heterocycl. Chem., Vol. 25 (1988) p. 1003; Tetrahedron Lett., Vol. 29 (1988) p. 1425]:

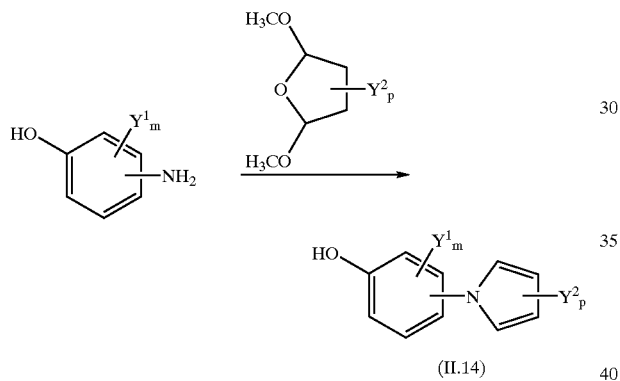
(II.14)

Phenols of the formula II in which X is pyrrol-2-yl are obtainable by methods known from the literature from aryl halides and pyrrol-2-yl Grignard compounds or the corresponding trimethyltin compounds [cf. Tetrahedron Lett., Vol. 27 (1986) p. 4407; Khim. Geterotsikl. Soedin (1991) p. 334; Tetrahedron Lett., Vol. 22 (1981) p. 5319].

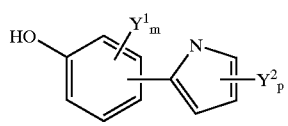
(II.15)

The starting materials required for preparing the compounds I are known from the literature or can be prepared according to the literature cited.

If individual compounds I cannot be obtained by the routes described above, they can be prepared by derivatization of other compounds I.

The reaction mixtures are worked up in the customary manner, for example by mixing with water, phase separation and, if appropriate, chromatographic purification of the crude products. In some cases, the intermediates and end products are obtained in the form of colorless or pale brown viscous oils, which are purified or freed from volatile components under reduced pressure and at moderately elevated temperature. If the intermediates and end products are obtained as solids, they can also be purified by recrystallization or digestion.

Due to their C=C- and C=N-double bonds, the compounds I can be obtained from the preparation in the form of E/Z isomer mixtures, it being possible for these mixtures to be separated into the individual compounds in the customary manner, for example by crystallization or chromatography.

However, if the synthesis yields isomer mixtures, separation is generally not absolutely necessary since in some cases the individual isomers can be converted into each other during formulation for use or upon use (for example when exposed to light, acids or bases). Similar conversions can also take place after use, for example in the case of the treatment of plants in the treated plants or in the harmful fungus or the animal pest to be controlled.

In the definitions of the symbols given in the above formulae, collective terms were used which generally represent the following substituents:

Halogen: fluorine, chlorine, bromine and iodine;

Alkyl: saturated, straight-chain or branched hydrocarbon radicals having 1 to 4 carbon atoms, such as methyl, ethyl, propyl, 1-methylethyl, butyl, 1-methylpropyl, 2-methylpropyl or 1,1-dimethylethyl;

Haloalkyl: straight-chain or branched alkyl groups having 1 to 4 carbon atoms (as mentioned above), it being possible for the hydrogen atoms in these groups to be partially or fully replaced by halogen atoms as mentioned above, for example $C_1$–$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkoxy: straight-chain or branched alkyl groups having 1 to 4 carbon atoms (as mentioned above), which are bonded to the skeleton via an oxygen atom (—O—);

Alkenyl: unsaturated, straight-chain or branched hydrocarbon radicals having 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1- butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Haloalkenyl: unsaturated, straight-chain or branched hydrocarbon radicals having 2 to 6 carbon atoms and a double bond in any position (as mentioned above), it being possible for the hydrogen atoms in these groups to be partially or fully replaced by halogen atoms as mentioned above, for example fluorine, chlorine and bromine;

Alkynyl: straight-chain or branched hydrocarbon groups having 2 to 6 carbon atoms and a triple bond in any position, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

Aryl: a mono- to trinuclear aromatic ring system containing 6 to 14 carbon ring members, for example phenyl, naphthyl and anthracenyl;

Five-membered hetaryl, containing one to four nitrogen atoms or one to three nitrogen atoms and one sulfur or oxygen atom: 5-membered hetaryl groups which, in addition to carbon atoms, may contain one to four nitrogen atoms or one to three nitrogen atoms and one sulfur or oxygen atom as ring members, for example 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 5-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

Alkylene: divalent unbranched chains of 3 to 5 $CH_2$ groups, for example $CH_2$, $CH_2CH_2$, $CH_2CH_2CH_2$, $CH_2CH_2CH_2CH_2$ and $CH_2CH_2CH_2CH_2CH_2$.

Customary groups are in particular the following substituents: halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-$C_1$–$C_4$-alkylamino and $C_1$–$C_4$-alkylthio.

With regard to the variables, the particularly preferred embodiments of the intermediates correspond to those of the radicals Q, X, $Y_n$, $Y^1_m$ and $Y^2_p$ of the formula I.

With a view to the intended use of the phenyl compounds of the formula I, particular preference is given to the following meanings of the substituents, in each case either alone or in combination:

Preference is given to compounds I'.

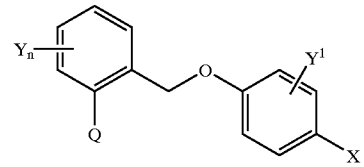

(I')

Particular preference is given to compounds I in which Q is $C(=CHOCH_3)$—$COOCH_3$, $C(=CHCH_3)$—$COOCH_3$, $C(=NOCH_3)$—$COOCH_3$, $C(=NOCH_3)$—$CONHCH_3$ or $N(—OCH_3)$—$COOCH_3$.

In addition, preference is given to compounds I in which $Y^1$ is ortho to the oxymethylene group.

Likewise, preference is given to compounds I in which $Y_n$ is 6-methyl.

Furthermore, preference is given to compounds I in which the index m is 1 or 2.

Additionally, preference is also given to compounds I".

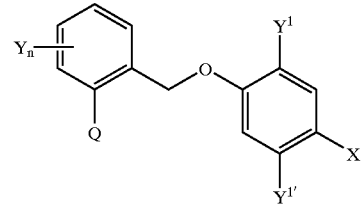

(I")

Particular preference is given to compounds I in which X is pyrazol-1-yl.

Particular preference is also given to compounds IA in which $Y^1$ is hydrogen, chlorine or methyl, $Y^{1'}$ is hydrogen, chlorine or methyl, X is pyrazol-1-yl, pyrazol-3-yl, pyrazol-5-yl, isoxazol-3-yl, isoxazol-5-yl, 1,2,4-triazol-3-yl, oxazol-2-yl, oxazol-4-yl or oxazol-5-yl, in each case substituted by customary groups.

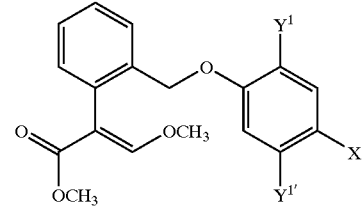

IA

Likewise, particular preference is given to compounds IB in which $R^A$ is hydrogen, chlorine, methyl or methoxy, $Y^1$ is hydrogen, chlorine or methyl, $Y^{1'}$ is hydrogen, chlorine or methyl, X is pyrazol-1-yl, pyrazol-3-yl, pyrazol-5-yl, isoxazol-3-yl, isoxazol-5-yl, 1,2,4-triazol-3-yl, oxazol-2-yl, oxazol-4-yl or oxazol-5-yl, in each case substituted by customary groups.

IB

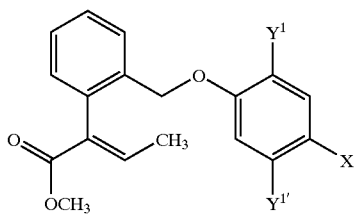

Additionally, particular preference is given to compounds IC in which $Y^1$ is hydrogen, chlorine or methyl, $Y^{1'}$ is hydrogen, chlorine or methyl, X is pyrazol-1-yl, pyrazol-3-yl, pyrazol-5-yl, isoxazol-3-yl, isoxazol-5-yl, 1,2,4-triazol-3-yl, oxazol-2-yl, oxazol-4-yl or oxazol-5-yl, each of which is substituted by customary groups.

IC

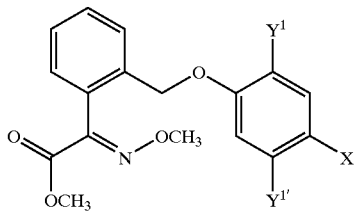

Particular preference is also given to compounds ID in which $Y^1$ is hydrogen, chlorine or methyl, $Y^{1'}$ is hydrogen, chlorine or methyl, $R^C$ is hydrogen or methyl, X is pyrazol-1-yl, pyrazol-3-yl, pyrazol-5-yl, isoxazol-3-yl, isoxazol-5-yl, 1,2,4-triazol-3-yl, oxazol-2-yl, oxazol-4-yl or oxazol-5-yl, in each case substituted by customary groups.

ID

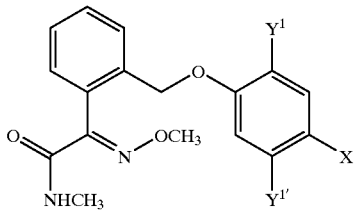

Furthermore, particular preference is given to compounds IE, in which $Y^1$ is hydrogen, chlorine or methyl, $Y^{1'}$ is hydrogen, chlorine or methyl, X is pyrazol-1-yl, pyrazol-3-yl, pyrazol-5-yl, isoxazol-3-yl, isoxazol-5-yl, 1,2,4-triazol-3-yl, oxazol-2-yl, oxazol-4-yl or oxazol-5-yl, in each case substituted by customary groups.

IE

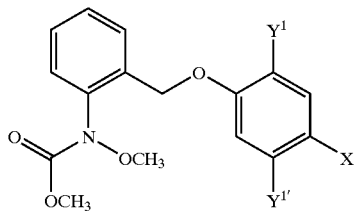

Moreover, particular preference is given to compounds IF''' in which $R^A$ is chlorine, methyl or methoxy, $Y^1$ is chlorine or methyl, $Y^{1'}$ is hydrogen, chlorine or methyl, X is pyrazol-1-yl, pyrazol-3-yl, pyrazol-5-yl, isoxazol-3-yl, isoxazol-5-yl, 1,2,4-triazol-3-yl, oxazol-2-yl, oxazol-4-yl or oxazol-5-yl, in each case substituted by customary groups.

IF'''

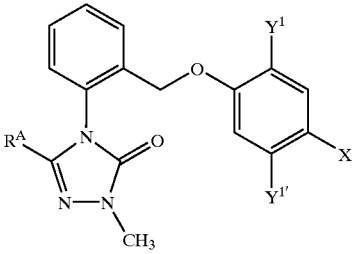

Likewise, particular preference is given to compounds IG'' in which $R^A$ is chlorine, methyl or methoxy, $Y^1$ is chlorine or methyl, $Y1'$ is hydrogen, chlorine or methyl, X is pyrazol-1-yl, pyrazol-3-yl, pyrazol-5-yl, isoxazol-3-yl, isoxazol-5-yl, 1,2,4-triazol-3-yl, oxazol-2-yl, oxazol-4-yl or oxazol-5-yl, in each case substituted by customary groups.

IG''

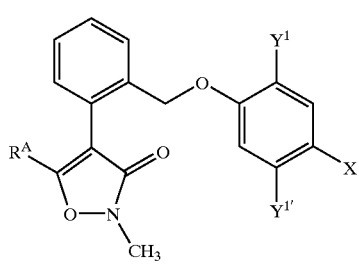

Additionally, particular preference is given to compounds 1H'' in which $Y^1$ is chlorine or methyl, $Y^{1'}$ is hydrogen, chlorine or methyl, X is pyrazol-1-yl, pyrazol-3-yl, pyrazol-5-yl, isoxazol-3-yl, isoxazol-5-yl, 1,2,4-triazol-3-yl, oxazol-2-yl, oxazol-4-yl or oxazol-5-yl, in each case substituted by customary groups.

IH''

Particular preference is also given to compounds IJ'' in which $R^A$ is chlorine, methyl or methoxy, $Y^1$ is chlorine or methyl, $Y^{1'}$ is hydrogen, chlorine or methyl, $R^C$ is hydrogen or methyl, X is pyrazol-1-yl, pyrazol-3-yl, pyrazol-5-yl, isoxazol-3-yl, isoxazol-5-yl, 1,2,4-triazol-3-yl, oxazol-2-yl, oxazol-4-yl or oxazol-5-yl, in each case substituted by customary groups.

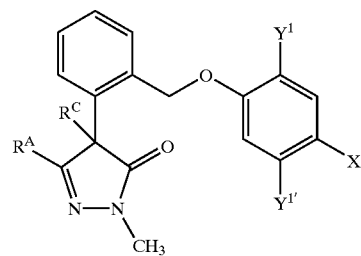

IJ''

Additionally, particular preference is given to compounds I.1 in which $Y^1$ is hydrogen, chlorine or methyl, $Y^{1'}$ is hydrogen, chlorine or methyl, and $R^1$, $R^2$ and $R^3$ are hydrogen, halogen, $C_1$–$C_4$-alkyl or trifluoromethyl.

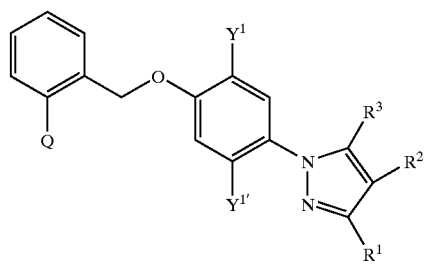

I.1

Likewise, particular preference is given to compounds I.2, in which $Y^1$ is hydrogen, chlorine or methyl, $Y^{1'}$ is hydrogen, chlorine or methyl and $R^1$, $R^2$ and $R^3$ are hydrogen, halogen, $C_1$–$C_4$-alkyl or trifluoromethyl.

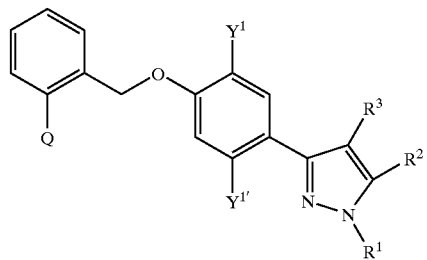

I.2

Additionally, particular preference is given to compounds I.3 in which $Y^1$ is hydrogen, chlorine or methyl, $Y^{1'}$ is hydrogen, chlorine or methyl and $R^1$, $R^2$ and $R^3$ are hydrogen, halogen, $C_1$–$C_4$-alkyl or trifluoromethyl.

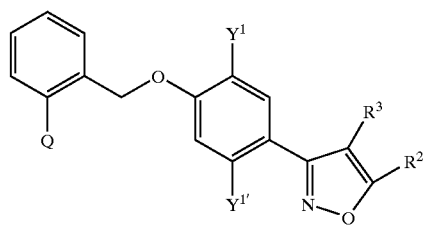

I.3

Furthermore, particular preference is given to compounds I.4 in which $Y^1$ is hydrogen, chlorine or methyl, $Y^{1'}$ is hydrogen, chlorine or methyl and $R^1$, $R^2$ and $R^3$ are hydrogen, halogen, $C_1$–$C_4$-alkyl or trifluoromethyl.

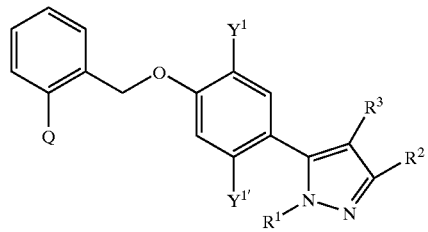

I.4

Additionally, particular preference is given to compounds I.5 in which $Y^1$ is hydrogen, chlorine or methyl, $Y^{1'}$ is hydrogen, chlorine or methyl and $R^1$, $R^2$ and $R^3$ are hydrogen, halogen, $C_1$–$C_4$-alkyl or trifluoromethyl.

I.5

Likewise, particular preference is given to compounds I.6, in which $Y^1$ is hydrogen, chlorine or methyl, $Y^{1'}$ is hydrogen, chlorine or methyl and $R^1$, $R^2$ and $R^3$ are hydrogen, halogen, $C_1$–$C_4$-alkyl or trifluoromethyl.

I.6

Additionally, particular preference is given to compounds I.7 in which $Y^1$ is hydrogen, chlorine or methyl, $Y^{1'}$ is hydrogen, chlorine or methyl and $R^1$, $R^2$ and $R^3$ are hydrogen, halogen, $C_1$–$C_4$-alkyl or trifluoromethyl.

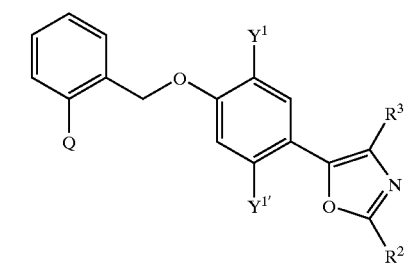

I.7

Likewise, particular preference is given to compounds I.8, in which $Y^1$ is hydrogen, chlorine or methyl, $Y^{1'}$ is hydrogen, chlorine or methyl and $R^1$, $R^2$ and $R^3$ are hydrogen, halogen, $C_1$–$C_4$-alkyl or trifluoromethyl.

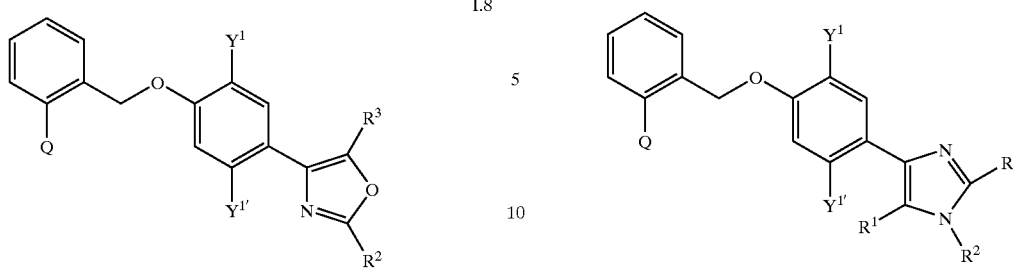

I.8

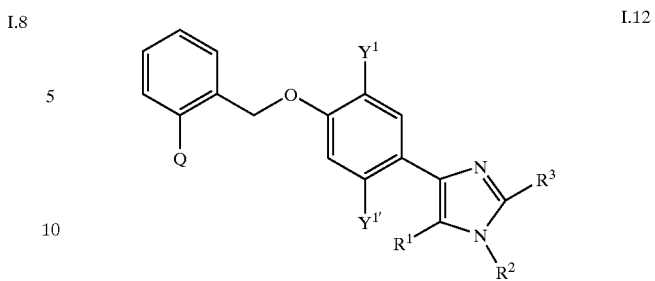

I.12

Additionally, particular preference is given to compounds I.9 in which $Y^1$ is hydrogen, chlorine or methyl, $Y^{1'}$ is hydrogen, chlorine or methyl and $R^1$, $R^2$ and $R^3$ are hydrogen, halogen, $C_1$–$C_4$-alkyl or trifluoromethyl.

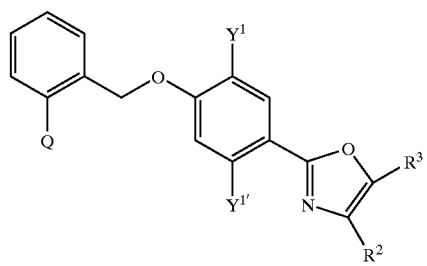

I.9

Particular preference is also given to compounds I.10 in which $Y^1$ is hydrogen, chlorine or methyl, $Y^{1'}$ is hydrogen, chlorine or methyl and $R^1$, $R^2$ and $R^3$ are hydrogen, halogen, $C_1$–$C_4$-alkyl or trifluoromethyl.

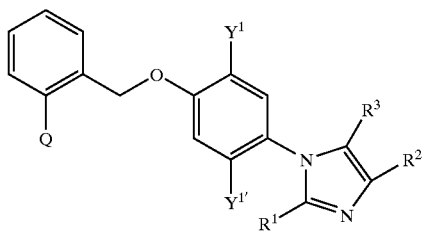

I.10

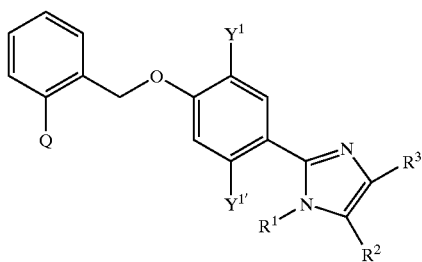

I.11

Additionally, particular preference is given to compounds I.11 in which $Y^1$ is hydrogen, chlorine or methyl, $Y^{1'}$ is hydrogen, chlorine or methyl and $R^1$, $R^2$ and $R^3$ are hydrogen, halogen, $C_1$–$C_4$-alkyl or trifluoromethyl.

Likewise, particular preference is given to compounds I.12, in which $Y^1$ is hydrogen, chlorine or methyl, $Y^{1'}$ is hydrogen, chlorine or methyl and $R^1$, $R^2$ and $R^3$ are hydrogen, halogen, $C_1$–$C_4$-alkyl or trifluoromethyl.

Additionally, particular preference is given to compounds I.13 in which $Y^1$ is hydrogen, chlorine or methyl, $Y^{1'}$ is hydrogen, chlorine or methyl and $R^1$, $R^2$ and $R^3$ are hydrogen, halogen, $C_1$–$C_4$-alkyl or trifluoromethyl.

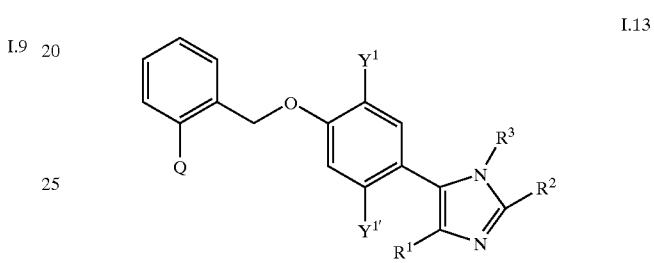

I.13

With respect to their use, the compounds I compiled in the tables below are particularly preferred. In addition, the groups mentioned for a substituent in the tables represent themselves, independently of the combination in which they are mentioned, a particularly preferred embodiment of the substituent in question.

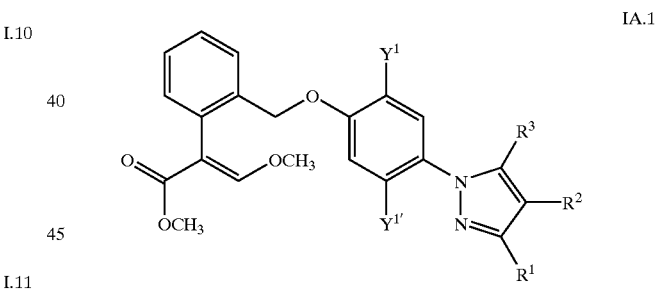

IA.1

Table 1

Compounds of the formula IA.1 in which $Y^1$ is chlorine, $Y^{1'}$ represents hydrogen and the combination of the radicals $R^1$, $R^2$ and $R^3$ corresponds for each compound to one row of Table A Table 2

Compounds of the formula IA.1 in which $Y^1$ is chlorine, $Y^{1'}$ is chlorine and the combination of the radicals $R^1$, $R^2$ and $R^3$ corresponds for each compound to one row of Table A Table 3

Compounds of the formula IA.1 in which $Y^1$ is chlorine, $Y^{1'}$ is methyl and the combination of the radicals $R^1$, $R^2$ and $R^3$ corresponds for each compound to one row of Table A Table 4

Compounds of the formula IA.1 in which $Y^1$ is methyl, $Y^{1'}$ is hydrogen and the combination of the radicals $R^1$, $R^2$ and $R^3$ corresponds for each compound to one row of Table A Table 5
Compounds of the formula IA.1 in which $Y^1$ is methyl, $Y^{1'}$ is chlorine and the combination of the radicals $R^1$, $R^2$ and $R^3$ corresponds for each compound to one row of Table A Table 6
Compounds of the formula IA.1 in which $Y^1$ is methyl, $Y^{1'}$ is methyl and the combination of the radicals $R^1$, $R^2$ and $R^3$ corresponds for each compound to one row of Table A Table 7
Compounds of the formula IA.1 in which $Y^1$ is hydrogen, $Y^{1'}$ is hydrogen and the combination of the radicals $R^1$, $R^2$ and $R^3$ corresponds for each compound to one row of Table A Table 8
Compounds of the formula IA.1 in which $Y^1$ is hydrogen, $Y^{1'}$ is chlorine and the combination of the radicals $R^1$, $R^2$ and $R^3$ corresponds for each compound to one row of Table A Table 9
Compounds of the formula IA.1 in which $Y^1$ is hydrogen, $Y^{1'}$ is methyl and the combination of the radicals $R^1$, $R^2$ and $R^3$ corresponds for each compound to one row of Table A Table 10
Compounds of the formula IA.2 in which $Y^1$ is chlorine, $Y^{1'}$ is hydrogen and the combination of the radicals $R^1$, $R^2$ and $R^3$ corresponds for each compound to one row of Table A

IA.2

Table 11
Compounds of the formula IA.2 in which $Y^1$ is chlorine, $Y^{1'}$ is chlorine and the combination of the radicals $R^1$, $R^2$ and $R^3$ corresponds for each compound to one row of Table A Table 12
Compounds of the formula IA.2 in which $Y^1$ is chlorine, $Y^{1'}$ is methyl and the combination of the radicals $R^1$, $R^2$ and $R^3$ corresponds for each compound to one row of Table A Table 13
Compounds of the formula IA.2 in which $Y^1$ is methyl, $Y^{1'}$ is hydrogen and the combination of the radicals $R^1$, $R^2$ and $R^3$ corresponds for each compound to one row of Table A Table 14
Compounds of the formula IA.2 in which $Y^1$ is methyl, $Y^{1'}$ is chlorine and the combination of the radicals $R^1$, $R^2$ and $R^3$ corresponds for each compound to one row of Table A Table 15
Compounds of the formula IA.2 in which $Y^1$ is methyl, $Y^{1'}$ is methyl and the combination of the radicals $R^1$, $R^2$ and $R^3$ corresponds for each compound to one row of Table A Table 16
Compounds of the formula IA.2 in which $Y^1$ is hydrogen, $Y^{1'}$ is hydrogen and the combination of the radicals $R^1$, $R^2$ and $R^3$ corresponds for each compound to one row of Table A Table 17
Compounds of the formula IA.2 in which $Y^1$ is hydrogen, $Y^{1'}$ is chlorine and the combination of the radicals $R^1$, $R^2$ and $R^3$ corresponds for each compound to one row of Table A Table 18
Compounds of the formula IA.2 in which $Y^1$ is hydrogen, $Y^{1'}$ is methyl and the combination of the radicals $R^1$, $R^2$ and $R^3$ corresponds for each compound to one row of Table A Table 19
Compounds of the formula IA.3 in which $Y^1$ is chlorine, $Y^{1'}$ is hydrogen and the combination of the radicals $R^2$ and $R^3$ corresponds for each compound to one row of Table B

IA.3

Table 20
Compounds of the formula IA.3 in which $Y^1$ is chlorine, $Y^{1'}$ is chlorine and the combination of the radicals $R^2$ and $R^3$ corresponds for each compound to one row of Table B Table 21
Compounds of the formula IA.3 in which $Y^1$ is chlorine, $Y^{1'}$ is methyl and the combination of the radicals $R^2$ and $R^3$ corresponds for each compound to one row of Table B Table 22
Compounds of the formula IA.3 in which $Y^1$ is methyl, $Y^{1'}$ is hydrogen and the combination of the radicals $R^2$ and $R^3$ corresponds for each compound to one row of Table B Table 23
Compounds of the formula IA.3 in which $Y^1$ is methyl, $Y^{1'}$ is chlorine and the combination of the radicals $R^2$ and $R^3$ corresponds for each compound to one row of Table B Table 24
Compounds of the formula IA.3 in which $Y^1$ is methyl, $Y^{1'}$ is methyl and the combination of the radicals $R^2$ and $R^3$ corresponds for each compound to one row of Table B Table 25
Compounds of the formula IA.3 in which $Y^1$ is hydrogen, $Y^{1'}$ is hydrogen and the combination of the radicals $R^2$ and $R^3$ corresponds for each compound to one row of Table B Table 26
Compounds of the formula IA.3 in which $Y^1$ is hydrogen, $Y^{1'}$ is chlorine and the combination of the radicals $R^2$ and $R^3$ corresponds for each compound to one row of Table B Table 27
Compounds of the formula IA.3 in which $Y^1$ is hydrogen, $Y^{1'}$ is methyl and the combination of the radicals $R^2$ and $R^3$ corresponds for each compound to one row of Table B Table 28
Compounds of the formula IA.4 in which $Y^1$ is chlorine, $Y^{1'}$ is hydrogen and the combination of the radicals $R^1$, $R^2$ and $R^3$ corresponds for each compound to one row of Table A

IA.4

Table 29
Compounds of the formula IA.4 in which $Y^1$ is chlorine, $Y^{1'}$ is chlorine and the combination of the radicals $R^1$, $R^2$ and $R^3$ corresponds for each compound to one row of Table A Table 30
Compounds of the formula IA.4 in which $Y^1$ is chlorine, $Y^{1'}$ is methyl and the combination of the radicals $R^1$, $R^2$ and $R^3$ corresponds for each compound to one row of Table A Table 31
Compounds of the formula IA.4 in which $Y^1$ is methyl, $Y^{1'}$ is hydrogen and the combination of the radicals $R^1$, $R^2$ and $R^3$ corresponds for each compound to one row of Table A Table 32
Compounds of the formula IA.4 in which $Y^1$ is methyl, $Y^{1'}$ is chlorine and the combination of the radicals $R^1$, $R^2$ and $R^3$ corresponds for each compound to one row of Table A Table 33
Compounds of the formula IA.4 in which $Y^1$ is methyl, $Y^{1'}$ is methyl and the combination of the radicals $R^1$, $R^2$ and $R^3$ corresponds for each compound to one row of Table A Table 34
Compounds of the formula IA.4 in which $Y^1$ is hydrogen, $Y^{1'}$ is hydrogen and the combination of the radicals $R^1$, $R^2$ and $R^3$ corresponds for each compound to one row of Table A Table 35
Compounds of the formula IA.4 in which $Y^1$ is hydrogen, $Y^{1'}$ is chlorine and the combination of the radicals $R^1$, $R^2$ and $R^3$ corresponds for each compound to one row of Table A Table 36
Compounds of the formula IA.4 in which $Y^1$ is hydrogen, $Y^{1'}$ is methyl and the combination of the radicals $R^1$, $R^2$ and $R^3$ corresponds for each compound to one row of Table A Table 37
Compounds of the formula IA.5 in which $Y^1$ is chlorine, $Y^{1'}$ is hydrogen and the combination of the radicals $R^2$ and $R^3$ corresponds for each compound to one row of Table B

IA.5

Table 38
Compounds of the formula IA.5 in which $Y^1$ is chlorine, $Y^{1'}$ is chlorine and the combination of the radicals $R^2$ and $R^3$ corresponds for each compound to one row of Table B Table 39
Compounds of the formula IA.5 in which $Y^1$ is chlorine, $Y^{1'}$ is methyl and the combination of the radicals $R^2$ and $R^3$ corresponds for each compound to one row of Table B Table 40
Compounds of the formula IA.5 in which $Y^1$ is methyl, $Y^{1'}$ is hydrogen and the combination of the radicals $R^2$ and $R^3$ corresponds for each compound to one row of Table B Table 41
Compounds of the formula IA.5 in which $Y^1$ is methyl, $Y^{1'}$ is chlorine and the combination of the radicals $R^2$ and $R^3$ corresponds for each compound to one row of Table B Table 42
Compounds of the formula IA.5 in which $Y^1$ is methyl, $Y^{1'}$ is methyl and the combination of the radicals $R^2$ and $R^3$ corresponds for each compound to one row of Table B Table 43
Compounds of the formula IA.5 in which $Y^1$ is hydrogen, $Y^{1'}$ is hydrogen and the combination of the radicals $R^2$ and $R^3$ corresponds for each compound to one row of Table B Table 44
Compounds of the formula IA.5 in which $Y^1$ is hydrogen, $Y^{1'}$ is chlorine and the combination of the radicals $R^2$ and $R^3$ corresponds for each compound to one row of Table B Table 45
Compounds of the formula IA.5 in which $Y^1$ is hydrogen, $Y^{1'}$ is methyl and the combination of the radicals $R^2$ and $R^3$ corresponds for each compound to one row of Table B Table 46
Compounds of the formula IA.6 in which $Y^1$ is chlorine, $Y^{1'}$ is hydrogen and the combination of the radicals $R^1$ and $R^2$ corresponds for each compound to one row of Table C

IA.6

Table 47
Compounds of the formula IA.6 in which $Y^1$ is chlorine, $Y^{1'}$ is chlorine and the combination of the radicals $R^1$ and $R^2$ corresponds for each compound to one row of Table C Table 48
Compounds of the formula IA.6 in which $Y^1$ is chlorine, $Y^{1'}$ is methyl and the combination of the radicals $R^1$ and $R^2$ corresponds for each compound to one row of Table C Table 49
Compounds of the formula IA.6 in which $Y^1$ is methyl, $Y^{1'}$ is hydrogen and the combination of the radicals $R^1$ and $R^2$ corresponds for each compound to one row of Table C Table 50
Compounds of the formula IA.6 in which $Y^1$ is methyl, $Y^{1'}$ is chlorine and the combination of the radicals $R^1$ and $R^2$ corresponds for each compound to one row of Table C Table 51
Compounds of the formula IA.6 in which $Y^1$ is methyl, $Y^{1'}$ is methyl and the combination of the radicals $R^1$ and $R^2$ corresponds for each compound to one row of Table C Table 52
Compounds of the formula IA.6 in which $Y^1$ is hydrogen, $Y^{1'}$ is hydrogen and the combination of the radicals $R^1$ and $R^2$ corresponds for each compound to one row of Table C Table 53
  Compounds of the formula IA.6 in which $Y^1$ is hydrogen, $Y^{1'}$ is chlorine and the combination of the radicals $R^1$ and $R^2$ corresponds for each compound to one row of Table C
Table 54
  Compounds of the formula IA.6 in which $Y^1$ is hydrogen, $Y^{1'}$ is methyl and the combination of the radicals $R^1$ and $R^2$ corresponds for each compound to one row of Table C

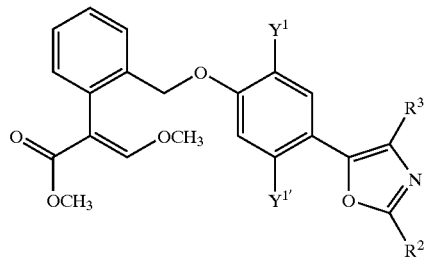

IA.7

Table 55
  Compounds of the formula IA.7 in which $Y^1$ is chlorine, $Y^{1'}$ is hydrogen and the combination of the radicals $R^2$ and $R^3$ corresponds for each compound to one row of Table B
Table 56
  Compounds of the formula IA.7 in which $Y^1$ is chlorine, $Y^{1'}$ is chlorine and the combination of the radicals $R^2$ and $R^3$ corresponds for each compound to one row of Table B
Table 57
  Compounds of the formula IA.7 in which $Y^1$ is chlorine, $Y^{1'}$ is methyl and the combination of the radicals $R^2$ and $R^3$ corresponds for each compound to one row of Table B
Table 58
  Compounds of the formula IA.7 in which $Y^1$ is methyl, $Y^{1'}$ is hydrogen and the combination of the radicals $R^2$ and $R^3$ corresponds for each compound to one row of Table B
Table 59
  Compounds of the formula IA.7 in which $Y^1$ is methyl, $Y^{1'}$ is chlorine and the combination of the radicals $R^2$ and $R^3$ corresponds for each compound to one row of Table B
Table 60
  Compounds of the formula IA.7 in which $Y^1$ is methyl, $Y^{1'}$ is methyl and the combination of the radicals $R^2$ and $R^3$ corresponds for each compound to one row of Table B
Table 61
  Compounds of the formula IA.7 in which $Y^1$ is hydrogen, $Y^{1'}$ is hydrogen and the combination of the radicals $R^2$ and $R^3$ corresponds for each compound to one row of Table B
Table 62
  Compounds of the formula IA.7 in which $Y^1$ is hydrogen, $Y^{1'}$ is chlorine and the combination of the radicals $R^2$ and $R^3$ corresponds for each compound to one row of Table B
Table 63
  Compounds of the formula IA.7 in which $Y^1$ is hydrogen, $Y^{1'}$ is methyl and the combination of the radicals $R^2$ and $R^3$ corresponds for each compound to one row of Table B
Table 64
  Compounds of the formula IA.8 in which $Y^1$ is chlorine, $Y^{1'}$ is hydrogen and the combination of the radicals $R^2$ and $R^3$ corresponds for each compound to one row of Table B

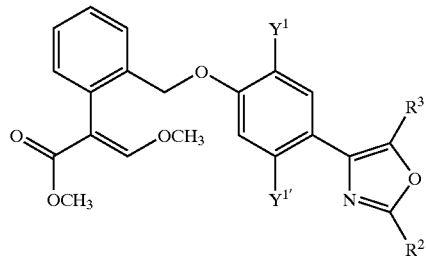

IA.8

Table 65
  Compounds of the formula IA.8 in which $Y^1$ is chlorine, $Y^{1'}$ is chlorine and the combination of the radicals $R^2$ and $R^3$ corresponds for each compound to one row of Table B
Table 66
  Compounds of the formula IA.8 in which $Y^1$ is chlorine, $Y^{1'}$ is methyl and the combination of the radicals $R^2$ and $R^3$ corresponds for each compound to one row of Table B
Table 67
  Compounds of the formula IA.8 in which $Y^1$ is methyl, $Y^{1'}$ is hydrogen and the combination of the radicals $R^2$ and $R^3$ corresponds for each compound to one row of Table B
Table 68
  Compounds of the formula IA.8 in which $Y^1$ is methyl, $Y^{1'}$ is chlorine and the combination of the radicals $R^2$ and $R^3$ corresponds for each compound to one row of Table B
Table 69
  Compounds of the formula IA.8 in which $Y^1$ is methyl, $Y^{1'}$ is methyl and the combination of the radicals $R^2$ and $R^3$ corresponds for each compound to one row of Table B
Table 70
  Compounds of the formula IA.8 in which $Y^1$ is hydrogen, $Y^{1'}$ is hydrogen and the combination of the radicals $R^2$ and $R^3$ corresponds for each compound to one row of Table B
Table 71
  Compounds of the formula IA.8 in which $Y^1$ is hydrogen, $Y^{1'}$ is chlorine and the combination of the radicals $R^2$ and $R^3$ corresponds for each compound to one row of Table B
Table 72
  Compounds of the formula IA.8 in which $Y^1$ is hydrogen, $Y^{1'}$ is methyl and the combination of the radicals $R^2$ and $R^3$ corresponds for each compound to one row of Table B
Table 73
  Compounds of the formula IA.9 in which $Y^1$ is chlorine, $Y^{1'}$ is hydrogen and the combination of the radicals $R^2$ and $R^3$ corresponds for each compound to one row of Table C

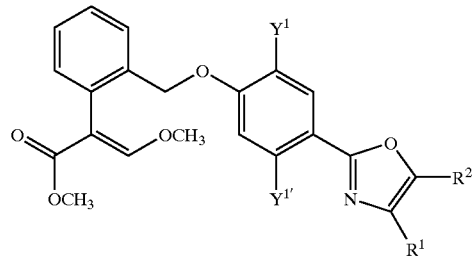

IA.9

Table 74
  Compounds of the formula IA.9 in which $Y^1$ is chlorine, $Y^{1'}$ is chlorine and the combination of the radicals $R^2$ and $R^3$ corresponds for each compound to one row of Table C Table 75
Compounds of the formula IA.9 in which $Y^1$ is chlorine, $Y^{1'}$ is methyl and the combination of the radicals $R^2$ and $R^3$ corresponds for each compound to one row of Table C Table 76
Compounds of the formula IA.9 in which $Y^1$ is methyl, $Y^{1'}$ is hydrogen and the combination of the radicals $R^2$ and $R^3$ corresponds for each compound to one row of Table C Table 77
Compounds of the formula IA.9 in which $Y^1$ is methyl, $Y^{1'}$ is chlorine and the combination of the radicals $R^2$ and $R^3$ corresponds for each compound to one row of Table C Table 78
Compounds of the formula IA.9 in which $Y^1$ is methyl, $Y^{1'}$ is methyl and the combination of the radicals $R^2$ and $R^3$ corresponds for each compound to one row of Table C Table 79
Compounds of the formula IA.9 in which $Y^1$ is hydrogen, $Y^{1'}$ is hydrogen and the combination of the radicals $R^2$ and $R^3$ corresponds for each compound to one row of Table C Table 80
Compounds of the formula IA.9 in which $Y^1$ is hydrogen, $Y^{1'}$ is chlorine and the combination of the radicals $R^2$ and $R^3$ corresponds for each compound to one row of Table C Table 81
Compounds of the formula IA.9 in which $Y^1$ is hydrogen, $Y^{1'}$ is methyl and the combination of the radicals $R^2$ and $R^3$ corresponds for each compound to one row of Table C Table 82
Compounds of the formula IA.10 in which $Y^1$ is chlorine, $Y^{1'}$ is hydrogen and the combination of the radicals $R^1$, $R^2$ and $R^3$ corresponds for each compound to one row of Table D

IA.10

Table 83
Compounds of the formula IA.10 in which $Y^1$ is chlorine, $Y^{1'}$ is chlorine and the combination of the radicals $R^1$, $R^2$ and $R^3$ corresponds for each compound to one row of Table D Table 84
Compounds of the formula IA.10 in which $Y^1$ is chlorine, $Y^{1'}$ is methyl and the combination of the radicals $R^1$, $R^2$ and $R^3$ corresponds for each compound to one row of Table D Table 85
Compounds of the formula IA.10 in which $Y^1$ is methyl, $Y^{1'}$ is hydrogen and the combination of the radicals $R^1$, $R^2$ and $R^3$ corresponds for each compound to one row of Table D Table 86
Compounds of the formula IA.10 in which $Y^1$ is methyl, $Y^{1'}$ is chlorine and the combination of the radicals $R^1$, $R^2$ and $R^3$ corresponds for each compound to one row of Table D Table 87
Compounds of the formula IA.10 in which $Y^1$ is methyl, $Y^{1'}$ is methyl and the combination of the radicals $R^1$, $R^2$ and $R^3$ corresponds for each compound to one row of Table D Table 88
Compounds of the formula IA.10 in which $Y^1$ is hydrogen, $Y^{1'}$ is hydrogen and the combination of the radicals $R^1$, $R^2$ and $R^3$ corresponds for each compound to one row of Table D Table 89
Compounds of the formula IA.10 in which $Y^1$ is hydrogen, $Y^{1'}$ is chlorine and the combination of the radicals $R^1$, $R^2$ and $R^3$ corresponds for each compound to one row of Table D Table 90
Compounds of the formula IA.10 in which $Y^1$ is hydrogen, $Y^{1'}$ is methyl and the combination of the radicals $R^1$, $R^2$ and $R^3$ corresponds for each compound to one row of Table D Table 91
Compounds of the formula IA.11 in which $Y^1$ is chlorine, $Y^{1'}$ is hydrogen and the combination of the radicals $R^1$, $R^2$ and $R^3$ corresponds for each compound to one row of Table D

IA.11

Table 92
Compounds of the formula IA.11 in which $Y^1$ is chlorine, $Y^{1'}$ is chlorine and the combination of the radicals $R^1$, $R^2$ and $R^3$ corresponds for each compound to one row of Table D Table 93
Compounds of the formula IA.11 in which $Y^1$ is chlorine, $Y^{1'}$ is methyl and the combination of the radicals $R^1$, $R^2$ and $R^3$ corresponds for each compound to one row of Table D Table 94
Compounds of the formula IA.11 in which $Y^1$ is methyl, $Y^{1'}$ is hydrogen and the combination of the radicals $R^1$, $R^2$ and $R^3$ corresponds for each compound to one row of Table D Table 95
Compounds of the formula IA.11 in which $Y^1$ is methyl, $Y^{1'}$ is chlorine and the combination of the radicals $R^1$, $R^2$ and $R^3$ corresponds for each compound to one row of Table D Table 96
Compounds of the formula IA.11 in which $Y^1$ is methyl, $Y^{1'}$ is methyl and the combination of the radicals $R^1$, $R^2$ and $R^3$ corresponds for each compound to one row of Table D Table 97
Compounds of the formula IA.11 in which $Y^1$ is hydrogen, $Y^{1'}$ is hydrogen and the combination of the radicals $R^1$, $R^2$ and $R^3$ corresponds for each compound to one row of Table D Table 98
Compounds of the formula IA.11 in which $Y^1$ is hydrogen, $Y^{1'}$ is chlorine and the combination of the radicals $R^1$, $R^2$ and $R^3$ corresponds for each compound to one row of Table D Table 99

Compounds of the formula IA.11 in which $Y^1$ is hydrogen, $Y^{1'}$ is methyl and the combination of the radicals $R^1$, $R^2$ and $R^3$ corresponds for each compound to one row of Table D Table 100

Compounds of the formula IA.12 in which $Y^1$ is chlorine, $Y^{1'}$ is hydrogen and the combination of the radicals $R^1$, $R^2$ and $R^3$ corresponds for each compound to one row of Table A

IA.12

Table 101

Compounds of the formula IA.12 in which $Y^1$ is chlorine, $Y^{1'}$ is chlorine and the combination of the radicals $R^1$, $R^2$ and $R^3$ corresponds for each compound to one row of Table A Table 102

Compounds of the formula IA.12 in which $Y^1$ is chlorine, $Y^{1'}$ is methyl and the combination of the radicals $R^1$, $R^2$ and $R^3$ corresponds for each compound to one row of Table A Table 103

Compounds of the formula IA.12 in which $Y^1$ is methyl, $Y^{1'}$ is hydrogen and the combination of the radicals $R^1$, $R^2$ and $R^3$ corresponds for each compound to one row of Table A Table 104

Compounds of the formula IA.12 in which $Y^1$ is methyl, $Y^{1'}$ is chlorine and the combination of the radicals $R^1$, $R^2$ and $R^3$ corresponds for each compound to one row of Table A Table 105

Compounds of the formula IA.12 in which $Y^1$ is methyl, $Y^{1'}$ is methyl and the combination of the radicals $R^1$, $R^2$ and $R^3$ corresponds for each compound to one row of Table A Table 106

Compounds of the formula IA.12 in which $Y^1$ is hydrogen, $Y^{1'}$ is hydrogen and the combination of the radicals $R^1$, $R^2$ and $R^3$ corresponds for each compound to one row of Table A Table 107

Compounds of the formula IA.12 in which $Y^1$ is hydrogen, $Y^{1'}$ is chlorine and the combination of the radicals $R^1$, $R^2$ and $R^3$ corresponds for each compound to one row of Table A Table 108

Compounds of the formula IA.12 in which $Y^1$ is hydrogen, $Y^{1'}$ is methyl and the combination of the radicals $R^1$, $R^2$ and $R^3$ corresponds for each compound to one row of Table A Table 109

Compounds of the formula IA.13 in which $Y^1$ is chlorine, $Y^{1'}$ is hydrogen and the combination of the radicals $R^1$, $R^2$ and $R^3$ corresponds for each compound to one row of Table A

IA.13

Table 110

Compounds of the formula IA.13 in which $Y^1$ is chlorine, $Y^{1'}$ is chlorine and the combination of the radicals $R^1$, $R^2$ and $R^3$ corresponds for each compound to one row of Table A Table 111

Compounds of the formula IA.13 in which $Y^1$ is chlorine, $Y^{1'}$ is methyl and the combination of the radicals $R^1$, $R^2$ and $R^3$ corresponds for each compound to one row of Table A Table 112

Compounds of the formula IA.13 in which $Y^1$ is methyl, $Y^{1'}$ is hydrogen and the combination of the radicals $R^1$, $R^2$ and $R^3$ corresponds for each compound to one row of Table A Table 113

Compounds of the formula IA.13 in which $Y^1$ is methyl, $Y^{1'}$ is chlorine and the combination of the radicals $R^1$, $R^2$ and $R^3$ corresponds for each compound to one row of Table A Table 114

Compounds of the formula IA.13 in which $Y^1$ is methyl, $Y^{1'}$ is methyl and the combination of the radicals $R^1$, $R^2$ and $R^3$ corresponds for each compound to one row of Table A Table 115

Compounds of the formula IA.13 in which $Y^1$ is hydrogen, $Y^{1'}$ is hydrogen and the combination of the radicals $R^1$, $R^2$ and $R^3$ corresponds for each compound to one row of Table A Table 116

Compounds of the formula IA.13 in which $Y^1$ is hydrogen, $Y^{1'}$ is chlorine and the combination of the radicals $R^1$, $R^2$ and $R^3$ corresponds for each compound to one row of Table A Table 117

Compounds of the formula IA.13 in which $Y^1$ is hydrogen, $Y^{1'}$ is methyl and the combination of the radicals $R^1$, $R^2$ and $R^3$ corresponds for each compound to one row of Table A Table 118

Compounds of the formula IB.1 in which $Y^1$ is chlorine, $Y^{1'}$ is hydrogen and the combination of the radicals $R^1$, $R^2$ and $R^3$ corresponds for each compound to one row of Table A

IB.1

[Structure IB.1]

Table 119

Compounds of the formula IB.1 in which $Y^1$ is chlorine, $Y^{1'}$ is chlorine and the combination of the radicals $R^1$, $R^2$ and $R^3$ corresponds for each compound to one row of Table A Table 120

Compounds of the formula IB.1 in which $Y^1$ is chlorine, $Y^{1'}$ is methyl and the combination of the radicals $R^1$, $R^2$ and $R^3$ corresponds for each compound to one row of Table A Table 121

Compounds of the formula IB.1 in which $Y^1$ is methyl, $Y^{1'}$ is hydrogen and the combination of the radicals $R^1$, $R^2$ and $R^3$ corresponds for each compound to one row of Table A Table 122

Compounds of the formula IB.1 in which $Y^1$ is methyl, $Y^{1'}$ is chlorine and the combination of the radicals $R^1$, $R^2$ and $R^3$ corresponds for each compound to one row of Table A Table 123

Compounds of the formula IB.1 in which $Y^1$ is methyl, $Y^{1'}$ is methyl and the combination of the radicals $R^1$, $R^2$ and $R^3$ corresponds for each compound to one row of Table A Table 124

Compounds of the formula IB.1 in which $Y^1$ is hydrogen, $Y^{1'}$ is hydrogen and the combination of the radicals $R^1$, $R^2$ and $R^3$ corresponds for each compound to one row of Table A Table 125

Compounds of the formula IB.1 in which $Y^1$ is hydrogen, $Y^{1'}$ is chlorine and the combination of the radicals $R^1$, $R^2$ and $R^3$ corresponds for each compound to one row of Table A Table 126

Compounds of the formula IB.1 in which $Y^1$ is hydrogen, $Y^{1'}$ is methyl and the combination of the radicals $R^1$, $R^2$ and $R^3$ corresponds for each compound to one row of Table A Table 127

Compounds of the formula IB.2 in which $Y^1$ is chlorine, $Y^{1'}$ is hydrogen and the combination of the radicals $R^1$, $R^2$ and $R^3$ corresponds for each compound to one row of Table A

IB.2

[Structure IB.2]

Table 128

Compounds of the formula IB.2 in which $Y^1$ is chlorine, $Y^{1'}$ is chlorine and the combination of the radicals $R^1$, $R^2$ and $R^3$ corresponds for each compound to one row of Table A Table 129

Compounds of the formula IB.2 in which $Y^1$ is chlorine, $Y^{1'}$ is methyl and the combination of the radicals $R^1$, $R^2$ and $R^3$ corresponds for each compound to one row of Table A Table 130

Compounds of the formula IB.2 in which $Y^1$ is methyl, $Y^{1'}$ is hydrogen and the combination of the radicals $R^1$, $R^2$ and $R^3$ corresponds for each compound to one row of Table A Table 131

Compounds of the formula IB.2 in which $Y^1$ is methyl, $Y^{1'}$ is chlorine and the combination of the radicals $R^1$, $R^2$ and $R^3$ corresponds for each compound to one row of Table A Table 132

Compounds of the formula IB.2 in which $Y^1$ is methyl, $Y^{1'}$ is methyl and the combination of the radicals $R^1$, $R^2$ and $R^3$ corresponds for each compound to one row of Table A Table 133

Compounds of the formula IB.2 in which $Y^1$ is hydrogen, $Y^{1'}$ is hydrogen and the combination of the radicals $R^1$, $R^2$ and $R^3$ corresponds for each compound to one row of Table A Table 134

Compounds of the formula IB.2 in which $Y^1$ is hydrogen, $Y^{1'}$ is chlorine and the combination of the radicals $R^1$, $R^2$ and $R^3$ corresponds for each compound to one row of Table A Table 135

Compounds of the formula IB.2 in which $Y^1$ is hydrogen, $Y^{1'}$ is methyl and the combination of the radicals $R^1$, $R^2$ and $R^3$ corresponds for each compound to one row of Table A Table 136

Compounds of the formula IB.3 in which $Y^1$ is chlorine, $Y^{1'}$ is hydrogen and the combination of the radicals $R^2$ and $R^3$ corresponds for each compound to one row of Table B

IB.3

[Structure IB.3]

Table 137

Compounds of the formula IB.3 in which $Y^1$ is chlorine, $Y^{1'}$ is chlorine and the combination of the radicals $R^2$ and $R^3$ corresponds for each compound to one row of Table B Table 138
Compounds of the formula IB.3 in which $Y^1$ is chlorine, $Y^{1'}$ is methyl and the combination of the radicals $R^2$ and $R^3$ corresponds for each compound to one row of Table B Table 139
Compounds of the formula IB.3 in which $Y^1$ is methyl, $Y^{1'}$ is hydrogen and the combination of the radicals $R^2$ and $R^3$ corresponds for each compound to one row of Table B Table 140
Compounds of the formula IB.3 in which $Y^1$ is methyl, $Y^{1'}$ is chlorine and the combination of the radicals $R^2$ and $R^3$ corresponds for each compound to one row of Table B Table 141
Compounds of the formula IB.3 in which $Y^1$ is methyl, $Y^{1'}$ is methyl and the combination of the radicals $R^2$ and $R^3$ corresponds for each compound to one row of Table B Table 142
Compounds of the formula IB.3 in which $Y^1$ is hydrogen, $Y^{1'}$ is hydrogen and the combination of the radicals $R^2$ and $R^3$ corresponds for each compound to one row of Table B Table 143
Compounds of the formula IB.3 in which $Y^1$ is hydrogen, $Y^{1'}$ is chlorine and the combination of the radicals $R^2$ and $R^3$ corresponds for each compound to one row of Table B Table 144
Compounds of the formula IB.3 in which $Y^1$ is hydrogen, $Y^{1'}$ is methyl and the combination of the radicals $R^2$ and $R^3$ corresponds for each compound to one row of Table B Table 145
Compounds of the formula IB.4 in which $Y^1$ is chlorine, $Y^{1'}$ is hydrogen and the combination of the radicals $R^1$, $R^2$ and $R^3$ corresponds for each compound to one row of Table A

IB.4

Table 146
Compounds of the formula IB.4 in which $Y^1$ is chlorine, $Y^{1'}$ is chlorine and the combination of the radicals $R^1$, $R^2$ and $R^3$ corresponds for each compound to one row of Table A Table 147
Compounds of the formula IB.4 in which $Y^1$ is chlorine, $Y^{1'}$ is methyl and the combination of the radicals $R^1$, $R^2$ and $R^3$ corresponds for each compound to one row of Table A Table 148
Compounds of the formula IB.4 in which $Y^1$ is methyl, $Y^{1'}$ is hydrogen and the combination of the radicals $R^1$, $R^2$ and $R^3$ corresponds for each compound to one row of Table A Table 149
Compounds of the formula IB.4 in which $Y^1$ is methyl, $Y^{1'}$ is chlorine and the combination of the radicals $R^1$, $R^2$ and $R^3$ corresponds for each compound to one row of Table A Table 150
Compounds of the formula IB.4 in which $Y^1$ is methyl, $Y^{1'}$ is methyl and the combination of the radicals $R^1$, $R^2$ and $R^3$ corresponds for each compound to one row of Table A Table 151
Compounds of the formula IB.4 in which $Y^1$ is hydrogen, $Y^{1'}$ is hydrogen and the combination of the radicals $R^1$, $R^2$ and $R^3$ corresponds for each compound to one row of Table A Table 152
Compounds of the formula IB.4 in which $Y^1$ is hydrogen, $Y^{1'}$ is chlorine and the combination of the radicals $R^1$, $R^2$ and $R^3$ corresponds for each compound to one row of Table A Table 153
Compounds of the formula IB.4 in which $Y^1$ is hydrogen, $Y^{1'}$ is methyl and the combination of the radicals $R^1$, $R^2$ and $R^3$ corresponds for each compound to one row of Table A Table 154
Compounds of the formula IB.5 in which $Y^1$ is chlorine, $Y^{1'}$ is hydrogen and the combination of the radicals $R^2$ and $R^3$ corresponds for each compound to one row of Table B

IB.5

Table 155
Compounds of the formula IB.5 in which $Y^1$ is chlorine, $Y^{1'}$ is chlorine and the combination of the radicals $R^2$ and $R^3$ corresponds for each compound to one row of Table B Table 156
Compounds of the formula IB.5 in which $Y^1$ is chlorine, $Y^{1'}$ is methyl and the combination of the radicals $R^2$ and $R^3$ corresponds for each compound to one row of Table B Table 157
Compounds of the formula IB.5 in which $Y^1$ is methyl, $Y^{1'}$ is hydrogen and the combination of the radicals $R^2$ and $R^3$ corresponds for each compound to one row of Table B Table 158
Compounds of the formula IB.5 in which $Y^1$ is methyl, $Y^{1'}$ is chlorine and the combination of the radicals $R^2$ and $R^3$ corresponds for each compound to one row of Table B Table 159
Compounds of the formula IB.5 in which $Y^1$ is methyl, $Y^{1'}$ is methyl and the combination of the radicals $R^2$ and $R^3$ corresponds for each compound to one row of Table B Table 160
Compounds of the formula IB.5 in which $Y^1$ is hydrogen, $Y^{1'}$ is hydrogen and the combination of the radicals $R^2$ and $R^3$ corresponds for each compound to one row of Table B Table 161
Compounds of the formula IB.5 in which $Y^1$ is hydrogen, $Y^{1'}$ is chlorine and the combination of the radicals $R^2$ and $R^3$ corresponds for each compound to one row of Table B Table 162
Compounds of the formula IB.5 in which $Y^1$ is hydrogen, $Y^{1'}$ is methyl and the combination of the radicals $R^2$ and $R^3$ corresponds for each compound to one row of Table B Table 163
Compounds of the formula IB.6 in which $Y^1$ is chlorine, $Y^{1'}$ is hydrogen and the combination of the radicals $R^1$ and $R^2$ corresponds for each compound to one row of Table C

IB.6

Table 164
Compounds of the formula IB.6 in which $Y^1$ is chlorine, $Y^{1'}$ is chlorine and the combination of the radicals $R^1$ and $R^2$ corresponds for each compound to one row of Table C Table 165
Compounds of the formula IB.6 in which $Y^1$ is chlorine, $Y^{1'}$ is methyl and the combination of the radicals $R^1$ and $R^2$ corresponds for each compound to one row of Table C Table 166
Compounds of the formula IB.6 in which $Y^1$ is methyl, $Y^{1'}$ is hydrogen and the combination of the radicals $R^1$ and $R^2$ corresponds for each compound to one row of Table C Table 167
Compounds of the formula IB.6 in which $Y^1$ is methyl, $Y^{1'}$ is chlorine and the combination of the radicals $R^1$ and $R^2$ corresponds for each compound to one row of Table C Table 168
Compounds of the formula IB.6 in which $Y^1$ is methyl, $Y^{1'}$ is methyl and the combination of the radicals $R^1$ and $R^2$ corresponds for each compound to one row of Table C Table 169
Compounds of the formula IB.6 in which $Y^1$ is hydrogen, $Y^{1'}$ is hydrogen and the combination of the radicals $R^1$ and $R^2$ corresponds for each compound to one row of Table C Table 170
Compounds of the formula IB.6 in which $Y^1$ is hydrogen, $Y^{1'}$ is chlorine and the combination of the radicals $R^1$ and $R^2$ corresponds for each compound to one row of Table C Table 171
Compounds of the formula IB.6 in which $Y^1$ is hydrogen, $Y^{1'}$ is methyl and the combination of the radicals $R^1$ and $R^2$ corresponds for each compound to one row of Table C Table 172
Compounds of the formula IB.7 in which $Y^1$ is chlorine, $Y^{1'}$ is hydrogen and the combination of the radicals $R^2$ and $R^3$ corresponds for each compound to one row of Table B

IB.7

Table 173
Compounds of the formula IB.7 in which $Y^1$ is chlorine, $Y^{1'}$ is chlorine and the combination of the radicals $R^2$ and $R^3$ corresponds for each compound to one row of Table B Table 174
Compounds of the formula IB.7 in which $Y^1$ is chlorine, $Y^{1'}$ is methyl and the combination of the radicals $R^2$ and $R^3$ corresponds for each compound to one row of Table B Table 175
Compounds of the formula IB.7 in which $Y^1$ is methyl, $Y^{1'}$ is hydrogen and the combination of the radicals $R^2$ and $R^3$ corresponds for each compound to one row of Table B Table 176
Compounds of the formula IB.7 in which $Y^1$ is methyl, $Y^{1'}$ is chlorine and the combination of the radicals $R^2$ and $R^3$ corresponds for each compound to one row of Table B Table 177
Compounds of the formula IB.7 in which $Y^1$ is methyl, $Y^{1'}$ is methyl and the combination of the radicals $R^2$ and $R^3$ corresponds for each compound to one row of Table B Table 178
Compounds of the formula IB.7 in which $Y^1$ is hydrogen, $Y^{1'}$ is hydrogen and the combination of the radicals $R^2$ and $R^3$ corresponds for each compound to one row of Table B Table 179
Compounds of the formula IB.7 in which $Y^1$ is hydrogen, $Y^{1'}$ is chlorine and the combination of the radicals $R^2$ and $R^3$ corresponds for each compound to one row of Table B Table 180
Compounds of the formula IB.7 in which $Y^1$ is hydrogen, $Y^{1'}$ is methyl and the combination of the radicals $R^2$ and $R^3$ corresponds for each compound to one row of Table B

IB.8

Table 181
Compounds of the formula IB.8 in which $Y^1$ is chlorine, $Y^{1'}$ is hydrogen and the combination of the radicals $R^2$ and $R^3$ corresponds for each compound to one row of Table B Table 182
Compounds of the formula IB.8 in which $Y^1$ is chlorine, $Y^{1'}$ is chlorine and the combination of the radicals $R^2$ and $R^3$ corresponds for each compound to one row of Table B Table 183
Compounds of the formula IB.8 in which $Y^1$ is chlorine, $Y^{1'}$ is methyl and the combination of the radicals $R^2$ and $R^3$ corresponds for each compound to one row of Table B Table 184
Compounds of the formula IB.8 in which $Y^1$ is methyl, $Y^{1'}$ is hydrogen and the combination of the radicals $R^2$ and $R^3$ corresponds for each compound to one row of Table B Table 185
Compounds of the formula IB.8 in which $Y^1$ is methyl, $Y^{1'}$ is chlorine and the combination of the radicals $R^2$ and $R^3$ corresponds for each compound to one row of Table B Table 186
Compounds of the formula IB.8 in which $Y^1$ is methyl, $Y^{1'}$ is methyl and the combination of the radicals $R^2$ and $R^3$ corresponds for each compound to one row of Table B Table 187
Compounds of the formula IB.8 in which $Y^1$ is hydrogen, $Y^{1'}$ is hydrogen and the combination of the radicals $R^2$ and $R^3$ corresponds for each compound to one row of Table B Table 188
Compounds of the formula IB.8 in which $Y^1$ is hydrogen, $Y^{1'}$ is chlorine and the combination of the radicals $R^2$ and $R^3$ corresponds for each compound to one row of Table B Table 189

Compounds of the formula IB.8 in which $Y^1$ is hydrogen, $Y^{1'}$ is methyl and the combination of the radicals $R^2$ and $R^3$ corresponds for each compound to one row of Table B Table 190

Compounds of the formula IB.9 in which $Y^1$ is chlorine, $Y^{1'}$ is hydrogen and the combination of the radicals $R^2$ and $R^3$ corresponds for each compound to one row of Table C

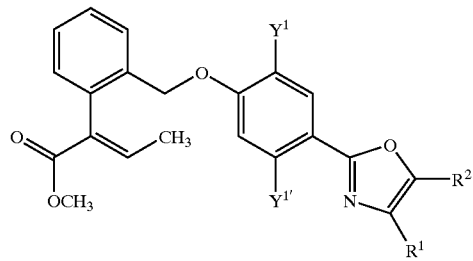

IB.9

Table 191

Compounds of the formula IB.9 in which $Y^1$ is chlorine, $Y^{1'}$ is chlorine and the combination of the radicals $R^2$ and $R^3$ corresponds for each compound to one row of Table C Table 192

Compounds of the formula IB.9 in which $Y^1$ is chlorine, $Y^{1'}$ is methyl and the combination of the radicals $R^2$ and $R^3$ corresponds for each compound to one row of Table C Table 193

Compounds of the formula IB.9 in which $Y^1$ is methyl, $Y^{1'}$ is hydrogen and the combination of the radicals $R^2$ and $R^3$ corresponds for each compound to one row of Table C Table 194

Compounds of the formula IB.9 in which $Y^1$ is methyl, $Y^{1'}$ is chlorine and the combination of the radicals $R^2$ and $R^3$ corresponds for each compound to one row of Table C Table 195

Compounds of the formula IB.9 in which $Y^1$ is methyl, $Y^{1'}$ is methyl and the combination of the radicals $R^2$ and $R^3$ corresponds for each compound to one row of Table C Table 196

Compounds of the formula IB.9 in which $Y^1$ is hydrogen, $Y^{1'}$ is hydrogen and the combination of the radicals $R^2$ and $R^3$ corresponds for each compound to one row of Table C Table 197

Compounds of the formula IB.9 in which $Y^1$ is hydrogen, $Y^{1'}$ is chlorine and the combination of the radicals $R^2$ and $R^3$ corresponds for each compound to one row of Table C Table 198

Compounds of the formula IB.9 in which $Y^1$ is hydrogen, $Y^{1'}$ is methyl and the combination of the radicals $R^2$ and $R^3$ corresponds for each compound to one row of Table C Table 199

Compounds of the formula IB.10 in which $Y^1$ is chlorine, $Y^{1'}$ is hydrogen and the combination of the radicals $R^1$, $R^2$ and $R^3$ corresponds for each compound to one row of Table D

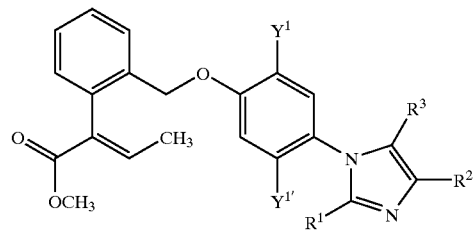

IB.10

Table 200

Compounds of the formula IB.10 in which $Y^1$ is chlorine, $Y^{1'}$ is chlorine and the combination of the radicals $R^1$, $R^2$ and $R^3$ corresponds for each compound to one row of Table D Table 201

Compounds of the formula IB.10 in which $Y^1$ is chlorine, $Y^{1'}$ is methyl and the combination of the radicals $R^1$, $R^2$ and $R^3$ corresponds for each compound to one row of Table D Table 202

Compounds of the formula IB.10 in which $Y^1$ is methyl, $Y^{1'}$ is hydrogen and the combination of the radicals Rim $R^2$ and $R^3$ corresponds for each compound to one row of Table D Table 203

Compounds of the formula IB.l0 in which $Y^1$ is methyl, $Y^{1'}$ is chlorine and the combination of the radicals $R^1$, $R^2$ and $R^3$ corresponds for each compound to one row of Table D Table 204

Compounds of the formula IB.10 in which $Y^1$ is methyl, $Y^{1'}$ is methyl and the combination of the radicals $R^1$, $R^2$ and $R^3$ corresponds for each compound to one row of Table D Table 205

Compounds of the formula IB.10 in which $Y^1$ is hydrogen, $Y^{1'}$ is hydrogen and the combination of the radicals $R^1$, $R^2$ and $R^3$ corresponds for each compound to one row of Table D Table 206

Compounds of the formula IB.10 in which $Y^1$ is hydrogen, $Y^{1'}$ is chlorine and the combination of the radicals $R^1$, $R^2$ and $R^3$ corresponds for each compound to one row of Table D Table 207

Compounds of the formula IB.10 in which $Y^1$ is hydrogen, $Y^{1'}$ is methyl and the combination of the radicals $R^1$, $R^2$ and $R^3$ corresponds for each compound to one row of Table D Table 208

Compounds of the formula IB.11 in which $Y^1$ is chlorine, $Y^{1'}$ is hydrogen and the combination of the radicals $R^1$, $R^2$ and $R^3$ corresponds for each compound to one row of Table D

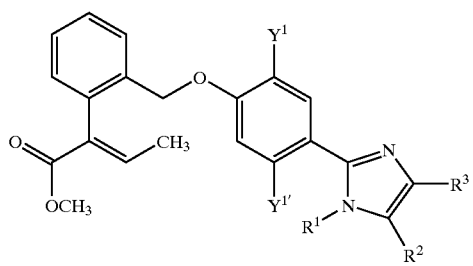

IB.11

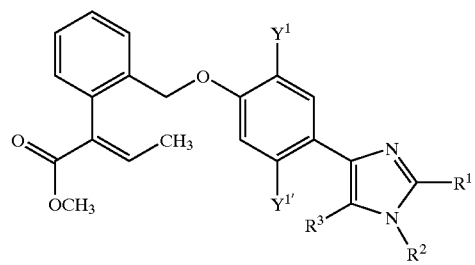

IB.12

Table 209

Compounds of the formula IB.11 in which $Y^1$ is chlorine, $Y^{1'}$ is chlorine and the combination of the radicals $R^1$, $R^2$ and $R^3$ corresponds for each compound to one row of Table D Table 210

Compounds of the formula IB.11 in which $Y^1$ is chlorine, $Y^{1'}$ is methyl and the combination of the radicals $R^1$, $R^2$ and $R^3$ corresponds for each compound to one row of Table D Table 211

Compounds of the formula IB.11 in which $Y^1$ is methyl, $Y^{1'}$ is hydrogen and the combination of the radicals $R^1$, $R^2$ and $R^3$ corresponds for each compound to one row of Table D Table 212

Compounds of the formula IB.11 in which $Y^1$ is methyl, $Y^{1'}$ is chlorine and the combination of the radicals $R^1$, $R^2$ and $R^3$ corresponds for each compound to one row of Table D Table 213

Compounds of the formula IB.11 in which $Y^1$ is methyl, $Y^{1'}$ is methyl and the combination of the radicals $R^1$, $R^2$ and $R^3$ corresponds for each compound to one row of Table D Table 214

Compounds of the formula IB.11 in which $Y^1$ is hydrogen, $Y^{1'}$ is hydrogen and the combination of the radicals $R^1$, $R^2$ and $R^3$ corresponds for each compound to one row of Table D Table 215

Compounds of the formula IB.11 in which $Y^1$ is hydrogen, $Y^{1'}$ is chlorine and the combination of the radicals $R^1$, $R^2$ and $R^3$ corresponds for each compound to one row of Table D Table 216

Compounds of the formula IB.11 in which $Y^1$ is hydrogen, $Y^{1'}$ is methyl and the combination of the radicals $R^1$, $R^2$ and $R^3$ corresponds for each compound to one row of Table D Table 217

Compounds of the formula IB.12 in which $Y^1$ is chlorine, $Y^{1'}$ is hydrogen and the combination of the radicals $R^1$, $R^2$ and $R^3$ corresponds for each compound to one row of Table A Table 218

Compounds of the formula IB.12 in which $Y^1$ is chlorine, $Y^{1'}$ is chlorine and the combination of the radicals $R^1$, $R^2$ and $R^3$ corresponds for each compound to one row of Table A Table 219

Compounds of the formula IB.12 in which $Y^1$ is chlorine, $Y^{1'}$ is methyl and the combination of the radicals $R^1$, $R^2$ and $R^3$ corresponds for each compound to one row of Table A Table 220

Compounds of the formula IB.12 in which $Y^1$ is methyl, $Y^{1'}$ is hydrogen and the combination of the radicals $R^1$, $R^2$ and $R^3$ corresponds for each compound to one row of Table A Table 221

Compounds of the formula IB.12 in which $Y^1$ is methyl, $Y^{1'}$ is chlorine and the combination of the radicals $R^1$, $R^2$ and $R^3$ corresponds for each compound to one row of Table A Table 222

Compounds of the formula IB.12 in which $Y^1$ is methyl, $Y^{1'}$ is methyl and the combination of the radicals $R^1$, $R^2$ and $R^3$ corresponds for each compound to one row of Table A Table 223

Compounds of the formula IB.12 in which $Y^1$ is hydrogen, $Y^{1'}$ is hydrogen and the combination of the radicals $R^1$, $R^2$ and $R^3$ corresponds for each compound to one row of Table A Table 224

Compounds of the formula IB.12 in which $Y^1$ is hydrogen, $Y^{1'}$ is chlorine and the combination of the radicals $R^1$, $R^2$ and $R^3$ corresponds for each compound to one row of Table A Table 225

Compounds of the formula IB.12 in which $Y^1$ is hydrogen, $Y^{1'}$ is methyl and the combination of the radicals $R^1$, $R^2$ and $R^3$ corresponds for each compound to one row of Table A Table 226

Compounds of the formula IB.13 in which $Y^1$ is chlorine, $Y^{1'}$ is hydrogen and the combination of the radicals $R^1$, $R^2$ and $R^3$ corresponds for each compound to one row of Table A

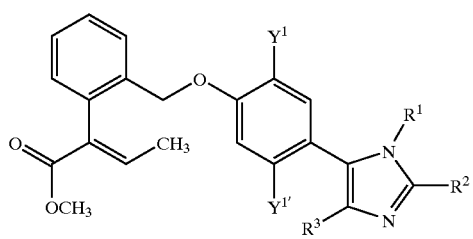

IB.13

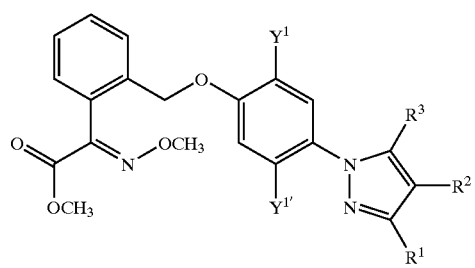

IC.1

Table 227

Compounds of the formula IB.13 in which $Y^1$ is chlorine, $Y^{1'}$ is chlorine and the combination of the radicals $R^1$, $R^2$ and $R^3$ corresponds for each compound to one row of Table A Table 228

Compounds of the formula IB.13 in which $Y^1$ is chlorine, $Y^{1'}$ is methyl and the combination of the radicals $R^1$, $R^2$ and $R^3$ corresponds for each compound to one row of Table A Table 229

Compounds of the formula IB.13 in which $Y^1$ is methyl, $Y^{1'}$ is hydrogen and the combination of the radicals $R^1$, $R^2$ and $R^3$ corresponds for each compound to one row of Table A Table 230

Compounds of the formula IB.13 in which $Y^1$ is methyl, $Y^{1'}$ is chlorine and the combination of the radicals $R^1$, $R^2$ and $R^3$ corresponds for each compound to one row of Table A Table 231

Compounds of the formula IB.13 in which $Y^1$ is methyl, $Y^{1'}$ is methyl and the combination of the radicals $R^1$, $R^2$ and $R^3$ corresponds for each compound to one row of Table A Table 232

Compounds of the formula IB.13 in which $Y^1$ is hydrogen, $Y^{1'}$ is hydrogen and the combination of the radicals $R^1$, $R^2$ and $R^3$ corresponds for each compound to one row of Table A Table 233

Compounds of the formula IB.13 in which $Y^1$ is hydrogen, $Y^{1'}$ is chlorine and the combination of the radicals $R^1$, $R^2$ and $R^3$ corresponds for each compound to one row of Table A Table 234

Compounds of the formula IB.13 in which $Y^1$ is hydrogen, $Y^{1'}$ is methyl and the combination of the radicals $R^1$, $R^2$ and $R^3$ corresponds for each compound to one row of Table A Table 235

Compounds of the formula IC.1 in which $Y^1$ is chlorine, $Y^{1'}$ is hydrogen and the combination of the radicals $R^1$, $R^2$ and $R^3$ corresponds for each compound to one row of Table A Table 236

Compounds of the formula IC.1 in which $Y^1$ is chlorine, $Y^{1'}$ is chlorine and the combination of the radicals $R^1$, $R^2$ and $R^3$ corresponds for each compound to one row of Table A Table 237

Compounds of the formula IC.1 in which $Y^1$ is chlorine, $Y^{1'}$ is methyl and the combination of the radicals $R^1$, $R^2$ and $R^3$ corresponds for each compound to one row of Table A Table 238

Compounds of the formula IC.1 in which $Y^1$ is methyl, $Y^{1'}$ is hydrogen and the combination of the radicals $R^1$, $R^2$ and $R^3$ corresponds for each compound to one row of Table A Table 239

Compounds of the formula IC.1 in which $Y^1$ is methyl, $Y^{1'}$ is chlorine and the combination of the radicals $R^1$, $R^2$ and $R^3$ corresponds for each compound to one row of Table A Table 240

Compounds of the formula IC.1 in which $Y^1$ is methyl, $Y^{1'}$ is methyl and the combination of the radicals $R^1$, $R^2$ and $R^3$ corresponds for each compound to one row of Table A Table 241

Compounds of the formula IC.1 in which $Y^1$ is hydrogen, $Y^{1'}$ is hydrogen and the combination of the radicals $R^1$, $R^2$ and $R^3$ corresponds for each compound to one row of Table A Table 242

Compounds of the formula IC.1 in which $Y^1$ is hydrogen, $Y^{1'}$ is chlorine and the combination of the radicals Rib $R^2$ and $R^3$ corresponds for each compound to one row of Table A Table 243

Compounds of the formula IC.1 in which $Y^1$ is hydrogen, $Y^{1'}$ is methyl and the combination of the radicals $R^1$, $R^2$ and $R^3$ corresponds for each compound to one row of Table A Table 244

Compounds of the formula IC.2 in which $Y^1$ is chlorine, $Y^{1'}$ is hydrogen and the combination of the radicals $R^1$, $R^2$ and $R^3$ corresponds for each compound to one row of Table A

IC.2

Table 245
Compounds of the formula IC.2 in which $Y^1$ is chlorine, $Y^{1'}$ is chlorine and the combination of the radicals $R^1$, $R^2$ and $R^3$ corresponds for each compound to one row of Table A Table 246
Compounds of the formula IC.2 in which $Y^1$ is chlorine, $Y^{1'}$ is methyl and the combination of the radicals $R^1$, $R^2$ and $R^3$ corresponds for each compound to one row of Table A Table 247
Compounds of the formula IC.2 in which $Y^1$ is methyl, $Y^{1'}$ is hydrogen and the combination of the radicals $R^1$, $R^2$ and $R^3$ corresponds for each compound to one row of Table A Table 248
Compounds of the formula IC.2 in which $Y^1$ is methyl, $Y^{1'}$ is chlorine and the combination of the radicals $R^1$, $R^2$ and $R^3$ corresponds for each compound to one row of Table A Table 249
Compounds of the formula IC.2 in which $Y^1$ is methyl, $Y^{1'}$ is methyl and the combination of the radicals $R^1$, $R^2$ and $R^3$ corresponds for each compound to one row of Table A Table 250
Compounds of the formula IC.2 in which $Y^1$ is hydrogen, $Y^{1'}$ is hydrogen and the combination of the radicals $R^1$, $R^2$ and $R^3$ corresponds for each compound to one row of Table A Table 251
Compounds of the formula IC.2 in which $Y^1$ is hydrogen, $Y^{1'}$ is chlorine and the combination of the radicals $R^1$, $R^2$ and $R^3$ corresponds for each compound to one row of Table A Table 252
Compounds of the formula IC.2 in which $Y^1$ is hydrogen, $Y^{1'}$ is methyl and the combination of the radicals $R^1$, $R^2$ and $R^3$ corresponds for each compound to one row of Table A Table 253
Compounds of the formula IC.3 in which $Y^1$ is chlorine, $Y^{1'}$ is hydrogen and the combination of the radicals $R^2$ and $R^3$ corresponds for each compound to one row of Table B

IC.3

Table 254
Compounds of the formula IC.3 in which $Y^1$ is chlorine, $Y^{1'}$ is chlorine and the combination of the radicals $R^2$ and $R^3$ corresponds for each compound to one row of Table B Table 255
Compounds of the formula IC.3 in which $Y^1$ is chlorine, $Y^{1'}$ is methyl and the combination of the radicals $R^2$ and $R^3$ corresponds for each compound to one row of Table B Table 256
Compounds of the formula IC.3 in which $Y^1$ is methyl, $Y^{1'}$ is hydrogen and the combination of the radicals $R^2$ and $R^3$ corresponds for each compound to one row of Table B Table 257
Compounds of the formula IC.3 in which $Y^1$ is methyl, $Y^{1'}$ is chlorine and the combination of the radicals $R^2$ and $R^3$ corresponds for each compound to one row of Table B Table 258
Compounds of the formula IC.3 in which $Y^1$ is methyl, $Y^{1'}$ is methyl and the combination of the radicals $R^2$ and $R^3$ corresponds for each compound to one row of Table B Table 259
Compounds of the formula IC.3 in which $Y^1$ is hydrogen, $Y^{1'}$ is hydrogen and the combination of the radicals $R^2$ and $R^3$ corresponds for each compound to one row of Table B Table 260
Compounds of the formula IC.3 in which $Y^1$ is hydrogen, $Y^{1'}$ is chlorine and the combination of the radicals $R^2$ and $R^3$ corresponds for each compound to one row of Table B Table 261
Compounds of the formula IC.3 in which $Y^1$ is hydrogen, $Y^{1'}$ is methyl and the combination of the radicals $R^2$ and $R^3$ corresponds for each compound to one row of Table B Table 262
Compounds of the formula IC.4 in which $Y^1$ is chlorine, $Y^{1'}$ is hydrogen and the combination of the radicals $R^1$, $R^2$ and $R^3$ corresponds for each compound to one row of Table A

IC.4

Table 263
Compounds of the formula IC.4 in which $Y^1$ is chlorine, $Y^{1'}$ is chlorine and the combination of the radicals $R^1$, $R^2$ and $R^3$ corresponds for each compound to one row of Table A Table 264
Compounds of the formula IC.4 in which $Y^1$ is chlorine, $Y^{1'}$ is methyl and the combination of the radicals $R^1$, $R^2$ and $R^3$ corresponds for each compound to one row of Table A Table 265
Compounds of the formula IC.4 in which $Y^1$ is methyl, $Y^{1'}$ is hydrogen and the combination of the radicals $R^1$, $R^2$ and $R^3$ corresponds for each compound to one row of Table A Table 266
Compounds of the formula IC.4 in which $Y^1$ is methyl, $Y^{1'}$ is chlorine and the combination of the radicals $R^1$, $R^2$ and $R^3$ corresponds for each compound to one row of Table A Table 267
Compounds of the formula IC.4 in which $Y^1$ is methyl, $Y^{1'}$ is methyl and the combination of the radicals $R^1$, $R^2$ and $R^3$ corresponds for each compound to one row of Table A Table 268
Compounds of the formula IC.4 in which $Y^1$ is hydrogen, $Y^{1'}$ is hydrogen and the combination of the radicals $R^1$, $R^2$ and $R^3$ corresponds for each compound to one row of Table A Table 269
Compounds of the formula IC.4 in which $Y^1$ is hydrogen, $Y^{1'}$ is chlorine and the combination of the radicals $R^1$, $R^2$ and $R^3$ corresponds for each compound to one row of Table A Table 270
Compounds of the formula IC.4 in which $Y^1$ is hydrogen, $Y^{1'}$ is methyl and the combination of the radicals $R^1$, $R^2$ and $R^3$ corresponds for each compound to one row of Table A Table 271
Compounds of the formula IC.5 in which $Y^1$ is chlorine, $Y^{1'}$ is hydrogen and the combination of the radicals $R^2$ and $R^3$ corresponds for each compound to one row of Table B

IC.5

Table 272
Compounds of the formula IC.5 in which $Y^1$ is chlorine, $Y^{1'}$ is chlorine and the combination of the radicals $R^2$ and $R^3$ corresponds for each compound to one row of Table B Table 273
Compounds of the formula IC.5 in which $Y^1$ is chlorine, $Y^{1'}$ is methyl and the combination of the radicals $R^2$ and $R^3$ corresponds for each compound to one row of Table B Table 274
Compounds of the formula IC.5 in which $Y^1$ is methyl, $Y^{1'}$ is hydrogen and the combination of the radicals $R^2$ and $R^3$ corresponds or each compound to one row of Table B Table 275
Compounds of the formula IC.5 in which $Y^1$ is methyl, $Y^{1'}$ is chlorine and the combination of the radicals $R^2$ and $R^3$ corresponds for each compound to one row of Table B Table 276
Compounds of the formula IC.5 in which $Y^1$ is methyl, $Y^{1'}$ is methyl and the combination of the radicals $R^2$ and $R^3$ corresponds for each compound to one row of Table B Table 277
Compounds of the formula IC.5 in which $Y^1$ is hydrogen, $Y^{1'}$ is hydrogen and the combination of the radicals $R^2$ and $R^3$ corresponds for each compound to one row of Table B Table 278
Compounds of the formula IC.5 in which $Y^1$ is hydrogen, $Y^{1'}$ is chlorine and the combination of the radicals $R^2$ and $R^3$ corresponds for each compound to one row of Table B Table 279
Compounds of the formula IC.5 in which $Y^1$ is hydrogen, $Y^{1'}$ is methyl and the combination of the radicals $R^2$ and $R^3$ corresponds for each compound to one row of Table B Table 280
Compounds of the formula IC.6 in which $Y^1$ is chlorine, $Y^{1'}$ is hydrogen and the combination of the radicals $R^1$ and $R^2$ corresponds for each compound to one row of Table C

IC.6

Table 281
Compounds of the formula IC.6 in which $Y^1$ is chlorine, $Y^{1'}$ is chlorine and the combination of the radicals $R^1$ and $R^2$ corresponds for each compound to one row of Table C Table 282
Compounds of the formula IC.6 in which $Y^1$ is chlorine, $Y^{1'}$ is methyl and the combination of the radicals $R^1$ and $R^2$ corresponds for each compound to one row of Table C Table 283
Compounds of the formula IC.6 in which $Y^1$ is methyl, $Y^{1'}$ is hydrogen and the combination of the radicals $R^1$ and $R^2$ corresponds for each compound to one row of Table C Table 284
Compounds of the formula IC.6 in which $Y^1$ is methyl, $Y^{1'}$ is chlorine and the combination of the radicals $R^1$ and $R^2$ corresponds for each compound to one row of Table C Table 285
Compounds of the formula IC.6 in which $Y^1$ is methyl, $Y^{1'}$ is methyl and the combination of the radicals $R^1$ and $R^2$ corresponds for each compouand to one row of Table C Table 286
Compounds of the formula IC.6 in which $Y^1$ is hydrogen, $Y^{1'}$ is hydrogen and the combination of the radicals $R^1$ and $R^2$ corresponds for each compound to one row of Table C Table 287
Compounds of the formula IC.6 in which $Y^1$ is hydrogen, $Y^{1'}$ is chlorine and the combination of the radicals $R^1$ and $R^2$ corresponds for each compound to one row of Table C Table 288
Compounds of the formula IC.6 in which $Y^1$ is hydrogen, $Y^{1'}$ is methyl and the combination of the radicals $R^1$ and $R^2$ corresponds for each compound to one row of Table C Table 289
Compounds of the formula IC.7 in which $Y^1$ is chlorine, $Y^{1'}$ is hydrogen and the combination of the radicals $R^2$ and $R^3$ corresponds for each compound to one row of Table B

IC.7

Table 290
Compounds of the formula IC.7 in which $Y^1$ is chlorine, $Y^{1'}$ is chlorine and the combination of the radicals $R^2$ and $R^3$ corresponds for each compound to one row of Table B Table 291
Compounds of the formula IC.7 in which $Y^1$ is chlorine, $Y^{1'}$ is methyl and the combination of the radicals $R^2$ and $R^3$ corresponds for each compound to one row of Table B Table 292
  Compounds of the formula IC.7 in which $Y^1$ is methyl, $Y^{1'}$ is hydrogen and the combination of the radicals $R^2$ and $R^3$ corresponds for each compound to one row of Table B Table 293
  Compounds of the formula IC.7 in which $Y^1$ is methyl, $Y^{1'}$ is chlorine and the combination of the radicals $R^2$ and $R^3$ corresponds for each compound to one row of Table B Table 294
  Compounds of the formula IC.7 in which $Y^1$ is methyl, $Y^{1'}$ is methyl and the combination of the radicals $R^2$ and $R^3$ corresponds for each compound to one row of Table B Table 295
  Compounds of the formula IC.7 in which $Y^1$ is hydrogen, $Y^{1'}$ is hydrogen and the combination of the radicals $R^2$ and $R^3$ corresponds for each compound to one row of Table B Table 296
  Compounds of the formula IC.7 in which $Y^1$ is hydrogen, $Y^{1'}$ is chlorine and the combination of the radicals $R^2$ and $R^3$ corresponds for each compound to one row of Table B Table 297
  Compounds of the formula IC.7 in which $Y^1$ is hydrogen, $Y^{1'}$ is methyl and the combination of the radicals $R^2$ and $R^3$ corresponds for each compound to one row of Table B Table 298
  Compounds of the formula IC.8 in which $Y^1$ is chlorine, $Y^{1'}$ is hydrogen and the combination of the radicals $R^2$ and $R^3$ corresponds for each compound to one row of Table B

IC.8

Table 299
  Compounds of the formula IC.8 in which $Y^1$ is chlorine, $Y^{1'}$ is chlorine and the combination of the radicals $R^2$ and $R^3$ corresponds for each compound to one row of Table B Table 300
  Compounds of the formula IC.8 in which $Y^1$ is chlorine, $Y^{1'}$ is methyl and the combination of the radicals $R^2$ and $R^3$ corresponds for each compound to one row of Table B Table 301
  Compounds of the formula IC.8 in which $Y^1$ is methyl, $Y^{1'}$ is hydrogen and the combination of the radicals $R^2$ and $R^3$ corresponds for each compound to one row of Table B Table 302
  Compounds of the formula IC.8 in which $Y^1$ is methyl, $Y^{1'}$ is chlorine and the combination of the radicals $R^2$ and $R^3$ corresponds for each compound to one row of Table B Table 303
  Compounds of the formula IC.8 in which $Y^1$ is methyl, $Y^{1'}$ is methyl and the combination of the radicals $R^2$ and $R^3$ corresponds for each compound to one row of Table B Table 304
  Compounds of the formula IC.8 in which $Y^1$ is hydrogen, $Y^{1'}$ is hydrogen and the combination of the radicals $R^2$ and $R^3$ corresponds for each compound to one row of Table B Table 305
  Compounds of the formula IC.8 in which $Y^1$ is hydrogen, $Y^{1'}$ is chlorine and the combination of the radicals $R^2$ and $R^3$ corresponds for each compound to one row of Table B Table 306
  Compounds of the formula IC.8 in which $Y^1$ is hydrogen, $Y^{1'}$ is methyl and the combination of the radicals $R^2$ and $R^3$ corresponds for each compound to one row of Table B Table 307
  Compounds of the formula IC.9 in which $Y^1$ is chlorine, $Y^{1'}$ is hydrogen and the combination of the radicals $R^2$ and $R^3$ corresponds for each compound to one row of Table C

IC.9

Table 308
  Compounds of the formula IC.9 in which $Y^1$ is chlorine, $Y^{1'}$ is chlorine and the combination of the radicals $R^2$ and $R^3$ corresponds for each compound to one row of Table C Table 309
  Compounds of the formula IC.9 in which $Y^1$ is chlorine, $Y^{1'}$ is methyl and the combination of the radicals $R^2$ and $R^3$ corresponds for each compound to one row of Table C Table 310
  Compounds of the formula IC.9 in which $Y^1$ is methyl, $Y^{1'}$ is hydrogen and the combination of the radicals $R^2$ and $R^3$ corresponds for each compound to one row of Table C Table 311
  Compounds of the formula IC.9 in which $Y^1$ is methyl, $Y^{1'}$ is chlorine and the combination of the radicals $R^2$ and $R^3$ corresponds for each compound to one row of Table C Table 312
  Compounds of the formula IC.9 in which $Y^1$ is methyl, $Y^{1'}$ is methyl and the combination of the radicals $R^2$ and $R^3$ corresponds for each compound to one row of Table C Table 313
  Compounds of the formula IC.9 in which $Y^1$ is hydrogen, $Y^{1'}$ is hydrogen and the combination of the radicals $R^2$ and $R^3$ corresponds for each compound to one row of Table C Table 314
  Compounds of the formula IC.9 in which $Y^1$ is hydrogen, $Y^{1'}$ is chlorine and the combination of the radicals $R^2$ and $R^3$ corresponds for each compound to one row of Table C Table 315
  Compounds of the formula IC.9 in which $Y^1$ is hydrogen, $Y^{1'}$ is methyl and the combination of the radicals $R^2$ and $R^3$ corresponds for each compound to one row of Table C Table 316
  Compounds of the formula IC.10 in which $Y^1$ is chlorine, $Y^{1'}$ is hydrogen and the combination of the radicals $R^1$, $R^2$ and $R^3$ corresponds for each compound to one row of Table D

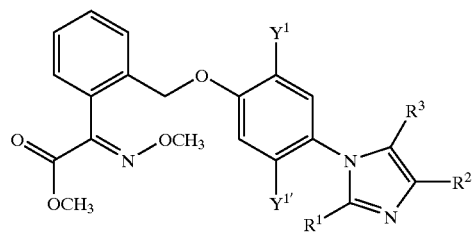

IC.10

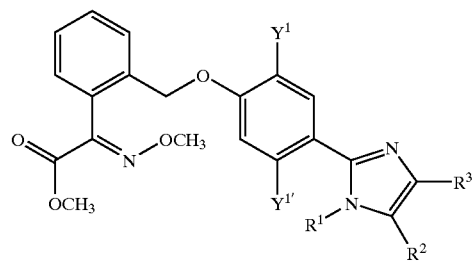

IC.11

Table 317

Compounds of the formula IC.10 in which $Y^1$ is chlorine, $Y^{1'}$ is chlorine and the combination of the radicals $R^1$, $R^2$ and $R^3$ corresponds for each compound to one row of Table D Table 318

Compounds of the formula IC.10 in which $Y^1$ is chlorine, $Y^{1'}$ is methyl and the combination of the radicals $R^1$, $R^2$ and $R^3$ corresponds for each compound to one row of Table D Table 319

Compounds of the formula IC.10 in which $Y^1$ is methyl, $Y^{1'}$ is hydrogen and the combination of the radicals $R^1$, $R^2$ and $R^3$ corresponds for each compound to one row of Table D Table 320

Compounds of the formula IC.10 in which $Y^1$ is methyl, $Y^{1'}$ is chlorine and the combination of the radicals $R^1$, $R^2$ and $R^3$ corresponds for each compound to one row of Table D Table 321

Compounds of the formula IC.10 in which $Y^1$ is methyl, $Y^{1'}$ is methyl and the combination of the radicals $R^1$, $R^2$ and $R^3$ corresponds for each compound to one row of Table D Table 322

Compounds of the formula IC.10 in which $Y^1$ is hydrogen, $Y^{1'}$ is hydrogen and the combination of the radicals $R^1$, $R^2$ and $R^3$ corresponds for each compound to one row of Table D Table 323

Compounds of the formula IC.10 in which $Y^1$ is hydrogen, $Y^{1'}$ is chlorine and the combination of the radicals $R^1$, $R^2$ and $R^3$ corresponds for each compound to one row of Table D Table 324

Compounds of the formula IC.10 in which $Y^1$ is hydrogen, $Y^{1'}$ is methyl and the combination of the radicals $R^1$, $R^2$ and $R^3$ corresponds for each compound to one row of Table D Table 325

Compounds of the formula IC.11 in which $Y^1$ is chlorine, $Y^{1'}$ is hydrogen and the combination of the radicals $R^1$, $R^2$ and $R^3$ corresponds for each compound to one row of Table D Table 326

Compounds of the formula IC.11 in which $Y^1$ is chlorine, $Y^{1'}$ is chlorine and the combination of the radicals $R^1$, $R^2$ and $R^3$ corresponds for each compound to one row of Table D Table 327

Compounds of the formula IC.11 in which $Y^1$ is chlorine, $Y^{1'}$ is methyl and the combination of the radicals $R^1$, $R^2$ and $R^3$ corresponds for each compound to one row of Table D Table 328

Compounds of the formula IC.11 in which $Y^1$ is methyl, $Y^{1'}$ is hydrogen and the combination of the radicals $R^1$, $R^2$ and $R^3$ corresponds for each compound to one row of Table D Table 329

Compounds of the formula IC.11 in which $Y^1$ is methyl, $Y^{1'}$ is chlorine and the combination of the radicals $R^1$, $R^2$ and $R^3$ corresponds for each compound to one row of Table D Table 330

Compounds of the formula IC.11 in which $Y^1$ is methyl, $Y^{1'}$ is methyl and the combination of the radicals $R^1$, $R^2$ and $R^3$ corresponds for each compound to one row of Table D Table 331

Compounds of the formula IC.11 in which $Y^1$ is hydrogen, $Y^{1'}$ is hydrogen and the combination of the radicals $R^1$, $R^2$ and $R^3$ corresponds for each compound to one row of Table D Table 332

Compounds of the formula IC.11 in which $Y^1$ is hydrogen, $Y^{1'}$ is chlorine and the combination of the radicals $R^1$, $R^2$ and $R^3$ corresponds for each compound to one row of Table D Table 333

Compounds of the formula IC.11 in which $Y^1$ is hydrogen, $Y^{1'}$ is methyl and the combination of the radicals $R^1$, $R^2$ and $R^3$ corresponds for each compound to one row of Table D Table 334

Compounds of the formula IC.12 in which $Y^1$ is chlorine, $Y^{1'}$ is hydrogen and the combination of the radicals $R^1$, $R^2$ and $R^3$ corresponds for each compound to one row of Table A

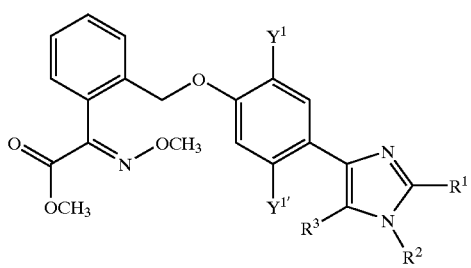

IC.12

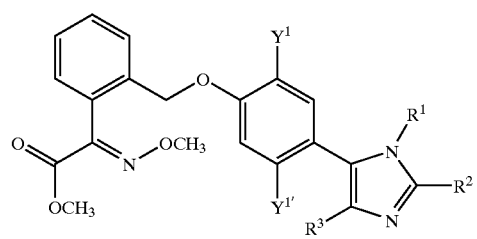

IC.13

Table 335

Compounds of the formula IC.12 in which $Y^1$ is chlorine, $Y^{1'}$ is chlorine and the combination of the radicals $R^1$, $R^2$ and $R^3$ corresponds for each compound to one row of Table A Table 336

Compounds of the formula IC.12 in which $Y^1$ is chlorine, $Y^{1'}$ is methyl and the combination of the radicals $R^1$, $R^2$ and $R^3$ corresponds for each compound to one row of Table A Table 337

Compounds of the formula IC.12 in which $Y^1$ is methyl, $Y^{1'}$ is hydrogen and the combination of the radicals $R^1$, $R^2$ and $R^3$ corresponds for each compound to one row of Table A Table 338

Compounds of the formula IC.12 in which $Y^1$ is methyl, $Y^{1'}$ is chlorine and the combination of the radicals $R^1$, $R^2$ and $R^3$ corresponds for each compound to one row of Table A Table 339

Compounds of the formula IC.12 in which $Y^1$ is methyl, $Y^{1'}$ is methyl and the combination of the radicals $R^1$, $R^2$ and $R^3$ corresponds for each compound to one row of Table A Table 340

Compounds of the formula IC.12 in which $Y^1$ is hydrogen, $Y^{1'}$ is hydrogen and the combination of the radicals $R^1$, $R^2$ and $R^3$ corresponds for each compound to one row of Table A Table 341

Compounds of the formula IC.12 in which $Y^1$ is hydrogen, $Y^{1'}$ is chlorine and the combination of the radicals $R^1$, $R^2$ and $R^3$ corresponds for each compound to one row of Table A Table 342

Compounds of the formula IC.12 in which $Y^1$ is hydrogen, $Y^{1'}$ is methyl and the combination of the radicals $R^1$, $R^2$ and $R^3$ corresponds for each compound to one row of Table A Table 343

Compounds of the formula IC.13 in which $Y^1$ is chlorine, $Y^{1'}$ is hydrogen and the combination of the radicals $R^1$, $R^2$ and $R^3$ corresponds for each compound to one row of Table A Table 344

Compounds of the formula IC.13 in which $Y^1$ is chlorine, $Y^{1'}$ is chlorine and the combination of the radicals $R^1$, $R^2$ and $R^3$ corresponds for each compound to one row of Table A Table 345

Compounds of the formula IC.13 in which $Y^1$ is chlorine, $Y^{1'}$ is methyl and the combination of the radicals $R^1$, $R^2$ and $R^3$ corresponds for each compound to one row of Table A Table 346

Compounds of the formula IC.13 in which $Y^1$ is methyl, $Y^{1'}$ is hydrogen and the combination of the radicals $R^1$, $R^2$ and $R^3$ corresponds for each compound to one row of Table A Table 347

Compounds of the formula IC.13 in which $Y^1$ is methyl, $Y^{1'}$ is chlorine and the combination of the radicals $R^1$, $R^2$ and $R^3$ corresponds for each compound to one row of Table A Table 348

Compounds of the formula IC.13 in which $Y^1$ is methyl, $Y^{1'}$ is methyl and the combination of the radicals $R^1$, $R^2$ and $R^3$ corresponds for each compound to one row of Table A Table 349

Compounds of the formula IC.13 in which $Y^1$ is hydrogen, $Y^{1'}$ is hydrogen and the combination of the radicals $R^1$, $R^2$ and $R^3$ corresponds for each compound to one row of Table A Table 350

Compounds of the formula IC.13 in which $Y^1$ is hydrogen, $Y^{1'}$ is chlorine and the combination of the radicals $R^1$, $R^2$ and $R^3$ corresponds for each compound to one row of Table A Table 351

Compounds of the formula IC.13 in which $Y^1$ is hydrogen, $Y^{1'}$ is methyl and the combination of the radicals $R^1$, $R^2$ and $R^3$ corresponds for each compound to one row of Table A Table 352

Compounds of the formula ID.1 in which $Y^1$ is chlorine, $Y^{1'}$ is hydrogen and the combination of the radicals $R^1$, $R^2$ and $R^3$ corresponds for each compound to one row of Table A

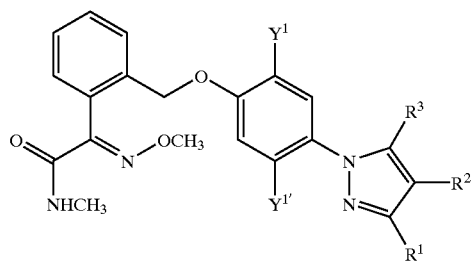

ID.1

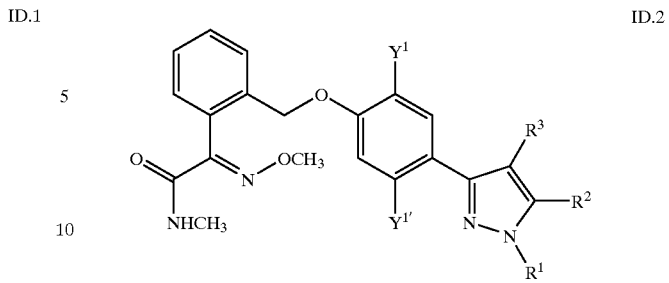

ID.2

Table 353

Compounds of the formula ID.1 in which $Y^1$ is chlorine, $Y^{1'}$ is chlorine and the combination of the radicals $R^1$, $R^2$ and $R^3$ corresponds for each compound to one row of Table A Table 354

Compounds of the formula ID.1 in which $Y^1$ is chlorine, $Y^{1'}$ is methyl and the combination of the radicals $R^1$, $R^2$ and $R^3$ corresponds for each compound to one row of Table A Table 355

Compounds of the formula ID.1 in which $Y^1$ is methyl, $Y^{1'}$ is hydrogen and the combination of the radicals $R^1$, $R^2$ and $R^3$ corresponds for each compound to one row of Table A Table 356

Compounds of the formula ID.1 in which $Y^1$ is methyl, $Y^{1'}$ is chlorine and the combination of the radicals $R^1$, $R^2$ and $R^3$ corresponds for each compound to one row of Table A Table 357

Compounds of the formula ID.1 in which $Y^1$ is methyl, $Y^{1'}$ is methyl and the combination of the radicals $R^1$, $R^2$ and $R^3$ corresponds for each compound to one row of Table A Table 358

Compounds of the formula ID.1 in which $Y^1$ is hydrogen, $Y^{1'}$ is hydrogen and the combination of the radicals $R^1$, $R^2$ and $R^3$ corresponds for each compound to one row of Table A Table 359

Compounds of the formula ID.1 in which $Y^1$ is hydrogen, $Y^{1'}$ is chlorine and the combination of the radicals $R^1$, $R^2$ and $R^3$ corresponds for each compound to one row of Table A Table 360

Compounds of the formula ID.1 in which $Y^1$ is hydrogen, $Y^{1'}$ is methyl and the combination of the radicals $R^1$, $R^2$ and $R^3$ corresponds for each compound to one row of Table A Table 361

Compounds of the formula ID.2 in which $Y^1$ is chlorine, $Y^{1'}$ is hydrogen and the combination of the radicals $R^1$, $R^2$ and $R^3$ corresponds for each compound to one row of Table A Table 362

Compounds of the formula ID.2 in which $Y^1$ is chlorine, $Y^{1'}$ is chlorine and the combination of the radicals $R^1$, $R^2$ and $R^3$ corresponds for each compound to one row of Table A Table 363

Compounds of the formula ID.2 in which $Y^1$ is chlorine, $Y^{1'}$ is methyl and the combination of the radicals $R^1$, $R^2$ and $R^3$ corresponds for each compound to one row of Table A Table 364

Compounds of the formula ID.2 in which $Y^1$ is methyl, $Y^{1'}$ is hydrogen and the combination of the radicals $R^1$, $R^2$ and $R^3$ corresponds for each compound to one row of Table A Table 365

Compounds of the formula ID.2 in which $Y^1$ is methyl, $Y^{1'}$ is chlorine and the combination of the radicals $R^1$, $R^2$ and $R^3$ corresponds for each compound to one row of Table A Table 366

Compounds of the formula ID.2 in which $Y^1$ is methyl, $Y^{1'}$ is methyl and the combination of the radicals $R^1$, $R^2$ and $R^3$ corresponds for each compound to one row of Table A Table 367

Compounds of the formula ID.2 in which $Y^1$ is hydrogen, $Y^{1'}$ is hydrogen and the combination of the radicals $R^1$, $R^2$ and $R^3$ corresponds for each compound to one row of Table A Table 368

Compounds of the formula ID.2 in which $Y^1$ is hydrogen, $Y^{1'}$ is chlorine and the combination of the radicals $R^1$, $R^2$ and $R^3$ corresponds for each compound to one row of Table A Table 369

Compounds of the formula ID.2 in which $Y^1$ is hydrogen, $Y^{1'}$ is methyl and the combination of the radicals $R^1$, $R^2$ and $R^3$ corresponds for each compound to one row of Table A Table 370

Compounds of the formula ID.3 in which $Y^1$ is chlorine, $Y^{1'}$ is hydrogen and the combination of the radicals $R^2$ and $R^3$ corresponds for each compound to one row of Table B

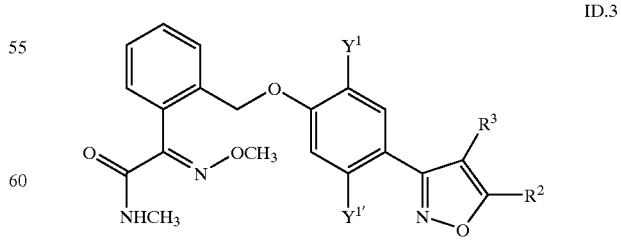

ID.3

Table 371

Compounds of the formula ID.3 in which $Y^1$ is chlorine, $Y^{1'}$ is chlorine and the combination of the radicals $R^2$ and $R^3$ corresponds for each compound to one row of Table B Table 372
Compounds of the formula ID.3 in which $Y^1$ is chlorine, $Y^{1'}$ is methyl and the combination of the radicals $R^2$ and $R^3$ corresponds for each compound to one row of Table B Table 373
Compounds of the formula ID.3 in which $Y^1$ is methyl, $Y^{1'}$ is hydrogen and the combination of the radicals $R^2$ and $R^3$ corresponds for each compound to one row of Table B Table 374
Compounds of the formula ID.3 in which $Y^1$ is methyl, $Y^{1'}$ is chlorine and the combination of the radicals $R^2$ and $R^3$ corresponds for each compound to one row of Table B Table 375
Compounds of the formula ID.3 in which $Y^1$ is methyl, $Y^{1'}$ is methyl and the combination of the radicals $R^2$ and $R^3$ corresponds for each compound to one row of Table B Table 376
Compounds of the formula ID.3 in which $Y^1$ is hydrogen, $Y^{1'}$ is hydrogen and the combination of the radicals $R^2$ and $R^3$ corresponds for each compound to one row of Table B Table 377
Compounds of the formula ID.3 in which $Y^1$ is hydrogen, $Y^{1'}$ is chlorine and the combination of the radicals $R^2$ and $R^3$ corresponds for each compound to one row of Table B Table 378
Compounds of the formula ID.3 in which $Y^1$ is hydrogen, $Y^{1'}$ is methyl and the combination of the radicals $R^2$ and $R^3$ corresponds for each compound to one row of Table B Table 379
Compounds of the formula ID.4 in which $Y^1$ is chlorine, $Y^{1'}$ is hydrogen and the combination of the radicals $R^1$, $R^2$ and $R^3$ corresponds for each compound to one row of Table A

ID.4

Table 380
Compounds of the formula ID.4 in which $Y^1$ is chlorine, $Y^{1'}$ is chlorine and the combination of the radicals $R^1$, $R^2$ and $R^3$ corresponds for each compound to one row of Table A Table 381
Compounds of the formula ID.4 in which $Y^1$ is chlorine, $Y^{1'}$ is methyl and the combination of the radicals $R^1$, $R^2$ and $R^3$ corresponds for each compound to one row of Table A Table 382
Compounds of the formula ID.4 in which $Y^1$ is methyl, $Y^{1'}$ is hydrogen and the combination of the radicals $R^1$, $R^2$ and $R^3$ corresponds for each compound to one row of Table A Table 383
Compounds of the formula ID.4 in which $Y^1$ is methyl, $Y^{1'}$ is chlorine and the combination of the radicals $R^1$, $R^2$ and $R^3$ corresponds for each compound to one row of Table A Table 384
Compounds of the formula ID.4 in which $Y^1$ is methyl, $Y^{1'}$ is methyl and the combination of the radicals $R^1$, $R^2$ and $R^3$ corresponds for each compound to one row of Table A Table 385
Compounds of the formula ID.4 in which $Y^1$ is hydrogen, $Y^{1'}$ is hydrogen and the combination of the radicals $R^1$, $R^2$ and $R^3$ corresponds for each compound to one row of Table A Table 386
Compounds of the formula ID.4 in which $Y^1$ is hydrogen, $Y^{1'}$ is chlorine and the combination of the radicals $R^1$, $R^2$ and $R^3$ corresponds for each compound to one row of Table A Table 387
Compounds of the formula ID.4 in which $Y^1$ is hydrogen, $Y^{1'}$ is methyl and the combination of the radicals $R^1$, $R^2$ and $R^3$ corresponds for each compound to one row of Table A Table 388
Compounds of the formula ID.5 in which $Y^1$ is chlorine, $Y^{1'}$ is hydrogen and the combination of the radicals $R^2$ and $R^3$ corresponds for each compound to one row of Table B

ID.5

Table 389
Compounds of the formula ID.5 in which $Y^1$ is chlorine, $Y^{1'}$ is chlorine and the combination of the radicals $R^2$ and $R^3$ corresponds for each compound to one row of Table B Table 390
Compounds of the formula ID.5 in which $Y^1$ is chlorine, $Y^{1'}$ is methyl and the combination of the radicals $R^2$ and $R^3$ corresponds for each compound to one row of Table B Table 391
Compounds of the formula ID.5 in which $Y^1$ is methyl, $Y^{1'}$ is hydrogen and the combination of the radicals $R^2$ and $R^3$ corresponds for each compound to one row of Table B Table 392
Compounds of the formula ID.5 in which $Y^1$ is methyl, $Y^{1'}$ is chlorine and the combination of the radicals $R^2$ and $R^3$ corresponds for each compound to one row of Table B Table 393
Compounds of the formula ID.5 in which $Y^1$ is methyl, $Y^{1'}$ is methyl and the combination of the radicals $R^2$ and $R^3$ corresponds for each compound to one row of Table B Table 394
Compounds of the formula ID.5 in which $Y^1$ is hydrogen, $Y^{1'}$ is hydrogen and the combination of the radicals $R^2$ and $R^3$ corresponds for each compound to one row of Table B Table 395
Compounds of the formula ID.5 in which $Y^1$ is hydrogen, $Y^{1'}$ is chlorine and the combination of the radicals $R^2$ and $R^3$ corresponds for each compound to one row of Table B Table 396
Compounds of the formula ID.5 in which $Y^1$ is hydrogen, $Y^{1'}$ is methyl and the combination of the radicals $R^2$ and $R^3$ corresponds for each compound to one row of Table B Table 397
Compounds of the formula ID.6 in which $Y^1$ is chlorine, $Y^{1'}$ is hydrogen and the combination of the radicals $R^1$ and $R^2$ corresponds for each compound to one row of Table C

ID.6

[Structure of formula ID.6]

Table 398
Compounds of the formula ID.6 in which $Y^1$ is chlorine, $Y^{1'}$ is chlorine and the combination of the radicals $R^1$ and $R^2$ corresponds for each compound to one row of Table C Table 399
Compounds of the formula ID.6 in which $Y^1$ is chlorine, $Y^{1'}$ is methyl and the combination of the radicals $R^1$ and $R^2$ corresponds for each compound to one row of Table C Table 400
Compounds of the formula ID.6 in which $Y^1$ is methyl, $Y^{1'}$ is hydrogen and the combination of the radicals $R^1$ and $R^2$ corresponds for each compound to one row of Table C Table 401
Compounds of the formula ID.6 in which $Y^1$ is methyl, $Y^{1'}$ is chlorine and the combination of the radicals $R^1$ and $R^2$ corresponds for each compound to one row of Table C Table 402
Compounds of the formula ID.6 in which $Y^1$ is methyl, $Y^{1'}$ is methyl and the combination of the radicals $R^1$ and $R^2$ corresponds for each compound to one row of Table C Table 403
Compounds of the formula ID.6 in which $Y^1$ is hydrogen, $Y^{1'}$ is hydrogen and the combination of the radicals $R^1$ and $R^2$ corresponds for each compound to one row of Table C Table 404
Compounds of the formula ID.6 in which $Y^1$ is hydrogen, $Y^{1'}$ is chlorine and the combination of the radicals $R^1$ and $R^2$ corresponds or each compound to one row of Table C Table 405
Compounds of the formula ID.6 in which $Y^1$ is hydrogen, $Y^{1'}$ is methyl and the combination of the radicals $R^1$ and $R^2$ corresponds for each compound to one row of Table C Table 406
Compounds of the formula ID.7 in which $Y^1$ is chlorine, $Y^{1'}$ is hydrogen and the combination of the radicals $R^2$ and $R^3$ corresponds for each compound to one row of Table B

ID.7

[Structure of formula ID.7]

Table 407
Compounds of the formula ID.7 in which $Y^1$ is chlorine, $Y^{1'}$ is chlorine and the combination of the radicals $R^2$ and $R^3$ corresponds for each compound to one row of Table B Table 408
Compounds of the formula ID.7 in which $Y^1$ is chlorine, $Y^{1'}$ is methyl and the combination of the radicals $R^2$ and $R^3$ corresponds for each compound to one row of Table B Table 409
Compounds of the formula ID.7 in which $Y^1$ is methyl, $Y^{1'}$ is hydrogen and the combination of the radicals $R^2$ and $R^3$ corresponds for each compound to one row of Table B Table 410
Compounds of the formula ID.7 in which $Y^1$ is methyl, $Y^{1'}$ is chlorine and the combination of the radicals $R^2$ and $R^3$ corresponds for each compound to one row of Table B Table 411
Compounds of the formula ID.7 in which $Y^1$ is methyl, $Y^{1'}$ is methyl and the combination of the radicals $R^2$ and $R^3$ corresponds for each compound to one row of Table B Table 412
Compounds of the formula ID.7 in which $Y^1$ is hydrogen, $Y^{1'}$ is hydrogen and the combination of the radicals $R^2$ and $R^3$ corresponds for each compound to one row of Table B Table 413
Compounds of the formula ID.7 in which $Y^1$ is hydrogen, $Y^{1'}$ is chlorine and the combination of the radicals $R^2$ and $R^3$ corresponds for each compound to one row of Table B Table 414
Compounds of the formula ID.7 in which $Y^1$ is hydrogen, $Y^{1'}$ is methyl and the combination of the radicals $R^2$ and $R^3$ corresponds for each compound to one row of Table B Table 415
Compounds of the formula ID.8 in which $Y^1$ is chlorine, $Y^{1'}$ is hydrogen and the combination of the radicals $R^2$ and $R^3$ corresponds for each compound to one row of Table B

ID.8

[Structure of formula ID.8]

Table 416
Compounds of the formula ID.8 in which $Y^1$ is chlorine, $Y^{1'}$ is chlorine and the combination of the radicals $R^2$ and $R^3$ corresponds for each compound to one row of Table B Table 417
Compounds of the formula ID.8 in which $Y^1$ is chlorine, $Y^{1'}$ is methyl and the combination of the radicals $R^2$ and $R^3$ corresponds for each compound to one row of Table B Table 418
Compounds of the formula ID.8 in which $Y^1$ is methyl, $Y^{1'}$ is hydrogen and the combination of the radicals $R^2$ and $R^3$ corresponds for each compound to one row of Table B Table 419
Compounds of the formula ID.8 in which $Y^1$ is methyl, $Y^{1'}$ is chlorine and the combination of the radicals $R^2$ and $R^3$ corresponds for each compound to one row of Table B Table 420
Compounds of the formula ID.8 in which $Y^1$ is methyl, $Y^{1'}$ is methyl and the combination of the radicals $R^2$ and $R^3$ corresponds for each compound to the one row of Table B Table 421
Compounds of the formula ID.8 in which $Y^1$ is hydrogen, $Y^{1'}$ is hydrogen and the combination of the radicals $R^2$ and $R^3$ corresponds for each compound to one row of Table B Table 422
Compounds of the formula ID.8 in which $Y^1$ is hydrogen, $Y^{1'}$ is chlorine and the combination of the radicals $R^2$ and $R^3$ corresponds for each compound to one row of Table B Table 423

Compounds of the formula ID.8 in which $Y^1$ is hydrogen, $Y^{1'}$ is methyl and the combination of the radicals $R^2$ and $R^3$ corresponds for each compound to one row of Table B Table 424

Compounds of the formula ID.9 in which $Y^1$ is chlorine, $Y^{1'}$ is hydrogen and the combination of the radicals $R^2$ and $R^3$ corresponds for each compound to one row of Table C

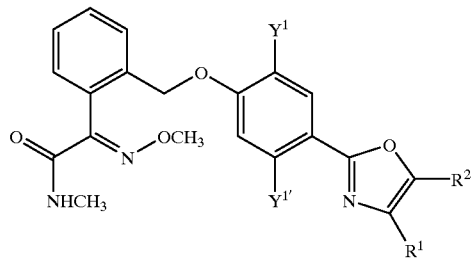

ID.9

Table 425

Compounds of the formula ID.9 in which $Y^1$ is chlorine, $Y^{1'}$ is chlorine and the combination of the radicals $R^2$ and $R^3$ corresponds for each compound to one row of Table C Table 426

Compounds of the formula ID.9 in which $Y^1$ is chlorine, $Y^{1'}$ is methyl and the combination of the radicals $R^2$ and $R^3$ corresponds for each compound to one row of Table C Table 427

Compounds of the formula ID.9 in which $Y^1$ is methyl, $Y^{1'}$ is hydrogen and the combination of the radicals $R^2$ and $R^3$ corresponds for each compound to one row of Table C Table 428

Compounds of the formula ID.9 in which $Y^1$ is methyl, $Y^{1'}$ is chlorine and the combination of the radicals $R^2$ and $R^3$ corresponds for each compound to one row of Table C Table 429

Compounds of the formula ID.9 in which $Y^1$ is methyl, $Y^{1'}$ is methyl and the combination of the radicals $R^2$ and $R^3$ corresponds for each compound to one row of Table C Table 430

Compounds of the formula ID.9 in which $Y^1$ is hydrogen, $Y^{1'}$ is hydrogen and the combination of the radicals $R^2$ and $R^3$ corresponds for each compound to one row of Table C Table 431

Compounds of the formula ID.9 in which $Y^1$ is hydrogen, $Y^{1'}$ is chlorine and the combination of the radicals $R^2$ and $R^3$ corresponds for each compound to one row of Table C Table 432

Compounds of the formula ID.9 in which $Y^1$ is hydrogen, $Y^{1'}$ is methyl and the combination of the radicals $R^2$ and $R^3$ corresponds for each compound to one row of Table C Table 433

Compounds of the formula ID.10 in which $Y^1$ is chlorine, $Y^{1'}$ is hydrogen and the combination of the radicals $R^1$, $R^2$ and $R^3$ corresponds for each compound to one row of Table D

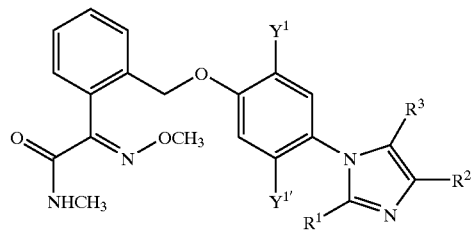

ID.10

Table 434

Compounds of the formula ID.10 in which $Y^1$ is chlorine, $Y^{1'}$ is chlorine and the combination of the radicals $R^1$, $R^2$ and $R^3$ corresponds for each compound to one row of Table D Table 435

Compounds of the formula ID.10 in which $Y^1$ is chlorine, $Y^{1'}$ is methyl and the combination of the radicals $R^1$, $R^2$ and $R^3$ corresponds for each compound to one row of Table D Table 436

Compounds of the formula ID.10 in which $Y^1$ is methyl, $Y^{1'}$ is hydrogen and the combination of the radicals $R^1$, $R^2$ and $R^3$ corresponds for each compound to one row of Table D Table 437

Compounds of the formula ID.10 in which $Y^1$ is methyl, $Y^{1'}$ is chlorine and the combination of the radicals $R^1$, $R^2$ and $R^3$ corresponds for each compound to one row of Table D Table 438

Compounds of the formula ID.10 in which $Y^1$ is methyl, $Y^{1'}$ is methyl and the combination of the radicals $R^1$, $R^2$ and $R^3$ corresponds for each compound to one row of Table D Table 439

Compounds of the formula ID.10 in which $Y^1$ is hydrogen, $Y^{1'}$ is hydrogen and the combination of the radicals $R^1$, $R^2$ and $R^3$ corresponds for each compound to one row of Table D Table 440

Compounds of the formula ID.10 in which $Y^1$ is hydrogen, $Y^{1'}$ is chlorine and the combination of the radicals $R^1$, $R^2$ and $R^3$ corresponds for each compound to one row of Table D Table 441

Compounds of the formula ID.10 in which $Y^1$ is hydrogen, $Y^{1'}$ is methyl and the combination of the radicals $R^1$, $R^2$ and $R^3$ corresponds for each compound to one row of Table D Table 442

Compounds of the formula ID.11 in which $Y^1$ is chlorine, $Y^{1'}$ is hydrogen and the combination of the radicals $R^1$, $R^2$ and $R^3$ corresponds for each compound to one row of Table D

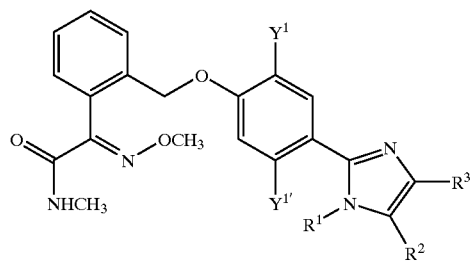

ID.11

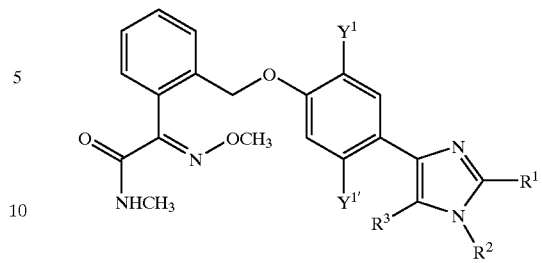

ID.12

Table 443

Compounds of the formula ID.11 in which $Y^1$ is chlorine, $Y^{1'}$ is chlorine and the combination of the radicals $R^1$, $R^2$ and $R^3$ corresponds for each compound to one row of Table D Table 444

Compounds of the formula ID.11 in which $Y^1$ is chlorine, $Y^{1'}$ is methyl and the combination of the radicals $R^1$, $R^2$ and $R^3$ corresponds for each compound to one row of Table D Table 445

Compounds of the formula ID.11 in which $Y^1$ is methyl, $Y^{1'}$ is hydrogen and the combination of the radicals $R^1$, $R^2$ and $R^3$ corresponds for each compound to one row of Table D Table 446

Compounds of the formula ID.11 in which $Y^1$ is methyl, $Y^{1'}$ is chlorine and the combination of the radicals $R^1$, $R^2$ and $R^3$ corresponds for each compound to one row of Table D Table 447

Compounds of the formula ID.11 in which $Y^1$ is methyl, $Y^{1'}$ is methyl and the combination of the radicals $R^1$, $R^2$ and $R^3$ corresponds for each compound to one row of Table D Table 448

Compounds of the formula ID.11 in which $Y^1$ is hydrogen, $Y^{1'}$ is hydrogen and the combination of the radicals $R^1$, $R^2$ and $R^3$ corresponds for each compound to one row of Table D Table 449

Compounds of the formula ID.11 in which $Y^1$ is hydrogen, $Y^{1'}$ is chlorine and the combination of the radicals $R^1$, $R^2$ and $R^3$ corresponds for each compound to one row of Table D Table 450

Compounds of the formula ID.11 in which $Y^1$ is hydrogen, $Y^{1'}$ is methyl and the combination of the radicals $R^1$, $R^2$ and $R^3$ corresponds for each compound to one row of Table D Table 451

Compounds of the formula ID.12 in which $Y^1$ is chlorine, $Y^{1'}$ is hydrogen and the combination of the radicals $R^1$, $R^2$ and $R^3$ corresponds for each compound to one row of Table A Table 452

Compounds of the formula ID.12 in which $Y^1$ is chlorine, $Y^{1'}$ is chlorine and the combination of the radicals $R^1$, $R^2$ and $R^3$ corresponds for each compound to one row of Table A Table 453

Compounds of the formula ID.12 in which $Y^1$ is chlorine, $Y^{1'}$ is methyl and the combination of the radicals $R^1$, $R^2$ and $R^3$ corresponds for each compound to one row of Table A Table 454

Compounds of the formula ID.12 in which $Y^1$ is methyl, $Y^{1'}$ is hydrogen and the combination of the radicals $R^1$, $R^2$ and $R^3$ corresponds for each compound to one row of Table A Table 455

Compounds of the formula ID.12 in which $Y^1$ is methyl, $Y^{1'}$ is chlorine and the combination of the radicals $R^1$, $R^2$ and $R^3$ corresponds for each compound to one row of Table A Table 456

Compounds of the formula ID.12 in which $Y^1$ is methyl, $Y^{1'}$ is methyl and the combination of the radicals $R^1$, $R^2$ and $R^3$ corresponds for each compound to one row of Table A Table 457

Compounds of the formula ID.12 in which $Y^1$ is hydrogen, $Y^{1'}$ is hydrogen and the combination of the radicals $R^1$, $R^2$ and $R^3$ corresponds for each compound to one row of Table A Table 458

Compounds of the formula ID.12 in which $Y^1$ is hydrogen, $Y^{1'}$ is chlorine and the combination of the radicals $R^1$, $R^2$ and $R^3$ corresponds for each compound to one row of Table A Table 459

Compounds of the formula ID.12 in which $Y^1$ is hydrogen, $Y^{1'}$ is methyl and the combination of the radicals $R^1$, $R^2$ and $R^3$ corresponds for each compound to one row of Table A Table 460

Compounds of the formula ID.13 in which $Y^1$ is chlorine, $Y^{1'}$ is hydrogen and the combination of the radicals $R^1$, $R^2$ and $R^3$ corresponds for each compound to one row of Table A

ID.13

Table 461

Compounds of the formula ID.13 in which $Y^1$ is chlorine, $Y^{1'}$ is chlorine and the combination of the radicals $R^1$, $R^2$ and $R^3$ corresponds for each compound to one row of Table A Table 462

Compounds of the formula ID.13 in which $Y^1$ is chlorine, $Y^{1'}$ is methyl and the combination of the radicals $R^1$, $R^2$ and $R^3$ corresponds for each compound to one row of Table A Table 463

Compounds of the formula ID.13 in which $Y^1$ is methyl, $Y^{1'}$ is hydrogen and the combination of the radicals $R^1$, $R^2$ and $R^3$ corresponds for each compound to one row of Table A Table 464

Compounds of the formula ID.13 in which $Y^1$ is methyl, $Y^{1'}$ is chlorine and the combination of the radicals $R^1$, $R^2$ and $R^3$ corresponds for each compound to one row of Table A Table 465

Compounds of the formula ID.13 in which $Y^1$ is methyl, $Y^{1'}$ is methyl and the combination of the radicals $R^1$, $R^2$ and $R^3$ corresponds for each compound to one row of Table A Table 466

Compounds of the formula ID.13 in which $Y^1$ is hydrogen, $Y^{1'}$ is hydrogen and the combination of the radicals $R^1$, $R^2$ and $R^3$ corresponds for each compound to one row of Table A Table 467

Compounds of the formula ID.13 in which $Y^1$ is hydrogen, $Y^{1'}$ is chlorine and the combination of the radicals $R^1$, $R^2$ and $R^3$ corresponds for each compound to one row of Table A Table 468

Compounds of the formula ID.13 in which $Y^1$ is hydrogen, $Y^{1'}$ is methyl and the combination of the radicals $R^1$, $R^2$ and $R^3$ corresponds for each compound to one row of Table A Table 469

Compounds of the formula IE.1 in which $Y^1$ is chlorine, $Y^{1'}$ is hydrogen and the combination of the radicals $R^1$, $R^2$ and $R^3$ corresponds for each compound to one row of Table A

IE.1

Table 470

Compounds of the formula IE.1 in which $Y^1$ is chlorine, $Y^{1'}$ is chlorine and the combination of the radicals $R^1$, $R^2$ and $R^3$ corresponds for each compound to one row of Table A Table 471

Compounds of the formula IE.1 in which $Y^1$ is chlorine, $Y^{1'}$ is methyl and the combination of the radicals $R^1$, $R^2$ and $R^3$ corresponds for each compound to one row of Table A Table 472

Compounds of the formula IE.1 in which $Y^1$ is methyl, $Y^{1'}$ is hydrogen and the combination of the radicals $R^1$, $R^2$ and $R^3$ corresponds for each compound to one row of Table A Table 473

Compounds of the formula IE.1 in which $Y^1$ is methyl, $Y^{1'}$ is chlorine and the combination of the radicals $R^1$, $R^2$ and $R^3$ corresponds for each compound to one row of Table A Table 474

Compounds of the formula IE.1 in which $Y^1$ is methyl, $Y^{1'}$ is methyl and the combination of the radicals $R^1$, $R^2$ and $R^3$ corresponds for each compound to one row of Table A Table 475

Compounds of the formula IE.1 in which $Y^1$ is hydrogen, $Y^{1'}$ is hydrogen and the combination of the radicals $R^1$, $R^2$ and $R^3$ corresponds for each compound to one row of Table A Table 476

Compounds of the formula IE.1 in which $Y^1$ is hydrogen, $Y^{1'}$ is chlorine and the combination of the radicals $R^1$, $R^2$ and $R^3$ corresponds for each compound to one row of Table A Table 477

Compounds of the formula IE.1 in which $Y^1$ is hydrogen, $Y^{1'}$ is methyl and the combination of the radicals $R^1$, $R^2$ and $R^3$ corresponds for each compound to one row of Table A Table 478

Compounds of the formula IE.2 in which $Y^1$ is chlorine, $Y^{1'}$ is hydrogen and the combination of the radicals $R^1$, $R^2$ and $R^3$ corresponds for each compound to one row of Table A

IE.2

Table 479

Compounds of the formula IE.2 in which $Y^1$ is chlorine, $Y^{1'}$ is chlorine and the combination of the radicals $R^1$, $R^2$ and $R^3$ corresponds for each compound to one row of Table A Table 480
Compounds of the formula IE.2 in which $Y^1$ is chlorine, $Y^{1'}$ is methyl and the combination of the radicals $R^1$, $R^2$ and $R^3$ corresponds for each compound to one row of Table A Table 481
Compounds of the formula IE.2 in which $Y^1$ is methyl, $Y^{1'}$ is hydrogen and the combination of the radicals $R^1$, $R^2$ and $R^3$ corresponds for each compound to one row of Table A Table 482
Compounds of the formula IE.2 in which $Y^1$ is methyl, $Y^{1'}$ is chlorine and the combination of the radicals $R^1$, $R^2$ and $R^3$ corresponds for each compound to one row of Table A Table 483
Compounds of the formula IE.2 in which $Y^1$ is methyl, $Y^{1'}$ is methyl and the combination of the radicals $R^1$, $R^2$ and $R^3$ corresponds for each compound to one row of Table A Table 484
Compounds of the formula IE.2 in which $Y^1$ is hydrogen, $Y^{1'}$ is hydrogen and the combination of the radicals $R^1$, $R^2$ and $R^3$ corresponds for each compound to one row of Table A Table 485
Compounds of the formula IE.2 in which $Y^1$ is hydrogen, $Y^{1'}$ is chlorine and the combination of the radicals $R^1$, $R^2$ and $R^3$ corresponds for each compound to one row of Table A Table 486
Compounds of the formula IE.2 in which $Y^1$ is hydrogen, $Y^{1'}$ is methyl and the combination of the radicals $R^1$, $R^2$ and $R^3$ corresponds for each compound to one row of Table A Table 487
Compounds of the formula IE.3 in which $Y^1$ is chlorine, $Y^{1'}$ is hydrogen and the combination of the radicals $R^2$ and $R^3$ corresponds for each compound to one row of Table B

IE.3

Table 488
Compounds of the formula IE.3 in which $Y^1$ is chlorine, $Y^{1'}$ is chlorine and the combination of the radicals $R^2$ and $R^3$ corresponds for each compound to one row of Table B Table 489
Compounds of the formula IE.3 in which $Y^1$ is chlorine, $Y^{1'}$ is methyl and the combination of the radicals $R^2$ and $R^3$ corresponds for each compound to one row of Table B Table 490
Compounds of the formula IE.3 in which $Y^1$ is methyl, $Y^{1'}$ is hydrogen and the combination of the radicals $R^2$ and $R^3$ corresponds for each compound to one row of Table B Table 491
Compounds of the formula IE.3 in which $Y^1$ is methyl, $Y^{1'}$ is chlorine and the combination of the radicals $R^2$ and $R^3$ corresponds for each compound to one row of Table B Table 492
Compounds of the formula IE.3 in which $Y^1$ is methyl, $Y^{1'}$ is methyl and the combination of the radicals $R^2$ and $R^3$ corresponds for each compound to one row of Table B Table 493
Compounds of the formula IE.3 in which $Y^1$ is hydrogen, $Y^{1'}$ is hydrogen and the combination of the radicals $R^2$ and $R^3$ corresponds for each compound to one row of Table B Table 494
Compounds of the formula IE.3 in which $Y^1$ is hydrogen, $Y^{1'}$ is chlorine and the combination of the radicals $R^2$ and $R^3$ corresponds for each compound to one row of Table B Table 495
Compounds of the formula IE.3 in which $Y^1$ is hydrogen, $Y^{1'}$ is methyl and the combination of the radicals $R^2$ and $R^3$ corresponds for each compound to one row of Table B Table 496
Compounds of the formula IE.4 in which $Y^1$ is chlorine, $Y^{1'}$ is hydrogen and the combination of the radicals $R^1$, $R^2$ and $R^3$ corresponds for each compound to one row of Table A

IE.4

Table 497
Compounds of the formula IE.4 in which $Y^1$ is chlorine, $Y^{1'}$ is chlorine and the combination of the radicals $R^1$, $R^2$ and $R^3$ corresponds for each compound to one row of Table A Table 498
Compounds of the formula IE.4 in which $Y^1$ is chlorine, $Y^{1'}$ is methyl and the combination of the radicals $R^1$, $R^2$ and $R^3$ corresponds for each compound to one row of Table A Table 499
Compounds of the formula IE.4 in which $Y^1$ is methyl, $Y^{1'}$ is hydrogen and the combination of the radicals $R^1$, $R^2$ and $R^3$ corresponds for each compound to one row of Table A Table 500
Compounds of the formula IE.4 in which $Y^1$ is methyl, $Y^{1'}$ is chlorine and the combination of the radicals $R^1$, $R^2$ and $R^3$ corresponds for each compound to one row of Table A Table 501
Compounds of the formula IE.4 in which $Y^1$ is methyl, $Y^{1'}$ is methyl and the combination of the radicals $R^1$, $R^2$ and $R^3$ corresponds for each compound to one row of Table A Table 502
Compounds of the formula IE.4 in which $Y^1$ is hydrogen, $Y^{1'}$ is hydrogen and the combination of the radicals $R^1$, $R^2$ and $R^3$ corresponds for each compound to one row of Table A Table 503
Compounds of the formula IE.4 in which $Y^1$ is hydrogen, $Y^{1'}$ is chlorine and the combination of the radicals $R^1$, $R^2$ and $R^3$ corresponds for each compound to one row of Table A Table 504
Compounds of the formula IE.4 in which $Y^1$ is hydrogen, $Y^{1'}$ is methyl and the combination of the radicals $R^1$, $R^2$ and $R^3$ corresponds for each compound to one row of Table A Table 505
Compounds of the formula IE.5 in which $Y^1$ is chlorine, $Y^{1'}$ is hydrogen and the combination of the radicals $R^2$ and $R^3$ corresponds for each compound to one row of Table B

IE.5

Table 506
Compounds of the formula IE.5 in which $Y^1$ is chlorine, $Y^{1'}$ is chlorine and the combination of the radicals $R^2$ and $R^3$ corresponds for each compound to one row of Table B Table 507
Compounds of the formula IE.5 in which $Y^1$ is chlorine, $Y^{1'}$ is methyl and the combination of the radicals $R^2$ and $R^3$ corresponds for each compound to one row of Table B Table 508
Compounds of the formula IE.5 in which $Y^1$ is methyl, $Y^{1'}$ is hydrogen and the combination of the radicals $R^2$ and $R^3$ corresponds for each compound to one row of Table B Table 509
Compounds of the formula IE.5 in which $Y^1$ is methyl, $Y^{1'}$ is chlorine and the combination of the radicals $R^2$ and $R^3$ corresponds for each compound to one row of Table B Table 510
Compounds of the formula IE.5 in which $Y^1$ is methyl, $Y^{1'}$ is methyl and the combination of the radicals $R^2$ and $R^3$ corresponds for each compound to one row of Table B Table 511
Compounds of the formula IE.5 in which $Y^1$ is hydrogen, $Y^{1'}$ is hydrogen and the combination of the radicals $R^2$ and $R^3$ corresponds for each compound to one row of Table B Table 512
Compounds of the formula IE.5 in which $Y^1$ is hydrogen, $Y^{1'}$ is chlorine and the combination of the radicals $R^2$ and $R^3$ corresponds for each compound to one row of Table B Table 513
Compounds of the formula IE.5 in which $Y^1$ is hydrogen, $Y^{1'}$ is methyl and the combination of the radicals $R^2$ and $R^3$ corresponds for each compound to one row of Table B Table 514
Compounds of the formula IE.6 in which $Y^1$ is chlorine, $Y^{1'}$ is hydrogen and the combination of the radicals $R^1$ and $R^2$ corresponds for each compound to one row of Table C

IE.6

Table 515
Compounds of the formula IE.6 in which $Y^1$ is chlorine, $Y^{1'}$ is chlorine and the combination of the radicals $R^1$ and $R^2$ corresponds for each compound to one row of Table C Table 516
Compounds of the formula IE.6 in which $Y^1$ is chlorine, $Y^{1'}$ is methyl and the combination of the radicals $R^1$ and $R^2$ corresponds for each compound to one row of Table C Table 517
Compounds of the formula IE.6 in which $Y^1$ is methyl, $Y^{1'}$ is hydrogen and the combination of the radicals $R^1$ and $R^2$ corresponds for each compound to one row of Table C Table 518
Compounds of the formula IE.6 in which $Y^1$ is methyl, $Y^{1'}$ is chlorine and the combination of the radicals $R^1$ and $R^2$ corresponds for each compound to one row of Table C Table 519
Compounds of the formula IE.6 in which $Y^1$ is methyl, $Y^{1'}$ is methyl and the combination of the radicals $R^1$ and $R^2$ corresponds for each compound to one row of Table C Table 520
Compounds of the formula IE.6 in which $Y^1$ is hydrogen, $Y^{1'}$ is hydrogen and the combination of the radicals $R^1$ and $R^2$ corresponds for each compound to one row of Table C Table 521
Compounds of the formula IE.6 in which $Y^1$ is hydrogen, $Y^{1'}$ is chlorine and the combination of the radicals $R^1$ and $R^2$ corresponds for each compound to one row of Table C Table 522
Compounds of the formula IE.6 in which $Y^1$ is hydrogen, $Y^{1'}$ is methyl and the combination of the radicals $R^1$ and $R^2$ corresponds for each compound to one row of Table C Table 523
Compounds of the formula IE.7 in which $Y^1$ is chlorine, $Y^{1'}$ is hydrogen and the combination of the radicals $R^2$ and $R^3$ corresponds for each compound to one row of Table B

IE.7

Table 524
Compounds of the formula IE.7 in which $Y^1$ is chlorine, $Y^{1'}$ is chlorine and the combination of the radicals $R^2$ and $R^3$ corresponds for each compound to one row of Table B Table 525
Compounds of the formula IE.7 in which $Y^1$ is chlorine, $Y^{1'}$ is methyl and the combination of the radicals $R^2$ and $R^3$ corresponds for each compound to one row of Table B Table 526
Compounds of the formula IE.7 in which $Y^1$ is methyl, $Y^{1'}$ is hydrogen and the combination of the radicals $R^2$ and $R^3$ corresponds for each compound to one row of Table B Table 527
Compounds of the formula IE.7 in which $Y^1$ is methyl, $Y^{1'}$ is chlorine and the combination of the radicals $R^2$ and $R^3$ corresponds for each compound to one row of Table B Table 528
Compounds of the formula IE.7 in which $Y^1$ is methyl, $Y^{1'}$ is methyl and the combination of the radicals $R^2$ and $R^3$ corresponds for each compound to one row of Table B Table 529
Compounds of the formula IE.7 in which $Y^1$ is hydrogen, $Y^{1'}$ is hydrogen and the combination of the radicals $R^2$ and $R^3$ corresponds for each compound to one row of Table B Table 530
Compounds of the formula IE.7 in which $Y^1$ is hydrogen, $Y^{1'}$ is chlorine and the combination of the radicals $R^2$ and $R^3$ corresponds for each compound to one row of Table B Table 531

Compounds of the formula IE.7 in which $Y^1$ is hydrogen, $Y^{1'}$ is methyl and the combination of the radicals $R^2$ and $R^3$ corresponds for each compound to one row of Table B Table 532

Compounds of the formula IE.8 in which $Y^1$ is chlorine, $Y^{1'}$ is hydrogen and the combination of the radicals $R^2$ and $R^3$ corresponds for each compound to one row of Table B

IE.8

Table 533

Compounds of the formula IE.8 in which $Y^1$ is chlorine, $Y^{1'}$ is chlorine and the combination of the radicals $R^2$ and $R^3$ corresponds for each compound to one row of Table B Table 534

Compounds of the formula IE.8 in which $Y^1$ is chlorine, $Y^{1'}$ is methyl and the combination of the radicals $R^2$ and $R^3$ corresponds for each compound to one row of Table B Table 535

Compounds of the formula IE.8 in which $Y^1$ is methyl, $Y^{1'}$ is hydrogen and the combination of the radicals $R^2$ and $R^3$ corresponds for each compound to one row of Table B Table 536

Compounds of the formula IE.8 in which $Y^1$ is methyl, $Y^{1'}$ is chlorine and the combination of the radicals $R^2$ and $R^3$ corresponds for each compound to one row of Table B Table 537

Compounds of the formula IE.8 in which $Y^1$ is methyl, $Y^{1'}$ is methyl and the combination of the radicals $R^2$ and $R^3$ corresponds for each compound to one row of Table B Table 538

Compounds of the formula IE.8 in which $Y^1$ is hydrogen, $Y^{1'}$ is hydrogen and the combination of the radicals $R^2$ and $R^3$ corresponds for each compound to one row of Table B Table 539

Compounds of the formula IE.8 in which $Y^1$ is hydrogen, $Y^{1'}$ is chlorine and the combination of the radicals $R^2$ and $R^3$ corresponds for each compound to one row of Table B Table 540

Compounds of the formula IE.8 in which $Y^1$ is hydrogen, $Y^{1'}$ is methyl and the combination of the radicals $R^2$ and $R^3$ corresponds for each compound to one row of Table B Table 541

Compounds of the formula IE.9 in which $Y^1$ is chlorine, $Y^{1'}$ is hydrogen and the combination of the radicals $R^2$ and $R^3$ corresponds for each compound to one row of Table C

IE.9

Table 542

Compounds of the formula IE.9 in which $Y^1$ is chlorine, $Y^{1'}$ is chlorine and the combination of the radicals $R^2$ and $R^3$ corresponds for each compound to one row of Table C Table 543

Compounds of the formula IE.9 in which $Y^1$ is chlorine, $Y^{1'}$ is methyl and the combination of the radicals $R^2$ and $R^3$ corresponds for each compound to one row of Table C Table 544

Compounds of the formula IE.9 in which $Y^1$ is methyl, $Y^{1'}$ is hydrogen and the combination of the radicals $R^2$ and $R^3$ corresponds for each compound to one row of Table C Table 545

Compounds of the formula IE.9 in which $Y^1$ is methyl, $Y^{1'}$ is chlorine and the combination of the radicals $R^2$ and $R^3$ corresponds for each compound to one row of Table C Table 546

Compounds of the formula IE.9 in which $Y^1$ is methyl, $Y^{1'}$ is methyl and the combination of the radicals $R^2$ and $R^3$ corresponds for each compound to one row of Table C Table 547

Compounds of the formula IE.9 in which $Y^1$ is hydrogen, $Y^{1'}$ is hydrogen and the combination of the radicals $R^2$ and $R^3$ corresponds for each compound to one row of Table C Table 548

Compounds of the formula IE.9 in which $Y^1$ is hydrogen, $Y^{1'}$ is chlorine and the combination of the radicals $R^2$ and $R^3$ corresponds for each compound to one row of Table C Table 549

Compounds of the formula IE.9 in which $Y^1$ is hydrogen, $Y^{1'}$ is methyl and the combination of the radicals $R^2$ and $R^3$ corresponds for each compound to one row of Table C Table 550

Compounds of the formula IE.10 in which $Y^1$ is chlorine, $Y^{1'}$ is hydrogen and the combination of the radicals $R^1$, $R^2$ and $R^3$ corresponds for each compound to one row of Table D

IE.10

Table 551

Compounds of the formula IE.10 in which $Y^1$ is chlorine, $Y^{1'}$ is chlorine and the combination of the radicals $R^1$, $R^2$ and $R^3$ corresponds for each compound to one row of Table D Table 552
Compounds of the formula IE.10 in which $Y^1$ is chlorine, $Y^{1'}$ is methyl and the combination of the radicals $R^1$, $R^2$ and $R^3$ corresponds for each compound to one row of Table D Table 553
Compounds of the formula IE.10 in which $Y^1$ is methyl, $Y^{1'}$ is hydrogen and the combination of the radicals $R^1$, $R^2$ and $R^3$ corresponds for each compound to one row of Table D Table 554
Compounds of the formula IE.10 in which $Y^1$ is methyl, $Y^{1'}$ is chlorine and the combination of the radicals $R^1$, $R^2$ and $R^3$ corresponds for each compound to one row of Table D Table 555
Compounds of the formula IE.10 in which $Y^1$ is methyl, $Y^{1'}$ is methyl and the combination of the radicals $R^1$, $R^2$ and $R^3$ corresponds for each compound to one row of Table D Table 556
Compounds of the formula IE.10 in which $Y^1$ is hydrogen, $Y^{1'}$ is hydrogen and the combination of the radicals $R^1$, $R^2$ and $R^3$ corresponds for each compound to one row of Table D Table 557
Compounds of the formula IE.10 in which $Y^1$ is hydrogen, $Y^{1'}$ is chlorine and the combination of the radicals $R^1$, $R^2$ and $R^3$ corresponds for each compound to one row of Table D Table 558
Compounds of the formula IE.10 in which $Y^1$ is hydrogen, $Y^{1'}$ is methyl and the combination of the radicals $R^1$, $R^2$ and $R^3$ corresponds for each compound to one row of Table D Table 559
Compounds of the formula IE.11 in which $Y^1$ is chlorine, $Y^{1'}$ is hydrogen and the combination of the radicals $R^1$, $R^2$ and $R^3$ corresponds for each compound to one row of Table D

IE.11

Table 560
Compounds of the formula IE.11 in which $Y^1$ is chlorine, $Y^{1'}$ is chlorine and the combination of the radicals $R^1$, $R^2$ and $R^3$ corresponds for each compound to one row of Table D Table 561
Compounds of the formula IE.11 in which $Y^1$ is chlorine, $Y^{1'}$ is methyl and the combination of the radicals $R^1$, $R^2$ and $R^3$ corresponds for each compound to one row of Table D Table 562
Compounds of the formula IE.11 in which $Y^1$ is methyl, $Y^{1'}$ is hydrogen and the combination of the radicals $R^1$, $R^2$ and $R^3$ corresponds for each compound to one row of Table D Table 563
Compounds of the formula IE.11 in which $Y^1$ is methyl, $Y^{1'}$ is chlorine and the combination of the radicals $R^1$, $R^2$ and $R^3$ corresponds for each compound to one row of Table D Table 564
Compounds of the formula IE.11 in which $Y^1$ is methyl, $Y^{1'}$ is methyl and the combination of the radicals $R^1$, $R^2$ and $R^3$ corresponds for each compound to one row of Table D Table 565
Compounds of the formula IE.11 in which $Y^1$ is hydrogen, $Y^{1'}$ is hydrogen and the combination of the radicals $R^1$, $R^2$ and $R^3$ corresponds for each compound to one row of Table D Table 566
Compounds of the formula IE.11 in which $Y^1$ is hydrogen, $Y^{1'}$ is chlorine and the combination of the radicals $R^1$, $R^2$ and $R^3$ corresponds for each compound to one row of Table D Table 567
Compounds of the formula IE.11 in which $Y^1$ is hydrogen, $Y^{1'}$ is methyl and the combination of the radicals $R^1$, $R^2$ and $R^3$ corresponds for each compound to one row of Table D Table 568
Compounds of the formula IE.12 in which $Y^1$ is chlorine, $Y^{1'}$ is hydrogen and the combination of the radicals $R^1$, $R^2$ and $R^3$ corresponds for each compound to one row of Table A

IE.12

Table 569
Compounds of the formula IE.12 in which $Y^1$ is chlorine, $Y^{1'}$ is chlorine and the combination of the radicals $R^1$, $R^2$ and $R^3$ corresponds for each compound to one row of Table A Table 570
Compounds of the formula IE.12 in which $Y^1$ is chlorine, $Y^{1'}$ is methyl and the combination of the radicals $R^1$, $R^2$ and $R^3$ corresponds for each compound to one row of Table A Table 571
Compounds of the formula IE.12 in which $Y^1$ is methyl, $Y^{1'}$ is hydrogen and the combination of the radicals $R^1$, $R^2$ and $R^3$ corresponds for each compound to one row of Table A Table 572
Compounds of the formula IE.12 in which $Y^1$ is methyl, $Y^{1'}$ is chlorine and the combination of the radicals $R^1$, $R^2$ and $R^3$ corresponds for each compound to one row of Table A Table 573
Compounds of the formula IE.12 in which $Y^1$ is methyl, $Y^{1'}$ is methyl and the combination of the radicals $R^1$, $R^2$ and $R^3$ corresponds for each compound to one row of Table A Table 574
Compounds of the formula IE.12 in which $Y^1$ is hydrogen, $Y^{1'}$ is hydrogen and the combination of the radicals $R^1$, $R^2$ and $R^3$ corresponds for each compound to one row of Table A Table 575
Compounds of the formula IE.12 in which $Y^1$ is hydrogen, $Y^{1'}$ is chlorine and the combination of the radicals $R^1$, $R^2$ and $R^3$ corresponds for each compound to one row of Table A Table 576
Compounds of the formula IE.12 in which $Y^1$ is hydrogen, $Y^{1'}$ is methyl and the combination of the radicals $R^1$, $R^2$ and $R^3$ corresponds for each compound to one row of Table A Table 577
Compounds of the formula IE.13 in which $Y^1$ is chlorine, $Y^{1'}$ is hydrogen and the combination of the radicals $R^1$, $R^2$ and $R^3$ corresponds for each compound to one row of Table A

IE.13

Table 578
Compounds of the formula IE.13 in which $Y^1$ is chlorine, $Y^{1'}$ is chlorine and the combination of the radicals $R^1$, $R^2$ and $R^3$ corresponds for each compound to one row of Table A Table 579
Compounds of the formula IE.13 in which $Y^1$ is chlorine, $Y^{1'}$ is methyl and the combination of the radicals $R^1$, $R^2$ and $R^3$ corresponds for each compound to one row of Table A Table 580
Compounds of the formula IE.13 in which $Y^1$ is methyl, $Y^{1'}$ is hydrogen and the combination of the radicals $R^1$, $R^2$ and $R^3$ corresponds for each compound to one row of Table A Table 581
Compounds of the formula IE.13 in which $Y^1$ is methyl, $Y^{1'}$ is chlorine and the combination of the radicals $R^1$, $R^2$ and $R^3$ corresponds for each compound to one row of Table A Table 582
Compounds of the formula IE.13 in which $Y^1$ is methyl, $Y^{1'}$ is methyl and the combination of the radicals $R^1$, $R^2$ and $R^3$ corresponds for each compound to one row of Table A Table 583
Compounds of the formula IE.13 in which $Y^1$ is hydrogen, $Y^{1'}$ is hydrogen and the combination of the radicals $R^1$, $R^2$ and $R^3$ corresponds for each compound to one row of Table A Table 584
Compounds of the formula IE.13 in which $Y^1$ is hydrogen, $Y^{1'}$ is chlorine and the combination of the radicals $R^1$, $R^2$ and $R^3$ corresponds for each compound to one row of Table A Table 585
Compounds of the formula IE.13 in which $Y^1$ is hydrogen, $Y^{1'}$ is methyl and the combination of the radicals $R^1$, $R^2$ and $R^3$ corresponds for each compound to one row of Table A Table 586
Compounds of the formula IF.1 in which $R^A$ is chlorine, $Y^1$ is chlorine, $Y^{1'}$ is hydrogen and the combination of the radicals $R^1$, $R^2$ and $R^3$ corresponds for each compound to one row of Table A

IF.1

Table 587
Compounds of the formula IF.1 in which $R^A$ is chlorine, $Y^1$ is chlorine, $Y^{1'}$ is chlorine and the combination of the radicals $R^1$, $R^2$ and $R^3$ corresponds for each compound to one row of Table A Table 588
Compounds of the formula IF.1 in which $R^A$ is chlorine, $Y^1$ is chlorine, $Y^{1'}$ is methyl and the combination of the radicals $R^1$, $R^2$ and $R^3$ corresponds for each compound to one row of Table A Table 589
Compounds of the formula IF.1 in which $R^A$ is chlorine, $Y^1$ is methyl, $Y^{1'}$ is hydrogen and the combination of the radicals $R^1$, $R^2$ and $R^3$ corresponds for each compound to one row of Table A Table 590
Compounds of the formula IF.1 in which $R^A$ is chlorine, $Y^1$ is methyl, $Y^{1'}$ is chlorine and the combination of the radicals $R^1$, $R^2$ and $R^3$ corresponds for each compound to one row of Table A Table 591
Compounds of the formula IF.1 in which $R^A$ is chlorine, $Y^1$ is methyl, $Y^{1'}$ is methyl and the combination of the radicals $R^1$, $R^2$ and $R^3$ corresponds for each compound to one row of Table A Table 592
Compounds of the formula IF.1 in which $R^A$ is methyl, $Y^1$ is chlorine, $Y^{1'}$ is hydrogen and the combination of the radicals $R^1$, $R^2$ and $R^3$ corresponds for each compound to one row of Table A Table 593
Compounds of the formula IF.1 in which $R^A$ is methyl, $Y^1$ is chlorine, $Y^{1'}$ is chlorine and the combination of the radicals $R^1$, $R^2$ and $R^3$ corresponds for each compound to one row of Table A Table 594
Compounds of the formula IF.1 in which $R^A$ is methyl, $Y^1$ is chlorine, $Y^{1'}$ is methyl and the combination of the radicals $R^1$, $R^2$ and $R^3$ corresponds for each compound to one row of Table A Table 595
Compounds of the formula IF.1 in which $R^A$ is methyl, $Y^1$ is methyl, $Y^{1'}$ is hydrogen and the combination of the radicals $R^1$, $R^2$ and $R^3$ corresponds for each compound to one row of Table A Table 596
Compounds of the formula IF.1 in which $R^A$ is methyl, $Y^1$ is methyl, $Y^{1'}$ is chlorine and the combination of the radicals $R^1$, $R^2$ and $R^3$ corresponds for each compound to one row of Table A Table 597
Compounds of the formula IF.1 in which $R^A$ is methyl, $Y^1$ is methyl, $Y^{1'}$ is methyl and the combination of the radicals $R^1$, $R^2$ and $R^3$ corresponds for each compound to one row of Table A Table 598
Compounds of the formula IF.1 in which $R^A$ is methoxy, $Y^1$ is chlorine, $Y^{1'}$ is hydrogen and the combination of the radicals $R^1$, $R^2$ and $R^3$ corresponds for each compound to one row of Table A Table 599
Compounds of the formula IF.1 in which $R^A$ is methoxy, $Y^1$ is chlorine, $Y^{1'}$ is chlorine and the combination of the radicals $R^1$, $R^2$ and $R^3$ corresponds for each compound to one row of Table A Table 600
Compounds of the formula IF.1 in which $R^A$ is methoxy, $Y^1$ is chlorine, $Y^{1'}$ is methyl and the combination of the radicals $R^1$, $R^2$ and $R^3$ corresponds for each compound to one row of Table A Table 601
Compounds of the formula IF.1 in which $R^A$ is methoxy, $Y^1$ is methyl, $Y^{1'}$ is hydrogen and the combination of the radicals $R^1$, $R^2$ and $R^3$ corresponds for each compound to one row of Table A Table 602
Compounds of the formula IF.1 in which $R^A$ is methoxy, $Y^1$ is methyl, $Y^{1'}$ is chlorine and the combination of the radicals $R^1$, $R^2$ and $R^3$ corresponds for each compound to one row of Table A Table 603
Compounds of the formula IF.1 in which $R^A$ is methoxy, $Y^1$ is methyl, $Y^{1'}$ is methyl and the combination of the radicals $R^1$, $R^2$ and $R^3$ corresponds for each compound to one row of Table A Table 604
Compounds of the formula IF.2 in which $R^A$ is chlorine, $Y^1$ is chlorine, $Y^{1'}$ is hydrogen and the combination of the radicals $R^1$, $R^2$ and $R^3$ corresponds for each compound to one row of Table A

IF.2

Table 605
Compounds of the formula IF.2 in which $R^A$ is chlorine, $Y^1$ is chlorine, $Y^{1'}$ is chlorine and the combination of the radicals $R^1$, $R^2$ and $R^3$ corresponds for each compound to one row of Table A Table 606
Compounds of the formula IF.2 in which $R^A$ is chlorine, $Y^1$ is chlorine, $Y^{1'}$ is methyl and the combination of the radicals $R^1$, $R^2$ and $R^3$ corresponds for each compound to one row of Table A Table 607
Compounds of the formula IF.2 in which $R^A$ is chlorine, $Y^1$ is methyl, $Y^{1'}$ is hydrogen and the combination of the radicals $R^1$, $R^2$ and $R^3$ corresponds for each compound to one row of Table A Table 608
Compounds of the formula IF.2 in which $R^A$ is chlorine, $Y^1$ is methyl, $Y^{1'}$ is chlorine and the combination of the radicals $R^1$, $R^2$ and $R^3$ corresponds for each compound to one row of Table A Table 609
Compounds of the formula IF.2 in which $R^A$ is chlorine, $Y^1$ is methyl, $Y^{1'}$ is methyl and the combination of the radicals $R^1$, $R^2$ and $R^3$ corresponds for each compound to one row of Table A Table 610
Compounds of the formula IF.2 in which $R^A$ is methyl, $Y^1$ is chlorine, $Y^{1'}$ is hydrogen and the combination of the radicals $R^1$, $R^2$ and $R^3$ corresponds for each compound to one row of Table A Table 611
Compounds of the formula IF.2 in which $R^A$ is methyl, $Y^1$ is chlorine, $Y^{1'}$ is chlorine and the combination of the radicals $R^1$, $R^2$ and $R^3$ corresponds for each compound to one row of Table A Table 612
Compounds of the formula IF.2 in which $R^A$ is methyl, $Y^1$ is chlorine, $Y^{1'}$ is methyl and the combination of the radicals $R^1$, $R^2$ and $R^3$ corresponds for each compound to one row of Table A Table 613
Compounds of the formula IF.2 in which $R^A$ is methyl, $Y^1$ is methyl, $Y^{1'}$ is hydrogen and the combination of the radicals $R^1$, $R^2$ and $R^3$ corresponds for each compound to one row of Table A Table 614
Compounds of the formula IF.2 in which $R^A$ is methyl, $Y^1$ is methyl, $Y^{1'}$ is chlorine and the combination of the radicals $R^1$, $R^2$ and $R^3$ corresponds for each compound to one row of Table A Table 615
Compounds of the formula IF.2 in which $R^A$ is methyl, $Y^1$ is methyl, $Y^{1'}$ is methyl and the combination of the radicals $R^1$, $R^2$ and $R^3$ corresponds for each compound to one row of Table A Table 616
Compounds of the formula IF.2 in which $R^A$ is methoxy, $Y^1$ is chlorine, $Y^{1'}$ is hydrogen and the combination of the radicals $R^1$, $R^2$ and $R^3$ corresponds for each compound to one row of Table A Table 617
Compounds of the formula IF.2 in which $R^A$ is methoxy, $Y^1$ is chlorine, $Y^{1'}$ is chlorine and the combination of the radicals $R^1$, $R^2$ and $R^3$ corresponds for each compound to one row of Table A Table 618
Compounds of the formula IF.2 in which $R^A$ is methoxy, $Y^1$ is chlorine, $Y^{1'}$ is methyl and the combination of the radicals $R^1$, $R^2$ and $R^3$ corresponds for each compound to one row of Table A Table 619
Compounds of the formula IF.2 in which $R^A$ is methoxy, $Y^1$ is methyl, $Y^{1'}$ is hydrogen and the combination of the radicals $R^1$, $R^2$ and $R^3$ corresponds for each compound to one row of Table A Table 620
Compounds of the formula IF.2 in which $R^A$ is methoxy, $Y^1$ is methyl, $Y^{1'}$ is chlorine and the combination of the radicals $R^1$, $R^2$ and $R^3$ corresponds for each compound to one row of Table A Table 621
Compounds of the formula IF.2 in which $R^A$ is methoxy, $Y^1$ is methyl, $Y^{1'}$ is methyl and the combination of the radicals $R^1$, $R^2$ and $R^3$ corresponds for each compound to one row of Table A Table 622
Compounds of the formula IF.3 in which $R^A$ is chlorine, $Y^1$ is chlorine, $Y^{1'}$ is hydrogen and the combination of the radicals R² and R³ corresponds for each compound to one row of Table B

IF.3

Table 623
Compounds of the formula IF.3 in which $R^A$ is chlorine, $Y^1$ is chlorine, $Y^{1'}$ is chlorine and the combination of the radicals R² and R³ corresponds for each compound to one row of Table B Table 624
Compounds of the formula IF.3 in which $R^A$ is chlorine, $Y^1$ is chlorine, $Y^{1'}$ is methyl and the combination of the radicals R² and R³ corresponds for each compound to one row of Table B Table 625
Compounds of the formula IF.3 in which $R^A$ is chlorine, $Y^1$ is methyl, $Y^{1'}$ is hydrogen and the combination of the radicals R² and R³ corresponds for each compound to one row of Table B Table 626
Compounds of the formula IF.3 in which $R^A$ is chlorine, $Y^1$ is methyl, $Y^{1'}$ is chlorine and the combination of the radicals R² and R³ corresponds for each compound to one row of Table B Table 627
Compounds of the formula IF.3 in which $R^A$ is chlorine, $Y^1$ is methyl, $Y^{1'}$ is methyl and the combination of the radicals R² and R³ corresponds for each compound to one row of Table B Table 628
Compounds of the formula IF.3 in which $R^A$ is methyl, $Y^1$ is chlorine, $Y^{1'}$ is hydrogen and the combination of the radicals R² and R³ corresponds for each compound to one row of Table B Table 629
Compounds of the formula IF.3 in which $R^A$ is methyl, $Y^1$ is chlorine, $Y^{1'}$ is chlorine and the combination of the radicals R² and R³ corresponds for each compound to one row of Table B Table 630
Compounds of the formula IF.3 in which $R^A$ is methyl, $Y^1$ is chlorine, $Y^{1'}$ is methyl and the combination of the radicals R² and R³ corresponds for each compound to one row of Table B Table 631
Compounds of the formula IF.3 in which $R^A$ is methyl, $Y^1$ is methyl, $Y^{1'}$ is hydrogen and the combination of the radicals R² and R³ corresponds for each compound to one row of Table B Table 632
Compounds of the formula IF.3 in which $R^A$ is methyl, $Y^1$ is methyl, $Y^{1'}$ is chlorine and the combination of the radicals R² and R³ corresponds for each compound to one row of Table B Table 633
Compounds of the formula IF.3 in which $R^A$ is methyl, $Y^1$ is methyl, $Y^{1'}$ is methyl and the combination of the radicals R² and R³ corresponds for each compound to one row of Table B Table 634
Compounds of the formula IF.3 in which $R^A$ is methoxy, $Y^1$ is chlorine, $Y^{1'}$ is hydrogen and the combination of the radicals R² and R³ corresponds for each compound to one row of Table B Table 635
Compounds of the formula IF.3 in which $R^A$ is methoxy, $Y^1$ is chlorine, $Y^{1'}$ is chlorine and the combination of the radicals R² and R³ corresponds for each compound to one row of Table B Table 636
Compounds of the formula IF.3 in which $R^A$ is methoxy, $Y^1$ is chlorine, $Y^{1'}$ is methyl and the combination of the radicals R² and R³ corresponds for each compound to one row of Table B Table 637
Compounds of the formula IF.3 in which $R^A$ is methoxy, $Y^1$ is methyl, $Y^{1'}$ is hydrogen and the combination of the radicals R² and R³ corresponds for each compound to one row of Table B Table 638
Compounds of the formula IF.3 in which $R^A$ is methoxy, $Y^1$ is methyl, $Y^{1'}$ is chlorine and the combination of the radicals R² and R³ corresponds for each compound to one row of Table B Table 639
Compounds of the formula IF.3 in which $R^A$ is methoxy, $Y^1$ is methyl, $Y^{1'}$ is methyl and the combination of the radicals R² and R³ corresponds for each compound to one row of Table B Table 640
Compounds of the formula IF.4 in which $R^A$ is chlorine, $Y^1$ is chlorine, $Y^{1'}$ is hydrogen and the combination of the radicals R¹, R² and R³ corresponds for each compound to one row of Table A

IF.4

Table 641
Compounds of the formula IF.4 in which $R^A$ is chlorine, $Y^1$ is chlorine, $Y^{1'}$ is chlorine and the combination of the radicals R¹, R² and R³ corresponds for each compound to one row of Table A Table 642
Compounds of the formula IF.4 in which $R^A$ is chlorine, $Y^1$ is chlorine, $Y^{1'}$ is methyl and the combination of the radicals R¹, R² and R³ corresponds for each compound to one row of Table A Table 643
Compounds of the formula IF.4 in which $R^A$ is chlorine, $Y^1$ is methyl, $Y^{1'}$ is hydrogen and the combination of the radicals R¹, R² and R³ corresponds for each compound to one row of Table A Table 644
Compounds of the formula IF.4 in which $R^A$ is chlorine, $Y^1$ is methyl, $Y^{1'}$ is chlorine and the combination of the radicals R¹, R² and R³ corresponds for each compound to one row of Table A Table 645
Compounds of the formula IF.4 in which $R^A$ is chlorine, $Y^1$ is methyl, $Y^{1'}$ is methyl and the combination of the radicals $R^1$, $R^2$ and $R^3$ corresponds for each compound to one row of Table A Table 646
Compounds of the formula IF.4 in which $R^A$ is methyl, $Y^1$ is chlorine, $Y^{1'}$ is hydrogen and the combination of the radicals $R^1$, $R^2$ and $R^3$ corresponds for each compound to one row of Table A Table 647
Compounds of the formula IF.4 in which $R^A$ is methyl, $Y^1$ is chlorine, $Y^{1'}$ is chlorine and the combination of the radicals $R^1$, $R^2$ and $R^3$ corresponds for each compound to one row of Table A Table 648
Compounds of the formula IF.4 in which $R^A$ is methyl, $Y^1$ is chlorine, $Y^{1'}$ is methyl and the combination of the radicals $R^1$, $R^2$ and $R^3$ corresponds for each compound to one row of Table A Table 649
Compounds of the formula IF.4 in which $R^A$ is methyl, $Y^1$ is methyl, $Y^{1'}$ is hydrogen and the combination of the radicals $R^1$, $R^2$ and $R^3$ corresponds for each compound to one row of Table A Table 650
Compounds of the formula IF.4 in which $R^A$ is methyl, $Y^1$ is methyl, $Y^{1'}$ is chlorine and the combination of the radicals $R^1$, $R^2$ and $R^3$ corresponds for each compound to one row of Table A Table 651
Compounds of the formula IF.4 in which $R^A$ is methyl, $Y^1$ is methyl, $Y^{1'}$ is methyl and the combination of the radicals $R^1$, $R^2$ and $R^3$ corresponds for each compound to one row of Table A Table 652
Compounds of the formula IF.4 in which $R^A$ is methoxy, $Y^1$ is chlorine, $Y^{1'}$ is hydrogen and the combination of the radicals $R^1$, $R^2$ and $R^3$ corresponds for each compound to one row of Table A Table 653
Compounds of the formula IF.4 in which $R^A$ is methoxy, $Y^1$ is chlorine, $Y^{1'}$ is chlorine and the combination of the radicals $R^1$, $R^2$ and $R^3$ corresponds for each compound to one row of Table A Table 654
Compounds of the formula IF.4 in which $R^A$ is methoxy, $Y^1$ is chlorine, $Y^{1'}$ is methyl and the combination of the radicals $R^1$, $R^2$ and $R^3$ corresponds for each compound to one row of Table A Table 655
Compounds of the formula IF.4 in which $R^A$ is methoxy, $Y^1$ is methyl, $Y^{1'}$ is hydrogen and the combination of the radicals $R^1$, $R^2$ and $R^3$ corresponds for each compound to one row of Table A Table 656
Compounds of the formula IF.4 in which $R^A$ is methoxy, $Y^1$ is methyl, $Y^{1'}$ is chlorine and the combination of the radicals $R^1$, $R^2$ and $R^3$ corresponds for each compound to one row of Table A Table 657
Compounds of the formula IF.4 in which $R^A$ is methoxy, $Y^1$ is methyl, $Y^{1'}$ is methyl and the combination of the radicals $R^1$, $R^2$ and $R^3$ corresponds for each compound to one row of Table A Table 658
Compounds of the formula IF.5 in which $R^A$ is chlorine, $Y^1$ is chlorine, $Y^{1'}$ is hydrogen and the combination of the radicals $R^2$ and $R^3$ corresponds for each compound to one row of Table B

IF.5

Table 659
Compounds of the formula IF.5 in which $R^A$ is chlorine, $Y^1$ is chlorine, $Y^{1'}$ is chlorine and the combination of the radicals $R^2$ and $R^3$ corresponds for each compound to one row of Table B Table 660
Compounds of the formula IF.5 in which $R^A$ is chlorine, $Y^1$ is chlorine, $Y^{1'}$ is methyl and the combination of the radicals $R^2$ and $R^3$ corresponds for each compound to one row of Table B Table 661
Compounds of the formula IF.5 in which $R^A$ is chlorine, $Y^1$ is methyl, $Y^{1'}$ is hydrogen and the combination of the radicals $R^2$ and $R^3$ corresponds for each compound to one row of Table B Table 662
Compounds of the formula IF.5 in which $R^A$ is chlorine, $Y^1$ is methyl, $Y^{1'}$ is chlorine and the combination of the radicals $R^2$ and $R^3$ corresponds for each compound to one row of Table B Table 663
Compounds of the formula IF.5 in which $R^A$ is chlorine, $Y^1$ is methyl, $Y^{1'}$ is methyl and the combination of the radicals $R^2$ and $R^3$ corresponds for each compound to one row of Table B Table 664
Compounds of the formula IF.5 in which $R^A$ is methyl, $Y^1$ is chlorine, $Y^{1'}$ is hydrogen and the combination of the radicals $R^2$ and $R^3$ corresponds for each compound to one row of Table B Table 665
Compounds of the formula IF.5 in which $R^A$ is methyl, $Y^1$ is chlorine, $Y^{1'}$ is chlorine and the combination of the radicals $R^2$ and $R^3$ corresponds for each compound to one row of Table B Table 666
Compounds of the formula IF.5 in which $R^A$ is methyl, $Y^1$ is chlorine, $Y^{1'}$ is methyl and the combination of the radicals $R^2$ and $R^3$ corresponds for each compound to one row of Table B Table 667
Compounds of the formula IF.5 in which $R^A$ is methyl, $Y^1$ is methyl, $Y^{1'}$ is hydrogen and the combination of the radicals $R^2$ and $R^3$ corresponds for each compound to one row of Table B Table 668
Compounds of the formula IF.5 in which $R^A$ is methyl, $Y^1$ is methyl, $Y^{1'}$ is chlorine and the combination of the radicals $R^2$ and $R^3$ corresponds for each compound to one row of Table B Table 669
Compounds of the formula IF.5 in which $R^A$ is methyl, $Y^1$ is methyl, $Y^{1'}$ is methyl and the combination of the radicals $R^2$ and $R^3$ corresponds for each compound to one row of Table B Table 670
Compounds of the formula IF.5 in which $R^A$ is methoxy, $Y^1$ is chlorine, $Y^{1'}$ is hydrogen and the combination of the radicals $R^2$ and $R^3$ corresponds for each compound to one row of Table B Table 671
Compounds of the formula IF.5 in which $R^A$ is methoxy, $Y^1$ is chlorine, $Y^{1'}$ is chlorine and the combination of the radicals $R^2$ and $R^3$ corresponds for each compound to one row of Table B Table 672
Compounds of the formula IF.5 in which $R^A$ is methoxy, $Y^1$ is chlorine, $Y^{1'}$ is methyl and the combination of the radicals $R^2$ and $R^3$ corresponds for each compound to one row of Table B Table 673
Compounds of the formula IF.5 in which $R^A$ is methoxy, $Y^1$ is methyl, $Y^{1'}$ is hydrogen and the combination of the radicals $R^2$ and $R^3$ corresponds for each compound to one row of Table B Table 674
Compounds of the formula IF.5 in which $R^A$ is methoxy, $Y^1$ is methyl, $Y^{1'}$ is chlorine and the combination of the radicals $R^2$ and $R^3$ corresponds for each compound to one row of Table B Table 675
Compounds of the formula IF.5 in which $R^A$ is methoxy, $Y^1$ is methyl, $Y^{1'}$ is methyl and the combination of the radicals $R^2$ and $R^3$ corresponds for each compound to one row of Table B Table 676
Compounds of the formula IF.6 in which $R^A$ is chlorine, $Y^{1'}$ is chlorine, $Y^1$ is hydrogen and the combination of the radicals $R^1$ and $R^2$ corresponds for each compound to one row of Table C

IF.6

Table 677
Compounds of the formula IF.6 in which $R^A$ is chlorine, $Y^1$ is chlorine, $Y^{1'}$ is chlorine and the combination of the radicals $R^1$ and $R^2$ corresponds for each compound to one row of Table C Table 678
Compounds of the formula IF.6 in which $R^A$ is chlorine, $Y^1$ is chlorine, $Y^{1'}$ is methyl and the combination of the radicals $R^1$ and $R^2$ corresponds for each compound to one row of Table C Table 679
Compounds of the formula IF.6 in which $R^A$ is chlorine, $Y^1$ is methyl, $Y^{1'}$ is hydrogen and the combination of the radicals $R^1$ and $R^2$ corresponds for each compound to one row of Table C Table 680
Compounds of the formula IF.6 in which $R^A$ is chlorine, $Y^1$ is methyl, $Y^{1'}$ is chlorine and the combination of the radicals $R^1$ and $R^2$ corresponds for each compound to one row of Table C Table 681
Compounds of the formula IF.6 in which $R^A$ is chlorine, $Y^1$ is methyl, $Y^{1'}$ is methyl and the combination of the radicals $R^1$ and $R^2$ corresponds for each compound to one row of Table C Table 682
Compounds of the formula IF.6 in which $R^A$ is methyl, $Y^1$ is chlorine, $Y^{1'}$ is hydrogen and the combination of the radicals $R^1$ and $R^2$ corresponds for each compound to one row of Table C Table 683
Compounds of the formula IF.6 in which $R^A$ is methyl, $Y^1$ is chlorine, $Y^{1'}$ is chlorine and the combination of the radicals $R^1$ and $R^2$ corresponds for each compound to one row of Table C Table 684
Compounds of the formula IF.6 in which $R^A$ is methyl, $Y^1$ is chlorine, $Y^{1'}$ is methyl and the combination of the radicals $R^1$ and $R^2$ corresponds for each compound to one row of Table C Table 685
Compounds of the formula IF.6 in which $R^A$ is methyl, $Y^1$ is methyl, $Y^{1'}$ is hydrogen and the combination of the radicals $R^2$ and $R^3$ corresponds for each compound to one row of Table C Table 686
Compounds of the formula IF.6 in which $R^A$ is methyl, $Y^1$ is methyl, $Y^{1'}$ is chlorine and the combination of the radicals $R^2$ and $R^3$ corresponds for each compound to one row of Table C Table 687
Compounds of the formula IF.6 in which $R^A$ is methyl, $Y^1$ is methyl, $Y^{1'}$ is methyl and the combination of the radicals $R^1$ and $R^2$ corresponds for each compound to one row of Table C Table 688
Compounds of the formula IF.6 in which $R^A$ is methoxy, $Y^1$ is chlorine, $Y^{1'}$ is hydrogen and the combination of the radicals $R^1$ and $R^2$ corresponds for each compound to one row of Table C Table 689
Compounds of the formula IF.6 in which $R^A$ is methoxy, $Y^1$ is chlorine, $Y^{1'}$ is chlorine and the combination of the radicals $R^1$ and $R^2$ corresponds for each compound to one row of Table C Table 690
Compounds of the formula IF.6 in which $R^A$ is methoxy, $Y^1$ is chlorine, $Y^{1'}$ is methyl and the combination of the radicals $R^1$ and $R^2$ corresponds for each compound to one row of Table C Table 691
Compounds of the formula IF.6 in which $R^A$ is methoxy, $Y^1$ is methyl, $Y^{1'}$ is hydrogen and the combination of the radicals $R^1$ and $R^2$ corresponds for each compound to one row of Table C Table 692
Compounds of the formula IF.6 in which $R^A$ is methoxy, $Y^1$ is methyl, $Y^{1'}$ is chlorine and the combination of the radicals $R^1$ and $R^2$ corresponds for each compound to one row of Table C Table 693
Compounds of the formula IF.6 in which $R^A$ is methoxy, $Y^1$ is methyl, $Y^{1'}$ is methyl and the combination of the radicals $R^1$ and $R^2$ corresponds for each compound to one row of Table C Table 694
Compounds of the formula IF.7 in which $R^A$ is chlorine, $Y^1$ is chlorine, $Y^{1'}$ is hydrogen and the combination of the radicals $R^2$ and $R^3$ corresponds for each compound to one row of Table B

IF.7

Table 695
Compounds of the formula IF.7 in which $R^A$ is chlorine, $Y^1$ is chlorine, $Y^{1'}$ is chlorine and the combination of the radicals $R^2$ and $R^3$ corresponds for each compound to one row of Table B Table 696
Compounds of the formula IF.7 in which $R^A$ is chlorine, $Y^1$ is chlorine, $Y^{1'}$ is methyl and the combination of the radicals $R^2$ and $R^3$ corresponds for each compound to one row of Table B Table 697
Compounds of the formula IF.7 in which $R^A$ is chlorine, $Y^1$ is methyl, $Y^{1'}$ is hydrogen and the combination of the radicals $R^2$ and $R^3$ corresponds for each compound to one row of Table B Table 698
Compounds of the formula IF.7 in which $R^A$ is chlorine, $Y^1$ is methyl, $Y^{1'}$ is chlorine and the combination of the radicals $R^2$ and $R^3$ corresponds for each compound to one row of Table B Table 699
Compounds of the formula IF.7 in which $R^A$ is chlorine, $Y^1$ is methyl, $Y^{1'}$ is methyl and the combination of the radicals $R^2$ and $R^3$ corresponds for each compound to one row of Table B Table 700
Compounds of the formula IF.7 in which $R^A$ is methyl, $Y^1$ is chlorine, $Y^{1'}$ is hydrogen and the combination of the radicals $R^2$ and $R^3$ corresponds for each compound to one row of Table B Table 701
Compounds of the formula IF.7 in which $R^A$ is methyl, $Y^1$ is chlorine, $Y^{1'}$ is chlorine and the combination of the radicals $R^2$ and $R^3$ corresponds for each compound to one row of Table B Table 702
Compounds of the formula IF.7 in which $R^A$ is methyl, $Y^1$ is chlorine, $Y^{1'}$ is methyl and the combination of the radicals $R^2$ and $R^3$ corresponds for each compound to one row of Table B Table 703
Compounds of the formula IF.7 in which $R^A$ is methyl, $Y^1$ is methyl, $Y^{1'}$ is hydrogen and the combination of the radicals $R^2$ and $R^3$ corresponds for each compound to one row of Table B Table 704
Compounds of the formula IF.7 in which $R^A$ is methyl, $Y^1$ is methyl, $Y^{1'}$ is chlorine and the combination of the radicals $R^2$ and $R^3$ corresponds for each compound to one row of Table B Table 705
Compounds of the formula IF.7 in which $R^A$ is methyl, $Y^1$ is methyl, $Y^{1'}$ is methyl and the combination of the radicals $R^2$ and $R^3$ corresponds for each compound to one row of Table B Table 706
Compounds of the formula IF.7 in which $R^A$ is methoxy, $Y^1$ is chlorine, $Y^{1'}$ is hydrogen and the combination of the radicals $R^2$ and $R^3$ corresponds for each compound to one row of Table B Table 707
Compounds of the formula IF.7 in which $R^A$ is methoxy, $Y^1$ is chlorine, $Y^{1'}$ is chlorine and the combination of the radicals $R^2$ and $R^3$ corresponds for each compound to one row of Table B Table 708
Compounds of the formula IF.7 in which $R^A$ is methoxy, $Y^1$ is chlorine, $Y^{1'}$ is methyl and the combination of the radicals $R^2$ and $R^3$ corresponds for each compound to one row of Table B Table 709
Compounds of the formula IF.7 in which $R^A$ is methoxy, $Y^1$ is methyl, $Y^{1'}$ is hydrogen and the combination of the radicals $R^2$ and $R^3$ corresponds for each compound to one row of Table B Table 710
Compounds of the formula IF.7 in which $R^A$ is methoxy, $Y^1$ is methyl, $Y^{1'}$ is chlorine and the combination of the radicals $R^2$ and $R^3$ corresponds for each compound to one row of Table B Table 711
Compounds of the formula IF.7 in which $R^A$ is methoxy, $Y^1$ is methyl, $Y^{1'}$ is methyl and the combination of the radicals $R^2$ and $R^3$ corresponds for each compound to one row of Table B Table 712
Compounds of the formula IF.8 in which $R^A$ is chlorine, $Y^1$ is chlorine, $Y^{1'}$ is hydrogen and the combination of the radicals $R^2$ and $R^3$ corresponds for each compound to one row of Table B

IF.8

Table 713
Compounds of the formula IF.8 in which $R^A$ is chlorine, $Y^1$ is chlorine, $Y^{1'}$ is chlorine and the combination of the radicals $R^2$ and $R^3$ corresponds for each compound to one row of Table B Table 714
Compounds of the formula IF.8 in which $R^A$ is chlorine, $Y^1$ is chlorine, $Y^{1'}$ is methyl and the combination of the radicals $R^2$ and $R^3$ corresponds for each compound to one row of Table B Table 715
Compounds of the formula IF.8 in which $R^A$ is chlorine, $Y^1$ is methyl, $Y^{1'}$ is hydrogen and the combination of the radicals $R^2$ and $R^3$ corresponds for each compound to one row of Table B Table 716
Compounds of the formula IF.8 in which $R^A$ is chlorine, $Y^1$ is methyl, $Y^{1'}$ is chlorine and the combination of the radicals $R^2$ and $R^3$ corresponds for each compound to one row of Table B Table 717
Compounds of the formula IF.8 in which $R^A$ is chlorine, $Y^1$ is methyl, $Y^{1'}$ is methyl and the combination of the radicals $R^2$ and $R^3$ corresponds for each compound to one row of Table B Table 718
Compounds of the formula IF.8 in which $R^A$ is methyl, $Y^1$ is chlorine, $Y^{1'}$ is hydrogen and the combination of the radicals $R^2$ and $R^3$ corresponds for each compound to one row of Table B Table 719
Compounds of the formula IF. 8 in which $R^A$ is methyl, $Y^1$ is chlorine, $Y^{1'}$ is chlorine and the combination of the radicals $R^2$ and $R^3$ corresponds for each compound to one row of Table B Table 720
Compounds of the formula IF.8 in which $R^A$ is methyl, $Y^1$ is chlorine, $Y^{1'}$ is methyl and the combination of the radicals $R^2$ and $R^3$ corresponds for each compound to one row of Table B Table 721
Compounds of the formula IF.8 in which $R^A$ is methyl, $Y^1$ is methyl, $Y^{1'}$ is hydrogen and the combination of the radicals $R^2$ and $R^3$ orresponds for each compound to one row of Table B Table 722
Compounds of the formula IF.8 in which $R^A$ is methyl, $Y^1$ is methyl, $Y^{1'}$ is chlorine and the combination of the radicals $R^2$ and $R^3$ corresponds for each compound to one row of Table B Table 723
Compounds of the formula IF.8 in which $R^A$ is methyl, $Y^1$ is methyl, $Y^{1'}$ is methyl and the combination of the radicals $R^2$ and $R^3$ corresponds for each compound to one row of Table B Table 724
Compounds of the formula IF.8 in which $R^A$ is methoxy, $Y^1$ is chlorine, $Y^{1'}$ is hydrogen and the combination of the radicals $R^2$ and $R^3$ corresponds for each compound to one row of Table B Table 725
Compounds of the formula IF.8 in which $R^A$ is methoxy, $Y^1$ is chlorine, $Y^{1'}$ is chlorine and the combination of the radicals $R^2$ and $R^3$ corresponds for each compound to one row of Table B Table 726
Compounds of the formula IF.8 in which $R^A$ is methoxy, $Y^1$ is chlorine, $Y^{1'}$ is methyl and the combination of the radicals $R^2$ and $R^3$ corresponds for each compound to one row of Table B Table 727
Compounds of the formula IF.8 in which $R^A$ is methoxy, $Y^1$ is methyl, $Y^{1'}$ is hydrogen and the combination of the radicals $R^2$ and $R^3$ corresponds for each compound to one row of Table B Table 728
Compounds of the formula IF.8 in which $R^A$ is methoxy, $Y^1$ is methyl, $Y^{1'}$ is chlorine and the combination of the radicals $R^2$ and $R^3$ corresponds for each compound to one row of Table B Table 729
Compounds of the formula IF.8 in which $R^A$ is methoxy, $Y^1$ is methyl, $Y^{1'}$ is methyl and the combination of the radicals $R^2$ and $R^3$ corresponds for each compound to one row of Table B Table 730
Compounds of the formula IF.9 in which $R^A$ is chlorine, $Y^1$ is chlorine, $Y^{1'}$ is hydrogen and the combination of the radicals $R^1$ and $R^2$ corresponds for each compound to one row of Table C

IF.9

Table 731
Compounds of the formula IF.9 in which $R^A$ is chlorine, $Y^1$ is chlorine, $Y^{1'}$ is chlorine and the combination of the radicals $R^1$ and $R^2$ corresponds for each compound to one row of Table C Table 732
Compounds of the formula IF.9 in which $R^A$ is chlorine, $Y^1$ is chlorine, $Y^{1'}$ is methyl and the combination of the radicals $R^1$ and $R^2$ corresponds for each compound to one row of Table C Table 733
Compounds of the formula IF.9 in which $R^A$ is chlorine, $Y^1$ is methyl, $Y^{1'}$ is hydrogen and the combination of the radicals $R^1$ and $R^2$ corresponds for each compound to one row of Table C Table 734
Compounds of the formula IF.9 in which $R^A$ is chlorine, $Y^1$ is methyl, $Y^{1'}$ is chlorine and the combination of the radicals $R^1$ and $R^2$ corresponds for each compound to one row of Table C Table 735
Compounds of the formula IF.9 in which $R^A$ is chlorine, $Y^1$ is methyl, $Y^{1'}$ is methyl and the combination of the radicals $R^1$ and $R^2$ corresponds for each compound to one row of Table C Table 736
Compounds of the formula IF.9 in which $R^A$ is methyl, $Y^1$ is chlorine, $Y^{1'}$ is hydrogen and the combination of the radicals $R^1$ and $R^2$ corresponds for each compound to one row of Table C Table 737
Compounds of the formula IF.9 in which $R^A$ is methyl, $Y^1$ is chlorine, $Y^{1'}$ is chlorine and the combination of the radicals $R^1$ and $R^2$ corresponds for each compound to one row of Table C Table 738
Compounds of the formula IF.9 in which $R^A$ is methyl, $Y^1$ is chlorine, $Y^{1'}$ is methyl and the combination of the radicals $R^1$ and $R^2$ corresponds for each compound to one row of Table C Table 739
Compounds of the formula IF.9 in which $R^A$ is methyl, $Y^1$ is methyl, $Y^{1'}$ is hydrogen and the combination of the radicals $R^1$ and $R^2$ corresponds for each compound to one row of Table C Table 740
Compounds of the formula IF.9 in which $R^A$ is methyl, $Y^1$ is methyl, $Y^{1'}$ is chlorine and the combination of the radicals $R^1$ and $R^2$ corresponds for each compound to one row of Table C Table 741
Compounds of the formula IP.9 in which $R^A$ is methyl, $Y^1$ is methyl, $Y^{1'}$ is methyl and the combination of the radicals $R^1$ and $R^2$ corresponds for each compound to one row of Table C Table 742
Compounds of the formula IF.9 in which $R^A$ is methoxy, $Y^1$ is chlorine, $Y^{1'}$ is hydrogen and the combination of the radicals $R^1$ and $R^2$ corresponds for each compound to one row of Table C Table 743
Compounds of the formula IF.9 in which $R^A$ is methoxy, $Y^1$ is chlorine, $Y^{1'}$ is chlorine and the combination of the radicals $R^1$ and $R^2$ corresponds for each compound to one row of Table C Table 744
Compounds of the formula IF.9 in which $R^A$ is methoxy, $Y^1$ is chlorine, $Y^{1'}$ is methyl and the combination of the radicals $R^1$ and $R^2$ corresponds for each compound to one row of Table C Table 745
Compounds of the formula IF.9 in which $R^A$ is methoxy, $Y^1$ is methyl, $Y^{1'}$ is hydrogen and the combination of the radicals $R^1$ and $R^2$ corresponds for each compound to one row of Table C Table 746
Compounds of the formula IF.9 in which $R^A$ is methoxy, $Y^1$ is methyl, $Y^{1'}$ is chlorine and the combination of the radicals $R^1$ and $R^2$ corresponds for each compound to one row of Table C Table 747
Compounds of the formula IF.9 in which $R^A$ is methoxy, $Y^1$ is methyl, $Y^{1'}$ is methyl and the combination of the radicals $R^1$ and $R^2$ corresponds for each compound to one row of Table C Table 748
Compounds of the formula IF.10 in which $R^A$ is chlorine, $Y^1$ is chlorine, $Y^{1'}$ is hydrogen and the combination of the radicals $R^1$, $R^2$ and $R^3$ corresponds for each compound to one row of Table D

IF.10

Table 749
Compounds of the formula IF.10 in which $R^A$ is chlorine, $Y^1$ is chlorine, $Y^{1'}$ is chlorine and the combination of the radicals $R^1$, $R^2$ and $R^3$ corresponds for each compound to one row of Table D Table 750
Compounds of the formula IF.10 in which $R^A$ is chlorine, $Y^1$ is chlorine, $Y^{1'}$ is methyl and the combination of the radicals $R^1$, $R^2$ and $R^3$ corresponds for each compound to one row of Table D Table 751
Compounds of the formula IF.10 in which $R^A$ is chlorine, $Y^1$ is methyl, $Y^{1'}$ is hydrogen and the combination of the radicals $R^1$, $R^2$ and $R^3$ corresponds for each compound to one row of Table D Table 752
Compounds of the formula IF.10 in which $R^A$ is chlorine, $Y^1$ is methyl, $Y^{1'}$ is chlorine and the combination of the radicals $R^1$, $R^2$ and $R^3$ corresponds for each compound to one row of Table D Table 753
Compounds of the formula IF.10 in which $R^A$ is chlorine, $Y^1$ is methyl, $Y^{1'}$ is methyl and the combination of the radicals $R^1$, $R^2$ and $R^3$ corresponds for each compound to one row of Table D Table 754
Compounds of the formula IF.10 in which $R^A$ is methyl, $Y^1$ is chlorine, $Y^{1'}$ is hydrogen and the combination of the radicals $R^1$, $R^2$ and $R^3$ corresponds for each compound to one row of Table D Table 755
Compounds of the formula IF.10 in which $R^A$ is methyl, $Y^1$ is chlorine, $Y^{1'}$ is chlorine and the combination of the radicals $R^1$, $R^2$ and $R^3$ corresponds for each compound to one row of Table D Table 756
Compounds of the formula IF.10 in which $R^A$ is methyl, $Y^1$ is chlorine, $Y^{1'}$ is methyl and the combination of the radicals $R^1$, $R^2$ and $R^3$ corresponds for each compound to one row of Table D Table 757
Compounds of the formula IF.10 in which $R^A$ is methyl, $Y^1$ is methyl, $Y^{1'}$ is hydrogen and the combination of the radicals $R^1$, $R^2$ and $R^3$ corresponds for each compound to one row of Table D Table 758
Compounds of the formula IF.10 in which $R^A$ is methyl, $Y^1$ is methyl, $Y^{1'}$ is chlorine and the combination of the radicals $R^1$, $R^2$ and $R^3$ corresponds for each compound to one row of Table D Table 759
Compounds of the formula IF.10 in which $R^A$ is methyl, $Y^1$ is methyl, $Y^{1'}$ is methyl and the combination of the radicals $R^1$, $R^2$ and $R^3$ corresponds for each compound to one row of Table D Table 760
Compounds of the formula IF.10 in which $R^A$ is methoxy, $Y^1$ is chlorine, $Y^{1'}$ is hydrogen and the combination of the radicals $R^1$, $R^2$ and $R^3$ corresponds for each compound to one row of Table D Table 761
Compounds of the formula IF.10 in which $R^A$ is methoxy, $Y^{1'}$ is chlorine, $Y^{1'}$ is chlorine and the combination of the radicals $R^1$, $R^2$ and $R^3$ corresponds for each compound to one row of Table D Table 762
Compounds of the formula IF.10 in which $R^A$ is methoxy, $Y^1$ is chlorine, $Y^{1'}$ is methyl and the combination of the radicals $R^1$, $R^2$ and $R^3$ corresponds for each compound to one row of Table D Table 763
Compounds of the formula IF.10 in which $R^A$ is methoxy, $Y^1$ is methyl, $Y^{1'}$ is hydrogen and the combination of the radicals $R^1$, $R^2$ and $R^3$ corresponds for each compound to one row of Table D Table 764
Compounds of the formula IF.10 in which $R^A$ is methoxy, $Y^1$ is methyl, $Y^{1'}$ is chlorine and the combination of the radicals $R^1$, $R^2$ and $R^3$ corresponds for each compound to one row of Table D Table 765
Compounds of the formula IF.10 in which $R^A$ is methoxy, $Y^1$ is methyl, $Y^{1'}$ is methyl and the combination of the radicals $R^1$, $R^2$ and $R^3$ corresponds for each compound to one row of Table D Table 766
Compounds of the formula IF.11 in which $R^A$ is chlorine, $Y^1$ is chlorine, $Y^{1'}$ is hydrogen and the combination of the radicals R¹, R² and R³ corresponds for each compound to one row of Table D

IF.11

Table 767
Compounds of the formula IF.11 in which $R^A$ is chlorine, $Y^1$ is chlorine, $Y^{1'}$ is chlorine and the combination of the radicals R¹, R² and R³ corresponds for each compound to one row of Table D Table 768
Compounds of the formula IF.11 in which $R^A$ is chlorine, $Y^1$ is chlorine, $Y^{1'}$ is methyl and the combination of the radicals R¹, R² and R³ corresponds for each compound to one row of Table D Table 769
Compounds of the formula IF.11 in which $R^A$ is chlorine, $Y^1$ is methyl, $Y^{1'}$ is hydrogen and the combination of the radicals R¹, R² and R³ corresponds for each compound to one row of Table D Table 770
Compounds of the formula IF.11 in which $R^A$ is chlorine, $Y^1$ is methyl, $Y^{1'}$ is chlorine and the combination of the radicals R¹, R² and R³ corresponds for each compound to one row of Table D Table 771
Compounds of the formula IF.11 in which $R^A$ is chlorine, $Y^1$ is methyl, $Y^{1'}$ is methyl and the combination of the radicals R¹, R² and R³ corresponds for each compound to one row of Table D Table 772
Compounds of the formula IF.11 in which $R^A$ is methyl, $Y^1$ is chlorine, $Y^{1'}$ is hydrogen and the combination of the radicals R¹, R² and R³ corresponds for each compound to one row of Table D Table 773
Compounds of the formula IF.11 in which $R^A$ is methyl, $Y^1$ is chlorine, $Y^{1'}$ is chlorine and the combination of the radicals R¹, R² and R³ corresponds for each compound to one row of Table D Table 774
Compounds of the formula IF.11 in which $R^A$ is methyl, $Y^1$ is chlorine, $Y^{1'}$ is methyl and the combination of the radicals R¹, R² and R³ corresponds for each compound to one row of Table D Table 775
Compounds of the formula IF.11 in which $R^A$ is methyl, $Y^1$ is methyl, $Y^{1'}$ is hydrogen and the combination of the radicals R¹, R² and R³ corresponds for each compound to one row of Table D Table 776
Compounds of the formula IF.11 in which $R^A$ is methyl, $Y^1$ is methyl, $Y^{1'}$ is chlorine and the combination of the radicals R¹, R² and R³ corresponds for each compound to one row of Table D Table 777
Compounds of the formula IF.11 in which $R^A$ is methyl, $Y^1$ is methyl, $Y^{1'}$ is methyl and the combination of the radicals R¹, R² and R³ corresponds for each compound to one row of Table D Table 778
Compounds of the formula IF.11 in which $R^A$ is methoxy, $Y^1$ is chlorine, $Y^{1'}$ is hydrogen and the combination of the radicals R¹, R² and R³ corresponds for each compound to one row of Table D Table 779
Compounds of the formula IF.11 in which $R^A$ is methoxy, $Y^1$ is chlorine, $Y^{1'}$ is chlorine and the combination of the radicals R¹, R² and R³ corresponds for each compound to one row of Table D Table 780
Compounds of the formula IF.11 in which $R^A$ is methoxy, $Y^1$ is chlorine, $Y^{1'}$ is methyl and the combination of the radicals R¹, R² and R³ corresponds for each compound to one row of Table D Table 781
Compounds of the formula IF.11 in which $R^A$ is methoxy, $Y^1$ is methyl, $Y^{1'}$ is hydrogen and the combination of the radicals R¹, R² and R³ corresponds for each compound to one row of Table D Table 782
Compounds of the formula IF.11 in which $R^A$ is methoxy, $Y^1$ is methyl, $Y^{1'}$ is chlorine and the combination of the radicals R¹, R² and R³ corresponds for each compound to one row of Table D Table 783
Compounds of the formula IF.11 in which $R^A$ is methoxy, $Y^1$ is methyl, $Y^{1'}$ is methyl and the combination of the radicals R¹, R² and R³ corresponds for each compound to one row of Table D Table 784
Compounds of the formula IF.12 in which $R^A$ is chlorine, $Y^1$ is chlorine, $Y^{1'}$ is hydrogen and the combination of the radicals R¹, R² and R³ corresponds for each compound to one row of Table A

IF.12

Table 785
Compounds of the formula IF.12 in which $R^A$ is chlorine, $Y^1$ is chlorine, $Y^{1'}$ is chlorine and the combination of the radicals R¹, R² and R³ corresponds for each compound to one row of Table A Table 786
Compounds of the formula IF.12 in which $R^A$ is chlorine, $Y^1$ is chlorine, $Y^{1'}$ is methyl and the combination of the radicals R¹, R² and R³ corresponds for each compound to one row of Table A Table 787
Compounds of the formula IF.12 in which $R^A$ is chlorine, $Y^1$ is methyl, $Y^{1'}$ is hydrogen and the combination of the radicals R¹, R² and R³ corresponds for each compound to one row of Table A Table 788
Compounds of the formula IF.12 in which $R^A$ is chlorine, $Y^1$ is methyl, $Y^{1'}$ is chlorine and the combination of the radicals $R^1$, $R^2$ and $R^3$ corresponds for each compound to one row of Table A Table 789
Compounds of the formula IF.12 in which $R^A$ is chlorine, $Y^1$ is methyl, $Y^{1'}$ is methyl and the combination of the radicals $R^1$, $R^2$ and $R^3$ corresponds for each compound to one row of Table A Table 790
Compounds of the formula IF.12 in which $R^A$ is methyl, $Y^1$ is chlorine, $Y^{1'}$ is hydrogen and the combination of the radicals $R^1$, $R^2$ and $R^3$ corresponds for each compound to one row of Table A Table 791
Compounds of the formula IF.12 in which $R^A$ is methyl, $Y^1$ is chlorine, $Y^{1'}$ is chlorine and the combination of the radicals $R^1$, $R^2$ and $R^3$ corresponds for each compound to one row of Table A Table 792
Compounds of the formula IF.12 in which $R^A$ is methyl, $Y^1$ is chlorine, $Y^{1'}$ is methyl and the combination of the radicals $R^1$, $R^2$ and $R^3$ corresponds for each compound to one row of Table A Table 793
Compounds of the formula IF.12 in which $R^A$ is methyl, $Y^1$ is methyl, $Y^{1'}$ is hydrogen and the combination of the radicals $R^1$, $R^2$ and $R^3$ corresponds for each compound to one row of Table A Table 794
Compounds of the formula IF.12 in which $R^A$ is methyl, $Y^1$ is methyl, $Y^{1'}$ is chlorine and the combination of the radicals $R^1$, $R^2$ and $R^3$ corresponds for each compound to one row of Table A Table 795
Compounds of the formula IF.12 in which $R^A$ is methyl, $Y^1$ is methyl, $Y^{1'}$ is methyl and the combination of the radicals $R^1$, $R^2$ and $R^3$ corresponds for each compound to one row of Table A Table 796
Compounds of the formula IF.12 in which $R^A$ is methoxy, $Y^1$ is chlorine, $Y^{1'}$ is hydrogen and the combination of the radicals $R^1$, $R^2$ and $R^3$ corresponds for each compound to one row of Table A Table 797
Compounds of the formula IF.12 in which $R^A$ is methoxy, $Y^1$ is chlorine, $Y^{1'}$ is chlorine and the combination of the radicals $R^1$, $R^2$ and $R^3$ corresponds for each compound to one row of Table A Table 798
Compounds of the formula IF.12 in which $R^A$ is methoxy, $Y^1$ is chlorine, $Y^{1'}$ is methyl and the combination of the radicals $R^1$, $R^2$ and $R^3$ corresponds for each compound to one row of Table A Table 799
Compounds of the formula IF.12 in which $R^A$ is methoxy, $Y^1$ is methyl, $Y^{1'}$ is hydrogen and the combination of the radicals $R^1$, $R^2$ and $R^3$ corresponds for each compound to one row of Table A Table 800
Compounds of the formula IF.12 in which $R^A$ is methoxy, $Y^1$ is methyl, $Y^{1'}$ is chlorine and the combination of the radicals $R^1$, $R^2$ and $R^3$ corresponds for each compound to one row of Table A Table 801
Compounds of the formula IF.12 in which $R^A$ is methoxy, $Y^1$ is methyl, $Y^{1'}$ is methyl and the combination of the radicals $R^1$, $R^2$ and $R^3$ corresponds for each compound to one row of Table A Table 802
Compounds of the formula IF.13 in which $R^A$ is chlorine, $Y^1$ is chlorine, $Y^{1'}$ is hydrogen and the combination of the radicals $R^1$, $R^2$ and $R^3$ corresponds for each compound to one row of Table A

IF.13

Table 803
Compounds of the formula IF.13 in which $R^A$ is chlorine, $Y^1$ is chlorine, $Y^{1'}$ is chlorine and the combination of the radicals $R^1$, $R^2$ and $R^3$ corresponds for each compound to one row of Table A Table 804
Compounds of the formula IF.13 in which $R^A$ is chlorine, $Y^1$ is chlorine, $Y^{1'}$ is methyl and the combination of the radicals $R^1$, $R^2$ and $R^3$ corresponds for each compound to one row of Table A Table 805
Compounds of the formula IF.13 in which $R^A$ is chlorine, $Y^1$ is methyl, $Y^{1'}$ is hydrogen and the combination of the radicals $R^1$, $R^2$ and $R^3$ corresponds for each compound to one row of Table A Table 806
Compounds of the formula IF.13 in which $R^A$ is chlorine, $Y^1$ is methyl, $Y^{1'}$ is chlorine and the combination of the radicals $R^1$, $R^2$ and $R^3$ corresponds for each compound to one row of Table A Table 807
Compounds of the formula IF.13 in which $R^A$ is chlorine, $Y^1$ is methyl, $Y^{1'}$ is methyl and the combination of the radicals $R^1$, $R^2$ and $R^3$ corresponds for each compound to one row of Table A Table 808
Compounds of the formula IF.13 in which $R^A$ is methyl, $Y^1$ is chlorine, $Y^{1'}$ is hydrogen and the combination of the radicals $R^1$, $R^2$ and $R^3$ corresponds for each compound to one row of Table A Table 809
Compounds of the formula IF.13 in which $R^A$ is methyl, $Y^1$ is chlorine, $Y^{1'}$ is chlorine and the combination of the radicals $R^1$, $R^2$ and $R^3$ corresponds for each compound to one row of Table A Table 810
Compounds of the formula IF.13 in which $R^A$ is methyl, $Y^1$ is chlorine, $Y^{1'}$ is methyl and the combination of the radicals $R^1$, $R^2$ and $R^3$ corresponds for each compound to one row of Table A Table 811
Compounds of the formula IF.13 in which $R^A$ is methyl, $Y^1$ is methyl, $Y^{1'}$ is hydrogen and the combination of the radicals $R^1$, $R^2$ and $R^3$ corresponds for each compound to one row of Table A Table 812
Compounds of the formula IF.13 in which $R^A$ is methyl, $Y^1$ is methyl, $Y^{1'}$ is chlorine and the combination of the radicals $R^1$, $R^2$ and $R^3$ corresponds for each compound to one row of Table A Table 813
Compounds of the formula IF.13 in which $R^A$ is methyl, $Y^1$ is methyl, $Y^{1'}$ is methyl and the combination of the radicals $R^1$, $R^2$ and $R^3$ corresponds for each compound to one row of Table A Table 814
Compounds of the formula IF.13 in which $R^A$ is methoxy, $Y^1$ is chlorine, $Y^{1'}$ is hydrogen and the combination of the radicals $R^1$, $R^2$ and $R^3$ corresponds for each compound to one row of Table A Table 815
Compounds of the formula IF.13 in which $R^A$ is methoxy, $Y^1$ is chlorine, $Y^{1'}$ is chlorine and the combination of the radicals $R^1$, $R^2$ and $R^3$ corresponds for each compound to one row of Table A Table 816
Compounds of the formula IF.13 in which $R^A$ is methoxy, $Y^1$ is chlorine, $Y^{1'}$ is methyl and the combination of the radicals $R^1$, $R^2$ and $R^3$ corresponds for each compound to one row of Table A Table 817
Compounds of the formula IF.13 in which $R^A$ is methoxy, $Y^1$ is methyl, $Y^{1'}$ is hydrogen and the combination of the radicals $R^1$, $R^2$ and $R^3$ corresponds for each compound to one row of Table A Table 818
Compounds of the formula IF.13 in which $R^A$ is methoxy, $Y^1$ is methyl, $Y^{1'}$ is chlorine and the combination of the radicals $R^1$, $R^2$ and $R^3$ corresponds for each compound to one row of Table A Table 819
Compounds of the formula IF.13 in which $R^A$ is methoxy, $Y^1$ is methyl, $Y^{1'}$ is methyl and the combination of the radicals $R^1$, $R^2$ and $R^3$ corresponds for each compound to one row of Table A Table 820
Compounds of the formula IG.1 in which $R^A$ is chlorine, $Y^1$ is chlorine, $Y^{1'}$ is hydrogen and the combination of the radicals $R^1$, $R^2$ and $R^3$ corresponds for each compound to one row of Table A

IG.1

Table 821
Compounds of the formula IG.1 in which $R^A$ is chlorine, $Y^1$ is chlorine, $Y^{1'}$ is chlorine and the combination of the radicals $R^1$, $R^2$ and $R^3$ corresponds for each compound to one row of Table A Table 822
Compounds of the formula IG.1 in which $R^A$ is chlorine, $Y^1$ is chlorine, $Y^{1'}$ is methyl and the combination of the radicals $R^1$, $R^2$ and $R^3$ corresponds for each compound to one row of Table A Table 823
Compounds of the formula IG.1 in which $R^A$ is chlorine, $Y^1$ is methyl, $Y^{1'}$ is hydrogen and the combination of the radicals $R^1$, $R^2$ and $R^3$ corresponds for each compound to one row of Table A Table 824
Compounds of the formula IG.1 in which $R^A$ is chlorine, $Y^1$ is methyl, $Y^{1'}$ is chlorine and the combination of the radicals $R^1$, $R^2$ and $R^3$ corresponds for each compound to one row of Table A Table 825
Compounds of the formula IG.1 in which $R^A$ is chlorine, $Y^1$ is methyl, $Y^{1'}$ is methyl and the combination of the radicals $R^1$, $R^2$ and $R^3$ corresponds for each compound to one row of Table A Table 826
Compounds of the formula IG.1 in which $R^A$ is methyl, $Y^1$ is chlorine, $Y^{1'}$ is hydrogen and the combination of the radicals $R^1$, $R^2$ and $R^3$ corresponds for each compound to one row of Table A Table 827
Compounds of the formula IG.1 in which $R^A$ is methyl, $Y^1$ is chlorine, $Y^{1'}$ is chlorine and the combination of the radicals $R^1$, $R^2$ and $R^3$ corresponds for each compound to one row of Table A Table 828
Compounds of the formula IG.1 in which $R^A$ is methyl, $Y^1$ is chlorine, $Y^{1'}$ is methyl and the combination of the radicals $R^1$, $R^2$ and $R^3$ corresponds for each compound to one row of Table A Table 829
Compounds of the formula IG.1 in which $R^A$ is methyl, $Y^1$ is methyl, $Y^{1'}$ is hydrogen and the combination of the radicals $R^1$, $R^2$ and $R^3$ corresponds for each compound to one row of Table A Table 830
Compounds of the formula IG.1 in which $R^A$ is methyl, $Y^1$ is methyl, $Y^{1'}$ is chlorine and the combination of the radicals $R^1$, $R^2$ and $R^3$ corresponds for each compound to one row of Table A Table 831
Compounds of the formula IG.1 in which $R^A$ is methyl, $Y^1$ is methyl, $Y^{1'}$ is methyl and the combination of the radicals $R^1$, $R^2$ and $R^3$ corresponds for each compound to one row of Table A Table 832
Compounds of the formula IG.1 in which $R^A$ is methoxy, $Y^1$ is chlorine, $Y^{1'}$ is hydrogen and the combination of the radicals $R^1$, $R^2$ and $R^3$ corresponds for each compound to one row of Table A Table 833
Compounds of the formula IG.1 in which $R^A$ is methoxy, $Y^1$ is chlorine, $Y^{1'}$ is chlorine and the combination of the radicals $R^1$, $R^2$ and $R^3$ corresponds for each compound to one row of Table A Table 834
Compounds of the formula IG.1 in which $R^A$ is methoxy, $Y^1$ is chlorine, $Y^{1'}$ is methyl and the combination of the radicals $R^1$, $R^2$ and $R^3$ corresponds for each compound to one row of Table A Table 835
Compounds of the formula IG.1 in which $R^A$ is methoxy, $Y^1$ is methyl, $Y^{1'}$ is hydrogen and the combination of the radicals $R^1$, $R^2$ and $R^3$ corresponds for each compound to one row of Table A Table 836
Compounds of the formula IG.1 in which $R^A$ is methoxy, $Y^1$ is methyl, $Y^{1'}$ is chlorine and the combination of the radicals $R^1$, $R^2$ and $R^3$ corresponds for each compound to one row of Table A Table 837
Compounds of the formula IG.1 in which $R^A$ is methoxy, $Y^1$ is methyl, $Y^{1'}$ is methyl and the combination of the radicals $R^1$, $R^2$ and $R^3$ corresponds for each compound to one row of Table A Table 838
Compounds of the formula IG.3 in which $R^A$ is chlorine, $Y^1$ is chlorine, $Y^{1'}$ is hydrogen and the combination of the radicals $R^2$ and $R^3$ corresponds for each compound to one row of Table B

IG.3

Table 839
Compounds of the formula IG.3 in which $R^A$ is chlorine, $Y^1$ is chlorine, $Y^{1'}$ is chlorine and the combination of the radicals $R^2$ and $R^3$ corresponds for each compound to one row of Table B Table 840
Compounds of the formula IG.3 in which $R^A$ is chlorine, $Y^1$ is chlorine, $Y^{1'}$ is methyl and the combination of the radicals $R^2$ and $R^3$ corresponds for each compound to one row of Table B Table 841
Compounds of the formula IG.3 in which $R^A$ is chlorine, $Y^1$ is methyl, $Y^{1'}$ is hydrogen and the combination of the radicals $R^2$ and $R^3$ corresponds for each compound to one row of Table B Table 842
Compounds of the formula IG.3 in which $R^A$ is chlorine, $Y^1$ is methyl, $Y^{1'}$ is chlorine and the combination of the radicals $R^2$ and $R^3$ corresponds for each compound to one row of Table B Table 843
Compounds of the formula IG.3 in which $R^A$ is chlorine, $Y^1$ is methyl, $Y^{1'}$ is methyl and the combination of the radicals $R^2$ and $R^3$ corresponds for each compound to one row of Table B Table 844
Compounds of the formula IG.3 in which $R^A$ is methyl, $Y^1$ is chlorine, $Y^{1'}$ is hydrogen and the combination of the radicals $R^2$ and $R^3$ corresponds for each compound to one row of Table B Table 845
Compounds of the formula IG.3 in which $R^A$ is methyl, $Y^1$ is chlorine, $Y^{1'}$ is chlorine and the combination of the radicals $R^2$ and $R^3$ corresponds for each compound to one row of Table B Table 846
Compounds of the formula IG.3 in which $R^A$ is methyl, $Y^1$ is chlorine, $Y^{1'}$ is methyl and the combination of the radicals $R^2$ and $R^3$ corresponds for each compound to one row of Table B Table 847
Compounds of the formula IG.3 in which $R^A$ is methyl, $Y^1$ is methyl, $Y^{1'}$ is hydrogen and the combination of the radicals $R^2$ and $R^3$ corresponds for each compound to one row of Table B Table 848
Compounds of the formula IG.3 in which $R^A$ is methyl, $Y^1$ is methyl, $Y^{1'}$ is chlorine and the combination of the radicals $R^2$ and $R^3$ corresponds for each compound to one row of Table B Table 849
Compounds of the formula IG.3 in which $R^A$ is methyl, $Y^1$ is methyl, $Y^{1'}$ is methyl and the combination of the radicals $R^2$ and $R^3$ corresponds for each compound to one row of Table B Table 850
Compounds of the formula IG.3 in which $R^A$ is methoxy, $Y^1$ is chlorine, $Y^{1'}$ is hydrogen and the combination of the radicals $R^2$ and $R^3$ corresponds for each compound to one row of Table B Table 851
Compounds of the formula IG.3 in which $R^A$ is methoxy, $Y^1$ is chlorine, $Y^{1'}$ is chlorine and the combination of the radicals $R^2$ and $R^3$ corresponds for each compound to one row of Table B Table 852
Compounds of the formula IG.3 in which $R^A$ is methoxy, $Y^1$ is chlorine, $Y^{1'}$ is methyl and the combination of the radicals $R^2$ and $R^3$ corresponds for each compound to one row of Table B Table 853
Compounds of the formula IG.3 in which $R^A$ is methoxy, $Y^1$ is methyl, $Y^{1'}$ is hydrogen and the combination of the radicals $R^2$ and $R^3$ corresponds for each compound to one row of Table B Table 854
Compounds of the formula IG.3 in which $R^A$ is methoxy, $Y^1$ is methyl, $Y^{1'}$ is chlorine and the combination of the radicals $R^2$ and $R^3$ corresponds for each compound to one row of Table B Table 855
Compounds of the formula IG.3 in which $R^A$ is methoxy, $Y^1$ is methyl, $Y^{1'}$ is methyl and the combination of the radicals $R^2$ and $R^3$ corresponds for each compound to one row of Table B Table 856
Compounds of the formula IG.4 in which $R^A$ is chlorine, $Y^1$ is chlorine, $Y^{1'}$ is hydrogen and the combination of the radicals $R^1$, $R^2$ and $R^3$ corresponds for each compound to one row of Table A

IG.4

Table 857
Compounds of the formula IG.4 in which $R^A$ is chlorine, $Y^1$ is chlorine, $Y^{1'}$ is chlorine and the combination of the radicals $R^1$, $R^2$ and $R^3$ corresponds for each compound to one row of Table A Table 858
Compounds of the formula IG.4 in which $R^A$ is chlorine, $Y^1$ is chlorine, $Y^{1'}$ is methyl and the combination of the radicals $R^1$, $R^2$ and $R^3$ corresponds for each compound to one row of Table A Table 859
Compounds of the formula IG.4 in which $R^A$ is chlorine, $Y^1$ is methyl, $Y^{1'}$ is hydrogen and the combination of the radicals $R^1$, $R^2$ and $R^3$ corresponds for each compound to one row of Table A Table 860
Compounds of the formula IG.4 in which $R^A$ is chlorine, $Y^1$ is methyl, $Y^{1'}$ is chlorine and the combination of the radicals $R^1$, $R^2$ and $R^3$ corresponds for each compound to one row of Table A Table 861
Compounds of the formula IG.4 in which $R^A$ is chlorine, $Y^1$ is methyl, $Y^{1'}$ is methyl and the combination of the radicals $R^1$, $R^2$ and $R^3$ corresponds for each compound to one row of Table A Table 862
Compounds of the formula IG.4 in which $R^A$ is methyl, $Y^1$ is chlorine, $Y^{1'}$ is hydrogen and the combination of the radicals $R^1$, $R^2$ and $R^3$ corresponds for each compound to one row of Table A Table 863
Compounds of the formula IG.4 in which $R^A$ is methyl, $Y^1$ is chlorine, $Y^{1'}$ is chlorine and the combination of the radicals $R^1$, $R^2$ and $R^3$ corresponds for each compound to one row of Table A Table 864
Compounds of the formula IG.4 in which $R^A$ is methyl, $Y^1$ is chlorine, $Y^{1'}$ is methyl and the combination of the radicals $R^1$, $R^2$ and $R^3$ corresponds for each compound to one row of Table A Table 865
Compounds of the formula IG.4 in which $R^A$ is methyl, $Y^1$ is methyl, $Y^{1'}$ is hydrogen and the combination of the radicals $R^1$, $R^2$ and $R^3$ corresponds for each compound to one row of Table A Table 866
Compounds of the formula IG.4 in which $R^A$ is methyl, $Y^1$ is methyl, $Y^{1'}$ is chlorine and the combination of the radicals $R^1$, $R^2$ and $R^3$ corresponds for each compound to one row of Table A Table 867
Compounds of the formula IG.4 in which $R^A$ is methyl, $Y^1$ is methyl, $Y^{1'}$ is methyl and the combination of the radicals $R^1$, $R^2$ and $R^3$ corresponds for each compound to one row of Table A Table 868
Compounds of the formula IG.4 in which $R^A$ is methoxy, $Y^1$ is chlorine, $Y^{1'}$ is hydrogen and the combination of the radicals $R^1$, $R^2$ and $R^3$ corresponds for each compound to one row of Table A Table 869
Compounds of the formula IG.4 in which $R^A$ is methoxy, $Y^1$ is chlorine, $Y^{1'}$ is chlorine and the combination of the radicals $R^1$, $R^2$ and $R^3$ corresponds for each compound to one row of Table A Table 870
Compounds of the formula IG.4 in which $R^A$ is methoxy, $Y^1$ is chlorine, $Y^{1'}$ is methyl and the combination of the radicals $R^1$, $R^2$ and $R^3$ corresponds for each compound to one row of Table A Table 871
Compounds of the formula IG.4 in which $R^A$ is methoxy, $Y^1$ is methyl, $Y^{1'}$ is hydrogen and the combination of the radicals $R^1$, $R^2$ and $R^3$ corresponds for each compound to one row of Table A Table 872
Compounds of the formula IG.4 in which $R^A$ is methoxy, $Y^1$ is methyl, $Y^{1'}$ is chlorine and the combination of the radicals $R^1$, $R^2$ and $R^3$ corresponds for each compound to one row of Table A Table 873
Compounds of the formula IG.4 in which $R^A$ is methoxy, $Y^1$ is methyl, $Y^{1'}$ is methyl and the combination of the radicals $R^1$, $R^2$ and $R^3$ corresponds for each compound to one row of Table A Table 874
Compounds of the formula IG.5 in which $R^A$ is chlorine, $Y^1$ is chlorine, $Y^{1'}$ is hydrogen and the combination of the radicals $R^2$ and $R^3$ corresponds for each compound to one row of Table B

IG.5

Table 875
Compounds of the formula IG.5 in which $R^A$ is chlorine, $Y^1$ is chlorine, $Y^{1'}$ is chlorine and the combination of the radicals $R^2$ and $R^3$ corresponds for each compound to one row of Table B Table 876
Compounds of the formula IG.5 in which $R^A$ is chlorine, $Y^1$ is chlorine, $Y^{1'}$ is methyl and the combination of the radicals $R^2$ and $R^3$ corresponds for each compound to one row of Table B Table 877
Compounds of the formula IG.5 in which $R^A$ is chlorine, $Y^1$ is methyl, $Y^{1'}$ is hydrogen and the combination of the radicals $R^2$ and $R^3$ corresponds for each compound to one row of Table B Table 878
Compounds of the formula IG.5 in which $R^A$ is chlorine, $Y^1$ is methyl, $Y^{1'}$ is chlorine and the combination of the radicals $R^2$ and $R^3$ corresponds for each compound to one row of Table B Table 879
Compounds of the formula IG.5 in which $R^A$ is chlorine, $Y^1$ is methyl, $Y^{1'}$ is methyl and the combination of the radicals $R^2$ and $R^3$ corresponds for each compound to one row of Table B Table 880
Compounds of the formula IG.5 in which $R^A$ is methyl, $Y^1$ is chlorine, $Y^{1'}$ is hydrogen and the combination of the radicals $R^2$ and $R^3$ corresponds for each compound to one row of Table B Table 881
Compounds of the formula IG.5 in which $R^A$ is methyl, $Y^1$ is chlorine, $Y^{1'}$ is chlorine and the combination of the radicals $R^2$ and $R^3$ corresponds for each compound to one row of Table B Table 882
Compounds of the formula IG.5 in which $R^A$ is methyl, $Y^1$ is chlorine, $Y^{1'}$ is methyl and the combination of the radicals $R^2$ and $R^3$ corresponds for each compound to one row of Table B Table 883
Compounds of the formula IG.5 in which $R^A$ is methyl, $Y^1$ is methyl, $Y^{1'}$ is hydrogen and the combination of the radicals $R^2$ and $R^3$ corresponds for each compound to one row of Table B Table 884
Compounds of the formula IG.5 in which $R^A$ is methyl, $Y^1$ is methyl, $Y^{1'}$ is chlorine and the combination of the radicals $R^2$ and $R^3$ corresponds for each compound to one row of Table B Table 885
Compounds of the formula IG.5 in which $R^A$ is methyl, $Y^1$ is methyl, $Y^{1'}$ is methyl and the combination of the radicals $R^2$ and $R^3$ corresponds for each compound to one row of Table B Table 886
Compounds of the formula IG.5 in which $R^A$ is methoxy, $Y^1$ is chlorine, $Y^{1'}$ is hydrogen and the combination of the radicals $R^2$ and $R^3$ corresponds for each compound to one row of Table B Table 887
Compounds of the formula IG.5 in which $R^A$ is methoxy, $Y^1$ is chlorine, $Y^{1'}$ is chlorine and the combination of the radicals $R^2$ and $R^3$ corresponds for each compound to one row of Table B Table 888
Compounds of the formula IG.5 in which $R^A$ is methoxy, $Y^1$ is chlorine, $Y^{1'}$ is methyl and the combination of the radicals $R^2$ and $R^3$ corresponds for each compound to one row of Table B Table 889
Compounds of the formula IG.5 in which $R^A$ is methoxy, $Y^1$ is methyl, $Y^{1'}$ is hydrogen and the combination of the radicals $R^2$ and $R^3$ corresponds for each compound to one row of Table B Table 890
Compounds of the formula IG.5 in which $R^A$ is methoxy, $Y^1$ is methyl, $Y^{1'}$ is chlorine and the combination of the radicals $R^2$ and $R^3$ corresponds for each compound to one row of Table B Table 891
Compounds of the formula IG.5 in which $R^A$ is methoxy, $Y^1$ is methyl, $Y^{1'}$ is methyl and the combination of the radicals $R^2$ and $R^3$ corresponds for each compound to one row of Table B Table 892
Compounds of the formula IG.9 in which $R^A$ is chlorine, $Y^1$ is chlorine, $Y^{1'}$ is hydrogen and the combination of the radicals $R^1$ and $R^2$ corresponds for each compound to one row of Table C

IG.9

Table 893
Compounds of the formula IG.9 in which $R^A$ is chlorine, $Y^1$ is chlorine, $Y^{1'}$ is chlorine and the combination of the radicals $R^1$ and $R^2$ corresponds for each compound to one row of Table C Table 894
Compounds of the formula IG.9 in which $R^A$ is chlorine, $Y^1$ is chlorine, $Y^{1'}$ is methyl and the combination of the radicals $R^1$ and $R^2$ corresponds for each compound to one row of Table C Table 895
Compounds of the formula IG.9 in which $R^A$ is chlorine, $Y^1$ is methyl, $Y^{1'}$ is hydrogen and the combination of the radicals $R^1$ and $R^2$ corresponds for each compound to one row of Table C Table 896
Compounds of the formula IG.9 in which $R^A$ is chlorine, $Y^1$ is methyl, $Y^{1'}$ is chlorine and the combination of the radicals $R^1$ and $R^2$ corresponds for each compound to one row of Table C Table 897
Compounds of the formula IG.9 in which $R^A$ is chlorine, $Y^1$ is methyl, $Y^{1'}$ is methyl and the combination of the radicals $R^1$ and $R^2$ corresponds for each compound to one row of Table C Table 898
Compounds of the formula IG.9 in which $R^A$ is methyl, $Y^1$ is chlorine, $Y^{1'}$ is hydrogen and the combination of the radicals $R^1$ and $R^2$ corresponds for each compound to one row of Table C Table 899
Compounds of the formula IG.9 in which $R^A$ is methyl, $Y^1$ is chlorine, $Y^{1'}$ is chlorine and the combination of the radicals $R^1$ and $R^2$ corresponds for each compound to one row of Table C Table 900
Compounds of the formula IG.9 in which $R^A$ is methyl, $Y^1$ is chlorine, $Y^{1'}$ is methyl and the combination of the radicals $R^1$ and $R^2$ corresponds for each compound to one row of Table C Table 901
Compounds of the formula IG.9 in which $R^A$ is methyl, $Y^1$ is methyl, $Y^{1'}$ is hydrogen and the combination of the radicals $R^2$ and $R^3$ corresponds for each compound to one row of Table C Table 902
Compounds of the formula IG.9 in which $R^A$ is methyl, $Y^1$ is methyl, $Y^{1'}$ is chlorine and the combination of the radicals $R^2$ and $R^3$ corresponds for each compound to one row of Table C Table 903
Compounds of the formula IG.9 in which $R^A$ is methyl, $Y^1$ is methyl, $Y^{1'}$ is methyl and the combination of the radicals $R^1$ and $R^2$ corresponds for each compound to one row of Table C Table 904
Compounds of the formula IG.9 in which $R^A$ is methoxy, $Y^1$ is chlorine, $Y^{1'}$ is hydrogen and the combination of the radicals $R^1$ and $R^2$ corresponds for each compound to one row of Table C Table 905
Compounds of the formula IG.9 in which $R^A$ is methoxy, $Y^1$ is chlorine, $Y^{1'}$ is chlorine and the combination of the radicals $R^1$ and $R^2$ corresponds for each compound to one row of Table C Table 906
Compounds of the formula IG.9 in which $R^A$ is methoxy, $Y^1$ is chlorine, $Y^{1'}$ is methyl and the combination of the radicals $R^1$ and $R^2$ corresponds for each compound to one row of Table C Table 907
Compounds of the formula IG.9 in which $R^A$ is methoxy, $Y^1$ is methyl, $Y^{1'}$ is hydrogen and the combination of the radicals $R^1$ and $R^2$ corresponds for each compound to one row of Table C Table 908
Compounds of the formula IG.9 in which $R^A$ is methoxy, $Y^1$ is methyl, $Y^{1'}$ is chlorine and the combination of the radicals $R^1$ and $R^2$ corresponds for each compound to one row of Table C Table 909
Compounds of the formula IG.9 in which $R^A$ is methoxy, $Y^1$ is methyl, $Y^{1'}$ is methyl and the combination of the radicals R¹ and R² corresponds for each compound to one row of Table C Table 910
Compounds of the formula IG.10 in which $R^A$ is chlorine, $Y^1$ is chlorine, $Y^{1'}$ is hydrogen and the combination of the radicals $R^1$, $R^2$ and $R^3$ corresponds for each compound to one row of Table D

IG.10

Table 911
Compounds of the formula IG.10 in which $R^A$ is chlorine, $Y^1$ is chlorine, $Y^{1'}$ is chlorine and the combination of the radicals $R^1$, $R^2$ and $R^3$ corresponds for each compound to one row of Table D Table 912
Compounds of the formula IG.10 in which $R^A$ is chlorine, $Y^1$ is chlorine, $Y^{1'}$ is methyl and the combination of the radicals $R^1$, $R^2$ and $R^3$ corresponds for each compound to one row of Table D Table 913
Compounds of the formula IG.10 in which $R^A$ is chlorine, $Y^1$ is methyl, $Y^{1'}$ is hydrogen and the combination of the radicals $R^1$, $R^2$ and $R^3$ corresponds for each compound to one row of Table D Table 914
Compounds of the formula IG.10 in which $R^A$ is chlorine, $Y^1$ is methyl, $Y^{1'}$ is chlorine and the combination of the radicals $R^1$, $R^2$ and $R^3$ corresponds for each compound to one row of Table D Table 915
Compounds of the formula IG.10 in which $R^A$ is chlorine, $Y^1$ is methyl, $Y^{1'}$ is methyl and the combination of the radicals $R^1$, $R^2$ and $R^3$ corresponds for each compound to one row of Table D Table 916
Compounds of the formula IG.10 in which $R^A$ is methyl, $Y^1$ is chlorine, $Y^{1'}$ is hydrogen and the combination of the radicals $R^1$, $R^2$ and $R^3$ corresponds for each compound to one row of Table D Table 917
Compounds of the formula IG.10 in which $R^A$ is methyl, $Y^1$ is chlorine, $Y^{1'}$ is chlorine and the combination of the radicals $R^1$, $R^2$ and $R^3$ corresponds for each compound to one row of Table D Table 918
Compounds of the formula IG.10 in which $R^A$ is methyl, $Y^1$ is chlorine, $Y^{1'}$ is methyl and the combination of the radicals $R^1$, $R^2$ and $R^3$ corresponds for each compound to one row of Table D Table 919
Compounds of the formula IG.10 in which $R^A$ is methyl, $Y^1$ is methyl, $Y^{1'}$ is hydrogen and the combination of the radicals $R^1$, $R^2$ and $R^3$ corresponds for each compound to one row of Table D Table 920
Compounds of the formula IG.10 in which $R^A$ is methyl, $Y^1$ is methyl, $Y^{1'}$ is chlorine and the combination of the radicals $R^1$, $R^2$ and $R^3$ corresponds for each compound to one row of Table D Table 921
Compounds of the formula IG.10 in which $R^A$ is methyl, $Y^1$ is methyl, $Y^{1'}$ is methyl and the combination of the radicals $R^1$, $R^2$ and $R^3$ corresponds for each compound to one row of Table D Table 922
Compounds of the formula IG.10 in which $R^A$ is methoxy, $Y^1$ is chlorine, $Y^{1'}$ is hydrogen and the combination of the radicals $R^1$, $R^2$ and $R^3$ corresponds for each compound to one row of Table D Table 923
Compounds of the formula IG.10 in which $R^A$ is methoxy, $Y^1$ is chlorine, $Y^{1'}$ is chlorine and the combination of the radicals $R^1$, $R^2$ and $R^3$ corresponds for each compound to one row of Table D Table 924
Compounds of the formula IG.10 in which $R^A$ is methoxy, $Y^1$ is chlorine, $Y^{1'}$ is methyl and the combination of the radicals $R^1$, $R^2$ and $R^3$ corresponds for each compound to one row of Table D Table 925
Compounds of the formula IG.10 in which $R^A$ is methoxy, $Y^1$ is methyl, $Y^{1'}$ is hydrogen and the combination of the radicals $R^1$, $R^2$ and $R^3$ corresponds for each compound to one row of Table D Table 926
Compounds of the formula IG.10 in which $R^A$ is methoxy, $Y^1$ is methyl, $Y^{1'}$ is chlorine and the combination of the radicals $R^1$, $R^2$ and $R^3$ corresponds for each compound to one row of Table D Table 927
Compounds of the formula IG.10 in which $R^A$ is methoxy, $Y^1$ is methyl, $Y^{1'}$ is methyl and the combination of the radicals $R^1$, $R^2$ and $R^3$ corresponds for each compound to one row of Table D Table 928
Compounds of the formula IH.1 in which $Y^1$ is chlorine, $Y^{1'}$ is hydrogen and the combination of the radicals $R^1$, $R^2$ and $R^3$ corresponds for each compound to one row of Table A

IH.1

Table 929
Compounds of the formula IH.1 in which $Y^1$ is chlorine, $Y^{1'}$ is chlorine and the combination of the radicals $R^1$, $R^2$ and $R^3$ corresponds for each compound to one row of Table A Table 930
Compounds of the formula IH.1 in which $Y^1$ is chlorine, $Y^{1'}$ is methyl and the combination of the radicals $R^1$, $R^2$ and $R^3$ corresponds for each compound to one row of Table A Table 931
Compounds of the formula IH.1 in which $Y^1$ is methyl, $Y^{1'}$ is hydrogen and the combination of the radicals $R^1$, $R^2$ and $R^3$ corresponds for each compound to one row of Table A Table 932

Compounds of the formula IH.1 in which $Y^1$ is methyl, $Y^{1'}$ is chlorine and the combination of the radicals $R^1$, $R^2$ and $R^3$ corresponds for each compound to one row of Table A Table 933

Compounds of the formula IH.1 in which $Y^1$ is methyl, $Y^{1'}$ is methyl and the combination of the radicals $R^1$, $R^2$ and $R^3$ corresponds for each compound to one row of Table A Table 934

Compounds of the formula IH.2 in which $Y^1$ is chlorine, $Y^{1'}$ is hydrogen and the combination of the radicals $R^1$, $R^2$ and $R^3$ corresponds for each compound to one row of Table A

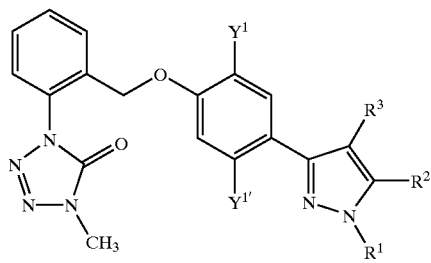

IH.2

Table 935

Compounds of the formula IH.2 in which $Y^1$ is chlorine, $Y^{1'}$ is chlorine and the combination of the radicals $R^1$, $R^2$ and $R^3$ corresponds for each compound to one row of Table A Table 936

Compounds of the formula IH.2 in which $Y^1$ is chlorine, $Y^{1'}$ is methyl and the combination of the radicals $R^1$, $R^2$ and $R^3$ corresponds for each compound to one row of Table A Table 937

Compounds of the formula IH.2 in which $Y^1$ is methyl, $Y^{1'}$ is hydrogen and the combination of the radicals $R^1$, $R^2$ and $R^3$ corresponds for each compound to one row of Table A Table 938

Compounds of the formula IH.2 in which $Y^1$ is methyl, $Y^{1'}$ is chlorine and the combination of the radicals $R^1$, $R^2$ and $R^3$ corresponds for each compound to one row of Table A Table 939

Compounds of the formula IH.2 in which $Y^1$ is methyl, $Y^{1'}$ is methyl and the combination of the radicals $R^1$, $R^2$ and $R^3$ corresponds for each compound to one row of Table A Table 940

Compounds of the formula IH.3 in which $Y^1$ is chlorine, $Y^{1'}$ is hydrogen and the combination of the radicals $R^2$ and $R^3$ corresponds for each compound to one row of Table B

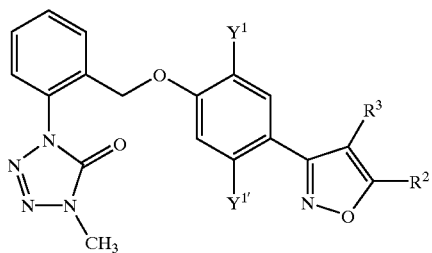

IH.3

Table 941

Compounds of the formula IH.3 in which $Y^1$ is chlorine, $Y^{1'}$ is chlorine and the combination of the radicals $R^2$ and $R^3$ corresponds for each compound to one row of Table B Table 942

Compounds of the formula IH.3 in which $Y^1$ is chlorine, $Y^{1'}$ is methyl and the combination of the radicals $R^2$ and $R^3$ corresponds for each compound to one row of Table B Table 943

Compounds of the formula IH.3 in which $Y^1$ is methyl, $Y^{1'}$ is hydrogen and the combination of the radicals $R^2$ and $R^3$ corresponds for each compound to one row of Table B Table 944

Compounds of the formula IH.3 in which $Y^1$ is methyl, $Y^{1'}$ is chlorine and the combination of the radicals $R^2$ and $R^3$ corresponds for each compound to one row of Table B Table 945

Compounds of the formula IH.3 in which $Y^1$ is methyl, $Y^{1'}$ is methyl and the combination of the radicals $R^2$ and $R^3$ corresponds for each compound to one row of Table B Table 946

Compounds of the formula IH.4 in which $Y^1$ is chlorine, $Y^{1'}$ is hydrogen and the combination of the radicals $R^1$, $R^2$ and $R^3$ corresponds for each compound to one row of Table A

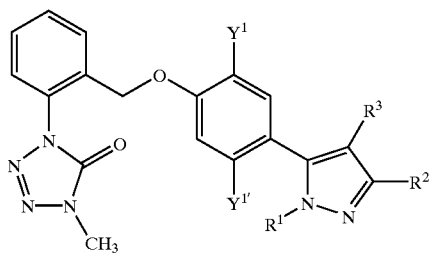

IH.4

Table 947

Compounds of the formula IH.4 in which $Y^1$ is chlorine, $Y^{1'}$ is chlorine and the combination of the radicals $R^1$, $R^2$ and $R^3$ corresponds for each compound to one row of Table A Table 948

Compounds of the formula IH.4 in which $Y^1$ is chlorine, $Y^{1'}$ is methyl and the combination of the radicals $R^1$, $R^2$ and $R^3$ corresponds for each compound to one row of Table A Table 949

Compounds of the formula IH.4 in which $Y^1$ is methyl, $Y^{1'}$ is hydrogen and the combination of the radicals $R^1$, $R^2$ and $R^3$ corresponds for each compound to one row of Table A Table 950

Compounds of the formula IH.4 in which $Y^1$ is methyl, $Y^{1'}$ is chlorine and the combination of the radicals $R^1$, $R^2$ and $R^3$ corresponds for each compound to one row of Table A Table 951
Compounds of the formula IH.4 in which $Y^1$ is methyl, $Y^{1'}$ is methyl and the combination of the radicals $R^1$, $R^2$ and $R^3$ corresponds for each compound to one row of Table A Table 952
Compounds of the formula IH.5 in which $Y^1$ is chlorine, $Y^{1'}$ is hydrogen and the combination of the radicals $R^2$ and $R^3$ corresponds for each compound to one row of Table B

IH.5

Table 953
Compounds of the formula IH.5 in which $Y^1$ is chlorine, $Y^{1'}$ is chlorine and the combination of the radicals $R^2$ and $R^3$ corresponds for each compound to one row of Table B Table 954
Compounds of the formula IH.5 in which $Y^1$ is chlorine, $Y^{1'}$ is methyl and the combination of the radicals $R^2$ and $R^3$ corresponds for each compound to one row of Table B Table 955
Compounds of the formula IH.5 in which $Y^1$ is methyl, $Y^{1'}$ is hydrogen and the combination of the radicals $R^2$ and $R^3$ corresponds for each compound to one row of Table B Table 956
Compounds of the formula IH.5 in which $Y^1$ is methyl, $Y^{1'}$ is chlorine and the combination of the radicals $R^2$ and $R^3$ corresponds for each compound to one row of Table B Table 957
Compounds of the formula IH.5 in which $Y^1$ is methyl, $Y^{1'}$ is methyl and the combination of the radicals $R^2$ and $R^3$ corresponds for each compound to one row of Table B Table 958
Compounds of the formula IH.6 in which $Y^1$ is chlorine, $Y^{1'}$ is hydrogen and the combination of the radicals $R^1$ and $R^2$ corresponds for each compound to one row of Table C

IH.6

Table 959
Compounds of the formula IH.6 in which $Y^1$ is chlorine, $Y^{1'}$ is chlorine and the combination of the radicals $R^1$ and $R^2$ corresponds for each compound to one row of Table C Table 960
Compounds of the formula IH.6 in which $Y^1$ is chlorine, $Y^{1'}$ is methyl and the combination of the radicals $R^1$ and $R^2$ corresponds for each compound to one row of Table C Table 961
Compounds of the formula IH.6 in which $Y^1$ is methyl, $Y^{1'}$ is hydrogen and the combination of the radicals $R^1$ and $R^2$ corresponds for each compound to one row of Table C Table 962
Compounds of the formula IH.6 in which $Y^1$ is methyl, $Y^{1'}$ is chlorine and the combination of the radicals $R^1$ and $R^2$ corresponds for each compound to one row of Table C Table 963
Compounds of the formula IH.6 in which $Y^1$ is methyl, $Y^{1'}$ is methyl and the combination of the radicals $R^1$ and $R^2$ corresponds for each compound to one row of Table C Table 964
Compounds of the formula IH.7 in which $Y^1$ is chlorine, $Y^{1'}$ is hydrogen and the combination of the radicals $R^2$ and $R^3$ corresponds for each compound to one row of Table B

IH.7

Table 965
Compounds of the formula IH.7 in which $Y^1$ is chlorine, $Y^{1'}$ is chlorine and the combination of the radicals $R^2$ and $R^3$ corresponds for each compound to one row of Table B Table 966
Compounds of the formula IH.7 in which $Y^1$ is chlorine, $Y^{1'}$ is methyl and the combination of the radicals $R^2$ and $R^3$ corresponds for each compound to one row of Table B Table 967
Compounds of the formula IH.7 in which $Y^1$ is methyl, $Y^{1'}$ is hydrogen and the combination of the radicals $R^2$ and $R^3$ corresponds for each compound to one row of Table B Table 968
Compounds of the formula IH.7 in which $Y^1$ is methyl, $Y^{1'}$ is chlorine and the combination of the radicals $R^2$ and $R^3$ corresponds for each compound to one row of Table B Table 969
Compounds of the formula IH.7 in which $Y^1$ is methyl, $Y^{1'}$ is methyl and the combination of the radicals $R^2$ and $R^3$ corresponds for each compound to one row of Table B Table 970
Compounds of the formula IH.8 in which $Y^1$ is chlorine, $Y^{1'}$ is hydrogen and the combination of the radicals $R^2$ and $R^3$ corresponds for each compound to one row of Table B

IH.8

Table 971
Compounds of the formula IH.8 in which $Y^1$ is chlorine, $Y^{1'}$ is chlorine and the combination of the radicals $R^2$ and $R^3$ corresponds for each compound to one row of Table B Table 972
Compounds of the formula IH.8 in which $Y^1$ is chlorine, $Y^{1'}$ is methyl and the combination of the radicals $R^2$ and $R^3$ corresponds for each compound to one row of Table B

Table 973

Compounds of the formula IH.8 in which $Y^1$ is methyl, $Y^{1'}$ is hydrogen and the combination of the radicals $R^2$ and $R^3$ corresponds for each compound to one row of Table B

Table 974

Compounds of the formula IH.8 in which $Y^1$ is methyl, $Y^{1'}$ is chlorine and the combination of the radicals $R^2$ and $R^3$ corresponds for each compound to one row of Table B

Table 975

Compounds of the formula IH.8 in which $Y^1$ is methyl, $Y^{1'}$ is methyl and the combination of the radicals $R^2$ and $R^3$ corresponds for each compound to one row of Table B

Table 976

Compounds of the formula IH.9 in which $Y^1$ is chlorine, $Y^{1'}$ is hydrogen and the combination of the radicals $R^1$ and $R^2$ corresponds for each compound to one row of Table C

IH.9

Table 977

Compounds of the formula IH.9 in which $Y^1$ is chlorine, $Y^{1'}$ is chlorine and the combination of the radicals $R^1$ and $R^2$ corresponds for each compound to one row of Table C

Table 978

Compounds of the formula IH.9 in which $Y^1$ is chlorine, $Y^{1'}$ is methyl and the combination of the radicals $R^1$ and $R^2$ corresponds for each compound to one row of Table C

Table 979

Compounds of the formula IH.9 in which $Y^1$ is methyl, $Y^{1'}$ is hydrogen and the combination of the radicals $R^1$ and $R^2$ corresponds for each compound to one row of Table C

Table 980

Compounds of the formula IH.9 in which $Y^1$ is methyl, $Y^{1'}$ is chlorine and the combination of the radicals $R^1$ and $R^2$ corresponds for each compound to one row of Table C

Table 981

Compounds of the formula IH.9 in which $Y^1$ is methyl, $Y^{1'}$ is methyl and the combination of the radicals $R^1$ and $R^2$ corresponds for each compound to one row of Table C

Table 982

Compounds of the formula IH.10 in which $Y^1$ is chlorine, $Y^{1'}$ is hydrogen and the combination of the radicals $R^1$, $R^2$ and $R^3$ corresponds for each compound to one row of Table D

IH.10

Table 983

Compounds of the formula IH.10 in which $Y^1$ is chlorine, $Y^{1'}$ is chlorine and the combination of the radicals $R^1$, $R^2$ and $R^3$ corresponds for each compound to one row of Table D

Table 984

Compounds of the formula IH.10 in which $Y^1$ is chlorine, $Y^{1'}$ is methyl and the combination of the radicals $R^1$, $R^2$ and $R^3$ corresponds for each compound to one row of Table D

Table 985

Compounds of the formula IH.10 in which $Y^1$ is methyl, $Y^{1'}$ is hydrogen and the combination of the radicals $R^1$, $R^2$ and $R^3$ corresponds for each compound to one row of Table D

Table 986

Compounds of the formula IH.10 in which $Y^1$ is methyl, $Y^{1'}$ is chlorine and the combination of the radicals $R^1$, $R^2$ and $R^3$ corresponds for each compound to one row of Table D

Table 987

Compounds of the formula IH.10 in which $Y^1$ is methyl, $Y^{1'}$ is methyl and the combination of the radicals $R^1$, $R^2$ and $R^3$ corresponds for each compound to one row of Table D

Table 988

Compounds of the formula IH.11 in which $Y^1$ is chlorine, $Y^{1'}$ is hydrogen and the combination of the radicals $R^1$, $R^2$ and $R^3$ corresponds for each compound to one row of Table D

IH.11

Table 989

Compounds of the formula IH.11 in which $Y^1$ is chlorine, $Y^{1'}$ is chlorine and the combination of the radicals $R^1$, $R^2$ and $R^3$ corresponds for each compound to one row of Table D

Table 990

Compounds of the formula IH.11 in which $Y^1$ is chlorine, $Y^{1'}$ is methyl and the combination of the radicals $R^1$, $R^2$ and $R^3$ corresponds for each compound to one row of Table D

Table 991

Compounds of the formula IH.11 in which $Y^1$ is methyl, $Y^{1'}$ is hydrogen and the combination of the radicals $R^1$, $R^2$ and $R^3$ corresponds for each compound to one row of Table D Table 992

Compounds of the formula IH.11 in which $Y^1$ is methyl, $Y^{1'}$ is chlorine and the combination of the radicals $R^1$, $R^2$ and $R^3$ corresponds for each compound to one row of Table D Table 993

Compounds of the formula IH.11 in which $Y^1$ is methyl, $Y^{1'}$ is methyl and the combination of the radicals $R^1$, $R^2$ and $R^3$ corresponds for each compound to one row of Table D Table 994

Compounds of the formula IH.12 in which $Y^1$ is chlorine, $Y^{1'}$ is hydrogen and the combination of the radicals $R^1$, $R^2$ and $R^3$ corresponds for each compound to one row of Table A

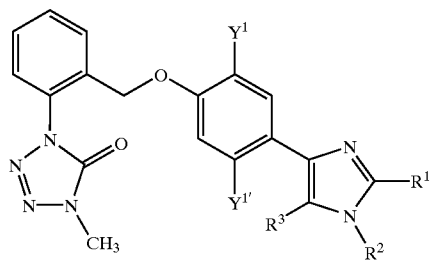

IH.12

Table 995

Compounds of the formula IH.12 in which $Y^1$ is chlorine, $Y^{1'}$ is chlorine and the combination of the radicals $R^1$, $R^2$ and $R^3$ corresponds for each compound to one row of Table A Table 996

Compounds of the formula IH.12 in which $Y^1$ is chlorine, $Y^{1'}$ is methyl and the combination of the radicals $R^1$, $R^2$ and $R^3$ corresponds for each compound to one row of Table A Table 997

Compounds of the formula IH.12 in which $Y^1$ is methyl, $Y^{1'}$ is hydrogen and the combination of the radicals $R^1$, $R^2$ and $R^3$ corresponds for each compound to one row of Table A Table 998

Compounds of the formula IH.12 in which $Y^1$ is methyl, $Y^{1'}$ is chlorine and the combination of the radicals $R^1$, $R^2$ and $R^3$ corresponds for each compound to one row of Table A Table 999

Compounds of the formula IH.12 in which $Y^1$ is methyl, $Y^{1'}$ is methyl and the combination of the radicals $R^1$, $R^2$ and $R^3$ corresponds for each compound to one row of Table A Table 1000

Compounds of the formula IH.13 in which $Y^1$ is chlorine, $Y^{1'}$ is hydrogen and the combination of the radicals $R^1$, $R^2$ and $R^3$ corresponds for each compound to one row of Table A

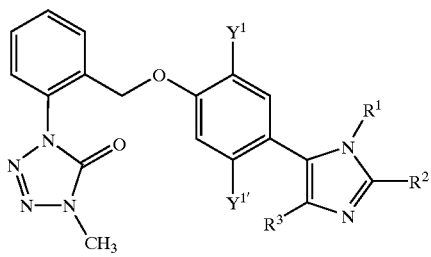

IH.13

Table 1001

Compounds of the formula IH.13 in which $Y^1$ is chlorine, $Y^{1'}$ is chlorine and the combination of the radicals $R^1$, $R^2$ and $R^3$ corresponds for each compound to one row of Table A Table 1002

Compounds of the formula IH.13 in which $Y^1$ is chlorine, Ylf is methyl and the combination of the radicals $R^1$, $R^2$ and $R^3$ corresponds for each compound to one row of Table A Table 1003

Compounds of the formula IH.13 in which $Y^1$ is methyl, $Y^{1'}$ is hydrogen and the combination of the radicals $R^1$, $R^2$ and $R^3$ corresponds for each compound to one row of Table A Table 1004

Compounds of the formula IH.13 in which $Y^1$ is methyl, $Y^{1'}$ is chlorine and the combination of the radicals $R^1$, $R^2$ and $R^3$ corresponds for each compound to one row of Table A Table 1005

Compounds of the formula IH.13 in which $Y^1$ is methyl, $Y^{1'}$ is methyl and the combination of the radicals $R^1$, $R^2$ and $R^3$ corresponds for each compound to one row of Table A

TABLE A

| No. | $R^1$ | $R^2$ | $R^3$ |
|---|---|---|---|
| A-1 | H | H | H |
| A-2 | F | H | H |
| A-3 | Cl | H | H |
| A-4 | Br | H | H |
| A-5 | $CH_3$ | H | H |
| A-6 | $C_2H_5$ | H | H |
| A-7 | $n-C_3H_7$ | H | H |
| A-8 | $i-C_3H_7$ | H | H |
| A-9 | $CF_3$ | H | H |
| A-10 | H | F | H |
| A-11 | F | F | H |
| A-12 | Cl | F | H |
| A-13 | Br | F | H |
| A-14 | $CH_3$ | F | H |
| A-15 | $C_2H_5$ | F | H |
| A-16 | $n-C_3H_7$ | F | H |
| A-17 | $i-C_3H_7$ | F | H |
| A-18 | $CF_3$ | F | H |
| A-19 | H | Cl | H |
| A-20 | F | Cl | H |
| A-21 | Cl | Cl | H |
| A-22 | Br | Cl | H |
| A-23 | $CH_3$ | Cl | H |
| A-24 | $C_2H_5$ | Cl | H |
| A-25 | $n-C_3H_7$ | Cl | H |
| A-26 | $i-C_3H_7$ | Cl | H |
| A-27 | $CF_3$ | Cl | H |
| A-28 | H | Br | H |
| A-29 | F | Br | H |
| A-30 | Cl | Br | H |
| A-31 | Br | Br | H |
| A-32 | $CH_3$ | Br | H |

TABLE A-continued

| No. | R¹ | R² | R³ |
|---|---|---|---|
| A-33 | $C_2H_5$ | Br | H |
| A-34 | $n\text{-}C_3H_7$ | Br | H |
| A-35 | $i\text{-}C_3H_7$ | Br | H |
| A-36 | $CF_3$ | Br | H |
| A-37 | H | $CH_3$ | H |
| A-38 | F | $CH_3$ | H |
| A-39 | Cl | $CH_3$ | H |
| A-40 | Br | $CH_3$ | H |
| A-41 | $CH_3$ | $CH_3$ | H |
| A-42 | $C_2H_5$ | $CH_3$ | H |
| A-43 | $n\text{-}C_3H_7$ | $CH_3$ | H |
| A-44 | $i\text{-}C_3H_7$ | $CH_3$ | H |
| A-45 | $CF_3$ | $CH_3$ | H |
| A-46 | H | $C_2H_5$ | H |
| A-47 | F | $C_2H_5$ | H |
| A-48 | Cl | $C_2H_5$ | H |
| A-49 | Br | $C_2H_5$ | H |
| A-50 | $CH_3$ | $C_2H_5$ | H |
| A-51 | $C_2H_5$ | $C_2H_5$ | H |
| A-52 | $n\text{-}C_3H_7$ | $C_2H_5$ | H |
| A-53 | $i\text{-}C_3H_7$ | $C_2H_5$ | H |
| A-54 | $CF_3$ | $C_2H_5$ | H |
| A-55 | H | $i\text{-}C_3H_7$ | H |
| A-56 | F | $i\text{-}C_3H_7$ | H |
| A-57 | Cl | $i\text{-}C_3H_7$ | H |
| A-58 | Br | $i\text{-}C_3H_7$ | H |
| A-59 | $CH_3$ | $i\text{-}C_3H_7$ | H |
| A-60 | $C_2H_5$ | $i\text{-}C_3H_7$ | H |
| A-61 | $n\text{-}C_3H_7$ | $i\text{-}C_3H_7$ | H |
| A-62 | $i\text{-}C_3H_7$ | $i\text{-}C_3H_7$ | H |
| A-63 | $CF_3$ | $i\text{-}C_3H_7$ | H |
| A-64 | $CHF_2$ | $i\text{-}C_3H_7$ | H |
| A-65 | $CH_2F$ | $i\text{-}C_3H_7$ | H |
| A-66 | H | $CF_3$ | H |
| A-67 | F | $CF_3$ | H |
| A-68 | Cl | $CF_3$ | H |
| A-69 | Br | $CF_3$ | H |
| A-70 | $CH_3$ | $CF_3$ | H |
| A-71 | $C_2H_5$ | $CF_3$ | H |
| A-72 | $n\text{-}C_3H_7$ | $CF_3$ | H |
| A-73 | $i\text{-}C_3H_7$ | $CF_3$ | H |
| A-74 | $CF_3$ | $CF_3$ | H |
| A-75 | $CHF_2$ | $CF_3$ | H |
| A-76 | H | H | Cl |
| A-77 | F | H | Cl |
| A-78 | Cl | H | Cl |
| A-79 | Br | H | Cl |
| A-80 | $CH_3$ | H | Cl |
| A-81 | $C_2H_5$ | H | Cl |
| A-82 | $n\text{-}C_3H_7$ | H | Cl |
| A-83 | $i\text{-}C_3H_7$ | H | Cl |
| A-84 | $CF_3$ | H | Cl |
| A-85 | H | F | Cl |
| A-86 | F | F | Cl |
| A-87 | Cl | F | Cl |
| A-88 | Br | F | Cl |
| A-89 | $CH_3$ | F | Cl |
| A-90 | $C_2H_5$ | F | Cl |
| A-91 | $n\text{-}C_3H_7$ | F | Cl |
| A-92 | $i\text{-}C_3H_7$ | F | Cl |
| A-93 | $CF_3$ | F | Cl |
| A-94 | H | Cl | Cl |
| A-95 | F | Cl | Cl |
| A-96 | Cl | Cl | Cl |
| A-97 | Br | Cl | Cl |
| A-98 | $CH_3$ | Cl | Cl |
| A-99 | $C_2H_5$ | Cl | Cl |
| A-100 | $n\text{-}C_3H_7$ | Cl | Cl |
| A-101 | $i\text{-}C_3H_7$ | Cl | Cl |
| A-102 | $CF_3$ | Cl | Cl |
| A-103 | H | Br | Cl |
| A-104 | F | Br | Cl |
| A-105 | Cl | Br | Cl |
| A-106 | Br | Br | Cl |
| A-107 | $CH_3$ | Br | Cl |
| A-108 | $C_2H_5$ | Br | Cl |
| A-109 | $n\text{-}C_3H_7$ | Br | Cl |
| A-110 | $i\text{-}C_3H_7$ | Br | Cl |
| A-111 | $CF_3$ | Br | Cl |
| A-112 | H | $CH_3$ | Cl |
| A-113 | F | $CH_3$ | Cl |
| A-114 | Cl | $CH_3$ | Cl |
| A-115 | Br | $CH_3$ | Cl |
| A-116 | $CH_3$ | $CH_3$ | Cl |
| A-117 | $C_2H_5$ | $CH_3$ | Cl |
| A-118 | $n\text{-}C_3H_7$ | $CH_3$ | Cl |
| A-119 | $i\text{-}C_3H_7$ | $CH_3$ | Cl |
| A-120 | $CF_3$ | $CH_3$ | Cl |
| A-121 | H | $C_2H_5$ | Cl |
| A-122 | F | $C_2H_5$ | Cl |
| A-123 | Cl | $C_2H_5$ | Cl |
| A-124 | Br | $C_2H_5$ | Cl |
| A-125 | $CH_3$ | $C_2H_5$ | Cl |
| A-126 | $C_2H_5$ | $C_2H_5$ | Cl |
| A-127 | $n\text{-}C_3H_7$ | $C_2H_5$ | Cl |
| A-128 | $i\text{-}C_3H_7$ | $C_2H_5$ | Cl |
| A-129 | $CF_3$ | $C_2H_5$ | Cl |
| A-130 | H | $i\text{-}C_3H_7$ | Cl |
| A-131 | F | $i\text{-}C_3H_7$ | Cl |
| A-132 | Cl | $i\text{-}C_3H_7$ | Cl |
| A-133 | Br | $i\text{-}C_3H_7$ | Cl |
| A-134 | $CH_3$ | $i\text{-}C_3H_7$ | Cl |
| A-135 | $C_2H_5$ | $i\text{-}C_3H_7$ | Cl |
| A-136 | $n\text{-}C_3H_7$ | $i\text{-}C_3H_7$ | Cl |
| A-137 | $i\text{-}C_3H_7$ | $i\text{-}C_3H_7$ | Cl |
| A-138 | $CF_3$ | $i\text{-}C_3H_7$ | Cl |
| A-139 | $CHF_2$ | $i\text{-}C_3H_7$ | Cl |
| A-140 | $CH_2F$ | $i\text{-}C_3H_7$ | Cl |
| A-141 | H | $CF_3$ | Cl |
| A-142 | F | $CF_3$ | Cl |
| A-143 | Cl | $CF_3$ | Cl |
| A-144 | Br | $CF_3$ | Cl |
| A-145 | $CH_3$ | $CF_3$ | Cl |
| A-146 | $C_2H_5$ | $CF_3$ | Cl |
| A-147 | $n\text{-}C_3H_7$ | $CF_3$ | Cl |
| A-148 | $i\text{-}C_3H_7$ | $CF_3$ | Cl |
| A-149 | $CF_3$ | $CF_3$ | Cl |
| A-150 | $CHF_2$ | $CF_3$ | Cl |
| A-151 | H | H | $CH_3$ |
| A-152 | F | H | $CH_3$ |
| A-153 | Cl | H | $CH_3$ |
| A-154 | Br | H | $CH_3$ |
| A-155 | $CH_3$ | H | $CH_3$ |
| A-156 | $C_2H_5$ | H | $CH_3$ |
| A-157 | $n\text{-}C_3H_7$ | H | $CH_3$ |
| A-158 | $i\text{-}C_3H_7$ | H | $CH_3$ |
| A-159 | $CF_3$ | H | $CH_3$ |
| A-160 | H | F | $CH_3$ |
| A-161 | F | F | $CH_3$ |
| A-162 | Cl | F | $CH_3$ |
| A-163 | Br | F | $CH_3$ |
| A-164 | $CH_3$ | F | $CH_3$ |
| A-165 | $C_2H_5$ | F | $CH_3$ |
| A-166 | $n\text{-}C_3H_7$ | F | $CH_3$ |
| A-167 | $i\text{-}C_3H_7$ | F | $CH_3$ |
| A-168 | $CF_3$ | F | $CH_3$ |
| A-169 | H | Cl | $CH_3$ |
| A-170 | F | Cl | $CH_3$ |
| A-171 | Cl | Cl | $CH_3$ |
| A-172 | Br | Cl | $CH_3$ |
| A-173 | $CH_3$ | Cl | $CH_3$ |
| A-174 | $C_2H_5$ | Cl | $CH_3$ |
| A-175 | $n\text{-}C_3H_7$ | Cl | $CH_3$ |
| A-176 | $i\text{-}C_3H_7$ | Cl | $CH_3$ |
| A-177 | $CF_3$ | Cl | $CH_3$ |
| A-178 | H | Br | $CH_3$ |
| A-179 | F | Br | $CH_3$ |
| A-180 | Cl | Br | $CH_3$ |
| A-181 | Br | Br | $CH_3$ |
| A-182 | $CH_3$ | Br | $CH_3$ |
| A-183 | $C_2H_5$ | Br | $CH_3$ |
| A-184 | $n\text{-}C_3H_7$ | Br | $CH_3$ |
| A-185 | $i\text{-}C_3H_7$ | Br | $CH_3$ |
| A-186 | $CF_3$ | Br | $CH_3$ |

TABLE A-continued

| No. | R$^1$ | R$^2$ | R$^3$ |
|---|---|---|---|
| A-187 | H | CH$_3$ | CH$_3$ |
| A-188 | F | CH$_3$ | CH$_3$ |
| A-189 | Cl | CH$_3$ | CH$_3$ |
| A-190 | Br | CH$_3$ | CH$_3$ |
| A-191 | CH$_3$ | CH$_3$ | CH$_3$ |
| A-192 | C$_2$H$_5$ | CH$_3$ | CH$_3$ |
| A-193 | n-C$_3$H$_7$ | CH$_3$ | CH$_3$ |
| A-194 | i-C$_3$H$_7$ | CH$_3$ | CH$_3$ |
| A-195 | CF$_3$ | CH$_3$ | CH$_3$ |
| A-196 | H | C$_2$H$_5$ | CH$_3$ |
| A-197 | F | C$_2$H$_5$ | CH$_3$ |
| A-198 | Cl | C$_2$H$_5$ | CH$_3$ |
| A-199 | Br | C$_2$H$_5$ | CH$_3$ |
| A-200 | CH$_3$ | C$_2$H$_5$ | CH$_3$ |
| A-201 | C$_2$H$_5$ | C$_2$H$_5$ | CH$_3$ |
| A-202 | n-C$_3$H$_7$ | C$_2$H$_5$ | CH$_3$ |
| A-203 | i-C$_3$H$_7$ | C$_2$H$_5$ | CH$_3$ |
| A-204 | CF$_3$ | C$_2$H$_5$ | CH$_3$ |
| A-205 | H | i-C$_3$H$_7$ | CH$_3$ |
| A-206 | F | i-C$_3$H$_7$ | CH$_3$ |
| A-207 | Cl | i-C$_3$H$_7$ | CH$_3$ |
| A-208 | Br | i-C$_3$H$_7$ | CH$_3$ |
| A-209 | CH$_3$ | i-C$_3$H$_7$ | CH$_3$ |
| A-210 | C$_2$H$_5$ | i-C$_3$H$_7$ | CH$_3$ |
| A-211 | n-C$_3$H$_7$ | i-C$_3$H$_7$ | CH$_3$ |
| A-212 | i-C$_3$H$_7$ | i-C$_3$H$_7$ | CH$_3$ |
| A-213 | CF$_3$ | i-C$_3$H$_7$ | CH$_3$ |
| A-214 | CHF$_2$ | i-C$_3$H$_7$ | CH$_3$ |
| A-215 | CH$_2$F | i-C$_3$H$_7$ | CH$_3$ |
| A-216 | H | CF$_3$ | CH$_3$ |
| A-217 | F | CF$_3$ | CH$_3$ |
| A-218 | Cl | CF$_3$ | CH$_3$ |
| A-219 | Br | CF$_3$ | CH$_3$ |
| A-220 | CH$_3$ | CF$_3$ | CH$_3$ |
| A-221 | C$_2$H$_5$ | CF$_3$ | CH$_3$ |
| A-222 | n-C$_3$H$_7$ | CF$_3$ | CH$_3$ |
| A-223 | i-C$_3$H$_7$ | CF$_3$ | CH$_3$ |
| A-224 | CF$_3$ | CF$_3$ | CH$_3$ |
| A-225 | CHF$_2$ | CF$_3$ | CH$_3$ |
| A-226 | H | H | i-C$_3$H$_7$ |
| A-227 | F | H | i-C$_3$H$_7$ |
| A-228 | Cl | H | i-C$_3$H$_7$ |
| A-229 | Br | H | i-C$_3$H$_7$ |
| A-230 | CH$_3$ | H | i-C$_3$H$_7$ |
| A-231 | C$_2$H$_5$ | H | i-C$_3$H$_7$ |
| A-232 | n-C$_3$H$_7$ | H | i-C$_3$H$_7$ |
| A-233 | i-C$_3$H$_7$ | H | i-C$_3$H$_7$ |
| A-234 | CF$_3$ | H | i-C$_3$H$_7$ |
| A-235 | H | F | i-C$_3$H$_7$ |
| A-236 | F | F | i-C$_3$H$_7$ |
| A-237 | Cl | F | i-C$_3$H$_7$ |
| A-238 | Br | F | i-C$_3$H$_7$ |
| A-239 | CH$_3$ | F | i-C$_3$H$_7$ |
| A-240 | C$_2$H$_5$ | F | i-C$_3$H$_7$ |
| A-241 | n-C$_3$H$_7$ | F | i-C$_3$H$_7$ |
| A-242 | i-C$_3$H$_7$ | F | i-C$_3$H$_7$ |
| A-243 | CF$_3$ | F | i-C$_3$H$_7$ |
| A-244 | H | Cl | i-C$_3$H$_7$ |
| A-245 | F | Cl | i-C$_3$H$_7$ |
| A-246 | Cl | Cl | i-C$_3$H$_7$ |
| A-247 | Br | Cl | i-C$_3$H$_7$ |
| A-248 | CH$_3$ | Cl | i-C$_3$H$_7$ |
| A-249 | C$_2$H$_5$ | Cl | i-C$_3$H$_7$ |
| A-250 | n-C$_3$H$_7$ | Cl | i-C$_3$H$_7$ |
| A-251 | i-C$_3$H$_7$ | Cl | i-C$_3$H$_7$ |
| A-252 | CF$_3$ | Cl | i-C$_3$H$_7$ |
| A-253 | H | Br | i-C$_3$H$_7$ |
| A-254 | F | Br | i-C$_3$H$_7$ |
| A-255 | Cl | Br | i-C$_3$H$_7$ |
| A-256 | Br | Br | i-C$_3$H$_7$ |
| A-257 | CH$_3$ | Br | i-C$_3$H$_7$ |
| A-258 | C$_2$H$_5$ | Br | i-C$_3$H$_7$ |
| A-259 | n-C$_3$H$_7$ | Br | i-C$_3$H$_7$ |
| A-260 | i-C$_3$H$_7$ | Br | i-C$_3$H$_7$ |
| A-261 | CF$_3$ | Br | i-C$_3$H$_7$ |
| A-262 | H | CH$_3$ | i-C$_3$H$_7$ |
| A-263 | F | CH$_3$ | i-C$_3$H$_7$ |
| A-264 | Cl | CH$_3$ | i-C$_3$H$_7$ |
| A-265 | Br | CH$_3$ | i-C$_3$H$_7$ |
| A-266 | CH$_3$ | CH$_3$ | i-C$_3$H$_7$ |
| A-267 | C$_2$H$_5$ | CH$_3$ | i-C$_3$H$_7$ |
| A-268 | n-C$_3$H$_7$ | CH$_3$ | i-C$_3$H$_7$ |
| A-269 | i-C$_3$H$_7$ | CH$_3$ | i-C$_3$H$_7$ |
| A-270 | CF$_3$ | CH$_3$ | i-C$_3$H$_7$ |
| A-271 | H | C$_2$H$_5$ | i-C$_3$H$_7$ |
| A-272 | F | C$_2$H$_5$ | i-C$_3$H$_7$ |
| A-273 | Cl | C$_2$H$_5$ | i-C$_3$H$_7$ |
| A-274 | Br | C$_2$H$_5$ | i-C$_3$H$_7$ |
| A-275 | CH$_3$ | C$_2$H$_5$ | i-C$_3$H$_7$ |
| A-276 | C$_2$H$_5$ | C$_2$H$_5$ | i-C$_3$H$_7$ |
| A-277 | n-C$_3$H$_7$ | C$_2$H$_5$ | i-C$_3$H$_7$ |
| A-278 | i-C$_3$H$_7$ | C$_2$H$_5$ | i-C$_3$H$_7$ |
| A-279 | CF$_3$ | C$_2$H$_5$ | i-C$_3$H$_7$ |
| A-280 | H | i-C$_3$H$_7$ | i-C$_3$H$_7$ |
| A-281 | F | i-C$_3$H$_7$ | i-C$_3$H$_7$ |
| A-282 | Cl | i-C$_3$H$_7$ | i-C$_3$H$_7$ |
| A-283 | Br | i-C$_3$H$_7$ | i-C$_3$H$_7$ |
| A-284 | CH$_3$ | i-C$_3$H$_7$ | i-C$_3$H$_7$ |
| A-285 | C$_2$H$_5$ | i-C$_3$H$_7$ | i-C$_3$H$_7$ |
| A-286 | n-C$_3$H$_7$ | i-C$_3$H$_7$ | i-C$_3$H$_7$ |
| A-287 | i-C$_3$H$_7$ | i-C$_3$H$_7$ | i-C$_3$H$_7$ |
| A-288 | CF$_3$ | i-C$_3$H$_7$ | i-C$_3$H$_7$ |
| A-289 | CHF$_2$ | i-C$_3$H$_7$ | i-C$_3$H$_7$ |
| A-290 | CH$_2$F | i-C$_3$H$_7$ | i-C$_3$H$_7$ |
| A-291 | H | CF$_3$ | i-C$_3$H$_7$ |
| A-292 | F | CF$_3$ | i-C$_3$H$_7$ |
| A-293 | Cl | CF$_3$ | i-C$_3$H$_7$ |
| A-294 | Br | CF$_3$ | i-C$_3$H$_7$ |
| A-295 | CH$_3$ | CF$_3$ | i-C$_3$H$_7$ |
| A-296 | C$_2$H$_5$ | CF$_3$ | i-C$_3$H$_7$ |
| A-297 | n-C$_3$H$_7$ | CF$_3$ | i-C$_3$H$_7$ |
| A-298 | i-C$_3$H$_7$ | CF$_3$ | i-C$_3$H$_7$ |
| A-299 | CF$_3$ | CF$_3$ | i-C$_3$H$_7$ |
| A-300 | CHF$_2$ | CF$_3$ | i-C$_3$H$_7$ |
| A-301 | H | H | CF$_3$ |
| A-302 | F | H | CF$_3$ |
| A-303 | Cl | H | CF$_3$ |
| A-304 | Br | H | CF$_3$ |
| A-305 | CH$_3$ | H | CF$_3$ |
| A-306 | C$_2$H$_5$ | H | CF$_3$ |
| A-307 | n-C$_3$H$_7$ | H | CF$_3$ |
| A-308 | i-C$_3$H$_7$ | H | CF$_3$ |
| A-309 | CF$_3$ | H | CF$_3$ |
| A-310 | H | F | CF$_3$ |
| A-311 | F | F | CF$_3$ |
| A-312 | Cl | F | CF$_3$ |
| A-313 | Br | F | CF$_3$ |
| A-314 | CH$_3$ | F | CF$_3$ |
| A-315 | C$_2$H$_5$ | F | CF$_3$ |
| A-316 | n-C$_3$H$_7$ | F | CF$_3$ |
| A-317 | i-C$_3$H$_7$ | F | CF$_3$ |
| A-318 | CF$_3$ | F | CF$_3$ |
| A-319 | H | Cl | CF$_3$ |
| A-320 | F | Cl | CF$_3$ |
| A-321 | Cl | Cl | CF$_3$ |
| A-322 | Br | Cl | CF$_3$ |
| A-323 | CH$_3$ | Cl | CF$_3$ |
| A-324 | C$_2$H$_5$ | Cl | CF$_3$ |
| A-325 | n-C$_3$H$_7$ | Cl | CF$_3$ |
| A-326 | i-C$_3$H$_7$ | Cl | CF$_3$ |
| A-327 | CF$_3$ | Cl | CF$_3$ |
| A-328 | H | Br | CF$_3$ |
| A-329 | F | Br | CF$_3$ |
| A-330 | Cl | Br | CF$_3$ |
| A-331 | Br | Br | CF$_3$ |
| A-332 | CH$_3$ | Br | CF$_3$ |
| A-333 | C$_2$H$_5$ | Br | CF$_3$ |
| A-334 | n-C$_3$H$_7$ | Br | CF$_3$ |
| A-335 | i-C$_3$H$_7$ | Br | CF$_3$ |
| A-336 | CF$_3$ | Br | CF$_3$ |
| A-337 | H | CH$_3$ | CF$_3$ |
| A-338 | F | CH$_3$ | CF$_3$ |
| A-339 | Cl | CH$_3$ | CF$_3$ |
| A-340 | Br | CH$_3$ | CF$_3$ |

TABLE A-continued

| No. | R¹ | R² | R³ |
|---|---|---|---|
| A-341 | $CH_3$ | $CH_3$ | $CF_3$ |
| A-342 | $C_2H_5$ | $CH_3$ | $CF_3$ |
| A-343 | $n\text{-}C_3H_7$ | $CH_3$ | $CF_3$ |
| A-344 | $i\text{-}C_3H_7$ | $CH_3$ | $CF_3$ |
| A-345 | $CF_3$ | $CH_3$ | $CF_3$ |
| A-346 | H | $C_2H_5$ | $CF_3$ |
| A-347 | F | $C_2H_5$ | $CF_3$ |
| A-348 | Cl | $C_2H_5$ | $CF_3$ |
| A-349 | Br | $C_2H_5$ | $CF_3$ |
| A-350 | $CH_3$ | $C_2H_5$ | $CF_3$ |
| A-351 | $C_2H_5$ | $C_2H_5$ | $CF_3$ |
| A-352 | $n\text{-}C_3H_7$ | $C_2H_5$ | $CF_3$ |
| A-353 | $i\text{-}C_3H_7$ | $C_2H_5$ | $CF_3$ |
| A-354 | $CF_3$ | $C_2H_5$ | $CF_3$ |
| A-355 | H | $i\text{-}C_3H_7$ | $CF_3$ |
| A-356 | F | $i\text{-}C_3H_7$ | $CF_3$ |
| A-357 | Cl | $i\text{-}C_3H_7$ | $CF_3$ |
| A-358 | Br | $i\text{-}C_3H_7$ | $CF_3$ |
| A-359 | $CH_3$ | $i\text{-}C_3H_7$ | $CF_3$ |
| A-360 | $C_2H_5$ | $i\text{-}C_3H_7$ | $CF_3$ |
| A-361 | $n\text{-}C_3H_7$ | $i\text{-}C_3H_7$ | $CF_3$ |
| A-362 | $i\text{-}C_3H_7$ | $i\text{-}C_3H_7$ | $CF_3$ |
| A-363 | $CF_3$ | $i\text{-}C_3H_7$ | $CF_3$ |
| A-364 | $CHF_2$ | $i\text{-}C_3H_7$ | $CF_3$ |
| A-365 | $CH_2F$ | $i\text{-}C_3H_7$ | $CF_3$ |
| A-366 | H | $CF_3$ | $CF_3$ |
| A-367 | F | $CF_3$ | $CF_3$ |
| A-368 | Cl | $CF_3$ | $CF_3$ |
| A-369 | Br | $CF_3$ | $CF_3$ |
| A-370 | $CH_3$ | $CF_3$ | $CF_3$ |
| A-371 | $C_2H_5$ | $CF_3$ | $CF_3$ |
| A-372 | $n\text{-}C_3H_7$ | $CF_3$ | $CF_3$ |
| A-373 | $i\text{-}C_3H_7$ | $CF_3$ | $CF_3$ |
| A-374 | $CF_3$ | $CF_3$ | $CF_3$ |
| A-375 | $CHF_2$ | $CF_3$ | $CF_3$ |

TABLE B

| No. | R² | R³ |
|---|---|---|
| B-1 | H | H |
| B-2 | F | H |
| B-3 | Cl | H |
| B-4 | Br | H |
| B-5 | $CH_3$ | H |
| B-6 | $C_2H_5$ | H |
| B-7 | $n\text{-}C_3H_7$ | H |
| B-8 | $i\text{-}C_3H_7$ | H |
| B-9 | $CF_3$ | H |
| B-10 | H | F |
| B-11 | F | F |
| B-12 | Cl | F |
| B-13 | Br | F |
| B-14 | $CH_3$ | F |
| B-15 | $C_2H_5$ | F |
| B-16 | $n\text{-}C_3H_7$ | F |
| B-17 | $i\text{-}C_3H_7$ | F |
| B-18 | $CF_3$ | F |
| B-19 | H | Cl |
| B-20 | F | Cl |
| B-21 | Cl | Cl |
| B-22 | Br | Cl |
| B-23 | $CH_3$ | Cl |
| B-24 | $C_2H_5$ | Cl |
| B-25 | $n\text{-}C_3H_7$ | Cl |
| B-26 | $i\text{-}C_3H_7$ | Cl |
| B-27 | H | Br |
| B-28 | F | Br |
| B-29 | Cl | Br |
| B-30 | Br | Br |
| B-31 | $CH_3$ | Br |
| B-32 | $C_2H_5$ | Br |
| B-33 | $n\text{-}C_3H_7$ | Br |
| B-34 | $i\text{-}C_3H_7$ | Br |

TABLE B-continued

| No. | R² | R³ |
|---|---|---|
| B-35 | $CF_3$ | Br |
| B-36 | H | $CH_3$ |
| B-37 | F | $CH_3$ |
| B-38 | Cl | $CH_3$ |
| B-39 | Br | $CH_3$ |
| B-40 | $CH_3$ | $CH_3$ |
| B-41 | $C_2H_5$ | $CH_3$ |
| B-42 | $n\text{-}C_3H_7$ | $CH_3$ |
| B-43 | $i\text{-}C_3H_7$ | $CH_3$ |
| B-44 | $CF_3$ | $CH_3$ |
| B-45 | H | $C_2H_5$ |
| B-46 | F | $C_2H_5$ |
| B-47 | Cl | $C_2H_5$ |
| B-48 | Br | $C_2H_5$ |
| B-49 | $CH_3$ | $C_2H_5$ |
| B-50 | $C_2H_5$ | $C_2H_5$ |
| B-51 | $n\text{-}C_3H_7$ | $C_2H_5$ |
| B-52 | $i\text{-}C_3H_7$ | $C_2H_5$ |
| B-53 | $CF_3$ | $C_2H_5$ |
| B-54 | H | $i\text{-}C_3H_7$ |
| B-55 | F | $i\text{-}C_3H_7$ |
| B-56 | Cl | $i\text{-}C_3H_7$ |
| B-57 | Br | $i\text{-}C_3H_7$ |
| B-58 | $CH_3$ | $i\text{-}C_3H_7$ |
| B-59 | $C_2H_5$ | $i\text{-}C_3H_7$ |
| B-60 | $n\text{-}C_3H_7$ | $i\text{-}C_3H_7$ |
| B-61 | $i\text{-}C_3H_7$ | $i\text{-}C_3H_7$ |
| B-62 | $CF_3$ | $i\text{-}C_3H_7$ |
| B-63 | $CHF_2$ | $i\text{-}C_3H_7$ |
| B-64 | $CH_2F$ | $i\text{-}C_3H_7$ |
| B-65 | H | $CF_3$ |
| B-66 | F | $CF_3$ |
| B-67 | Cl | $CF_3$ |
| B-68 | Br | $CF_3$ |
| B-69 | $CH_3$ | $CF_3$ |
| B-70 | $C_2H_5$ | $CF_3$ |
| B-71 | $n\text{-}C_3H_7$ | $CF_3$ |
| B-72 | $i\text{-}C_3H_7$ | $CF_3$ |
| B-73 | $CF_3$ | $CF_3$ |
| B-74 | $CHF_2$ | $CF_3$ |

TABLE C

| No. | R¹ | R² |
|---|---|---|
| C-1 | H | H |
| C-2 | F | H |
| C-3 | Cl | H |
| C-4 | Br | H |
| C-5 | $CH_3$ | H |
| C-6 | $C_2H_5$ | H |
| C-7 | $n\text{-}C_3H_7$ | H |
| C-8 | $i\text{-}C_3H_7$ | H |
| C-9 | $CF_3$ | H |
| C-10 | H | F |
| C-11 | F | F |
| C-12 | Cl | F |
| C-13 | Br | F |
| C-14 | $CH_3$ | F |
| C-15 | $C_2H_5$ | F |
| C-16 | $n\text{-}C_3H_7$ | F |
| C-17 | $i\text{-}C_3H_7$ | F |
| C-18 | $CF_3$ | F |
| C-19 | H | Cl |
| C-20 | F | Cl |
| C-21 | Cl | Cl |
| C-22 | Br | Cl |
| C-23 | $CH_3$ | Cl |
| C-24 | $C_2H_5$ | Cl |
| C-25 | $n\text{-}C_3H_7$ | Cl |
| C-26 | $i\text{-}C_3H_7$ | Cl |
| C-27 | $CF_3$ | Cl |
| C-28 | H | Br |
| C-29 | F | Br |

TABLE C-continued

| No. | R¹ | R² |
|---|---|---|
| C-30 | Cl | Br |
| C-31 | Br | Br |
| C-32 | CH$_3$ | Br |
| C-33 | C$_2$H$_5$ | Br |
| C-34 | n-C$_3$H$_7$ | Br |
| C-35 | i-C$_3$H$_7$ | Br |
| C-36 | CF$_3$ | Br |
| C-37 | H | CH$_3$ |
| C-38 | F | CH$_3$ |
| C-39 | Cl | CH$_3$ |
| C-40 | Br | CH$_3$ |
| C-41 | CH$_3$ | CH$_3$ |
| C-42 | C$_2$H$_5$ | CH$_3$ |
| C-43 | n-C$_3$H$_7$ | CH$_3$ |
| C-44 | i-C$_3$H$_7$ | CH$_3$ |
| C-45 | CF$_3$ | CH$_3$ |
| C-46 | H | C$_2$H$_5$ |
| C-47 | F | C$_2$H$_5$ |
| C-48 | Cl | C$_2$H$_5$ |
| C-49 | Br | C$_2$H$_5$ |
| C-50 | CH$_3$ | C$_2$H$_5$ |
| C-51 | C$_2$H$_5$ | C$_2$H$_5$ |
| C-52 | n-C$_3$H$_7$ | C$_2$H$_5$ |
| C-53 | i-C$_3$H$_7$ | C$_2$H$_5$ |
| C-54 | CF$_3$ | C$_2$H$_5$ |
| C-55 | H | i-C$_3$H$_7$ |
| C-56 | F | i-C$_3$H$_7$ |
| C-57 | Cl | i-C$_3$H$_7$ |
| C-58 | Br | i-C$_3$H$_7$ |
| C-59 | CH$_3$ | i-C$_3$H$_7$ |
| C-60 | C$_2$H$_5$ | i-C$_3$H$_7$ |
| C-61 | n-C$_3$H$_7$ | i-C$_3$H$_7$ |
| C-62 | i-C$_3$H$_7$ | i-C$_3$H$_7$ |
| C-63 | CF$_3$ | i-C$_3$H$_7$ |
| C-64 | CHF$_2$ | i-C$_3$H$_7$ |
| C-65 | CH$_2$F | i-C$_3$H$_7$ |
| C-66 | H | CF$_3$ |
| C-67 | F | CF$_3$ |
| C-68 | Cl | CF$_3$ |
| C-69 | Br | CF$_3$ |
| C-70 | CH$_3$ | CF$_3$ |
| C-71 | C$_2$H$_5$ | CF$_3$ |
| C-72 | n-C$_3$H$_7$ | CF$_3$ |
| C-73 | i-C$_3$H$_7$ | CF$_3$ |
| C-74 | CF$_3$ | CF$_3$ |
| C-75 | CHF$_2$ | CF$_3$ |

TABLE D

| No. | R¹ | R² | R³ |
|---|---|---|---|
| D-1 | H | H | H |
| D-2 | F | H | H |
| D-3 | Cl | H | H |
| D-4 | Br | H | H |
| D-5 | CH$_3$ | H | H |
| D-6 | C$_2$H$_5$ | H | H |
| D-7 | n-C$_3$H$_7$ | H | H |
| D-8 | i-C$_3$H$_7$ | H | H |
| D-9 | CF$_3$ | H | H |
| D-10 | H | F | H |
| D-11 | F | F | H |
| D-12 | Cl | F | H |
| D-13 | Br | F | H |
| D-14 | CH$_3$ | F | H |
| D-15 | C$_2$H$_5$ | F | H |
| D-16 | n-C$_3$H$_7$ | F | H |
| D-17 | i-C$_3$H$_7$ | F | H |
| D-18 | CF$_3$ | F | H |
| D-19 | H | Cl | H |
| D-20 | F | Cl | H |
| D-21 | Cl | Cl | H |
| D-22 | Br | Cl | H |
| D-23 | CH$_3$ | Cl | H |
| D-24 | C$_2$H$_5$ | Cl | H |
| D-25 | n-C$_3$H$_7$ | Cl | H |
| D-26 | CF$_3$ | Cl | H |
| D-27 | H | Br | H |
| D-28 | F | Br | H |
| D-29 | Cl | Br | H |
| D-30 | Br | Br | H |
| D-31 | CH$_3$ | Br | H |
| D-32 | C$_2$H$_5$ | Br | H |
| D-33 | n-C$_3$H$_7$ | Br | H |
| D-34 | i-C$_3$H$_7$ | Br | H |
| D-35 | CF$_3$ | Br | H |
| D-36 | H | CH$_3$ | H |
| D-37 | F | CH$_3$ | H |
| D-38 | Cl | CH$_3$ | H |
| D-39 | Br | CH$_3$ | H |
| D-40 | CH$_3$ | CH$_3$ | H |
| D-41 | C$_2$H$_5$ | CH$_3$ | H |
| D-42 | n-C$_3$H$_7$ | CH$_3$ | H |
| D-43 | i-C$_3$H$_7$ | CH$_3$ | H |
| D-44 | CF$_3$ | CH$_3$ | H |
| D-45 | H | C$_2$H$_5$ | H |
| D-46 | F | C$_2$H$_5$ | H |
| D-47 | Cl | C$_2$H$_5$ | H |
| D-48 | Br | C$_2$H$_5$ | H |
| D-49 | CH$_3$ | C$_2$H$_5$ | H |
| D-50 | C$_2$H$_5$ | C$_2$H$_5$ | H |
| D-51 | n-C$_3$H$_7$ | C$_2$H$_5$ | H |
| D-52 | i-C$_3$H$_7$ | C$_2$H$_5$ | H |
| D-53 | CF$_3$ | C$_2$H$_5$ | H |
| D-54 | H | i-C$_3$H$_7$ | H |
| D-55 | F | i-C$_3$H$_7$ | H |
| D-56 | Cl | i-C$_3$H$_7$ | H |
| D-57 | Br | i-C$_3$H$_7$ | H |
| D-58 | CH$_3$ | i-C$_3$H$_7$ | H |
| D-59 | C$_2$H$_5$ | i-C$_3$H$_7$ | H |
| D-60 | n-C$_3$H$_7$ | i-C$_3$H$_7$ | H |
| D-61 | i-C$_3$H$_7$ | i-C$_3$H$_7$ | H |
| D-62 | CF$_3$ | i-C$_3$H$_7$ | H |
| D-63 | CHF$_2$ | i-C$_3$H$_7$ | H |
| D-64 | CH$_2$F | i-C$_3$H$_7$ | H |
| D-65 | CHF$_2$ | t-C$_4$H$_9$ | H |
| D-66 | H | CF$_3$ | H |
| D-67 | F | CF$_3$ | H |
| D-68 | Cl | CF$_3$ | H |
| D-69 | Br | CF$_3$ | H |
| D-70 | CH$_3$ | CF$_3$ | H |
| D-71 | C$_2$H$_5$ | CF$_3$ | H |
| D-72 | n-C$_3$H$_7$ | CF$_3$ | H |
| D-73 | i-C$_3$H$_7$ | CF$_3$ | H |
| D-74 | CF$_3$ | CF$_3$ | H |
| D-75 | CHF$_2$ | CF$_3$ | H |
| D-76 | H | H | F |
| D-77 | F | H | F |
| D-78 | Cl | H | F |
| D-79 | Br | H | F |
| D-80 | CH$_3$ | H | F |
| D-81 | C$_2$H$_5$ | H | F |
| D-82 | n-C$_3$H$_7$ | H | F |
| D-83 | i-C$_3$H$_7$ | H | F |
| D-84 | CF$_3$ | H | F |
| D-85 | H | F | F |
| D-86 | F | F | F |
| D-87 | Cl | F | F |
| D-88 | Br | F | F |
| D-89 | CH$_3$ | F | F |
| D-90 | C$_2$H$_5$ | F | F |
| D-91 | n-C$_3$H$_7$ | F | F |
| D-92 | i-C$_3$H$_7$ | F | F |
| D-93 | CF$_3$ | F | F |
| D-94 | H | Cl | F |
| D-95 | F | Cl | F |
| D-96 | Cl | Cl | F |
| D-97 | Br | Cl | F |
| D-98 | CH$_3$ | Cl | F |
| D-99 | C$_2$H$_5$ | Cl | F |
| D-100 | n-C$_3$H$_7$ | Cl | F |

TABLE D-continued

| No. | R¹ | R² | R³ |
|---|---|---|---|
| D-101 | i-C$_3$H$_7$ | Cl | F |
| D-102 | CF$_3$ | Cl | F |
| D-103 | H | Br | F |
| D-104 | F | Br | F |
| D-105 | Cl | Br | F |
| D-106 | Br | Br | F |
| D-107 | CH$_3$ | Br | F |
| D-108 | C$_2$H$_5$ | Br | F |
| D-109 | n-C$_3$H$_7$ | Br | F |
| D-110 | i-C$_3$H$_7$ | Br | F |
| D-111 | CF$_3$ | Br | F |
| D-112 | H | CH$_3$ | F |
| D-113 | F | CH$_3$ | F |
| D-114 | Cl | CH$_3$ | F |
| D-115 | Br | CH$_3$ | F |
| D-116 | CH$_3$ | CH$_3$ | F |
| D-117 | C$_2$H$_5$ | CH$_3$ | F |
| D-118 | n-C$_3$H$_7$ | CH$_3$ | F |
| D-119 | i-C$_3$H$_7$ | CH$_3$ | F |
| D-120 | CF$_3$ | CH$_3$ | F |
| D-121 | H | C$_2$H$_5$ | F |
| D-122 | F | C$_2$H$_5$ | F |
| D-123 | Cl | C$_2$H$_5$ | F |
| D-124 | Br | C$_2$H$_5$ | F |
| D-125 | CH$_3$ | C$_2$H$_5$ | F |
| D-126 | C$_2$H$_5$ | C$_2$H$_5$ | F |
| D-127 | n-C$_3$H$_7$ | C$_2$H$_5$ | F |
| D-128 | i-C$_3$H$_7$ | C$_2$H$_5$ | F |
| D-129 | CF$_3$ | C$_2$H$_5$ | F |
| D-130 | H | i-C$_3$H$_7$ | F |
| D-131 | F | i-C$_3$H$_7$ | F |
| D-132 | Cl | i-C$_3$H$_7$ | F |
| D-133 | Br | i-C$_3$H$_7$ | F |
| D-134 | CH$_3$ | i-C$_3$H$_7$ | F |
| D-135 | C$_2$H$_5$ | i-C$_3$H$_7$ | F |
| D-136 | n-C$_3$H$_7$ | i-C$_3$H$_7$ | F |
| D-137 | i-C$_3$H$_7$ | i-C$_3$H$_7$ | F |
| D-138 | CF$_3$ | i-C$_3$H$_7$ | F |
| D-139 | CHF$_2$ | i-C$_3$H$_7$ | F |
| D-140 | CH$_2$F | i-C$_3$H$_7$ | F |
| D-141 | H | CF$_3$ | F |
| D-142 | F | CF$_3$ | F |
| D-143 | Cl | CF$_3$ | F |
| D-144 | Br | CF$_3$ | F |
| D-145 | CH$_3$ | CF$_3$ | F |
| D-146 | C$_2$H$_5$ | CF$_3$ | F |
| D-147 | n-C$_3$H$_7$ | CF$_3$ | F |
| D-148 | i-C$_3$H$_7$ | CF$_3$ | F |
| D-149 | CF$_3$ | CF$_3$ | F |
| D-150 | CHF$_2$ | CF$_3$ | F |
| D-151 | H | H | Cl |
| D-152 | F | H | Cl |
| D-153 | Cl | H | Cl |
| D-154 | Br | H | Cl |
| D-155 | CH$_3$ | H | Cl |
| D-156 | C$_2$H$_5$ | H | Cl |
| D-157 | n-C$_3$H$_7$ | H | Cl |
| D-158 | i-C$_3$H$_7$ | H | Cl |
| D-159 | CF$_3$ | H | Cl |
| D-160 | H | F | Cl |
| D-161 | F | F | Cl |
| D-162 | Cl | F | Cl |
| D-163 | Br | F | Cl |
| D-164 | CH$_3$ | F | Cl |
| D-165 | C$_2$H$_5$ | F | Cl |
| D-166 | n-C$_3$H$_7$ | F | Cl |
| D-167 | i-C$_3$H$_7$ | F | Cl |
| D-168 | CF$_3$ | F | Cl |
| D-169 | H | Cl | Cl |
| D-170 | F | Cl | Cl |
| D-171 | Cl | Cl | Cl |
| D-172 | Br | Cl | Cl |
| D-173 | CH$_3$ | Cl | Cl |
| D-174 | C$_2$H$_5$ | Cl | Cl |
| D-175 | n-C$_3$H$_7$ | Cl | Cl |
| D-176 | i-C$_3$H$_7$ | Cl | Cl |
| D-177 | CF$_3$ | Cl | Cl |
| D-178 | H | Br | Cl |
| D-179 | F | Br | Cl |
| D-180 | Cl | Br | Cl |
| D-181 | Br | Br | Cl |
| D-182 | CH$_3$ | Br | Cl |
| D-183 | C$_2$H$_5$ | Br | Cl |
| D-184 | n-C$_3$H$_7$ | Br | Cl |
| D-185 | i-C$_3$H$_7$ | Br | Cl |
| D-186 | CF$_3$ | Br | Cl |
| D-187 | H | CH$_3$ | Cl |
| D-188 | F | CH$_3$ | Cl |
| D-189 | Cl | CH$_3$ | Cl |
| D-190 | Br | CH$_3$ | Cl |
| D-191 | CH$_3$ | CH$_3$ | Cl |
| D-192 | C$_2$H$_5$ | CH$_3$ | Cl |
| D-193 | n-C$_3$H$_7$ | CH$_3$ | Cl |
| D-194 | i-C$_3$H$_7$ | CH$_3$ | Cl |
| D-195 | CF$_3$ | CH$_3$ | Cl |
| D-196 | H | C$_2$H$_5$ | Cl |
| D-197 | F | C$_2$H$_5$ | Cl |
| D-198 | Cl | C$_2$H$_5$ | Cl |
| D-199 | Br | C$_2$H$_5$ | Cl |
| D-200 | CH$_3$ | C$_2$H$_5$ | Cl |
| D-201 | C$_2$H$_5$ | C$_2$H$_5$ | Cl |
| D-202 | n-C$_3$H$_7$ | C$_2$H$_5$ | Cl |
| D-203 | i-C$_3$H$_7$ | C$_2$H$_5$ | Cl |
| D-204 | CF$_3$ | C$_2$H$_5$ | Cl |
| D-205 | H | i-C$_3$H$_7$ | Cl |
| D-206 | F | i-C$_3$H$_7$ | Cl |
| D-207 | Cl | i-C$_3$H$_7$ | Cl |
| D-208 | Br | i-C$_3$H$_7$ | Cl |
| D-209 | CH$_3$ | i-C$_3$H$_7$ | Cl |
| D-210 | C$_2$H$_5$ | i-C$_3$H$_7$ | Cl |
| D-211 | n-C$_3$H$_7$ | i-C$_3$H$_7$ | Cl |
| D-212 | i-C$_3$H$_7$ | i-C$_3$H$_7$ | Cl |
| D-213 | CF$_3$ | i-C$_3$H$_7$ | Cl |
| D-214 | CHF$_2$ | i-C$_3$H$_7$ | Cl |
| D-215 | CH$_2$F | i-C$_3$H$_7$ | Cl |
| D-216 | H | CF$_3$ | Cl |
| D-217 | F | CF$_3$ | Cl |
| D-218 | Cl | CF$_3$ | Cl |
| D-219 | Br | CF$_3$ | Cl |
| D-220 | CH$_3$ | CF$_3$ | Cl |
| D-221 | C$_2$H$_5$ | CF$_3$ | Cl |
| D-222 | n-C$_3$H$_7$ | CF$_3$ | Cl |
| D-223 | i-C$_3$H$_7$ | CF$_3$ | Cl |
| D-224 | CF$_3$ | CF$_3$ | Cl |
| D-225 | CHF$_2$ | CF$_3$ | Cl |
| D-226 | H | H | Br |
| D-227 | F | H | Br |
| D-228 | Cl | H | Br |
| D-229 | Br | H | Br |
| D-230 | CH$_3$ | H | Br |
| D-231 | C$_2$H$_5$ | H | Br |
| D-232 | n-C$_3$H$_7$ | H | Br |
| D-233 | i-C$_3$H$_7$ | H | Br |
| D-234 | CF$_3$ | H | Br |
| D-235 | H | F | Br |
| D-236 | F | F | Br |
| D-237 | Cl | F | Br |
| D-238 | Br | F | Br |
| D-239 | CH$_3$ | F | Br |
| D-240 | C$_2$H$_5$ | F | Br |
| D-241 | n-C$_3$H$_7$ | F | Br |
| D-242 | i-C$_3$H$_7$ | F | Br |
| D-243 | CF$_3$ | F | Br |
| D-244 | H | Cl | Br |
| D-245 | F | Cl | Br |
| D-246 | Cl | Cl | Br |
| D-247 | Br | Cl | Br |
| D-248 | CH$_3$ | Cl | Br |
| D-249 | C$_2$H$_5$ | Cl | Br |
| D-250 | n-C$_3$H$_7$ | Cl | Br |
| D-251 | i-C$_3$H$_7$ | Cl | Br |
| D-252 | CF$_3$ | Cl | Br |
| D-253 | H | Br | Br |
| D-254 | F | Br | Br |

TABLE D-continued

| No. | R¹ | R² | R³ |
|---|---|---|---|
| D-255 | Cl | Br | Br |
| D-256 | Br | Br | Br |
| D-257 | CH$_3$ | Br | Br |
| D-258 | C$_2$H$_5$ | Br | Br |
| D-259 | n-C$_3$H$_7$ | Br | Br |
| D-260 | i-C$_3$H$_7$ | Br | Br |
| D-261 | CF$_3$ | Br | Br |
| D-262 | H | CH$_3$ | Br |
| D-263 | F | CH$_3$ | Br |
| D-264 | Cl | CH$_3$ | Br |
| D-265 | Br | CH$_3$ | Br |
| D-266 | CH$_3$ | CH$_3$ | Br |
| D-267 | C$_2$H$_5$ | CH$_3$ | Br |
| D-268 | n-C$_3$H$_7$ | CH$_3$ | Br |
| D-269 | i-C$_3$H$_7$ | CH$_3$ | Br |
| D-270 | CF$_3$ | CH$_3$ | Br |
| D-271 | H | C$_2$H$_5$ | Br |
| D-272 | F | C$_2$H$_5$ | Br |
| D-273 | Cl | C$_2$H$_5$ | Br |
| D-274 | Br | C$_2$H$_5$ | Br |
| D-275 | CH$_3$ | C$_2$H$_5$ | Br |
| D-276 | C$_2$H$_5$ | C$_2$H$_5$ | Br |
| D-277 | n-C$_3$H$_7$ | C$_2$H$_5$ | Br |
| D-278 | i-C$_3$H$_7$ | C$_2$H$_5$ | Br |
| D-279 | CF$_3$ | C$_2$H$_5$ | Br |
| D-280 | H | i-C$_3$H$_7$ | Br |
| D-281 | F | i-C$_3$H$_7$ | Br |
| D-282 | Cl | i-C$_3$H$_7$ | Br |
| D-283 | Br | i-C$_3$H$_7$ | Br |
| D-284 | CH$_3$ | i-C$_3$H$_7$ | Br |
| D-285 | C$_2$H$_5$ | i-C$_3$H$_7$ | Br |
| D-286 | n-C$_3$H$_7$ | i-C$_3$H$_7$ | Br |
| D-287 | i-C$_3$H$_7$ | i-C$_3$H$_7$ | Br |
| D-288 | CF$_3$ | i-C$_3$H$_7$ | Br |
| D-289 | CHF$_2$ | i-C$_3$H$_7$ | Br |
| D-290 | CH$_2$F | i-C$_3$H$_7$ | Br |
| D-291 | H | CF$_3$ | Br |
| D-292 | F | CF$_3$ | Br |
| D-293 | Cl | CF$_3$ | Br |
| D-294 | Br | CF$_3$ | Br |
| D-295 | CH$_3$ | CF$_3$ | Br |
| D-296 | C$_2$H$_5$ | CF$_3$ | Br |
| D-297 | n-C$_3$H$_7$ | CF$_3$ | Br |
| D-298 | i-C$_3$H$_7$ | CF$_3$ | Br |
| D-299 | CF$_3$ | CF$_3$ | Br |
| D-300 | CHF$_2$ | CF$_3$ | Br |
| D-301 | H | H | CH$_3$ |
| D-302 | F | H | CH$_3$ |
| D-303 | Cl | H | CH$_3$ |
| D-304 | Br | H | CH$_3$ |
| D-305 | CH$_3$ | H | CH$_3$ |
| D-306 | C$_2$H$_5$ | H | CH$_3$ |
| D-307 | n-C$_3$H$_7$ | H | CH$_3$ |
| D-308 | i-C$_3$H$_7$ | H | CH$_3$ |
| D-309 | s-C$_4$H$_9$ | H | CH$_3$ |
| D-310 | i-C$_4$H$_9$ | H | CH$_3$ |
| D-311 | t-C$_4$H$_9$ | H | CH$_3$ |
| D-312 | n-C$_5$H$_{11}$ | H | CH$_3$ |
| D-313 | CF$_3$ | H | CH$_3$ |
| D-314 | H | F | CH$_3$ |
| D-315 | F | F | CH$_3$ |
| D-316 | Cl | F | CH$_3$ |
| D-317 | Br | F | CH$_3$ |
| D-318 | CH$_3$ | F | CH$_3$ |
| D-319 | C$_2$H$_5$ | F | CH$_3$ |
| D-320 | n-C$_3$H$_7$ | F | CH$_3$ |
| D-321 | i-C$_3$H$_7$ | F | CH$_3$ |
| D-322 | CF$_3$ | F | CH$_3$ |
| D-323 | H | Cl | CH$_3$ |
| D-324 | F | Cl | CH$_3$ |
| D-325 | Cl | Cl | CH$_3$ |
| D-326 | Br | Cl | CH$_3$ |
| D-327 | CH$_3$ | Cl | CH$_3$ |
| D-328 | C$_2$H$_5$ | Cl | CH$_3$ |
| D-329 | n-C$_3$H$_7$ | Cl | CH$_3$ |
| D-330 | i-C$_3$H$_7$ | Cl | CH$_3$ |
| D-331 | CF$_3$ | Cl | CH$_3$ |
| D-332 | H | Br | CH$_3$ |
| D-333 | F | Br | CH$_3$ |
| D-334 | Cl | Br | CH$_3$ |
| D-335 | Br | Br | CH$_3$ |
| D-336 | CH$_3$ | Br | CH$_3$ |
| D-337 | C$_2$H$_5$ | Br | CH$_3$ |
| D-338 | n-C$_3$H$_7$ | Br | CH$_3$ |
| D-339 | i-C$_3$H$_7$ | Br | CH$_3$ |
| D-340 | s-C$_4$H$_9$ | Br | CH$_3$ |
| D-341 | CF$_3$ | Br | CH$_3$ |
| D-342 | H | CH$_3$ | CH$_3$ |
| D-343 | F | CH$_3$ | CH$_3$ |
| D-344 | Cl | CH$_3$ | CH$_3$ |
| D-345 | Br | CH$_3$ | CH$_3$ |
| D-346 | CH$_3$ | CH$_3$ | CH$_3$ |
| D-347 | C$_2$H$_5$ | CH$_3$ | CH$_3$ |
| D-348 | n-C$_3$H$_7$ | CH$_3$ | CH$_3$ |
| D-349 | i-C$_3$H$_7$ | CH$_3$ | CH$_3$ |
| D-350 | CF$_3$ | CH$_3$ | CH$_3$ |
| D-351 | H | C$_2$H$_5$ | CH$_3$ |
| D-352 | F | C$_2$H$_5$ | CH$_3$ |
| D-353 | Cl | C$_2$H$_5$ | CH$_3$ |
| D-354 | Br | C$_2$H$_5$ | CH$_3$ |
| D-355 | CH$_3$ | C$_2$H$_5$ | CH$_3$ |
| D-356 | C$_2$H$_5$ | C$_2$H$_5$ | CH$_3$ |
| D-357 | n-C$_3$H$_7$ | C$_2$H$_5$ | CH$_3$ |
| D-358 | i-C$_3$H$_7$ | C$_2$H$_5$ | CH$_3$ |
| D-359 | CF$_3$ | C$_2$H$_5$ | CH$_3$ |
| D-360 | H | i-C$_3$H$_7$ | CH$_3$ |
| D-361 | F | i-C$_3$H$_7$ | CH$_3$ |
| D-362 | Cl | i-C$_3$H$_7$ | CH$_3$ |
| D-363 | Br | i-C$_3$H$_7$ | CH$_3$ |
| D-364 | CH$_3$ | i-C$_3$H$_7$ | CH$_3$ |
| D-365 | C$_2$H$_5$ | i-C$_3$H$_7$ | CH$_3$ |
| D-366 | n-C$_3$H$_7$ | i-C$_3$H$_7$ | CH$_3$ |
| D-367 | i-C$_3$H$_7$ | i-C$_3$H$_7$ | CH$_3$ |
| D-368 | CF$_3$ | i-C$_3$H$_7$ | CH$_3$ |
| D-369 | CHF$_2$ | i-C$_3$H$_7$ | CH$_3$ |
| D-370 | CH$_2$F | i-C$_3$H$_7$ | CH$_3$ |
| D-371 | H | CF$_3$ | CH$_3$ |
| D-372 | F | CF$_3$ | CH$_3$ |
| D-373 | Cl | CF$_3$ | CH$_3$ |
| D-374 | Br | CF$_3$ | CH$_3$ |
| D-375 | CH$_3$ | CF$_3$ | CH$_3$ |
| D-376 | C$_2$H$_5$ | CF$_3$ | CH$_3$ |
| D-377 | n-C$_3$H$_7$ | CF$_3$ | CH$_3$ |
| D-378 | i-C$_3$H$_7$ | CF$_3$ | CH$_3$ |
| D-379 | CF$_3$ | CF$_3$ | CH$_3$ |
| D-380 | CHF$_2$ | CF$_3$ | CH$_3$ |
| D-381 | H | H | C$_2$H$_5$ |
| D-382 | F | H | C$_2$H$_5$ |
| D-383 | Cl | H | C$_2$H$_5$ |
| D-384 | Br | H | C$_2$H$_5$ |
| D-385 | CH$_3$ | H | C$_2$H$_5$ |
| D-386 | C$_2$H$_5$ | H | C$_2$H$_5$ |
| D-387 | n-C$_3$H$_7$ | H | C$_2$H$_5$ |
| D-388 | i-C$_3$H$_7$ | H | C$_2$H$_5$ |
| D-389 | CF$_3$ | H | C$_2$H$_5$ |
| D-390 | H | F | C$_2$H$_5$ |
| D-391 | F | F | C$_2$H$_5$ |
| D-392 | Cl | F | C$_2$H$_5$ |
| D-393 | Br | F | C$_2$H$_5$ |
| D-394 | CH$_3$ | F | C$_2$H$_5$ |
| D-395 | C$_2$H$_5$ | F | C$_2$H$_5$ |
| D-396 | n-C$_3$H$_7$ | F | C$_2$H$_5$ |
| D-397 | i-C$_3$H$_7$ | F | C$_2$H$_5$ |
| D-398 | CF$_3$ | F | C$_2$H$_5$ |
| D-399 | H | Cl | C$_2$H$_5$ |
| D-400 | F | Cl | C$_2$H$_5$ |
| D-401 | Cl | Cl | C$_2$H$_5$ |
| D-402 | Br | Cl | C$_2$H$_5$ |
| D-403 | CH$_3$ | Cl | C$_2$H$_5$ |
| D-404 | C$_2$H$_5$ | Cl | C$_2$H$_5$ |
| D-405 | n-C$_3$H$_7$ | Cl | C$_2$H$_5$ |
| D-406 | i-C$_3$H$_7$ | Cl | C$_2$H$_5$ |
| D-407 | CF$_3$ | Cl | C$_2$H$_5$ |
| D-408 | H | Br | C$_2$H$_5$ |

TABLE D-continued

| No. | R¹ | R² | R³ |
|---|---|---|---|
| D-409 | F | Br | $C_2H_5$ |
| D-410 | Cl | Br | $C_2H_5$ |
| D-411 | Br | Br | $C_2H_5$ |
| D-412 | $CH_3$ | Br | $C_2H_5$ |
| D-413 | $C_2H_5$ | Br | $C_2H_5$ |
| D-414 | $n-C_3H_7$ | Br | $C_2H_5$ |
| D-415 | $i-C_3H_7$ | Br | $C_2H_5$ |
| D-416 | $CF_3$ | Br | $C_2H_5$ |
| D-417 | H | $CH_3$ | $C_2H_5$ |
| D-418 | F | $CH_3$ | $C_2H_5$ |
| D-419 | Cl | $CH_3$ | $C_2H_5$ |
| D-420 | Br | $CH_3$ | $C_2H_5$ |
| D-421 | $CH_3$ | $CH_3$ | $C_2H_5$ |
| D-422 | $C_2H_5$ | $CH_3$ | $C_2H_5$ |
| D-423 | $n-C_3H_7$ | $CH_3$ | $C_2H_5$ |
| D-424 | $i-C_3H_7$ | $CH_3$ | $C_2H_5$ |
| D-425 | $CF_3$ | $CH_3$ | $C_2H_5$ |
| D-426 | H | $C_2H_5$ | $C_2H_5$ |
| D-427 | F | $C_2H_5$ | $C_2H_5$ |
| D-428 | Cl | $C_2H_5$ | $C_2H_5$ |
| D-429 | Br | $C_2H_5$ | $C_2H_5$ |
| D-430 | $CH_3$ | $C_2H_5$ | $C_2H_5$ |
| D-431 | $C_2H_5$ | $C_2H_5$ | $C_2H_5$ |
| D-432 | $n-C_3H_7$ | $C_2H_5$ | $C_2H_5$ |
| D-433 | $i-C_3H_7$ | $C_2H_5$ | $C_2H_5$ |
| D-434 | $CF_3$ | $C_2H_5$ | $C_2H_5$ |
| D-435 | H | $i-C_3H_7$ | $C_2H_5$ |
| D-436 | F | $i-C_3H_7$ | $C_2H_5$ |
| D-437 | Cl | $i-C_3H_7$ | $C_2H_5$ |
| D-438 | Br | $i-C_3H_7$ | $C_2H_5$ |
| D-439 | $CH_3$ | $i-C_3H_7$ | $C_2H_5$ |
| D-440 | $C_2H_5$ | $i-C_3H_7$ | $C_2H_5$ |
| D-441 | $n-C_3H_7$ | $i-C_3H_7$ | $C_2H_5$ |
| D-442 | $i-C_3H_7$ | $i-C_3H_7$ | $C_2H_5$ |
| D-443 | $CF_3$ | $i-C_3H_7$ | $C_2H_5$ |
| D-444 | $CHF_2$ | $i-C_3H_7$ | $C_2H_5$ |
| D-445 | $CH_2F$ | $i-C_3H_7$ | $C_2H_5$ |
| D-446 | H | $CF_3$ | $C_2H_5$ |
| D-447 | F | $CF_3$ | $C_2H_5$ |
| D-448 | Cl | $CF_3$ | $C_2H_5$ |
| D-449 | Br | $CF_3$ | $C_2H_5$ |
| D-450 | $CH_3$ | $CF_3$ | $C_2H_5$ |
| D-451 | $C_2H_5$ | $CF_3$ | $C_2H_5$ |
| D-452 | $n-C_3H_7$ | $CF_3$ | $C_2H_5$ |
| D-453 | $i-C_3H_7$ | $CF_3$ | $C_2H_5$ |
| D-454 | $CF_3$ | $CF_3$ | $C_2H_5$ |
| D-455 | $CHF_2$ | $CF_3$ | $C_2H_5$ |
| D-456 | H | H | $i-C_3H_7$ |
| D-457 | F | H | $i-C_3H_7$ |
| D-458 | Cl | H | $i-C_3H_7$ |
| D-459 | Br | H | $i-C_3H_7$ |
| D-460 | $CH_3$ | H | $i-C_3H_7$ |
| D-461 | $C_2H_5$ | H | $i-C_3H_7$ |
| D-462 | $n-C_3H_7$ | H | $i-C_3H_7$ |
| D-463 | $i-C_3H_7$ | H | $i-C_3H_7$ |
| D-464 | $CF_3$ | H | $i-C_3H_7$ |
| D-465 | H | F | $i-C_3H_7$ |
| D-466 | F | F | $i-C_3H_7$ |
| D-467 | Cl | F | $i-C_3H_7$ |
| D-468 | Br | F | $i-C_3H_7$ |
| D-469 | $CH_3$ | F | $i-C_3H_7$ |
| D-470 | $C_2H_5$ | F | $i-C_3H_7$ |
| D-471 | $n-C_3H_7$ | F | $i-C_3H_7$ |
| D-472 | $i-C_3H_7$ | F | $i-C_3H_7$ |
| D-473 | $CF_3$ | F | $i-C_3H_7$ |
| D-474 | H | Cl | $i-C_3H_7$ |
| D-475 | F | Cl | $i-C_3H_7$ |
| D-476 | Cl | Cl | $i-C_3H_7$ |
| D-477 | Br | Cl | $i-C_3H_7$ |
| D-478 | $CH_3$ | Cl | $i-C_3H_7$ |
| D-479 | $C_2H_5$ | Cl | $i-C_3H_7$ |
| D-480 | $n-C_3H_7$ | Cl | $i-C_3H_7$ |
| D-481 | $i-C_3H_7$ | Cl | $i-C_3H_7$ |
| D-482 | $CF_3$ | Cl | $i-C_3H_7$ |
| D-483 | H | Br | $i-C_3H_7$ |
| D-484 | F | Br | $i-C_3H_7$ |
| D-485 | Cl | Br | $i-C_3H_7$ |
| D-486 | Br | Br | $i-C_3H_7$ |
| D-487 | $CH_3$ | Br | $i-C_3H_7$ |
| D-488 | $C_2H_5$ | Br | $i-C_3H_7$ |
| D-489 | $n-C_3H_7$ | Br | $i-C_3H_7$ |
| D-490 | $i-C_3H_7$ | Br | $i-C_3H_7$ |
| D-491 | $CF_3$ | Br | $i-C_3H_7$ |
| D-492 | H | $CH_3$ | $i-C_3H_7$ |
| D-493 | F | $CH_3$ | $i-C_3H_7$ |
| D-494 | Cl | $CH_3$ | $i-C_3H_7$ |
| D-495 | Br | $CH_3$ | $i-C_3H_7$ |
| D-496 | $CH_3$ | $CH_3$ | $i-C_3H_7$ |
| D-497 | $C_2H_5$ | $CH_3$ | $i-C_3H_7$ |
| D-498 | $n-C_3H_7$ | $CH_3$ | $i-C_3H_7$ |
| D-499 | $i-C_3H_7$ | $CH_3$ | $i-C_3H_7$ |
| D-500 | $CF_3$ | $CH_3$ | $i-C_3H_7$ |
| D-501 | H | $C_2H_5$ | $i-C_3H_7$ |
| D-502 | F | $C_2H_5$ | $i-C_3H_7$ |
| D-503 | Cl | $C_2H_5$ | $i-C_3H_7$ |
| D-504 | Br | $C_2H_5$ | $i-C_3H_7$ |
| D-505 | $CH_3$ | $C_2H_5$ | $i-C_3H_7$ |
| D-506 | $C_2H_5$ | $C_2H_5$ | $i-C_3H_7$ |
| D-507 | $n-C_3H_7$ | $C_2H_5$ | $i-C_3H_7$ |
| D-508 | $i-C_3H_7$ | $C_2H_5$ | $i-C_3H_7$ |
| D-509 | $CF_3$ | $C_2H_5$ | $i-C_3H_7$ |
| D-510 | H | $i-C_3H_7$ | $i-C_3H_7$ |
| D-511 | F | $i-C_3H_7$ | $i-C_3H_7$ |
| D-512 | Cl | $i-C_3H_7$ | $i-C_3H_7$ |
| D-513 | Br | $i-C_3H_7$ | $i-C_3H_7$ |
| D-514 | $CH_3$ | $i-C_3H_7$ | $i-C_3H_7$ |
| D-515 | $C_2H_5$ | $i-C_3H_7$ | $i-C_3H_7$ |
| D-516 | $n-C_3H_7$ | $i-C_3H_7$ | $i-C_3H_7$ |
| D-517 | $i-C_3H_7$ | $i-C_3H_7$ | $i-C_3H_7$ |
| D-518 | $CF_3$ | $i-C_3H_7$ | $i-C_3H_7$ |
| D-519 | $CHF_2$ | $i-C_3H_7$ | $i-C_3H_7$ |
| D-520 | $CH_2F$ | $i-C_3H_7$ | $i-C_3H_7$ |
| D-521 | H | $CF_3$ | $i-C_3H_7$ |
| D-522 | F | $CF_3$ | $i-C_3H_7$ |
| D-523 | Cl | $CF_3$ | $i-C_3H_7$ |
| D-524 | Br | $CF_3$ | $i-C_3H_7$ |
| D-525 | $CH_3$ | $CF_3$ | $i-C_3H_7$ |
| D-526 | $C_2H_5$ | $CF_3$ | $i-C_3H_7$ |
| D-527 | $n-C_3H_7$ | $CF_3$ | $i-C_3H_7$ |
| D-528 | $i-C_3H_7$ | $CF_3$ | $i-C_3H_7$ |
| D-529 | $CF_3$ | $CF_3$ | $i-C_3H_7$ |
| D-530 | $CHF_2$ | $CF_3$ | $i-C_3H_7$ |

The compounds I are suitable as fungicides. They are distinguished by outstanding activity against a broad spectrum of phytopathogenic fungi, in particular from the classes of the Ascomycetes, Deuteromycetes, Phycomycetes and Basidiomycetes. Some of them act systemically, and they can be employed in crop protection as foliar- and soil-acting fungicides.

They are especially important for controlling a large number of fungi on a variety of crop plants such as wheat, rye, barley, oats, rice, maize, grass, bananas, cotton, soya, coffee, sugar cane, grapevines, fruit species, ornamentals and vegetables such as cucumbers, beans, tomatoes, potatoes and cucurbits, and on the seeds of these plants.

Specifically, they are suitable for controlling the following plant diseases:

Alternaria species on vegetables and fruit,
*Botrytis cinerea* (gray mold) on strawberries, vegetables, ornamentals and grapevines,
*Cercospora arachidicola* on peanuts,
*Erysiphe cichoracearum* and *Sphaerotheca fuliginea* on cucurbits,
*Erysiphe graminis* (powdery mildew) on cereals,
Fusarium and Verticillium species on various plants,
Helminthosporium species on cereals, Mycosphaerella species on bananas and peanuts,

*Phytophthora infestans* on potatoes and tomatoes,

*Plasmopara viticola* on grapevines,

*Podosphaera leucotricha* on apples,

*Pseudocercosporella herpotrichoides* on wheat and barley,

Pseudocercosporella species on hops and cucumbers,

Puccinia species on cereals,

*Pyricularia oryzae* on rice,

Rhizoctonia species on cotton, rice and lawns,

*Septoria nodorum* on wheat,

*Uncinula necator* on grapevines,

Ustilago species on cereals and sugar cane, and

*Venturia inaequalis* (scab) on apples and pears.

Moreover, the compounds I are suitable for controlling harmful fungi such as *Paecilomyces variotii* in the protection of materials (eg. wood, paper, paint dispersions, fibers and tissues) and in the protection of stored products.

The compounds I are applied by treating the fungi, or the plants, seeds, materials or the soil to be protected against fungal infection, with a fungicidally active amount of the active ingredients. Application can be effected both before and after infection of the materials, plants or seeds by the fungi.

In general, the fungicidal compositions comprise from 0.1 to 95, preferably 0.5 to 90%, by weight of active ingredient.

When used in crop protection, the rates of application are from 0.01 to 2.0 kg of active ingredient per ha, depending on the nature of the effect desired.

In the treatment of seed, amounts of active ingredient of from 0.001 to 0.1 g, preferably 0.01 to 0.05 g, are generally required per kilogram of seed.

When used in the protection of materials or stored products, the rate of application of active ingredient depends on the nature of the field of application and on the effect desired. Rates of application conventionally used in the protection of materials are, for example, from 0.001 g to 2 kg, preferably 0.005 g to 1 kg, of active ingredient per cubic meter of material treated.

Moreover, the compounds of the formula I are suitable for efficiently controlling animal pests from the classes of the insects, arachnids and nematodes. They can be employed in crop protection and in the hygiene, stored-product and veterinary sector for controlling animal pests. In particular, they are suitable for controlling the following animal pests:

insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis*, beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllotreta chrysocephala,* Phyllophaga sp., *Phyllopertha horticola, Phyllotreta nemorum, Phyllotreta striolata, Popillia japonica, Sitona lineatus* and *Sitophilus granaria*, dipterans (Diptera), for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa*, thrips (Thysanoptera), eg. *Frankliniella fusca, Frankliniella occidentalis, Frankliniella tritici, Scirtothrips citri, Thrips oryzae, Thrips palmi* and *Thrips tabaci*, hymenopterans (Hymenoptera), eg. *Athalia rosae, Atta cephalotes, Atta sexdens, Atta texana, Hoplocampa minuta, Hoplocampa testudinea, Monomorium pharaonis, Solenopsis geminata* and *Solenopsis invicta*, heteropterans (Heteroptera), eg. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor*, homopterans (Homoptera), eg. *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii,*

*Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii,* termites (Isoptera), eg. *Calotermes flavicollis, Leucotermes flavipes, Reticulitermes lucifugus* und *Termes natalensis,* orthopterans (Orthoptera), eg. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus,*

Arachnoidea, such as arachnids (Acarina), eg. *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius* and *Tetranychus urticae,* nematodes such as root knot nematodes, eg. *Meloidogyne hapla, Meloidogyne incognita, Meloidogyne javanica,* cyst-forming nematodes, eg. *Globodera rostochiensis, Heterodera avenae, Heterodera glycines, Heterodera schachtii, Heterodera trifolii,* stem eelworms and foliar nematodes, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

The rate of application of active ingredient for controlling animal pests is from 0.1 to 2.0, preferably 0.2 to 1.0, kg/ha under field conditions.

The compounds I can be converted into the customary formulations, eg. solutions, emulsions, suspensions, dusts, powders, pastes and granules. The use form depends on the particular purpose; in any case, it should ensure a fine and uniform distribution of the compound according to the invention.

The formulations are prepared in a known manner, eg. by extending the active ingredient with solvents and/or carriers, if desired using emulsifiers and dispersants, it also being possible to use other organic solvents as auxiliary solvents if water is used as the diluent. Auxiliaries which are suitable are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly-disperse silica, silicates); emulsifiers such as non-ionic and anionic emulsifiers (eg. polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of napthalenesulfonic acid with phenol or formaldehyde, polyoxyethylene octylphenol ether, ethoxylated isooctylphenol, octylphenol, nonylphenol, alkylphenol polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, eg. benzene, toluene, xylene, paraffin, tetrahydro-naphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone and water.

Powders, materials for spreading and dusts can be prepared by mixing or concomitantly grinding the active substances with a solid carrier.

Granules, eg. coated granules, impregnated granules and homogeneous granules, can be prepared by binding the active ingredients to solid carriers. Examples of solid carriers are mineral earths, such as silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, eg. ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

The following are exemplary formulations:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which had been sprayed onto the surface of this silica gel.

This gives a formulation of the active ingredient with good adhesion properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-a-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

The active ingredients can be used as such, in the form of their formulations or the use forms prepared therefrom, eg. in the form of directly sprayable solutions, powders, suspensions or dispersions, emulsions, oil dispersions, pastes, dusts, materials for spreading or granules, by means of spraying, atomizing, dusting, spreading or pouring. The use forms depend entirely on the intended purposes; in any case, they are intended to guarantee the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances as such, or dissolved in an oil or solvent, can be homogenized in water by means of a wetting agent, tackifier, dispersant or emulsifier. Alternatively, it is possible to prepare concentrates composed of an active substance, wetter, tackifier, dispersant or emulsifier and, if appropriate, solvent or oil, and such concentrates are suitable for dilution with water.

The active ingredient concentrations in the ready-to-use products can be varied within substantial ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even the active ingredient without additives.

Various types of oils, herbicides, fungicides, other pesticides or bactericides may be added to the active ingredients, if appropriate also only immediately prior to use (tank mix). These agents can be admixed with the agents according to the invention 45 in a weight ratio of 1:10 to 10:1.

In the use form as fungicides, the compositions according to the invention can also be present together with other active ingredients, eg. with herbicides, insecticides, growth regulators, fungicides or else with fertilizers. Mixing the compounds I or the compositions comprising them in the use form as fungicides with other fungicides frequently results in a broader fungicidal spectrum of action.

The following list of fungicides together with which the compounds according to the invention can be used is intended to illustrate the possible combinations, but not to impose any limitation:

sulfur, dithiocarbamates and their derivatives, such as iron (III) dimethyldithiocarbamate, zinc dimethyldithiocarbamate, zinc ethylenebisdithiocarbamate, manganese ethylenebisdithiocarbamate, manganese zinc ethylenediamine-bisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl)disulfide;

nitro derivatives, such as dinitro-(1-methylheptyl)phenyl crotonate, 2-sec-butyl-4,6-dinitrophenyl 3,3-dimethylacrylate, 2-sec-butyl-4,6-dinitrophenylisopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis-(dimethylamino)phosphinyl]-3-phenyl-1,2,4-triazole, 2,3-dicyano-1,4-dithioanthraquinone, 2-thio-1,3-dithiolo-[4,5-b] quinoxaline, methyl 1-(butylcarbamoyl)-2-benzimidazole-carbamate, 2-methoxycarbonylaminobenzimidazole, 2-(2-furyl)-benzimidazole, 2-(4-thiazolyl)benzimidazole, N-(1,1,2,2-tetrachloroethylthio)tetrahydrophthalimide, N-trichloromethylthio-tetrahydrophthalimide, N-trichloromethylthiophthalimide, N-dichlorofluoromethylthio-N',N'-dimethyl-N-phenylsulfodiamide, 5-ethoxy-3-trichloromethyl-1,2,3-thiadiazole, 2-thiocyanatomethylthiobenzothiazole, 1,4-dichloro-2,5-dimethoxy-benzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H pyran-3-carboxanilide, 2-methylfuran-3-carboxanilide, 2,5-dimethylfuran-3-carboxanilide, 2,4,5-tri-methylfuran-3-carboxanilide, N-cyclohexyl-2,5-dimethylfuran-3-carboxamide, N-cyclohexyl-N-methoxy-2,5- dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-1-formylamino-2,2,2-trichlorethane, 2,6-dimethyl-N-tridecylmorpholine or its salts, 2,6-dimethyl-N-cyclododecylmorpholine or its salts, N-[3-(p-tert-butyl-phenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H 1,2,4-triazole, 1-[2-(2,4-dichlorophenyl)-4-n-propyl-1,3-dioxolan-2-ylethyl]-1H 1,2,4-triazole, N-(n-propyl)-N-(2,4,6-trichlorophenoxyethyl)-N'-imidazolylurea, 1-(4-chlorophenoxy)-3,3-dimethyl-1-(1H 1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, strobilurines such as methyl E-methoxyimino-[α-(o-tolyloxy)-o-tolyl]acetate, methyl E-2-{2-[6-(2-cyanophenoxy)pyrimidin-4-yloxy]phenyl}-3-methoxyacrylate, methyl-E-methoxyimino-[α-(2-phenoxyphenyl)]acetamide, methyl E-methoxyimino-[α-(2,5-dimethylphenoxy)-o-tolyl]acetamide, anilinopyrimidines such as N-(4,6-dimethylpyrimidin-2-yl)aniline, N-[4-methyl-6-(1-propynyl)pyrimidin-2-yl]aniline, N-[4-methyl-6-cyclopropylpyrimidin-2-yl]aniline, phenylpyrroles such as 4-(2,2-difluoro-1,3-benzodioxol-4-yl)-pyrrole-3-carbonitrile, cinnamamides such as 3-(4-chlorophenyl)-3-(3,4-dimethoxy-phenyl)acryloylmorpholide, and a variety of fungicides such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl) alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropyl-carbamoylhydantoin, N-(3,5-dichlorophenyl)-1,2-dimethyl-cyclopropane-1,2-dicarboximide, 2-cyano-[N-(ethyl-aminocarbonyl)-2-methoximino]acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-amino-pyridine, 1-((bis(4-fluorophenyl)methylsilyl)methyl)-1H-1,2,4-triazole.

SYNTHESIS EXAMPLES

With due modification of the starting compounds, the protocols shown in the synthesis examples below were used for obtaining further compounds I. The resulting compounds, together with physical data, are listed in the Tables which follow.

Example 1

Preparation of 2-chloro-4-(3,5-dimethylpyrazol-1-yl)phenol

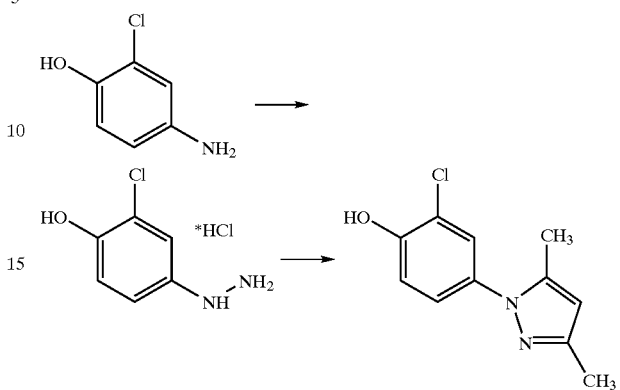

At from −5 to −10° C., a suspension of 123 g (858 mmol) of 2-chloro-4-aminophenol in 190 ml of conc. HCl was added dropwise to a solution of 71 g (1 mol) of $NaNO_2$ in 190 ml of water. At from −5 to −10° C., this suspension was added to a solution of 354 g (1.72 mol) of $SnCl_2 \cdot 2H_2O$ in 800 ml of conc. HCl. The mixture was stirred at about 20–25° C. for approximately 14 hours and the crystalline material was filtered off and washed with water. After drying, 85 g of 3-chloro-4-hydroxyphenyldiazonium hydrochloride were obtained.

A suspension of 39 g (0.2 mol) of the diazonium salt in 200 ml of ethanol was admixed with 17 g (0.2 mol) of acetylacetone and the mixture was refluxed for two hours. The solvent was distilled off and the residue was then digested in a water/methylene chloride mixture. The crystalline material was filtered off and then washed with methylene chloride, giving 17 g of the title compound as HCl salt.

Example 2

Preparation of methyl 2-{2-chloro-[4-(3,5-dimethyl)-pyrazol-1-yl]phenoxymethylene}phenylglyoxylate O-methyloxime [I-12]

A solution of 1.2 g (5 mmol) of the phenylpyrazole from Example 1, 1.6 g (5 mmol) of methyl 2-bromomethylphenylglyoxylate O-methyloxime [cf. EP-A 254 426] and 2.2 g (16 mmol) of potassium carbonate in 30 ml of dimethylformamide (DMF) was stirred at 20–25° C. for approximately 14 hours. The reaction mixture was taken up in water and extracted with methyl tert-butyl ether (MTBE). The combined organic phases were washed with water and dried. The solvent was distilled off and the residue was chromatographed over silica gel (cyclohexane/ethyl acetate 1:1), giving 1.7 g of the title compound in the form of colorless crystals.

Example 3

Preparation of N-methyl-2-{2-chloro-[4-(3,5-dimethyl)pyrazol-1-yl]phenoxymethylene}-phenylglyoxamide O-methyloxime [I-11]

A solution of 1.7 g (4 mmol) of the ester II-12 and 1 ml of 40% strength aqueous methylamine solution were dissolved in 25 ml of tetrahydrofuran and the mixture was stirred at 20–25° C. for about 3.5 hours. The solvent was distilled off and the residue was crystallized from diisopropyl ether, giving 1.3 g of the title compound.

Example 4

Preparation of 1-methyl-4-{ortho-[2-chloro-4-(3,5-dimethylpyrazol-1-yl)phenoxymethylene]phenyl}-tetrazol-5-one [II-1]

0.12 g of sodium hydride was added to a solution of 1.02 g (4.6 mmol) of 2-chloro-4-(3,5-dimethylpyrazol-1-yl)phenol in 25 ml of anhydrous dimethylformamide. The mixture was stirred at 20–25° C. for 1 hour, after which a solution of 1.24 g of 1-methyl-4-(orthobromomethylene)phenyltetrazol-5-one in 10 ml of anhydrous dimethylformamide was added, and stirring was continued at 20–25° C. for 20 hours. 250 ml of dil. NaCl solution were subsequently added. The mixture was extracted with ethyl acetate, and the organic phase was washed with water, dried and freed of solvents. Recrystallization of the residue from methyl tert-butyl ether/hexane gave 1.3 g of the title compound as light-beige crystals of m.p. 122–124° C.

IR [$cm^{-1}$]: 1737, 1510, 1457, 1427, 1396, 1282, 1242, 1063, 1031, 747.

Example 5

Preparation of 1-methyl-4-[ortho-(4-iodo-2-methylphenoxymethylene)phenyl]tetrazol-5-one A solution of 5.38 g (20 mmol) of 1-methyl-4-(orthobromomethylene)phenyltetrazol-5-one, 4.68 g (20 mmol) of 4-iodo-2-methylphenol and 4.14 g (60 mmol) of potassium carbonate in 60 ml of anhydrous dimethylformamide was stirred at approximately 85° C. for 4 hours. 600 ml of dil. sodium chloride solution were subsequently added. The reaction solution was extracted with ethyl acetate and the organic phase was washed with water, dried and freed of the solvent. This gave 8.2 g of the title compound as colorless crystals of m.p. 128–130° C.

Example 6

Preparation of 1-methyl-4-(ortho-(2-methyl-4-(1-phenylpyrazol-4-yl)-phenoxymethylene)phenyl)-tetrazol-5-one [II-9]

A solution of 1.48 g (3.5 mmol) of the tetrazolone from Example 5, 1.51 g of (1-phenylpyrazol-4-yl)tributylstannane and 0.2 g of tetrakis(triphenylphosphine)palladium(0) in 20 ml of anhydrous toluene was stirred at 70° C. for 2 hours and then refluxed for 2 hours. The solvent was distilled off and the residue was chromatographed over silica gel (cyclohexane:methyl tert-butyl ether mixture 1:1), giving 0.24 g of the title compound of m.p. 152–153° C.

IR [$cm^{-1}$]: 1717, 1498, 1411, 1245, 1139, 1015, 813, 753.

TABLE I

| No. | Formula $Y_n = H$ | $Y^1$ | $Y^{1'}$ | X | Phys. data (m.p. [° C.]; IR [$cm^{-1}$]; $^1$H NMR (CDCl$_3$) δ [ppm]) |
|---|---|---|---|---|---|
| I-1 | IC | Cl | H | pyrazol-1-yl | 1727, 1521, 1503, 1279, 1223, 1069, 1045, 1018 |
| I-2 | ID | Cl | H | pyrazol-1-yl | 116–118 |
| I-3 | IA | Cl | H | pyrazol-1-yl | 146–148 |
| I-4 | IB | Cl | H | pyrazol-1-yl | 117–119 |
| I-5 | IE | Cl | H | pyrazol-1-yl | 110–114 |
| I-6 | ID | Cl | H | 3,5-(CF$_3$)$_2$-pyrazol-1-yl | 110–113 |
| I-7 | IC | Cl | H | 3,5-(CF$_3$)$_2$-pyrazol-1-yl | 103–106 |
| I-8 | IA | Cl | H | 3,5-(CF$_3$)$_2$-pyrazol-1-yl | 129–132 |
| I-9 | IB | Cl | H | 3,5-(CF$_3$)$_2$-pyrazol-1-yl | 1.1; 1.6(d, 3H); 3.7(s, 3H); 5.0(s, 2H); 6.9–7.5(m, 9H) |
| I-10 | IE | Cl | H | 3,5-(CF$_3$)$_2$-pyrazol-1-yl | 104–106 |
| I-11 | ID | Cl | H | 3,5-(CH$_3$)$_2$-pyrazol-1-yl | 1671, 1555, 1410, 1281, 1260, 1231, 1062, 1037, 978 |
| I-12 | IC | Cl | H | 3,5-(CH$_3$)$_2$-pyrazol-1-yl | 1673, 1512, 1285, 1260, 1233, 1060, 1033, 1017 |
| I-13 | IA | Cl | H | 3,5-(CH$_3$)$_2$-pyrazol-1-yl | 93–96 |
| I-14 | IB | Cl | H | 3,5-(CH$_3$)$_2$-pyrazol-1-yl | 99–103 |
| I-15 | IE | Cl | H | 3,5-(CH$_3$)$_2$-pyrazol-1-yl | 1739, 1710, 1456, 1440, 1335, 1308, 1286, 1258, 1062 |
| I-16 | ID | Cl | H | 3,5-(CH$_3$)$_2$-4-Cl-pyrazol-1-yl | 1675, 1509, 1289, 1259, 1233, 1060, 1033, 1014, 984 |
| I-17 | IC | Cl | H | 3-CH$_3$-pyrazol-1-yl | 121–126 |
| I-18 | ID | Cl | H | 5-CH$_3$-pyrazol-1-yl | 84–89 |
| I-19 | IC | Cl | H | 3-CH$_3$-pyrazol-1-yl | 113–117 |
| I-20 | IA | Cl | H | 3-CH$_3$-pyrazol-1-yl | 127–131 |
| I-21 | IB | Cl | H | 3-CH$_3$-pyrazol-1-yl | 114–119 |
| I-22 | IE | Cl | H | 3-CH$_3$-pyrazol-1-yl | 108–110 |
| I-23 | IC | Cl | H | 3-CF$_3$-5-CH$_3$-pyrazol-1-yl | 1728, 1508, 1489, 1463, 1248, 1233, 1179, 1135, 1069, 1019 |
| I-24 | ID | Cl | H | 3-CF$_3$-5-CH$_3$-pyrazol-1-yl | 95–98 |
| I-25 | IA | Cl | H | 3-CF$_3$-5-CH$_3$-pyrazol-1-yl | 139–148 |
| I-26 | IB | Cl | H | 3-CF$_3$-5-CH$_3$-pyrazol-1-yl | 79–83 |
| I-27 | IE | Cl | H | 3-CF$_3$-5-CH$_3$-pyrazol-1-yl | 1740, 1508, 1490, 1459, 1248, 1235, 1179, 1135, 1101 |
| I-28 | ID | CH$_3$ | H | 3,5-(CF$_3$)$_2$-pyrazol-1-yl | 118–121 |
| I-29 | ID | CH$_3$ | H | pyrazol-1-yl | 75–78 |
| I-30 | IC | CH$_3$ | H | pyrazol-1-yl | 111–115 |
| I-31 | IA | CH$_3$ | H | pyrazol-1-yl | 97–101 |
| I-32 | IB | CH$_3$ | H | pyrazol-1-yl | 85–89 |

TABLE II

| No. | Formula ($Y_n$ = H) | $R^A$ | $R^B$ | $(Y^1)_m$*) | X | Phys. data (m.p. [° C.]; IR [cm$^{-1}$]) |
|---|---|---|---|---|---|---|
| II-1 | IH | — | $CH_3$ | 2-Cl | 3,5-$(CH_3)_2$-pyrazol-1-yl | cf. Example 4 |
| II-2 | IF | $OCH_3$ | $CH_3$ | 2-Cl | 3,5-$(CH_3)_2$-pyrazol-1-yl | m.p. = 143–144° C.<br>IR: 1733, 1613, 1515, 1474, 1465, 1414, 1314, 1275, 1267, 1062 |
| II-3 | IF | $OCH_3$ | $CH_3$ | 2-$CH_3$ | pyrazol-1-yl | IR: 1722, 1615, 1519, 1504, 1479, 1414, 1393, 1235, 1235, 753, 743 |
| II-4 | IF | $OCH_3$ | $CH_3$ | 2-$CH_3$ | 5-$CH_3$-pyrazol-1-yl | IR: 1723, 1615, 1531, 1506, 1478, 1458, 1414, 1234, 1049, 974 |
| II-5 | IF | $OCH_3$ | $CH_3$ | 2-Cl | 3,5-$(CF_3)_2$-pyrazol-1-yl | m.p. = 135–137° C.<br>IR: 1735, 1616, 1513, 1480, 1282, 1260, 1235, 1174, 1143, 1107 |
| II-6 | IH | — | $CH_3$ | 2-Cl | 3,5-$(CF_3)_2$-pyrazol-1-yl | m.p. = 138–139° C.<br>IR: 1718, 1513, 1281, 1260, 1246, 1236, 1183, 1169, 1133, 1109 |
| II-7 | IH | — | $CH_3$ | 2-$CH_3$ | 3-$CF_3$-pyrazol-1-yl | m.p. = 122–124° C.<br>IR: 1718, 1514, 1390, 1263, 1246, 1176, 1154, 1144, 1113, 752 |
| II-8 | IH | — | $CH_3$ | 3-$CH_3$ | pyrrol-1-yl | m.p. = 136–139° C.<br>IR: 1730, 1513, 1501, 1383, 1236, 1165, 1148, 1030, 737, 728 |
| II-9 | IH | — | $CH_3$ | 2-$CH_3$ | 1-phenylpyrazol-4-yl | cf. Example 6 |
| II-10 | IF | $OCH_3$ | $CH_3$ | 2-$CH_3$ | 3-$CF_3$-pyrazol-1-yl | m.p. = 86–88° C.<br>IR: 1722, 1616, 1506, 1480, 1415, 1388, 1258, 1239, 1170, 1133 |
| II-11 | IH | — | $CH_3$ | 2-$CH_3$ | 4-$CH_3$-oxazol-2-yl | m.p. = 152–153° C.<br>IR: 1723, 1617, 1503, 1399, 1348, 1274, 1262, 1252, 1130, 749 |
| II-12 | IH | — | $CH_3$ | 2-$CH_3$ | pyrazol-1-yl | m.p. = 150–152° C.<br>IR: 1716, 1522, 1506, 1403, 1258, 1236, 1052, 1038, 758, 748 |

*)position of $(Y^1)_m$ relative to the oxymethylene bridge

Examples for the Action Against Harmful Fungi

The fungicidal action of the compounds of the formula I was demonstrated by the following experiments:

The active ingredients, separately or together, were prepared as a 10% strength emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Wettol® EM (nonionic emulsifier based on ethoxylated castor oil) and diluted with water to the desired concentration.

The compounds A and B known from EP-A 280 185 and WO-A 93/15046, respectively, served as comparative active ingredients:

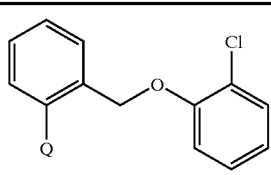

| No. | known from | Q |
|---|---|---|
| A | EP-A 280 185, No. 126 of the table | C(=CHCH$_3$)COOCH$_3$ |
| B | WO-A 93/15046, No. I-8 of Table 8 | N(—OCH$_3$)COOCH$_3$ |

Use Example 1
Activity Against Powdery Mildew of Wheat

Leaves of potted wheat seedlings c.v. "Frühgold" were sprayed to runoff point with an aqueous spray liquor which had been prepared using a stock solution of 10% of active ingredient, 63% of cyclohexanone and 27% of emulsifier and, 24 hours after the spray coating had dried on, dusted with spores of powdery mildew of wheat (Erysiphe graminis form a specialis tritici). The test plants were subsequently placed in a greenhouse at 20–24° C. and 60–90% relative atmospheric humidity. After 7 days, the extent of the mildew development was scored visually in % infection of the total leaf area.

In this test, the plants which had been treated with 16 ppm of the active ingredients No. I-2, I-4, I-5, I-6, I-7, I-9, I-10, I-12, I-13, I-15, I-17, I-18, I-22, I-24 and I-27 of Table I showed at most 15% infection, while the plants which had been treated with 16 ppm of the comparative active ingredient A showed 40% infection and the untreated plants 80% infection.

Use Example 2
Activity Against *Plasmopara viticola*

Leaves of potted grapevines c.v. "Müller-Thurgau" were sprayed to runoff point with an aqueous spray liquor which had been prepared using a stock solution of 10% of active compound, 63% of cyclohexanone and 27% of emulsifier. To be able to assess the persistency of the substances, the plants were, after the spray coating had dried on, kept in a greenhouse for 7 days. Only then were the leaves inoculated with an aqueous zoospore suspension of *Plasmopara viticola*. The grapevines were then initially kept in a water-vapor-saturated chamber at 24° C. for 48 hours and subsequently kept in a greenhouse at 20–30° C. for 5 days. After this period of time, the plants were once more placed in a humid chamber for 16 hours to accelerate Sporangiophore eruption. The extent of the disease development on the undersides of the leaves was then determined visually.

In this test, the plants which had been treated with 16 ppm of the active ingredients Nos. I-1, I-2, I-3, I-6, I-11, I-13, I-15, I-18, I-19, I-20 and I-24 of Table I showed at most 15% infection, while the plants which had been treated with 16 ppm of the comparative active ingredient B showed 25% infection and the untreated plants 75% infection.

Use Example 3

Curative Activity Against *Puccinia recondita* on Wheat (Leaf Rust of Wheat)

Leaves of potted wheat seedlings c.v. "Frühgold" were dusted with leaf rust spores (*Puccinia recondite*). The pots were then placed for 24 hours into a chamber with high atmospheric humidity (90 to 95%) at 20 to 25° C. During this time, the spores germinated, and the germinal tubes penetrated the leaf tissue. The next day, the infected plants were sprayed to runoff point with an aqueous spray liquor which had been prepared using a stock solution of 10% of active ingredient, 63% of cyclohexanone and 27% of emulsifier. After the spray coating had dried on, the test plants were cultivated for 7 days in a greenhouse at from 20 to 22° C. and a relative atmospheric humidity of 65 to 70%. The extent of rust development on the leaves was then determined.

In this test, the plants which had been treated with 16 ppm of the active ingredients Nos. I-2, I-11, I-12, I-13, I-14, I-15 and I-18 of Table I showed no infection, while the plants which had been treated with 16 ppm of the comparative active ingredient B showed 55% infection and the untreated plants 80% infection.

Use Example 4

Activity Against *Pyricularia oryzae* (Protective)

Leaves of potted rice seedlings c.v. "Tai-Nong 67" were sprayed to runoff point with an aqueous preparation of active ingredient which had been prepared using a stock solution of 10% of active ingredient, 63% of cyclohexanone and 27% of emulsifier. The next day, the plants were inoculated with an aqueous spore suspension of *Pyricularia oryzae*. The test plants were subsequently placed for 6 days into controlled-environment cabinets at 22–24° C. and a relative atmospheric humidity of 95–99%. The extent of the disease development on the leaves was then determined visually.

In this test, the plants which had been treated with 16 ppm of the active ingredients Nos. I-1, I-2, I-6, I-7, I-11, I-12, I-13, I-14, I-15, I-17, I-18, I-19, I-20, I-21 and I-22 of Table I showed at most 15% infection, while the plants which had been treated with 16 ppm of the comparative active ingredient A showed 60% infection and the untreated plants 85% infection.

Use Example 5

Activity Against *Botrytis cinerea* on Bell Pepper Leaves

Bell pepper seedlings c.v. "Neusiedler Ideal Elite" were, after 4 to 5 leaves were well developed, sprayed to runoff point with an aqueous preparation of active ingredient which had been prepared using a stock solution of 10% of active ingredient, 63% of cyclohexanone and 27% of emulsifier. The next day, the treated plants were innoculated with a spore suspension of *Botrytis cinerea* which contained 1.7× 10$^6$ spores/ml in a 2% strength aqueus Biomalz solution. The test plants were subsequently placed into controlled-environment cabinets at 22–24° C. and high atmospheric humidity. After 5 days, the extent of the fungal infection on the leaves could be determined visually in %.

In this test, the plants which had been treated with 250 ppm of the active ingredients II-4, II-5 and II-11 showed 10% infection, while the untreated plants showed 80% infection.

Examples of the Action Against Animal Pests

The action of the compounds of the formula I against animal pests was demonstrated by the following experiments:

The active ingredients were formulated
a. as a 0.1% strength solution in acetone or
b. as a 10% strength emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Wettol® EM (nonionic emulsifier based on ethoxylated castor oil)

and the formulations were diluted to give the desired concentration, using acetone in the case of a. or water in the case of b..

After the experiments had been concluded, in each case the lowest concentration was determined at which the compounds still caused an 80 to 100% inhibition or mortality in comparison with untreated controls (limit or minimal concentration).

Action Against *Tetranycus urticae* (Greenhouse Red Spider Mite)

Potted bush beans which showed the second pair of adult leaves were sprayed to runoff point with the aqueous preparation of active ingredient. The plants were strongly infested by adult mites and had eggs deposited on them. After 5 days in a greenhouse, the infestation was determined using a binocular.

In this test, the active ingredient I-9 showed a limit concentration of 100 ppm, while the comparative active ingredient A showed a limit concentration of 400 ppm.

We claim:

1. A benzyl phenyl ether of formula I

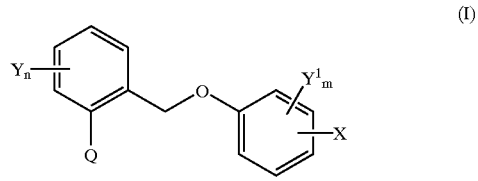

(I)

wherein
Q is C(=CHOCH$_3$)—COOCH$_3$, C(=CHCH$_3$)—COOCH$_3$, C(=NOCH$_3$)—COOCH$_3$, C(=NOCH$_3$)—CONHCH$_3$ or N(—OCH$_3$)—COOCH$_3$;

X is pyrazolyl which is unsubstituted or substituted by a group Y$^2_p$;

Y, Y$^1$ are halogen, cyano, nitro, C$_1$14 C$_4$-alkyl, C$_1$14 C$_4$-haloalkyl, C$_2$–C$_6$-alkenyl, C$_2$–C$_6$-haloalkenyl or C$_1$–C$_4$-alkoxy;

Y$^2$ is halogen, cyano, nitro, C$_1$–C$_4$-alkyl, C$_1$–C$_4$-haloalkyl, C$_2$–C$_6$-alkenyl, C$_2$–C$_6$-haloalkenyl, C$_2$–C$_6$-alkynyl, C$_1$–C$_4$-alkoxy, C$_1$–C$_4$-haloalkoxy, C$_1$–C$_4$-alkylamino, di-C$_1$–C$_4$-alkylamino or C$_1$–C$_4$-alkylthio, or phenyl, phenoxy or benzyl, where the aromatic rings may be partially or fully halogenated or may carry one to three groups R$^4$:

R$^4$ is halogen, cyano, nitro, hydroxyl, mercapto, amino, carboxyl, aminocarbonyl, aminothiocarbonyl, alkyl, haloalkyl, alkenyl, alkenyloxy, alkynyloxy, alkoxy, haloalkoxy, alkylthio, alkylamino, dialkylamio, formyl, alkylcarbonyl, alkylsulfonyl, alkylsulfoxyl, alkoxycarbonyl, alkylcarbonyloxy, alkylaminocarbonyl, dialkylaminocarbonyl, alkylaminothiocarbonyl, dialkylaminothiocarbonyl, where the alkyl groups in these radicals contain 1 to 6 carbon atoms and the abovementioned alkenyl or alkynyl groups in these radicals contain 2 to 8 carbon atoms;

and/or one to three of the following radicals cycloalkyl, cycloalkoxy, heterocyclyl, heterocyclyloxy, where the cyclic systems contain 3 to 10 ring members; aryl, aryloxy, arylthio, aryl-$C_1$–$C_6$-alkoxy, aryl-$C_1$–$C_6$-alkyl, hetaryl, hetaryloxy, hetarylthio, where the aryl radicals preferably contain 6 to 10 ring members, the hetaryl radicals 5 or 6 ring members, where the cyclic systems may be partially or fully halogenated or may be substituted by one to three groups $R^5$ or by one or two groups $R^6$:

$R^5$ is halogen, cyano, nitro, hydroxyl, $C_1$–$C_6$-alkyl, $C_1$–$C_6$-haloalkyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_3$–$C_6$-alkynyloxy and $C_1$–$C_4$-alkylenedioxy which may be halogenated; and $R^6$ is C($=$NOR$^d$)-$\Gamma_1$-R$^{d'}$, where R$^d$ is hydrogen or $C_1$–$C_6$-alkyl, $\Gamma$ is oxygen, sulfur or NR$^d$ and 1 is 0 or 1;

m, n are 0, 1 or 2, where the radicals Y and $Y^1$ may be different if m or n=2;

p is 0, 1, 2 or 3, where the radicals $Y^2$ may be different if p=2 or 3;

with the proviso that if Q is C($=$CHOCH$_3$)—COOCH$_3$, C($=$CHOCH$_3$)—CONHCH$_3$ or C($=$NOCH$_3$)—COOCH$_3$, the index m is 1 or 2;

or a salt thereof.

2. The benzyl phenyl ether of formula I defined in claim 1 which is represented by formula I'

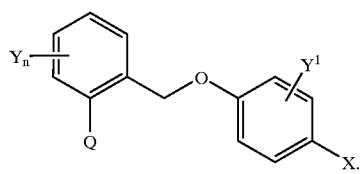

3. The benzyl phenyl ether of formula I defined in claim 1 which is represented by formula I"

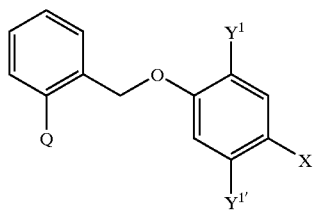

wherein $Y^{1'}$ is hydrogen.

4. A process for preparing the benzyl phenyl ether of formula I defined in claim 1, which comprises reacting a phenol of formula II

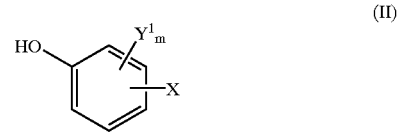

with a benzyl compound of formula III

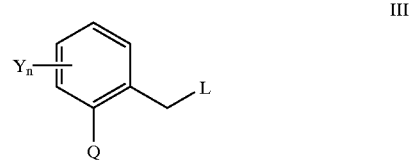

wherein L represents a nucleophilically cleavable group.

5. A composition suitable for controlling animal pests or harmful fungi which comprises a solid or liquid carrier and an effective amount of the benzyl phenyl ether of formula I defined in claim 1.

6. A method for controlling harmful fungi, which comprises treating the fungi, or materials, plants, soil or seeds to be protected against fungal attack, with an effective amount of the benzyl phenyl ether of formula I defined in claim 1.

7. A method for controlling animal pests, which comprises treating the animal pests, or materials, plants, soil or seeds to be protected against the pests, with an effective amount of the benzyl phenyl ether of formula I defined in claim 1.

8. The benzyl phenyl ether of formula I defined in claim 1, wherein $Y^2$ is halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-$C_1$–$C_4$-alkylamino and $C_1$–$C_4$-alkylthio.

9. The benzyl phenyl ether of formula I' defined in claim 2, wherein $Y^2$ is halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-$C_1$–$C_4$-alkylamino and $C_1$–$C_4$-alkylthio.

10. The benzyl phenyl ether of formula I" defined in claim 4, wherein $Y^2$ is halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-$C_1$–$C_4$-alkylamino and $C_1$–$C_4$-alkylthio.

* * * * *

UNITED STATES PATENT AND TRADEMARK OFFICE
CERTIFICATE OF CORRECTION

PATENT NO. : 6,583,090 B1
DATED : June 24, 2003
INVENTOR(S) : Gewehr et al.

It is certified that error appears in the above-identified patent and that said Letters Patent is hereby corrected as shown below:

<u>Column 152,</u>
Line 45, "$C_114$ $C_4$-alkyl, $C_114$" should be -- $C_1$-$C_4$-alkyl, $C_1$- --.

Signed and Sealed this

Twenty-fifth Day of November, 2003

JAMES E. ROGAN
*Director of the United States Patent and Trademark Office*